United States Patent
Slepushkin et al.

(10) Patent No.: US 11,866,725 B2
(45) Date of Patent: *Jan. 9, 2024

(54) OPTIMIZED LENTIVIRAL TRANSFER VECTORS AND USES THEREOF

(71) Applicants: Novartis AG, Basel (CH); The Trustees of the University of Pennsylvania, Philadelphia, PA (US)

(72) Inventors: Vladimir Slepushkin, Everett, MA (US); Dmitriy Lukashev, Ashland, MA (US)

(73) Assignees: Novartis AG, Basel (CH); The Trustees of the University of Pennsylvania, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/534,032

(22) Filed: Nov. 23, 2021

(65) Prior Publication Data

US 2022/0145326 A1    May 12, 2022

Related U.S. Application Data

(63) Continuation of application No. 16/881,523, filed on May 22, 2020, now abandoned, which is a continuation of application No. 15/778,046, filed as application No. PCT/US2016/063700 on Nov. 23, 2016, now Pat. No. 10,711,282.

(60) Provisional application No. 62/258,798, filed on Nov. 23, 2015.

(51) Int. Cl.
| | |
|---|---|
| C07K 14/705 | (2006.01) |
| C07K 16/28 | (2006.01) |
| C12N 15/86 | (2006.01) |
| C12N 15/63 | (2006.01) |
| C12N 15/49 | (2006.01) |
| C07K 14/725 | (2006.01) |

(52) U.S. Cl.
CPC .......... *C12N 15/86* (2013.01); *C07K 14/7051* (2013.01); *C07K 14/70578* (2013.01); *C07K 16/2803* (2013.01); *C07K 2317/622* (2013.01); *C07K 2319/02* (2013.01); *C07K 2319/03* (2013.01); *C12N 2740/15043* (2013.01); *C12N 2740/16043* (2013.01)

(58) Field of Classification Search
CPC .......... C07K 2319/02; C07K 14/70578; C07K 14/7051; C12N 15/86; C12N 2740/15043
See application file for complete search history.

(56) References Cited

U.S. PATENT DOCUMENTS

| | | |
|---|---|---|
| 10,711,282 B2 | 7/2020 | Slepushkin et al. |
| 2019/0062783 A1 | 2/2019 | Slepushkin et al. |
| 2020/0399655 A1 | 12/2020 | Slepushkin et al. |

FOREIGN PATENT DOCUMENTS

| | | |
|---|---|---|
| EP | 0635062 A1 | 1/1995 |
| WO | WO-93/20212 A1 | 10/1993 |
| WO | WO-2015/164759 A2 | 10/2015 |

OTHER PUBLICATIONS

Chen et al., "Construction of Anti-CD20 Single-Chain Antibody-CD28-CD137-TCRZeta Recombinant Genetic Modified T Cells and its Treatment Effect on B Cell Lymphoma," Med. Sci. Monit. 21:2110-2115 (2015).
Dull et al., "A third-generation lentivirus vector with a conditional packaging system," J. Virol. 72(11):8463-8471 (1998).
International Preliminary Report on Patentability dated Jun. 7, 2018 for International Application No. PCT/US2016/063700, Slepushkin et al., "Optimized Lentiviral Transfer Vectors and Uses Thereof," filed Nov. 23, 2016 (14 pages).
International Search Report and Written Opinion dated Apr. 21, 2017 for International Application No. PCT/US2016/063700, Slepushkin et al., "Optimized Lentiviral Transfer Vectors and Uses Thereof," filed Nov. 23, 2016 (25 pages).
Koldej et al., "Refinement of lentiviral vector for improved RNA processing and reduced rates of self inactivation repair," BMC Biotechnol. 9:86 (2009).
Lima et al., "Malignant transformation in melanocytes is associated with increased production of procoagulant microvesicles," Thromb. Haemost. 106(4):712-723 (2011).
Milone et al., "Chimeric receptors containing CD137 signal transduction domains mediate enhanced survival of T cells and increased antileukemic efficacy in vivo," Mol. Ther. 17(8):1453-1464 (2009).
Schneider et al., "Inactivation of the human immunodeficiency virus type 1 inhibitory elements allows Rev-independent expression of Gag and Gag/protease and particle formation," J. Virol. 71(7):4892-4903 (1997).

*Primary Examiner* — Barry A Chestnut
(74) *Attorney, Agent, or Firm* — Clark & Elbing LLP; Susan M. Michaud

(57) ABSTRACT

The invention features lentiviral transfer vectors that include heterologous nucleic acids to be introduced into a cell. The lentiviral transfer vector may be characterized by the following features: (a) including a cytomegalovirus (CMV) promoter; (b) including a polynucleotide encoding a partial gag protein that includes a mutated INS1 inhibitory sequence that reduces restriction of nuclear export of RNA; (c) not including a polynucleotide encoding the INS2, INS3, and INS4 inhibitory sequences of gag; (d) not including an SV40 origin of replication and/or an f1 origin of replication; (e) including a cPPT sequence that contains splice site; (f) including an EF1alpha promoter with intact splice donor and acceptor sites; and (g) including hepatitis B PRE with mutation in start codon of X protein ORF.

27 Claims, 19 Drawing Sheets

Specification includes a Sequence Listing.

FIG. 5A- 5E
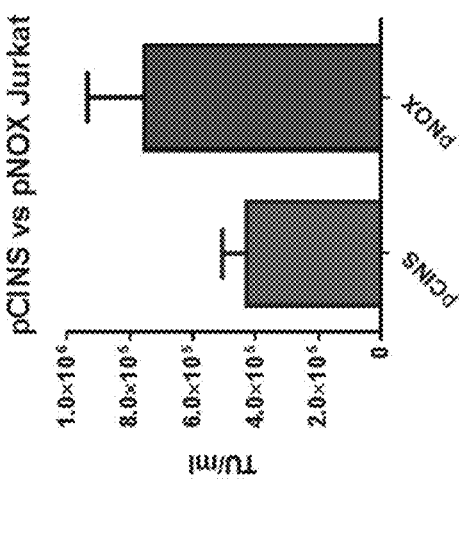
FIG. 5A
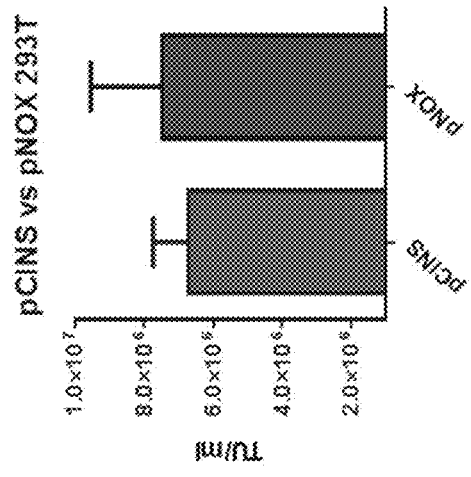
FIG. 5B
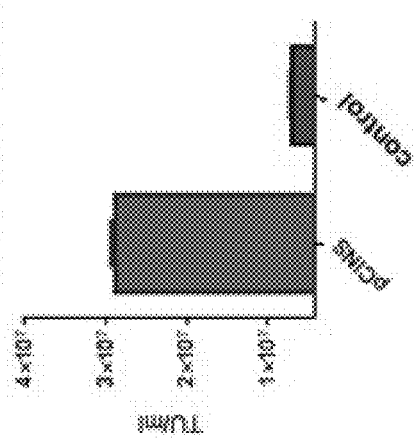
FIG. 5C
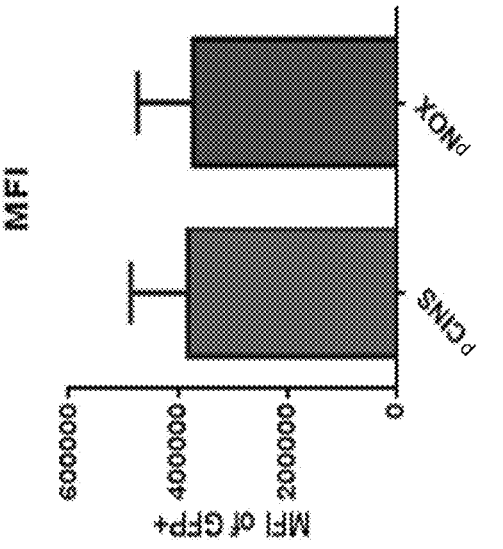
FIG. 5D
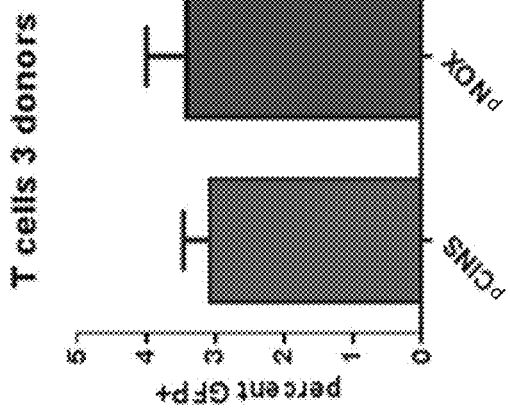
FIG. 5E

FIG. 7A-7B
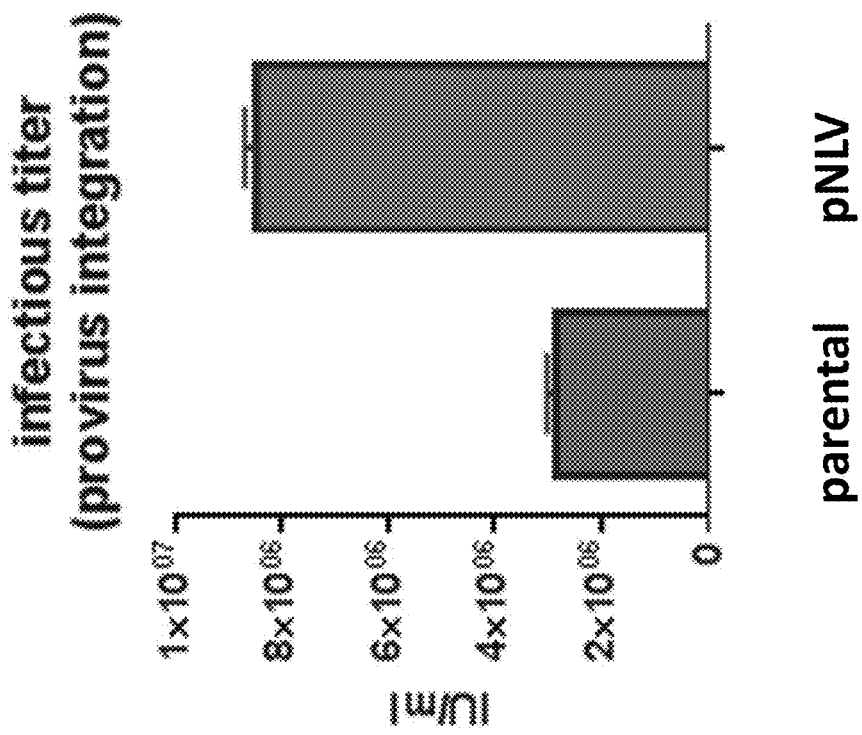
FIG. 7A
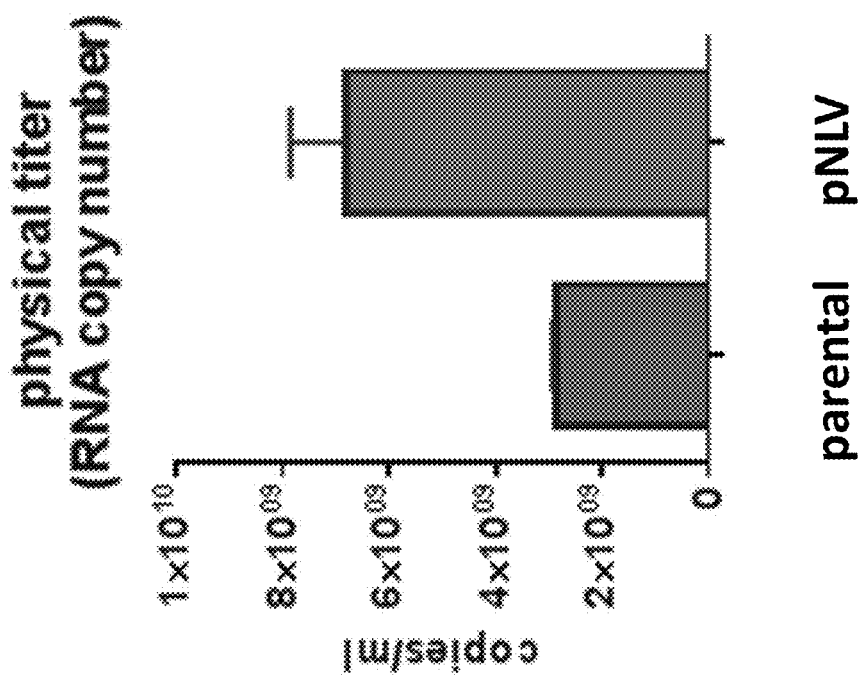
FIG. 7B

FIG. 8A-8C
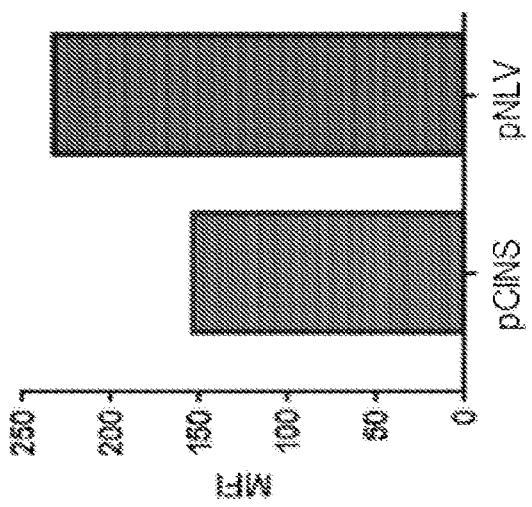
FIG. 8C
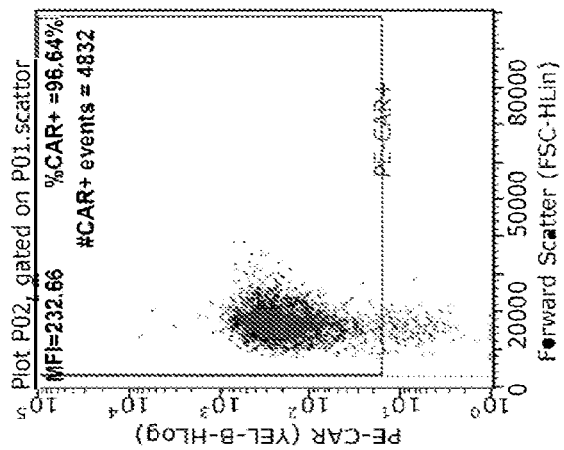
FIG. 8B
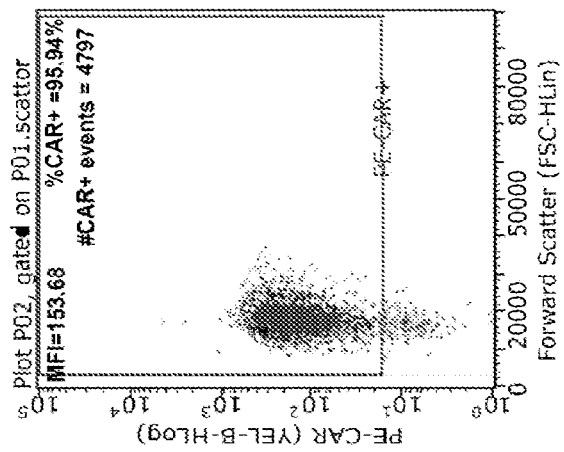
FIG. 8A

FIG. 10A-10B
FIG. 10A
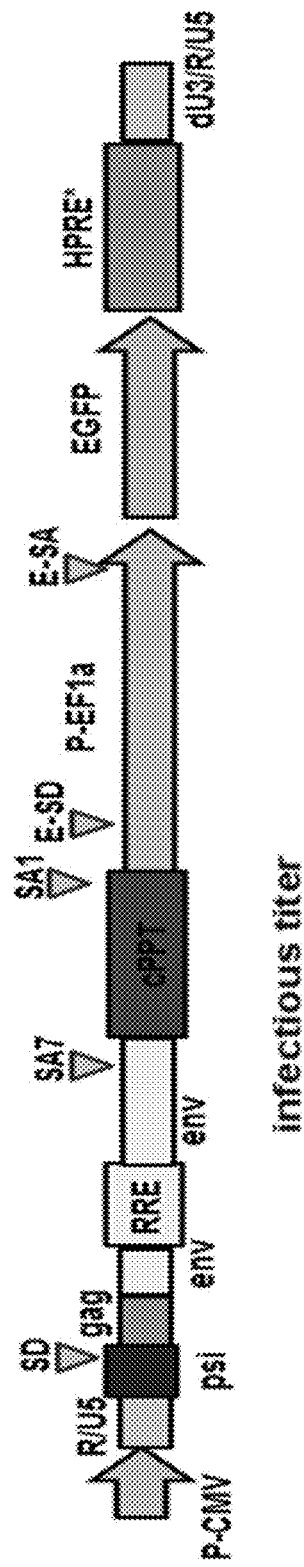
FIG. 10B
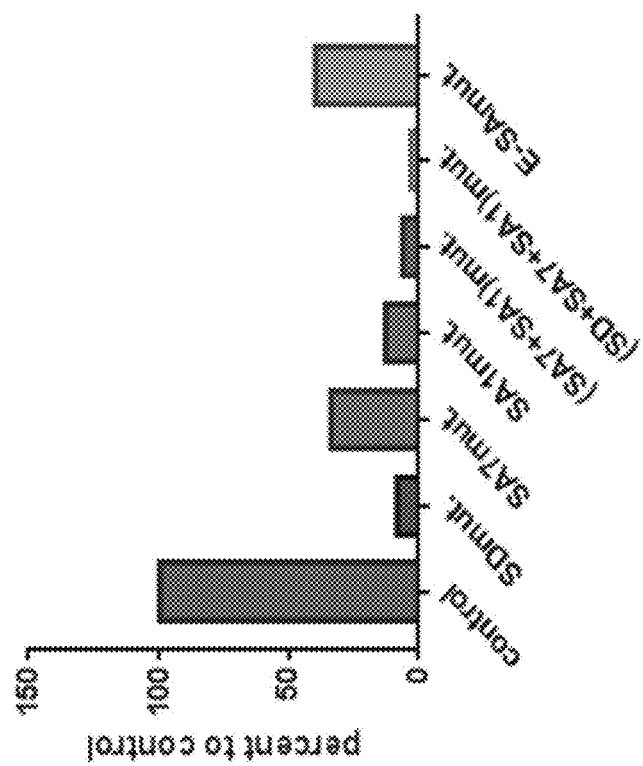

FIG. 11A-11B
FIG. 11A
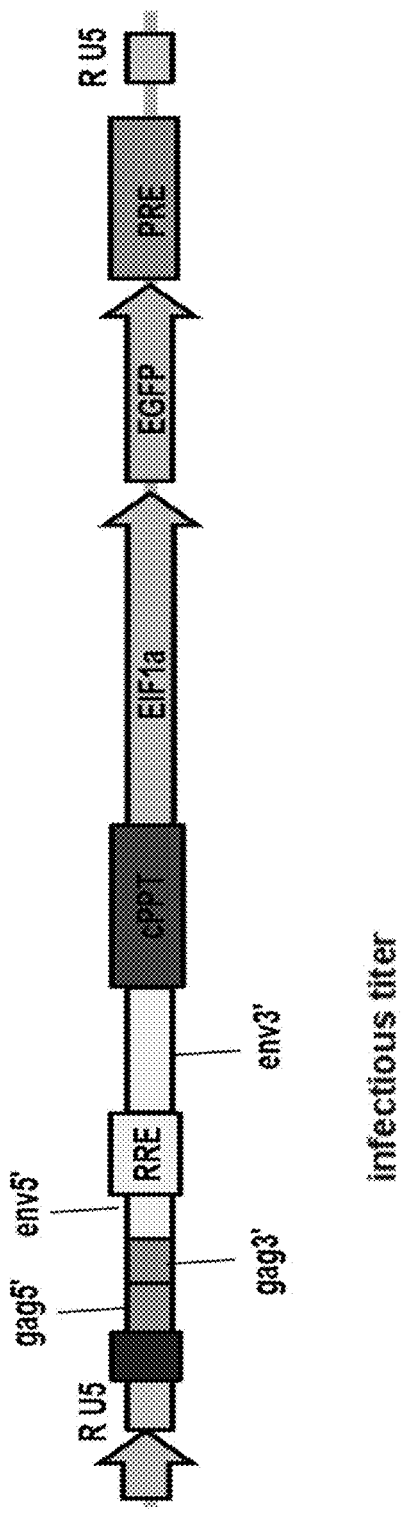
FIG. 11B
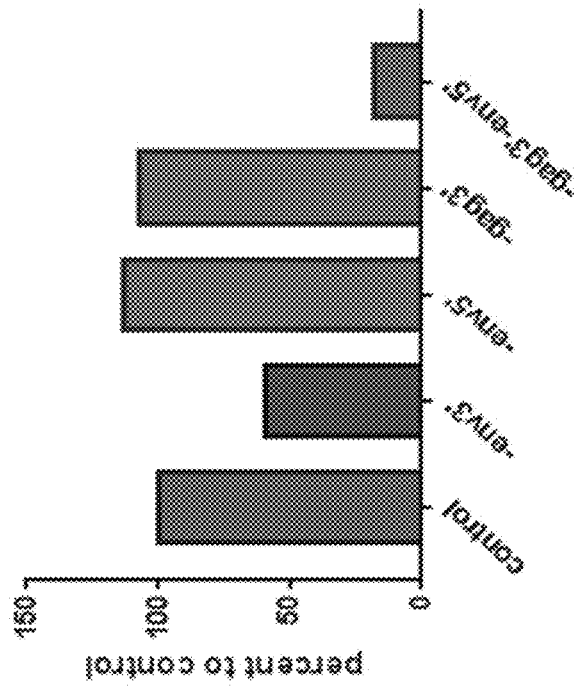

```
                                                                                                                          *
                                                                                                *
pNLV     TGATCTTCAGACCTGGAGGAGGCGATATGAG 1113
         |||||||||||  ||||||||||||||||||
pRRLSIN  tgatcttcagacctggaggagatatgag 960
                                                                                                *
                                                                                                                          *

1114 GGACAATTGGAGAAGTGAATTATATAAATATAAAGTAGTAAAAATTGAACCATTAGGAGTAGCACCCACCAAGGCAAAGAGAAGAGTGGTGCAGAGAGAA 1213
     |||||||||||||||||||||||  |||||||||||| |||||||||||||||||||||  |||||||||||||||||||||||||| ||||||||||
 961 ggacaattggagaagtgaattatataaatataaagtagtaaaaattgaaccattaggagtagcacccaccaaggcaaagagaagagtgtgcagagagaa 1060

1214 AAAAGAGCAGTGGGA
     |||||||||||||||
1061 aaaagagcagtggga
```

FIG. 12D

```
            *         *         *         *         *         *
pNLV    AGGAGCTTTGTTCCTTGGGTTCTTGGGAGCAGCAGGAAGCACTATGGGCGCAGCGTCAATGACGCTGACGGTACAGG 1313
        ||||||||||||||||||||||||||||||||||||||||||||||||||||||||||||||||     |||||||
pRRLSIN aggagctttgttccttgggttcttgggagcagcaggaagcactatgggcgcagcgtcaatgacgctga cggtacagg 1154
            *         *         *         *         *         *

*         *         *         *         *         *
1314 CCAGACAATTATTGTCTGATATAGTGCAGCAGCAGAACAATTTGCTGAGGGCTATTGAGGCGCAACAGCATCTGTTGCAACTCACAGTCTGGGGCATCAA 1413
     |||||||||||||||||    |||||||||||||||||||||||||||||||||||||||||||||||||||||||||||||||||||||||||||||
1155 ccagacaattattgtctggtatagtgcagcagcagaacaatttgctgagggctattgaggcgcaacagcatctgttgcaactcacagtctggggcatcaa 1254
         *         *         *         *         *         *

*         *         *
1414 ACAGCTCCAGGCAAGAATCCTGGCTGTGGAAAGATACCTAAAGGATCAACAGCTCCT
     ||||||||||||||||||||||||||||||||||||||||||||||||||||||||
1255 gcagctccaggcaagaatcctggctgtgaaagatacctaaaggatcaacagctcct
         *         *         *
```

FIG. 12E

```
                                                               *          *          *          *
                                                    pNLV   GGATTTGGGGTTGCTCTGGAAAACTCATTTGCACC 1513
                                                               ||||||||||||||||||||||||||||||||
                                                 pRRLSIN   ggatttggggttgctctggaaaactcatttgcacc 1348
                                                               *          *          *          *

*          *          *          *          *          *          *          *          *          *
1514 ACTGCTGCCTTGGAATGCTAGTTGGAGTAATAAATCTCTGAACAGATTTGGAGTAACATGACCTGGATGGAGTGGGACAGAGAAATTAACAATTACA 1613
     |||||||||||||||||||||||||||||||||||||||||||||||||| ||||||||||||||||||||||||||||||||||||||||||||||
1349 actgctgccttggaatgctagttggagtaataaatctctgaacagatttggagtaacatgacctggatggagtgggacagagaaattaacaattaca 1448
        *          *          *          *          *          *          *          *          *          *

1614 CAAGCTTAATACACTCCTTAATTGAAGAATCGCAAAACCAGCAAGAAAAGAATGAACAAGAATTATTGGAATTAGATAAATGGCAAGTTTGTGGAATTG 1713
     ||||||||||||||||||||||||||||||||||||||||||||||||||||||||||||||||||||||||||||||||||||||||||||||||||
1449 caagcttaatacactccttaattgaagaatcgcaaaaccagcaagaaaagaatgaacaagaattattggaattagataaatggcaagtttgtggaattg 1548
        *          *          *          *          *          *          *          *          *          *

1714 GTTTAACATAACAAATTGCCTGTGTGTATATAAAATTATTCATAATGATAGTAGGAGGCTTGGTAGGTTTAAGAATAGTTTTTGCTGTACTTTCTATAGTG 1813
     ||||||||||||||||||||||||||||||||||||||||||||||||||||||||||||||||||||||||||||||||||||||||||||||||||
1549 gtttaacataacaaattgcctgtgtgtatataaaattattcataatgatagtaggaggcttggtaggtttaagaatagttttgctgtactttctatagtg 1648
        *          *          *          *          *          *          *          *          *          *

1814 AATAGAGTTAGGCAGGATATTCACCATTATCGTTTCAGACCCACCTCCGAGGGGACCCGACAGGCCCGAAGGAATAGAAGAAGAAGGTGGAG 1913
     ||||||||||||||||||||||||||||||||||||||||||||||||| ||||||||||||||||||||||||||||||||||||||||||
1649 aatagagttaggcaggatattcaccattatcgtttcagacccaccctccgagggaccccgacaggcccgaaggaatagaagaagaaggtggag 1748
        *          *          *          *          *          *          *          *          *

1914 AGAGAGACAGAGACAGATCCATTCGATTAGTGAACGGATCTCGACGGT
     ||||||||||||||||||||||||||||||||||||||||||||||||
1749 agagagacagagacagatccattcgattagtgaacggatctcgacggt
        *          *          *          *          *
```

FIG. 12F

```
                          *         *         *         *         *         *
pNLV      AGTACAAATGGCAGTATTCATCCACAATTTTAAAAGAAAAGGG 2013
          ||                       ||  ||  |||||||||||||
pRRLSIN  -gt----------ta-------ac--ttttaaagaaaaggg 1822

*         *         *         *         *         *
2014  GGGATTGGGGGTACAGTGCAGGGGAAAGAATAGTAGACATAATAGCAACAGACATACAAACTAAAGAATTACAAAAACAAATTACAAAAATTCAAAATT 2113
      |||||||||||||||||||||||||||||||||||||||||||||||||||||||||||||||||||||||||||||||||||||||||||||||||
1823  gggattggggggtacagtgcaggggaagaatagtagacataatagcaacagacatacaaactaaagaattacaaaaacaattacaaaattcaaaatt 1922

*         *         *
2114  TTCGGGTTTATTACAGGGACAGCAGAGATCCACTTTGG
      ||                                   
1923  tt----------------------------------
```

OPTIMIZED LENTIVIRAL TRANSFER VECTORS AND USES THEREOF

SEQUENCE LISTING

The instant application contains a Sequence Listing which has been submitted electronically in ASCII format and is hereby incorporated by reference in its entirety. Said ASCII copy, created Nov. 22, 2021 is named 51093-004004_Sequence_Listing_11_22_21_ST25 and is 119,978 bytes in size.

FIELD OF THE INVENTION

The present invention relates to lentiviral transfer vectors and methods of using such vectors.

BACKGROUND OF THE INVENTION

Expression of heterologous genes in cells is desirable for many therapeutically relevant applications. One method of introducing a heterologous gene into a cell involves the use of transfer vectors which, when transfected into a host cell, induce the host cell to produce viral particles including the heterologous gene. The viral particles can then be used to infect a target cell, thereby inducing the target cell to express the heterologous gene. Viruses useful in such methods include lentiviruses, adenoviruses, and adeno-associated viruses. Some existing lentiviral vectors exhibit low gene expression levels and may be extremely large. In addition, there can be biosafety and toxicity concerns with respect to such vectors. As such, transfection and viral production using such vectors may be slow, inefficient, laborious, and expensive. Thus, a need exists for improved lentiviral vectors suitable for rapid and efficient production of viruses that are useful for inducing heterologous gene expression in target cells.

SUMMARY OF THE INVENTION

In a first aspect, the invention provides lentiviral transfer vectors, optionally including one or more heterologous nucleic acid sequences (which are optionally downstream from a Kozak sequence), and being characterized by at least two of the following features: (a) including a cytomegalovirus (CMV) promoter, (b) including a polynucleotide encoding at least a portion of a gag protein that includes a mutated INS1 inhibitory sequence that reduces restriction of nuclear export of RNA relative to wild-type INS1, (c) not including a polynucleotide encoding the INS2, INS3, and INS4 inhibitory sequences of gag, and (d) not including an SV40 origin of replication and/or an f1 origin of replication. In various embodiments, lentiviral transfer vector is characterized by at least three or all four of features (a)-(d).

In various examples, the lentiviral transfer includes a polynucleotide encoding a 150-250 (e.g., 168) nucleotide portion of a gag protein that (i) includes a mutated INS1 inhibitory sequence that reduces restriction of nuclear export of RNA relative to wild-type INS1, (ii) contains two nucleotide insertion that results in frame shift and premature termination, and/or (iii) does not include INS2, INS3, and INS4 inhibitory sequences of gag.

In additional examples, the lentiviral transfer vector further includes one or more elements selected from the group consisting of a packaging signal (psi), a partial gag sequence adjacent to or partially overlapping with psi, a rev-response element, a partial env sequence, and a cPPT sequence from pol, the sequences of which optionally originate from HIV-1 isolate NL4-3 or SF3. In various examples, the cPPT sequence includes about 150-250 (e.g., 178-181) nucleotides and includes splice acceptor SA1 sequence.

The lentiviral transfer vectors can optionally include one or more restriction sites positioned between elements of the vector (see, e.g., Tables 3-5 below for exemplary locations).

Further, the lentiviral transfer vectors can optionally include a post-transcriptional regulatory element (PRE). For example, a woodchuck hepatitis virus PRE (WPRE; having, e.g., at least 95%, 96%, 97%, 98%, 99%, or 100% sequence identity to SEQ ID NO: 78), or a hepatitis B virus isolate bba6 PRE (HPRE; having, e.g., at least 95%, 96%, 97%, 98%, 99%, or 100% sequence identity to SEQ ID NO: 79), and optionally wherein the HPRE including an inactivating mutation in an X protein-encoding sequence.

The lentiviral transfer vectors further can include a sub-genomic promoter that can be used to drive expression of a transgene. In one example, the promoter is an EF1a promoter (e.g., an EF1a promoter having a nucleic acid sequence having at least 95%, 96%, 97%, 98%, 99%, or 100% identity to SEQ ID NO: 71). The EF1a promoter optionally is full length and includes intact splice donor and splice acceptor sequences (SEQ ID NOs:72 and 73, respectively) (see, e.g., SEQ ID NO:95).

The lentiviral components of the lentiviral transfer vectors can optionally originate from HIV-1 (e.g., HIV-1 strain NL4-3 or SF3). In various embodiments, in the lentiviral transfer vectors, the sequence encoding the partial gag protein has less than 90% sequence identity to a corresponding region of gag protein encoded by a packaging plasmid used with the lentiviral transfer vector (e.g., pMDLgpRRE packaging plasmid).

In another aspect, the invention includes lentiviral transfer vectors that include one or more (e.g., 2, 3, 4, 5, 6, 7, 8, 9, 10, 11, 12, 13, 14, 15, 16, 17, 18, 19, 20, 21, or 22) of the following features: (i) a CMV promoter including a nucleic acid sequence having at least 95% identity to SEQ ID NO: 52, (ii) an LTR R region including a nucleic acid sequence having at least 95% identity to SEQ ID NO: 53, (iii) an LTR U5 region including a nucleic acid sequence having at least 95% identity to SEQ ID NO: 54, (iv) a primer binding site including a nucleic acid sequence having at least 95% identity to SEQ ID NO: 55, (v) a packaging signal including a nucleic acid sequence having at least 95% identity to SEQ ID NO: 56, (vi) a major splice donor site including a nucleic acid sequence having at least 95% identity to SEQ ID NO: 57, which is within the packaging signal, (vii) a partial gag sequence including a nucleic acid sequence having at least 95% identity to SEQ ID NO:58, (viii) a partial env sequence including a nucleic acid sequence having at least 95% identity to SEQ ID NO:60, (ix) a rev-response element including a nucleic acid sequence having at least 95% identity to SEQ ID NO: 62, (x) a partial env sequence including a nucleic acid sequence having at least 95% identity to SEQ ID NO:64, (xi) a splice acceptor site including a nucleic acid sequence having at least 95% identity to SEQ ID NO: 65, which is within the partial env sequence of part (x), (xii) a central polypurine tract including a nucleic acid sequence having at least 95% identity to SEQ ID NO: 67, 92, or 93, (xiii) a splice acceptor site including a nucleic acid sequence having at least 95% identity to SEQ ID NO: 68 or 94, which is within the central polypurine tract, (xiv) an EF1alpha promoter having at least 95% sequence identity to SEQ ID NO:71 or 95, (xv) a constitutive splice donor (CD) site including a nucleic acid sequence having at least 95% identity to SEQ ID NO: 72, which is within the EF1alpha promoter, (xvi) a constitutive splice acceptor (CA) site including a nucleic acid sequence having at least 95% identity to SEQ ID NO: 73, which is within the EF1alpha promoter, (xvii) a polynucleotide encoding an EGFP including a nucleic acid sequence having at least 95% identity to SEQ ID NO: 76 and/or a transgene sequence, (xviii) a PRE sequence including a nucleic acid sequence having at least 95% sequence identity to SEQ ID NO: 78 or 79, (xix) a partial nef sequence including a nucleic acid sequence having at least 95% sequence identity to SEQ ID NO:83, (xx) a dU3 sequence including a nucleic acid sequencing having at least 95% sequence identity to SEQ ID NO:84, (xxi) an LTR R region including a nucleic acid sequence having at least 95% identity to SEQ ID NO: 85, and (xxii) an LTR U5 region including a nucleic acid sequence having at least 95% identity to SEQ ID NO: 86. The sequence identities of these components can optionally be 96%, 97%, 98%, 99%, or 100%. Examples of combinations include those containing: i, vii, viii, ix, x, xii, xiv, and xviii; wherein x optionally includes xi, xii optionally includes xiii, and xiv optionally includes xv and xvi. In addition, the combination may also include ii, iii, iv, v, xix, xx, xxi, and/or xxv, optionally wherein v includes vi. Further, any of these combinations may also include xvii.

The lentiviral transfer vectors of the invention can optionally include a heterologous nucleic acid sequence that encodes a protein, e.g., EGFP and or a chimeric antigen receptor (CAR). In the case of a CAR, the CAR can optionally include, in a N-terminal to C-terminal direction, an antigen binding domain (e.g., an scFv), a transmembrane domain, and one or more signaling domains (e.g., one or more primary signaling domains (e.g., a CD3-zeta stimulatory domain) and/or one or more costimulatory signaling domains (e.g., an intracellular domain selected from a costimulatory protein selected from the group consisting of CD27, CD28, 4-1BB (CD137), OX40, GITR, CD30, CD40, ICOS, BAFFR, HVEM, ICAM-1, lymphocyte function-associated antigen-1 (LFA-1), CD2, CDS, CD7, CD287, LIGHT, NKG2C, NKG2D, SLAMF7, NKp80, NKp30, NKp44, NKp46, CD160, B7-H3, and a ligand that specifically binds with CD83)).

In various examples, the antigen binding domain binds to an antigen selected from the group consisting of CD19; CD123; CD22; CD30; CD171; CS-1; C-type lectin-like molecule-1, CD33; epidermal growth factor receptor variant III (EGFRvIII); ganglioside G2 (GD2); ganglioside GD3; TNF receptor family member B cell maturation (BCMA); Tn antigen ((Tn Ag) or (GalNAcα-Ser/Thr)); prostate-specific membrane antigen (PSMA); Receptor tyrosine kinase-like orphan receptor 1 (ROR1); Fms-Like Tyrosine Kinase 3 (FLT3); Tumor-associated glycoprotein 72 (TAG72); CD38; CD44v6; Carcinoembryonic antigen (CEA); Epithelial cell adhesion molecule (EPCAM); B7H3 (CD276); KIT (CD117); Interleukin-13 receptor subunit alpha-2; mesothelin; Interleukin 11 receptor alpha (IL-11 Ra); prostate stem cell antigen (PSCA); Protease Serine 21; vascular endothelial growth factor receptor 2 (VEGFR2); Lewis(Y) antigen; CD24; Platelet-derived growth factor receptor beta (PDGFR-beta); Stage-specific embryonic antigen-4 (SSEA-4); CD20; Folate receptor alpha; Receptor tyrosine-protein kinase ERBB2 (Her2/neu); Mucin 1, cell surface associated (MUC1); epidermal growth factor receptor (EGFR); neural cell adhesion molecule (NCAM); Prostase; prostatic acid phosphatase (PAP); elongation factor 2 mutated (ELF2M); Ephrin B2; fibroblast activation protein alpha (FAP); insulin-like growth factor 1 receptor (IGF-I receptor), carbonic anhydrase IX (CAIX); Proteasome (Prosome, Macropain) Subunit, Beta Type, 9 (LMP2); glycoprotein 100 (gp100); oncogene fusion protein consisting of breakpoint cluster region (BCR) and Abelson murine leukemia viral oncogene homolog 1 (Abl) (bcr-abl); tyrosinase; ephrin type-A receptor 2 (EphA2); Fucosyl GM1; sialyl Lewis adhesion molecule (sLe); ganglioside GM3; transglutaminase 5 (TGS5); high molecular weight-melanoma-associated antigen (HMWMAA); o-acetyl-G D2 ganglioside (OAcGD2); Folate receptor beta; tumor endothelial marker 1 (TEM1/CD248); tumor endothelial marker 7-related (TEM7R); claudin 6 (CLDN6); thyroid stimulating hormone receptor (TSHR); G protein-coupled receptor class C group 5, member D (GPRC5D); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (OR51E2); TCR Gamma Alternate Reading Frame Protein (TARP); Wilms tumor protein (WT1); Cancer/testis antigen 1 (NY-ESO-1); Cancer/testis antigen 2 (LAGE-1a); Melanoma-associated antigen 1 (MAGE-A1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); melanoma cancer testis antigen-1 (MAD-CT-1); melanoma cancer testis antigen-2 (MAD-CT-2); Fos-related antigen 1; tumor protein p53 (p53); p53 mutant; prostein; surviving; telomerase; prostate carcinoma tumor antigen-1, melanoma antigen recognized by T cells 1; Rat sarcoma (Ras) mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin B1; v-myc avian myelocytomatosis viral oncogene neuroblastoma derived homolog (MYCN); Ras Homolog Family Member C (RhoC); Tyrosinase-related protein 2 (TRP-2); Cytochrome P450 1B1 (CYP1B1); CCCTC-Binding Factor (Zinc Finger Protein)-Like, Squamous Cell Carcinoma Antigen Recognized By T Cells 3 (SART3); Paired box protein Pax-5 (PAX5); proacrosin binding protein sp32 (OY-TES1); lymphocyte-specific protein tyrosine kinase (LCK); A kinase anchor protein 4 (AKAP-4); synovial sarcoma, X breakpoint 2 (SSX2); Receptor for Advanced Glycation Endproducts (RAGE-1); renal ubiquitous 1 (RU1); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2); CD79a; CD79b; CD72; Leukocyte-associated immunoglobulin-like receptor 1 (LAIR1); Fc fragment of IgA receptor (FCAR or CD89); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); and immunoglobulin lambda-like polypeptide 1 (IGLL1).

In a specific example, the CAR includes an anti-CD19 antibody or a fragment thereof, a 4-1BB (CD137) transmembrane domain, and a CD3-zeta signaling domain.

In another aspect, the invention includes lentiviral transfer vectors including, from 5' to 3', one or more (e.g., all) of the following elements in operable association: a promoter, a packaging signal (psi) including a major splice donor site (SD), a partial gag sequence, a partial env sequence, a Rev-response element (RRE), a partial env sequence including splice acceptor site (SA7), a central polypurine tract (cPPT) including a splice acceptor site (SA1), an EF1a promoter, which comprises a constitutive splice donor site (CD) and a constitutive splice acceptor site (CD), optionally a gene encoding EGFP and/or a heterologous nucleic acid sequence, and a post-transcriptional regulatory element.

In one example, the invention includes lentiviral transfer vector including, from 5' to 3', one or more of the following elements in operable association: a CMV promoter, an LTR R region, an LTR U5 region, a primer binding site (PBS), a packaging signal (psi) including a major splice donor site (SD), a partial gag sequence, a partial env sequence, a Rev-response element (RRE), a partial env sequence including splice acceptor site (SA7), a central polypurine tract (cPPT) including a splice acceptor site (SA1), an EF1a promoter, optionally a gene encoding EGFP and/or a heterologous nucleic acid sequence, a post-transcriptional regulatory element, an LTR R region, an LTR U5 region, an SV40 polyA tail, a kanamycin resistance gene (nptII), and a pUC origin of replication.

In various examples, the post-transcriptional regulatory element is a woodchuck hepatitis virus PRE (WPRE) or a hepatitis B virus isolate bba6 PRE (HPRE), as described herein.

In further examples, the heterologous nucleic acid sequence encodes a chimeric antigen receptor (CAR), as described herein. In one example, the CAR can include an anti-CD19 antibody or a fragment thereof, a 4-1BB (CD137) transmembrane domain, and a CD3-zeta signaling domain.

In another aspect, the invention includes a host cell (e.g., a 293T cell, a Jurkat T cell, or a primary human T cell) including a lentiviral transfer vector as described herein. Optionally, the host call can further include one or more lentiviral packaging vectors.

In a further aspect, the invention includes compositions including a lentiviral transfer vector as described herein and one or more packaging vectors.

In an additional aspect, the invention includes methods of producing a lentivirus capable of expressing a heterologous nucleic acid sequence. These methods can optionally include (a) introducing into a cell (e.g., a 293T cell, a Jurkat T cell, or a primary human T cell): (i) a lentiviral transfer vector as described herein, and (ii) one or more lentiviral packaging vectors; and (b) expressing viral proteins encoded by the lentiviral transfer vector and/or the packaging vector in the cell, thereby producing a lentivirus including the heterologous nucleic acid sequence of the lentiviral transfer vector.

Definitions

The term "Chimeric Antigen Receptor" or alternatively a "CAR" refers to a set of polypeptides, typically two in the simplest embodiments, which when in an immune effector cell, provides the cell with specificity for a target cell, typically a cancer cell, and with intracellular signal generation. In some embodiments, a CAR comprises at least an extracellular antigen binding domain, a transmembrane domain and a cytoplasmic signaling domain (also referred to herein as "an intracellular signaling domain") comprising a functional signaling domain derived from a stimulatory molecule and/or costimulatory molecule as defined below. In some aspects, the set of polypeptides are contiguous with each other. In some embodiments, the set of polypeptides include a dimerization switch that, upon the presence of a dimerization molecule, can couple the polypeptides to one another, e.g., can couple an antigen binding domain to an intracellular signaling domain. In one aspect, the stimulatory molecule is the zeta chain associated with the T cell receptor complex. In one aspect, the cytoplasmic signaling domain further comprises one or more functional signaling domains derived from at least one costimulatory molecule as defined below. In one aspect, the costimulatory molecule is chosen from the costimulatory molecules described herein, e.g., 4-1BB (i.e., CD137), CD27 and/or CD28. In one aspect, the CAR comprises a chimeric fusion protein comprising an extracellular antigen binding domain, a transmembrane domain and an intracellular signaling domain comprising a functional signaling domain derived from a stimulatory molecule. In one aspect, the CAR comprises a chimeric fusion protein comprising an extracellular antigen binding domain, a transmembrane domain and an intracellular signaling domain comprising a functional signaling domain derived from a costimulatory molecule and a functional signaling domain derived from a stimulatory molecule. In one aspect, the CAR comprises a chimeric fusion protein comprising an extracellular antigen binding domain, a transmembrane domain and an intracellular signaling domain comprising two functional signaling domains derived from one or more costimulatory molecule(s) and a functional signaling domain derived from a stimulatory molecule. In one aspect, the CAR comprises a chimeric fusion protein comprising an extracellular antigen binding domain, a transmembrane domain and an intracellular signaling domain comprising at least two functional signaling domains derived from one or more costimulatory molecule(s) and a functional signaling domain derived from a stimulatory molecule. In one aspect the CAR comprises an optional leader sequence at the amino-terminus (N-ter) of the CAR fusion protein. In one aspect, the CAR further comprises a leader sequence at the N-terminus of the extracellular antigen binding domain, wherein the leader sequence is optionally cleaved from the antigen binding domain (e.g., a scFv) during cellular processing and localization of the CAR to the cellular membrane.

A CAR that comprises an antigen binding domain (e.g., a scFv, or TCR) that targets a specific tumor maker X, such as those described herein, is also referred to as XCAR. For example, a CAR that comprises an antigen binding domain that targets CD19 is referred to as CD19CAR.

The term "signaling domain" refers to the functional portion of a protein which acts by transmitting information within the cell to regulate cellular activity via defined signaling pathways by generating second messengers or functioning as effectors by responding to such messengers.

The term "antibody," as used herein, refers to a protein, or polypeptide sequence derived from an immunoglobulin molecule which specifically binds with an antigen. Antibodies can be polyclonal or monoclonal, multiple or single chain, or intact immunoglobulins, and may be derived from natural sources or from recombinant sources. Antibodies can be tetramers of immunoglobulin molecules.

The term "antibody fragment" refers to at least one portion of an antibody, that retains the ability to specifically interact with (e.g., by binding, steric hinderance, stabilizing/destabilizing, spatial distribution) an epitope of an antigen. Examples of antibody fragments include, but are not limited to, Fab, Fab', F(ab')$_2$, Fv fragments, scFv antibody fragments, disulfide-linked Fvs (sdFv), a Fd fragment consisting of the VH and CH1 domains, linear antibodies, single domain antibodies such as sdAb (either VL or VH), camelid VHH domains, multi-specific antibodies formed from antibody fragments such as a bivalent fragment comprising two Fab fragments linked by a disulfide bridge at the hinge region, and an isolated CDR or other epitope binding fragments of an antibody. An antigen binding fragment can also be incorporated into single domain antibodies, maxibodies, minibodies, nanobodies, intrabodies, diabodies, triabodies, tetrabodies, v-NAR and bis-scFv (see, e.g., Hollinger and Hudson, Nature Biotechnology 23:1126-1136, 2005). Antigen binding fragments can also be grafted into scaffolds based on polypeptides such as a fibronectin type III (Fn3)(see U.S. Pat. No. 6,703,199, which describes fibronectin polypeptide minibodies).

The term "scFv" refers to a fusion protein comprising at least one antibody fragment comprising a variable region of a light chain and at least one antibody fragment comprising a variable region of a heavy chain, wherein the light and heavy chain variable regions are contiguously linked, e.g., via a synthetic linker, e.g., a short flexible polypeptide linker, and capable of being expressed as a single chain polypeptide, and wherein the scFv retains the specificity of the intact antibody from which it is derived. Unless specified, as used herein an scFv may have the VL and VH variable regions in either order, e.g., with respect to the N-terminal and C-terminal ends of the polypeptide, the scFv may comprise VL-linker-VH or may comprise VH-linker-VL.

The portion of the CAR of the invention comprising an antibody or antibody fragment thereof may exist in a variety of forms where the antigen binding domain is expressed as part of a contiguous polypeptide chain including, for example, a single domain antibody fragment (sdAb), a single chain antibody (scFv), a humanized antibody or bispecific antibody (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426). In one aspect, the antigen binding domain of a CAR composition of the invention comprises an antibody fragment. In a further aspect, the CAR comprises an antibody fragment that comprises a scFv. The precise amino acid sequence boundaries of a given CDR can be determined using any of a number of well-known schemes, including those described by Kabat et al. (1991), "Sequences of Proteins of Immunological Interest," 5th Ed. Public Health Service, National Institutes of Health, Bethesda, MD ("Kabat" numbering scheme), Al-Lazikani et al., (1997) JMB 273, 927-948 ("Chothia" numbering scheme), or a combination thereof.

As used herein, the term "binding domain" or "antibody molecule" refers to a protein, e.g., an immunoglobulin chain or fragment thereof, comprising at least one immunoglobulin variable domain sequence. The term "binding domain" or "antibody molecule" encompasses antibodies and antibody fragments. In an embodiment, an antibody molecule is a multispecific antibody molecule, e.g., it comprises a plurality of immunoglobulin variable domain sequences, wherein a first immunoglobulin variable domain sequence of the plurality has binding specificity for a first epitope and a second immunoglobulin variable domain sequence of the plurality has binding specificity for a second epitope. In an embodiment, a multispecific antibody molecule is a bispecific antibody molecule. A bispecific antibody has specificity for no more than two antigens. A bispecific antibody molecule is characterized by a first immunoglobulin variable domain sequence which has binding specificity for a first epitope and a second immunoglobulin variable domain sequence that has binding specificity for a second epitope.

The portion of the CAR of the invention comprising an antibody or antibody fragment thereof may exist in a variety of forms where the antigen binding domain is expressed as part of a contiguous polypeptide chain including, for example, a single domain antibody fragment (sdAb), a single chain antibody (scFv), a humanized antibody, or bispecific antibody (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, NY; Houston et al., 1988, Proc. Natl. Acad. Sci. USA 85:5879-5883; Bird et al., 1988, Science 242:423-426). In one aspect, the antigen binding domain of a CAR composition of the invention comprises an antibody fragment. In a further aspect, the CAR comprises an antibody fragment that comprises a scFv.

The term "antibody heavy chain," refers to the larger of the two types of polypeptide chains present in antibody molecules in their naturally occurring conformations, and which normally determines the class to which the antibody belongs.

The term "antibody light chain," refers to the smaller of the two types of polypeptide chains present in antibody molecules in their naturally occurring conformations. Kappa (K) and lambda (A) light chains refer to the two major antibody light chain isotypes.

The term "recombinant antibody" refers to an antibody which is generated using recombinant DNA technology, such as, for example, an antibody expressed by a bacteriophage or yeast expression system. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using recombinant DNA or amino acid sequence technology which is available and well known in the art.

The term "antigen" or "Ag" refers to a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to encode polypeptides that elicit the desired immune response. Moreover, a skilled artisan will understand that an antigen need not be encoded by a "gene" at all. It is readily apparent that an antigen can be generated synthesized or can be derived from a biological sample, or might be macromolecule besides a polypeptide. Such a biological sample can include, but is not limited to a tissue sample, a tumor sample, a cell or a fluid with other biological components.

The term "autologous" refers to any material derived from the same individual (e.g., a cell or organism) to whom it is later to be re-introduced into the individual. The term "heterologous" may refer to any material derived from a different individual (e.g., a cell or organism) than the individual to whom the material is introduced. In some instances, the term "heterologous" may refer to any material derived from an individual (e.g., a cell or organism) of a different species than the individual to whom the material is introduced.

An "intracellular signaling domain," as the term is used herein, refers to an intracellular portion of a molecule. The intracellular signaling domain generates a signal that promotes an immune effector function of the CAR containing cell, e.g., a CART cell. Examples of immune effector function, e.g., in a CART cell, include cytolytic activity and helper activity, including the secretion of cytokines.

In an embodiment, the intracellular signaling domain can comprise a primary intracellular signaling domain. Exemplary primary intracellular signaling domains include those derived from the molecules responsible for primary stimulation, or antigen dependent simulation. In an embodiment, the intracellular signaling domain can comprise a costimulatory intracellular signaling domain. Exemplary costimulatory intracellular signaling domains include those derived from molecules responsible for costimulatory signals, or antigen independent stimulation. For example, in the case of a CART, a primary intracellular signaling domain can comprise a cytoplasmic sequence of a T cell receptor, and a costimulatory intracellular signaling domain can comprise cytoplasmic sequence from co-receptor or costimulatory molecule.

A primary intracellular signaling domain can comprise a signaling motif which is known as an immunoreceptor tyrosine-based activation motif or ITAM. Examples of ITAM containing primary cytoplasmic signaling sequences include, but are not limited to, those derived from CD3 zeta, common FcR gamma (FCER1G), Fc gamma RIIa, FcR beta (Fc Epsilon R1 b), CD3 gamma, CD3 delta, CD3 epsilon, CD79a, CD79b, DAP10, and DAP12.

The term "zeta" or alternatively "zeta chain", "CD3-zeta" or "TCR-zeta" is defined as the protein provided as GenBan Acc. No. BAG36664.1, or the equivalent residues from a non-human species, e.g., mouse, rodent, monkey, ape and the like, and a "zeta stimulatory domain" or alternatively a "CD3-zeta stimulatory domain" or a "TCR-zeta stimulatory domain" is defined as the amino acid residues from the cytoplasmic domain of the zeta chain, or functional derivatives thereof, that are sufficient to functionally transmit an initial signal necessary for T cell activation. In one aspect the cytoplasmic domain of zeta comprises residues 52 through 164 of GenBank Acc. No. BAG36664.1 or the equivalent residues from a non-human species, e.g., mouse, rodent, monkey, ape and the like, that are functional orthologs thereof.

The term a "costimulatory molecule" refers to a cognate binding partner on a T cell that specifically binds with a costimulatory ligand, thereby mediating a costimulatory response by the T cell, such as, but not limited to, proliferation. Costimulatory molecules are cell surface molecules other than antigen receptors or their ligands that contribute to an efficient immune response. Costimulatory molecules include, but are not limited to an MHC class I molecule, BTLA and a Toll ligand receptor, as well as OX40, CD27, CD28, CDS, ICAM-1, LFA-1 (CD11a/CD18), ICOS (CD278), and 4-1BB (CD137). Further examples of such costimulatory molecules include CDS, ICAM-1, GITR, BAFFR, HVEM (LIGHTR), SLAMF7, NKp80 (KLRF1), NKp44, NKp30, NKp46, CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11 b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83.

A costimulatory intracellular signaling domain can be the intracellular portion of a costimulatory molecule. A costimulatory molecule can be represented in the following protein families: TNF receptor proteins, Immunoglobulin-like proteins, cytokine receptors, integrins, signaling lymphocytic activation molecules (SLAM proteins), and activating NK cell receptors. Examples of such molecules include CD27, CD28, 4-1BB (CD137), OX40, GITR, CD30, CD40, ICOS, BAFFR, HVEM, ICAM-1, lymphocyte function-associated antigen-1 (LFA-1), CD2, CDS, CD7, CD287, LIGHT, NKG2C, NKG2D, SLAMF7, NKp80, NKp30, NKp44, NKp46, CD160, B7-H3, and a ligand that specifically binds with CD83, and the like.

The intracellular signaling domain can comprise the entire intracellular portion, or the entire native intracellular signaling domain, of the molecule from which it is derived, or a functional fragment or derivative thereof.

The term "4-1BB" refers to a member of the TNFR superfamily with an amino acid sequence provided as GenBank Acc. No. AAA62478.2, or the equivalent residues from a non-human species, e.g., mouse, rodent, monkey, ape and the like; and a "4-1BB costimulatory domain" is defined as amino acid residues 214-255 of GenBank Acc. No. AAA62478.2, or the equivalent residues from a non-human species, e.g., mouse, rodent, monkey, ape and the like.

The term "encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (e.g., rRNA, tRNA and mRNA) or a defined sequence of amino acids and the biological properties resulting therefrom. Thus, a gene, cDNA, or RNA, encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

The term "expression" refers to the transcription and/or translation of a particular nucleotide sequence driven by a promoter.

The term "transfer vector" refers to a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "transfer vector" includes an autonomously replicating plasmid. The term should also be construed to further include non-plasmid and non-viral compounds which facilitate transfer of transgene into cells. In some instances, a transfer vector is a plasmid DNA construct encoding transgene and lentiviral cis-elements required for packaging and insertion into host genome.

The term "lentivirus" refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses.

The term "lentiviral vector" refers to a vector including one or more nucleic acid sequences derived from at least a portion of a lentivirus genome. A lentiviral vector may contains non-coding sequences of one or more proteins from a lentivirus (e.g., HIV-1). A "lentiviral transfer vector" may include a heterologous nucleic acid sequence, for example, to be transferred into a cell, and may further include, for example, one or more lentiviral genes, or portions thereof. A "lentiviral packaging vector" may include one or more genes encoding lentiviral proteins, or portions thereof. For example, a lentiviral envelope protein may include a gene encoding an env protein, or a portion thereof. Transfection of host cells with a transfer vector and one or more packaging vectors can be carried out in order to produce a virus, which in turn to be used to infect target cells to express one or more transgenes comprised within a heterologous nucleic acid sequence within the target cells. A "transgene" thus refers to a heterologous gene that is transferred into a target cell, for example, using a lentiviral transfer vector of the invention. In certain examples described herein, a transgene is a gene encoding a chimeric antigen receptor, such as those described herein.

The term "isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

The terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. A polypeptide includes a natural peptide, a recombinant peptide, or a combination thereof.

The term "promoter" refers to a DNA sequence recognized by the synthetic machinery of the cell, or introduced synthetic machinery, required to initiate the specific transcription of a polynucleotide sequence.

The term "promoter/regulatory sequence" refers to a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

As used herein, a "poly(A)" is a series of adenosines attached by polyadenylation to the mRNA. In the preferred embodiment of a construct for transient expression, the polyA is between 50 and 5000 nucleotides in length, preferably greater than 64 nucleotides, more preferably greater than 100 nucleotides, most preferably greater than 300 or 400 nucleotides. Poly(A) sequences can be modified chemically or enzymatically to modulate mRNA functionality such as localization, stability or efficiency of translation.

As used herein, "polyadenylation" refers to the covalent linkage of a polyadenylyl moiety, or its modified variant, to a messenger RNA molecule. In eukaryotic organisms, most messenger RNA (mRNA) molecules are polyadenylated at the 3' end. The 3' poly(A) tail is a long sequence of adenine nucleotides (often several hundred) added to the pre-mRNA through the action of an enzyme, polyadenylate polymerase. In higher eukaryotes, the poly(A) tail is added onto transcripts that contain a specific sequence, the polyadenylation signal. The poly(A) tail and the protein bound to it aid in protecting mRNA from degradation by exonucleases. Polyadenylation is also important for transcription termination, export of the mRNA from the nucleus, and translation. Polyadenylation occurs in the nucleus immediately after transcription of DNA into RNA, but additionally can also occur later in the cytoplasm. After transcription has been terminated, the mRNA chain is cleaved through the action of an endonuclease complex associated with RNA polymerase. The cleavage site is usually characterized by the presence of the base sequence AAUAAA near the cleavage site. After the mRNA has been cleaved, adenosine residues are added to the free 3' end at the cleavage site.

The term "subject" is intended to include a living organism (e.g., mammals, human). In some instances, a subject may be a subject in which an immune response can be elicited.

The term "transfected" or "transformed" or "transduced" refers to a process by which exogenous nucleic acid is transferred or introduced into the host cell. A "transfected" or "transformed" or "transduced" cell is one which has been transfected, transformed, or transduced with exogenous nucleic acid. The cell includes the primary subject cell and its progeny. An "infected" cell is one that has be transfected, transformed, or transduced with a pathogen, for example, a virus (e.g., a lentivirus). In some instances, one or more viral nucleic acid elements may be integrated into the genome of an infected cell.

The invention provides several advantages. For example, the viral transfer vectors of the invention can be used to achieve increased production of viral genomic RNA in packaging cells, increased nuclear export of RNA, and increased viral titer. In addition, the viral transfer vectors can be of a size that is relatively small, compared to prior vectors, which facilitates ease of use and permits the insertion of larger heterologous sequences.

Other features and advantages of the invention will be apparent from the following detailed description, the drawings, and the claims.

BRIEF DESCRIPTION OF THE DRAWINGS

FIG. 5A-5E is a series of graphs showing the performance of the GFP-encoding pCINS and pNOX vectors relative to each other and in comparison to other lentiviral vectors. The following packaging vectors were used in these experiments: pNVS-MDG-VSVG-Kan; pNVS-MDLgp-RRE; pNVS RSV Rev-Kan. FIG. 5A Use of the pCINS transfer vector results in viral titer several times higher than that generated using the parental transfer vector before optimization. FIG. 5B The pCINS and pNOX vectors generate similar viral titers in 293T cells. FIG. 5C pNOX generated higher viral titers in Jurkat cells compared to pCINS. FIG. 5D Transduction of primary human T cells with pCINS or pNOX resulted in the generation similar percentages of GFP-expressing T cells, indicating that pCINS and pNOX generate similar infectious titers in primary human T cells. FIG. 5E A population of T cells that had been transduced with pNOX, which contains the HPRE post-transcriptional regulatory element, showed similar quantities of GFP+ cells after integration of lentiviral vector sequences compared to a population of T cells transduced with pCINS, which contains the WPRE post-transcriptional regulatory element.

FIG. 7A-7B is a set of graphs showing the performance of the parental transfer vector and pNLV transfer vectors relative to each other. FIG. 7A Use of the pNLV lentiviral backbone produces more packaged lentiviral genomic RNA than the control GFP vector lentiviral backbone, as measured by qRT-PCR using Lenti-X qRT-PCR Titration Kit (Clontech). FIG. 7B Transduction of 293T cells with the pNLV vector generated higher viral titers compared to the control transfer vector, as measured by proviral integration assay using qPCR.

FIG. 8A-8C is a series of plots showing FACS measurements of transgene expression in SupT1 cells transduced with pCINS or pNLV lentiviral vectors expressing a transgene (e.g., a CAR). FIG. 8A FACS plot of cells transduced with a pCINS lentiviral vector containing a transgene, using a PE-conjugated antibody as a detection reagent for the transgene on the surface. FIG. 8B FACS plot of cells transduced with a pNLV lentiviral vector containing a transgene, using a PE-conjugated antibody as a detection reagent for the transgene. FIG. 8C Plot comparing the MFI measured in the FACS analyses of FIG. 8A and FIG. 8B, showing higher surface expression of the transgene in cells transduced with the pNLV transfer vector.

FIG. 9A The second generation pLVX (Clontech) lentiviral vector was produced with Tat-expressing construct and transduced into 293T cells and was found to have a slightly higher viral titer than a control transfer vector. FIG. 9B The pLenti6.2 (Life Technologies) lentiviral vector was transduced into cells and was found to have a large decrease in viral titer compared to the control transfer vector. FIG. 9C The pD2109 (DNA2.0) lentiviral vector was transduced into cells and was found to have a small decrease in viral titer compared to the control transfer vector. FIG. 9D The pCINS lentiviral vector was transduced into cells and was found to have a much higher viral titer than the control transfer vector. FIG. 9E The pNLV lentiviral vector was transduced into cells and was found to have a higher viral titer than the pCINS transfer vector.

FIG. 10A-10B is a schematic and plot comparing the effects of different splice site mutations in control non-optimized transfer construct on viral titer. FIG. 10A Panel A shows a schematic showing the lentiviral backbone with labeled arrowheads denoting the location of the splice donor and splice acceptor sites that were mutated for subsequent viral titer determination. FIG. 10B The various splice donor and splice acceptor site mutants of the indicated transfer vector were transduced into cells and the viral titer was compared across the panel of mutants to a control transfer vector. All of the mutations led to a large decrease in viral titer, with the SA7mut and E-SAmut transfer vectors having slightly improved titers.

FIG. 11A-11B is a schematic and plot of a transfer vector backbone containing gag and/or env-derived sequence deletions and comparing the subsequent effects on viral titer. FIG. 11A Panel A shows a schematic of the lentiviral backbone with annotations indicating the approximate location of gag and/or env deletions. FIG. 11B Transfer vector constructs with deletions in the env and/or gag regions were transduced into cells and the viral titer was determined. Compared to a control transfer vector, the −env3' and −gag3'-env5' mutants had a decrease in viral titer, while the −env5' and −gag3' showed little difference in viral titer.

FIG. 12A-12F is a series of schematics representing several sequence alignments between the pNLV transfer vector and the pRRLSIN transfer vector across key viral cis elements. FIG. 12A Panel A shows a schematic of the alignment between the psi regions of the two vectors, with the shaded regions denoting areas of sequence variation. FIG. 12B Panel B shows a schematic of the alignment between the gag regions of the two vectors, with the shaded regions denoting areas of sequence variation. FIG. 12C Panel C shows a schematic of the alignment between the env regions of the two vectors, with the shaded regions denoting areas of sequence variation. FIG. 12D Panel D shows a schematic of the alignment between the RRE regions of the two vectors, with the shaded regions denoting areas of sequence variation. FIG. 12E Panel E shows a schematic of the alignment between the env (with major splice acceptor site 7) regions of the two vectors, with the shaded regions denoting areas of sequence variation. FIG. 12F Panel F shows a schematic of the alignment between the pol (with cPPT and major splice acceptor site 1) regions of the two vectors, with the shaded regions denoting areas of sequence variation. #=Single-nucleotide substitution. Top row=pNLV; bottom row=pRRLSIN. pRRLSIN sequence corresponds to the sequence of the pRRLSIN.cPPT.PGK-GFP.WPRE vector (Addgene Plasmid #12252). The pNLV cPPT sequence is that of SEQ ID NO:92.

DETAILED DESCRIPTION OF THE INVENTION

Figure 1:
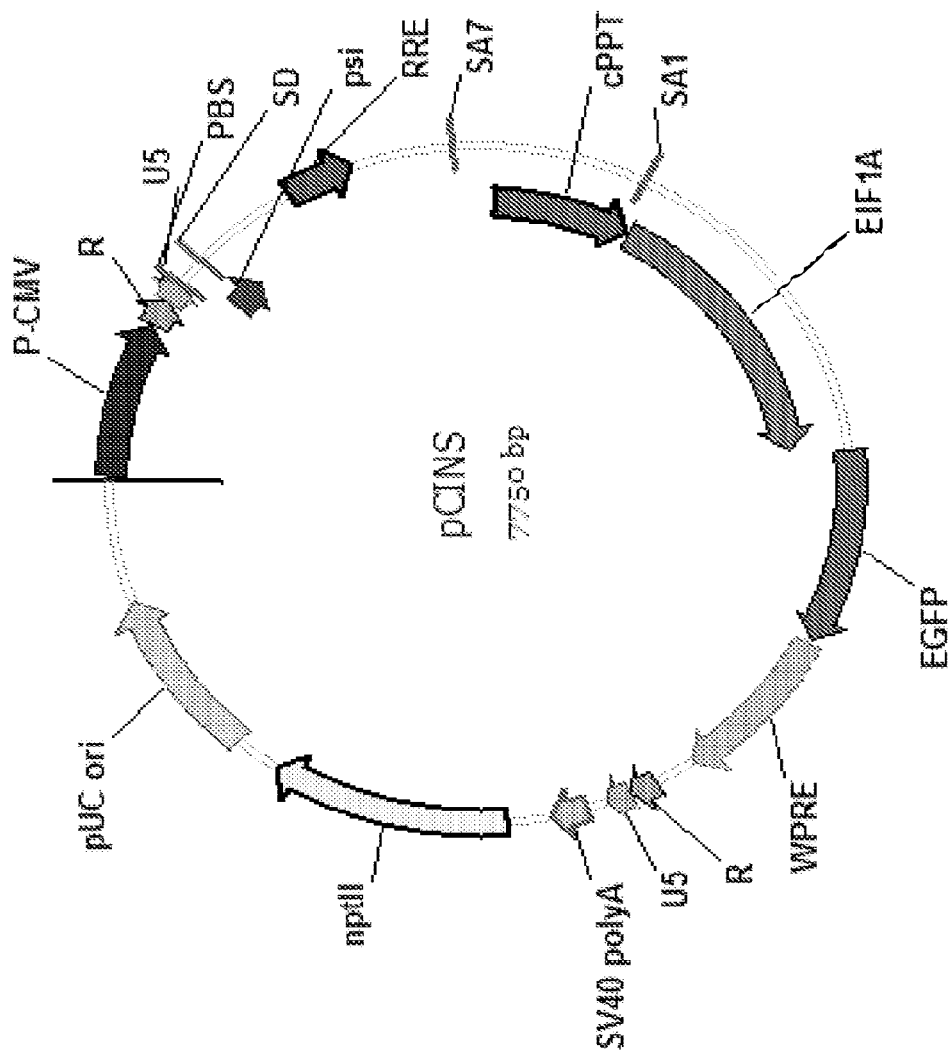
FIG. 1 is a schematic showing the feature map of the pCINS lentiviral transfer vector. P-CMV=cytomegalovirus (CMV) promoter; R=LTR R region, U5=LTR U5 region, PBS=primer binding site; SD=major splice donor site; psi=packaging signal; RRE=Rev-response element; SA7=splice acceptor site; cPPT=central polypurine tract; SA1=splice acceptor site; EF1A=human EF1alpha promoter; EGFP=GFP reporter open reading frame (ORF); WPRE=woodchuck hepatitis virus post-transcriptional regulatory element; SV40 polyA=SV40 polyadenylation sequence; nptII=kanamycin resistance gene; pUC ori=origin of replication from pUC.

The present invention provides lentiviral transfer vectors and uses thereof. Generally, the lentiviral transfer vectors of the invention include a heterologous nucleic acid sequence, such as, for example, a sequence encoding a transgene (e.g., a gene encoding a chimeric antigen receptor (CAR); see below). The lentiviral transfer vectors further include a combination of two or more additional desirable features, as described below.

The lentiviral transfer vectors of the invention can be useful, for example, in providing a heterologous nucleic acid sequence to a host cell for packaging into a virus, which in turn can be used for expressing a transgene within the heterologous nucleic acid sequence in a desired target cell. For example, the lentiviral transfer vectors may be introduced into a host cell in combination with, for example, one or more packaging vectors, such that the host cell produces a lentivirus. The lentivirus can then be used, for example, to infect a desired target cell. In certain instances, lentiviral infection of the desired target cell may result in integration of one or more nucleic acid sequences from the lentiviral transfer vector (e.g., a heterologous nucleic acid encoding a transgene) into the genome of the desired target cell (e.g., a T cell). Thus, the transduced cell may be capable of expressing one or more genes (e.g., a CAR gene) present in the heterologous nucleic acid and/or the viral elements, and this capability may be passed on to the progeny of the transduced cell.

Introduction of nucleic acid sequences from the lentiviral transfer vector of the invention into a target cell, via a lentivirus generated in a host cell, can enable expression, by the target cell, of elements from the lentiviral transfer vector (e.g., the heterologous nucleic acid encoding the transgene).

Transfer Vector Elements

Lentiviral transfer vectors of the invention include elements suitable for enabling transfer of heterologous nucleic acids present in the lentiviral transfer vector into a cell (e.g., a cell transfected with the lentiviral transfer vector, and optionally one or more additional vectors, such as packaging vectors). In particular, lentiviral transfer vectors of the invention are generally characterized by at least two of the following features: (a) including a cytomegalovirus (CMV) promoter; (b) including a polynucleotide encoding at least a portion of a gag protein that includes a mutated INS1 inhibitory sequence that reduces restriction of nuclear export of RNA relative to wild-type INS1; (c) not including a polynucleotide encoding INS2, INS3, and INS4 inhibitory sequences of gag; and (d) not including an SV40 origin of replication and/or an f1 origin of replication. In some instances, a lentiviral transfer vector of the invention includes a cPPT element having a length of about 178 nucleotides (e.g., about 100, 110, 120, 125, 130, 140, 150, 160, 170, 175, 178, 180, 190, 200, 225, or 250 nucleotides). In one instance, the cPPT element has a length of 178 nucleotides. In certain instances, the vector includes a Kozak sequence positioned upstream (e.g., immediately upstream) of a heterologous nucleic acid or transgene to be transferred into a host cell.

In some instances, the lentiviral transfer vectors may include one or more of the following: a promoter (e.g., a CMV, RSV, or EF1a promoter) driving expression of one or more viral sequences, long terminal repeat (LTR) regions (e.g., an R region or an U5 region), a primer binding site (PBS), a packaging signal (psi) (e.g., a packaging signal including a major splice donor site (SD)), a partial gag sequence (e.g., as described herein), a partial env sequence, a Rev-response element (RRE), additional partial env sequence, optionally including a splice acceptor site (e.g., an SA7 splice acceptor), a partial pol sequence including a central polypurine tract (cPPT) (e.g., a cPPT comprising a splice acceptor site, e.g., SA1), a subgenomic promoter (e.g., P-EF1a), a heterologous nucleic acid (e.g., a heterologous nucleic acid including a gene encoding EGFP and/or a transgene of interest (e.g., a CAR gene)), a post-transcriptional regulatory element (e.g., a WPRE or HPRE, optionally including an X protein mutation), a polyA sequence (e.g., an SV40 polyA tail), a selectable marker (e.g., a kanamycin resistance gene (nptII), ampicilin resistance gene, or a chloramphenicol resistance gene), and an origin of replication (e.g., a pUC origin of replication, an SV40 origin of replication, or an f1 origin of replication). As noted above, the lentiviral transfer vectors may include an EF1a promoter, which can be used to drive expression of the transgene. In particular instances, the EF1a promoter includes a wild-type EF1a promoter sequence having the nucleic acid sequence of SEQ ID NO: 95. In some instances, cells transfected with a lentiviral transfer vector of the invention and/or a packaging vector as described herein produce lentiviral RNA that is primarily spliced. Lentiviral vectors of the invention may also include additional sequences (e.g., vector backbone sequences), such as well known in the art. In certain instances, lentiviral vectors of the invention may include or incorporate sequences from the vectors described herein (e.g., pNOX, pCINS, and/or pNLV). In particular instances, lentiviral vectors of the invention may include or incorporate vector backbone sequences, or portions thereof, from vectors described herein (e.g., pNOX, pCINS, and/or pNLV). In one example, a lentiviral vector of the invention incorporates a vector backbone sequence, or portion thereof, from pNLV.

The lentiviral transfer vector may also include elements suitable for driving expression of the heterologous protein in a cell. In certain instances, a Kozak sequence is positioned upstream of the heterologous protein open reading frame. For example, the lentiviral transfer vector may include a promoter (e.g., a CMV, RSV, or EF1a promoter) that controls the expression of the heterologous nucleic acid. Other promoters suitable for use in the lentiviral transfer vector include, for example, constitutive promoters or tissue/cell type-specific promoters. In some instances, the lentiviral transfer vector includes a means of selectively marking a gene product (e.g., a polypeptide or RNA) encoded by at least a portion of the heterologous nucleic acid (e.g., a gene product of interest). For example, the lentiviral transfer vector may include a marker gene (e.g., a gene encoding a selectable marker, such as a fluorescent protein (e.g., GFP, YFP, RFP, dsRed, mCherry, or any derivative thereof)). The marker gene may be expressed independently of the gene product of interest. Alternatively, the marker gene may be co-expressed with the gene product of interest. For example, the marker gene may be under the control of the same or different promoter as the gene product of interest. In another example, the marker gene may be fused to the gene product of interest. The elements of the lentiviral transfer vectors of the invention are, in general, in operable association with one another, to enable the transfer vectors to participate in the formation of a lentivirus in a transfected cell, together with one or more packaging vectors.

Viral Proteins

Figure 12A:
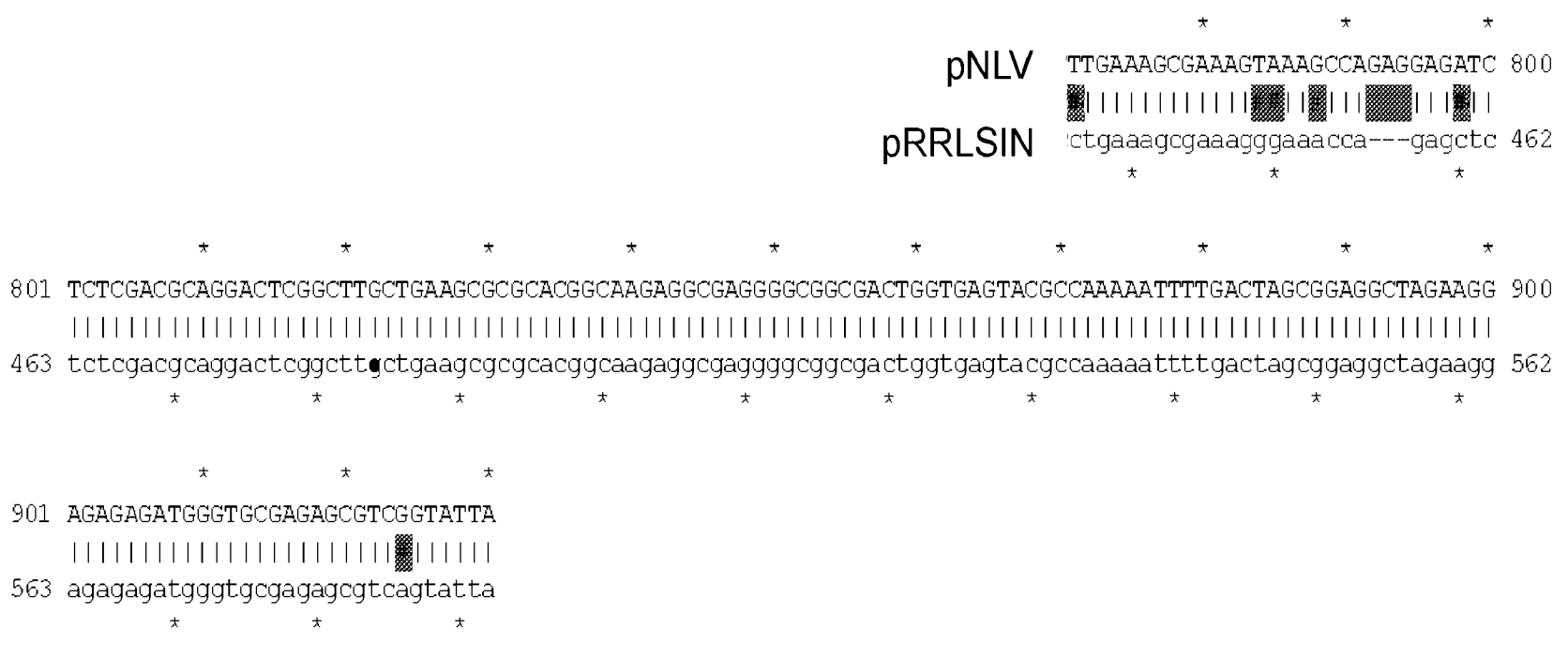
Figure 12B:
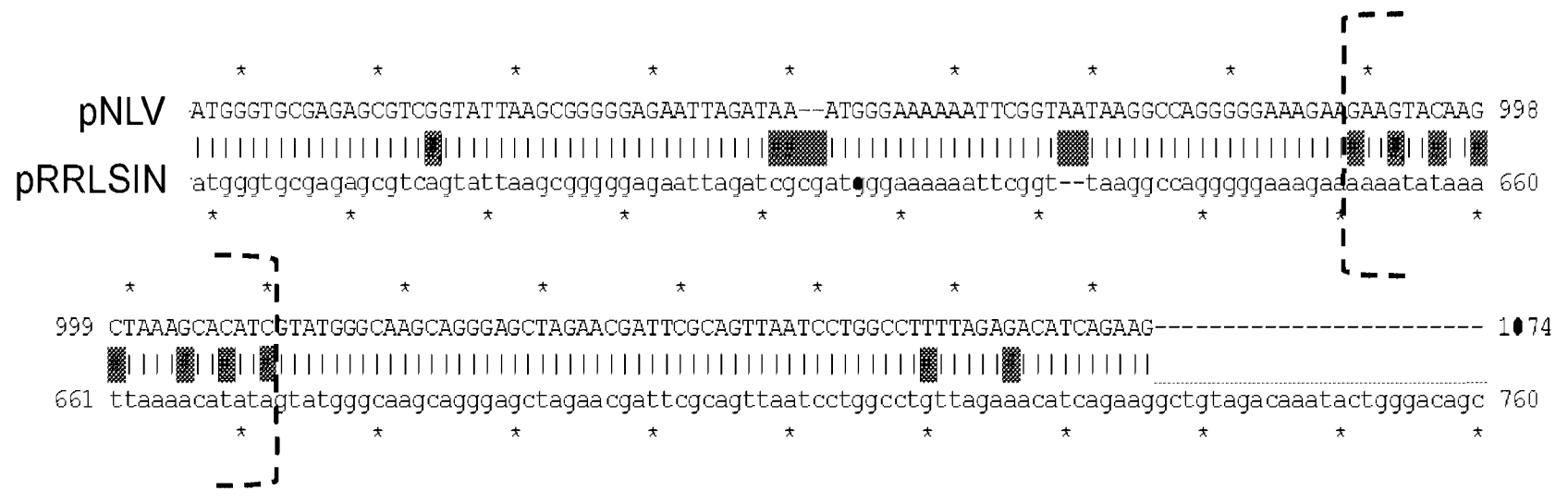

In some instances, a lentiviral transfer vector of the invention may include one or more genes encoding viral proteins, or portions thereof. For example, the lentiviral transfer vector may include a polynucleotide encoding at least a portion of a gag protein (e.g., an HIV-1 gag protein). In various examples, the sequence encoding the gag protein comprises 250 nucleotides or less, e.g., 200 nucleotides or less, 175 nucleotides or less, or 150 nucleotides or less. In one example, the sequence encoding the gag protein comprises or consists of 168 nucleotides. The nucleotide sequence encoding gag can include INS1 sequences (e.g., with the mutations noted below), but lack INS2, INS3, and INS4 sequences. The polynucleotide encoding the gag protein, or portion thereof, may include mutations that inactivate one or more inhibitory sequences, for example, as described herein. Mutations in one or more (e.g., all) of the following nucleotides of the INS1 region can be included: G989, G992, C995, G998, C999, G1004, C1007T, and C1010 (using the pNLV sequence of FIG. 12B as a reference (pNLV)). In specific examples, these mutations are as follows: G989A, G992A, C995T, G998A, C999T, G1004A, C1007T, and C1010A. Furthermore, sequences encoding gag can include an insertion resulting in a frameshift and premature termination (see, e.g., FIG. 12B, below) of undesirable production of gag protein. In certain instances, a lentiviral transfer vector may include a partial gag sequence (e.g., a partial gag sequence positioned adjacent to and/or overlapping with a packaging signal in the lentiviral transfer vector), a partial env sequence, and/or a partial pol sequence (e.g., a central polypurine tract from pol). The partial gag, partial env, and/or partial pol sequences may, in certain instances, originate from HIV-1 (e.g., HIV-1 isolate NL4-3 or SF3). In one example, the lentiviral transfer vector may include a partial gag sequence under the control of a CMV promoter.

Post-Transcriptional Regulatory Elements (PREs)

A lentiviral transfer vector of the invention may include a post-transcriptional regulatory element (PRE). PREs are nucleic acid sequences that contribute to regulation of expression of a DNA sequence within which the PRE is located. For example, a PRE may be transcribed along with the rest of the DNA sequence. The portion of the resulting mRNA molecule transcribed from the PRE may form a tertiary structure that enhances expression of the gene product. A PRE may include, in some instances, three components (alpha, beta, and gamma). The activity of the PRE may depend on how many of the components are present. For example, a full tripartite PRE may be more active than the alpha component alone. PREs suitable for inclusion in the lentiviral transfer vectors of the invention include, for example, woodchuck hepatitis virus PRE (WPRE) and/or hepatitis B virus PRE (HPRE). In certain instances, an HPRE may include a natural HPRE sequence (e.g., a natural HPRE sequence derived from hepatitis B virus isolate bba6, complete genome; GenBank: KP341007.1). In some instances, a PRE in a lentiviral transfer vector of the invention may be modified to inactivate an X protein, as described herein.

Omitted Elements

The present invention features lentiviral transfer vectors that have been optimized over existing vectors. In some instances, it is desirable to reduce the size of a vector, such as a lentiviral transfer vector of the invention. For example, redundant sequences or elements may be removed from a vector to reduce its size. In certain instances, unneeded origins of replication (e.g., an SV40 ori sequence and/or an f1 ori sequence) may be removed from a lentiviral vector. Thus, in various examples, the lentiviral transfer vectors of the invention may be less than 8000 nucleotides in length, e.g., less than 7900, 7800, or 7700 nucleotides in length.

In some instances, portions of elements or genes encoded by a vector may be deleted from the vector. For example, protein-coding genes may include inhibitory sequences. Such inhibitory sequences may inhibit the expression, processing, and/or function of a gene. For example, the HIV-1 gag protein includes a series of inhibitory RNA elements known as INS elements (e.g., INS1, INS2, INS3, and INS4). Such INS elements are described, for example, in *J. Virol.* 71(7):4892-4903, 1997; *J. Virol.* 66(12):7176-7182, 1992; and *J. Virol.* 68(6):3784-3793, 1994; each of which is incorporated herein by reference. In one example, INS1 is involved in restricting nuclear export of unspliced viral RNA (see, e.g., *J. Virol.* 66(12):7176-7182, 1992). Removal or mutation of one or more (e.g., 1, 2, 3, or 4) of these inhibitory sequences (e.g., by mutation of the nucleotides forming a particular INS element; see, e.g., above) from a gene (e.g., a gene encoding a gag protein, or a portion thereof) may therefore increase the expression, processing, and/or function of the gene, or its gene product. In one example, mutation of the INS1 element in a gene encoding a gag protein, or a portion thereof, results in increased nuclear export of unspliced viral RNAs.

In some instances, entire elements or genes encoded by a vector may be deleted from the vector. For example, some post-transcriptional regulatory elements, such as WPRE, include a polynucleotide encoding an X protein, or a portion thereof. The X protein has been implicated in generation of liver cancers (see, e.g., *Gene Ther.* 12(1):3-4, 2005; incorporated herein by reference). As such, it may be beneficial from a biosafety standpoint to prevent X protein activity, function, and/or expression from the PRE of a lentiviral transfer vector of the invention. For example, the X protein-encoding gene may be deleted from the vector. Alternatively, the start codon of the X protein-encoding gene may be mutated (e.g., from ATG to AGG), thereby preventing translation of the X protein. In another alternative, one or more inactivating mutations may be introduced into the X protein amino acid sequence that prevents its function. Further approaches for inactivating the X protein include mutation methods well known in the art.

Packaging Vectors

The lentiviral transfer vectors of the invention may be co-transfected into a cell together with one or more additional vectors. In some instances, the one or more additional vectors may include lentiviral packaging vectors. In certain instances, the one or more additional plasmids may include an envelope plasmid (e.g., an envelope plasmid encoding VSV-G, such as pMD.G). Generally, a packaging vector includes one or more polynucleotide sequences encoding lentiviral proteins (e.g., gag, pol, env, tat, rev, vif, vpu, vpr, and/or nef protein, or a derivative, combination, or portion thereof). A packaging vector to be co-transfected into a cell with a lentiviral transfer vector of the invention may include sequence(s) encoding one or more lentiviral proteins not encoded by the lentiviral transfer vector. For example, a lentiviral transfer vector may be co-transfected with a first packaging vector encoding gag and pol and a second packaging vector encoding rev. Thus, co-transfection of a lentiviral transfer vector with such packaging vector(s) may result in the introduction of all genes required for viral particle formation into the cell, thereby enabling the cell to produce viral particles that may be isolated. Appropriate packaging vectors for use in the invention can be selected by those of skill in the art based on, for example, consideration of the features selected for a lentiviral transfer vector of the invention. For examples of packaging vectors that can be used or adapted for use in the invention see, e.g., WO 03/064665, WO 2009/153563, U.S. Pat. No. 7,419,829, WO 2004/022761, U.S. Pat. No. 5,817,491, WO 99/41397, U.S. Pat. Nos. 6,924,123, 7,056,699, WO 99/32646, WO 98/51810, and WO 98/17815. In some instances, a packaging plasmid may encode a gag and/or pol protein, and may optionally include an RRE sequence (e.g., an pMDLgpRRE vector; see, e.g., Dull et al., J. Virol. 72(11):8463-8471, 1998). In certain instances, a packaging vector may encode a rev protein (e.g., a pRSV-Rev vector).

Host Cells for Lentivirus Production

A lentiviral transfer vector of the invention may be introduced into a host cell (packaging cell). The lentiviral transfer vector is generally co-transfected into the host cell together with one or more additional vectors (e.g., one or more packaging vectors). The one or more additional vectors may encode viral proteins and/or regulatory proteins. Co-transfection of the lentiviral transfer vector and the one or more additional vectors enables the host cell to produce a lentivirus (e.g., a lentivirus encoding a heterologous nucleic acid sequence from the lentiviral transfer vector). Lentiviruses produced by a host cell as described herein may be used to infect another cell. The heterologous nucleic acid and/or one or more additional elements (e.g., promoters and viral elements) may be integrated into the genome of the infected cell, thereby permitting the cell and its progeny to express gene(s) originating from the lentiviral transfer vector.

A packaging cell suitable for transfection with the lentiviral transfer vector (and one or more packaging vectors) may be a eukaryotic cell, such as a mammalian cell. The host cell may originate from a cell line (e.g., an immortalized cell line). For example, the host cell may be a HEK 293 cell (e.g., a 293T cell including the SV40 large T-antigen). Information regarding cells that are transduced by the lentiviruses is provided below.

Target cell is the cell, which is infected (transduced) with lentiviral vector (lentivirus) encoding transgene of interest. After transduction, transgene of interest is stably inserted into target cell genome and can be detected by molecular biology methods such as PCR and Southern blot. Transgene can be expressed in target cell and detected by flow cytometry or Western blot. In some instances, target cell is a human cell. In certain instances, the host cell is a particular cell type of interest, e.g., a primary T cell, SupT1 cell, Jurkat cell, or 293T cell.

Methods of Producing Lentiviruses

The lentiviral transfer vectors of the invention may be useful for producing lentiviruses in cells (e.g., a host cell as described herein). A method of producing a lentivirus using a lentiviral transfer vector described herein will generally involve introducing the lentiviral transfer vector and one or more additional vectors (e.g., a lentiviral packaging vector) into the cell. The vectors may be introduced into the cell using transfection methods well known in the art. After transfection, the cell may be permitted to express viral proteins encoded by the lentiviral transfer vector and/or the one or more additional vectors (e.g., by incubating the cell under standard conditions known in the art for inducing viral gene expression). In some instances, the viral genes are expressed under the control of a constitutive or inducible promoter. In the latter case, viral gene expression may be selectively induced by incubating the cell under conditions suitable for activating the inducible promoter. Viral proteins produced by the cell may subsequently form a viral particle, which buds from the cell surface and can be isolated from the solution (e.g., according to methods well known in the art). During formation of the virus, a polynucleotide including the sequence of the heterologous nucleic acid may be incorporated into the viral particle. Thus, this process yields a lentivirus that includes the heterologous nucleic acid originating from the lentiviral transfer vector.

Heterologous Nucleic Acids

The present invention features a lentiviral transfer vector that includes a heterologous nucleic acid. The heterologous nucleic acid may include a transgene of interest (e.g., a gene encoding a polypeptide or a gene for a noncoding RNA) that is to be expressed in a cell. In some instances, the heterologous protein ORF is positioned downstream of a Kozak sequence. The gene of interest may be, in certain instances, associated with (e.g., fused to) a marker gene, as described herein. In some instances, the heterologous nucleic acid of the lentiviral transfer vector will be present in a lentivirus produced in a cell transfected with the lentiviral transfer vector and, optionally, one or more additional vectors (e.g., packaging vectors). In certain instances, the heterologous nucleic acid may be integrated into the genome of a cell infected with the lentivirus. Integration of the heterologous nucleic acid into the genome of such a cell may permit the cell and its progeny to express the gene of interest. The gene of interest may be any gene known in the art. Exemplary genes of interest include, without limitation, genes encoding chimeric antigen receptors (CARs), binding moieties (e.g., antibodies and antibody fragments), signaling proteins, cell surface proteins (e.g., T cell receptors), proteins involved in disease (e.g., cancers, autoimmune diseases, neurological disorders, or any other disease known in the art), or any derivative or combination thereof.

Chimeric Antigen Receptors

A lentiviral transfer vector of the invention may be used to induce the production of a chimeric antigen receptor (CAR) in a cell. A CAR may be a transmembrane protein including (i) an extracellular antigen binding domain, (ii) a transmembrane domain, and (iii) an intracellular signaling domain. A CAR encoded by a lentiviral transfer vector of the present invention may be any CAR known in the art. In one embodiment, the CAR includes an anti-CD19 antibody or a fragment thereof, a 4-1BB (CD137) transmembrane domain, and a CD3-zeta signaling domain.

Antigen Binding Domain

The present invention can be used to make immune effector cells (e.g., T cells, NK cells) that are engineered to contain one or more CARs that direct the immune effector cells to undesired cells (e.g., cancer cells). This is achieved through an antigen binding domain on the CAR that is specific for a cancer associated antigen. There are two classes of cancer associated antigens (tumor antigens) that can be targeted by the CARs of the instant invention: (1) cancer associated antigens that are expressed on the surface of cancer cells; and (2) cancer associated antigens that itself is intracelluar, however, a fragment of such antigen (peptide) is presented on the surface of the cancer cells by MHC (major histocompatibility complex).

In some instances, the antigen binding domain is capable of specifically binding to an antigen selected from the group consisting of CD19; CD123; CD22; CD30; CD171; CS-1; C-type lectin-like molecule-1, CD33; epidermal growth factor receptor variant III (EGFRvIII); ganglioside G2 (GD2); ganglioside GD3; TNF receptor family member B cell maturation (BCMA); Tn antigen ((Tn Ag) or (GalNAcα-Ser/Thr)); prostate-specific membrane antigen (PSMA); Receptor tyrosine kinase-like orphan receptor 1 (ROR1); Fms-Like Tyrosine Kinase 3 (FLT3); Tumor-associated glycoprotein 72 (TAG72); CD38; CD44v6; Carcinoembryonic antigen (CEA); Epithelial cell adhesion molecule (EPCAM); B7H3 (CD276); KIT (CD117); Interleukin-13 receptor subunit alpha-2; mesothelin; Interleukin 11 receptor alpha (IL-11 Ra); prostate stem cell antigen (PSCA); Protease Serine 21; vascular endothelial growth factor receptor 2 (VEGFR2); Lewis(Y) antigen; CD24; Platelet-derived growth factor receptor beta (PDGFR-beta); Stage-specific embryonic antigen-4 (SSEA-4); CD20; Folate receptor alpha; Receptor tyrosine-protein kinase ERBB2 (Her2/neu); Mucin 1, cell surface associated (MUC1); epidermal growth factor receptor (EGFR); neural cell adhesion molecule (NCAM); Prostase; prostatic acid phosphatase (PAP); elongation factor 2 mutated (ELF2M); Ephrin B2; fibroblast activation protein alpha (FAP); insulin-like growth factor 1 receptor (IGF-I receptor), carbonic anhydrase IX (CAIX); Proteasome (Prosome, Macropain) Subunit, Beta Type, 9 (LMP2); glycoprotein 100 (gp100); oncogene fusion protein consisting of breakpoint cluster region (BCR) and Abelson murine leukemia viral oncogene homolog 1 (Abl) (bcr-abl); tyrosinase; ephrin type-A receptor 2 (EphA2); Fucosyl GM1; sialyl Lewis adhesion molecule (sLe); ganglioside GM3; transglutaminase 5 (TGS5); high molecular weight-melanoma-associated antigen (HMWMAA); o-acetyl-GD2 ganglioside (OAcGD2); Folate receptor beta; tumor endothelial marker 1 (TEM1/CD248); tumor endothelial marker 7-related (TEM7R); claudin 6 (CLDN6); thyroid stimulating hormone receptor (TSHR); G protein-coupled receptor class C group 5, member D (GPRC5D); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (OR51E2); TCR Gamma Alternate Reading Frame Protein (TARP); Wilms tumor protein (WT1); Cancer/testis antigen 1 (NY-ESO-1); Cancer/testis antigen 2 (LAGE-1a); Melanoma-associated antigen 1 (MAGE-A1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); melanoma cancer testis antigen-1 (MAD-CT-1); melanoma cancer testis antigen-2 (MAD-CT-2); Fos-related antigen 1; tumor protein p53 (p53); p53 mutant; prostein; surviving; telomerase; prostate carcinoma tumor antigen-1, melanoma antigen recognized by T cells 1; Rat sarcoma (Ras) mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin B1; v-myc avian myelocytomatosis viral oncogene neuroblastoma derived homolog (MYCN); Ras Homolog Family Member C (RhoC); Tyrosinase-related protein 2 (TRP-2); Cytochrome P450 1B1 (CYP1B1); CCCTC-Binding Factor (Zinc Finger Protein)-Like, Squamous Cell Carcinoma Antigen Recognized By T Cells 3 (SART3); Paired box protein Pax-5 (PAX5); proacrosin binding protein sp32 (OY-TES1); lymphocyte-specific protein tyrosine kinase (LCK); A kinase anchor protein 4 (AKAP-4); synovial sarcoma, X breakpoint 2 (SSX2); Receptor for Advanced Glycation Endproducts (RAGE-1); renal ubiquitous 1 (RU1); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2); CD79a; CD79b; CD72; Leukocyte-associated immunoglobulin-like receptor 1 (LAIR1); Fc fragment of IgA receptor (FCAR or CD89); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); and immunoglobulin lambda-like polypeptide 1 (IGLL1).

A CAR described herein can comprise an antigen binding domain (e.g., antibody or antibody fragment, TCR or TCR fragment) that binds to a tumor-supporting antigen (e.g., a tumor-supporting antigen as described herein). In some embodiments, the tumor-supporting antigen is an antigen present on a stromal cell or a myeloid-derived suppressor cell (MDSC). Stromal cells can secrete growth factors to promote cell division in the microenvironment. MDSC cells can inhibit T cell proliferation and activation. Without wishing to be bound by theory, in some embodiments, the CAR-expressing cells destroy the tumor-supporting cells, thereby indirectly inhibiting tumor growth or survival.

In embodiments, the stromal cell antigen is chosen from one or more of: bone marrow stromal cell antigen 2 (BST2), fibroblast activation protein (FAP) and tenascin. In an embodiment, the FAP-specific antibody is, competes for binding with, or has the same CDRs as, sibrotuzumab. In embodiments, the MDSC antigen is chosen from one or more of: CD33, CD11b, C14, CD15, and CD66b. Accordingly, in some embodiments, the tumor-supporting antigen is chosen from one or more of: bone marrow stromal cell antigen 2 (BST2), fibroblast activation protein (FAP) or tenascin, CD33, CD11b, C14, CD15, and CD66b.

Antigen Binding Domain Structures

The antigen binding domain of a CAR may include, for example, any polypeptide binding moiety known in the art. For example, the antigen binding domain may include an antibody or antibody fragment (e.g., an scFv, a Fv, a Fab, a (Fab')2, a single domain antibody (SDAB), a VH or VL domain, a camelid VHH domain or a bi-functional (e.g. bi-specific) hybrid antibody). In preferred instances, the antigen binding domain includes an scFv. In some instances, the antigen binding domain may include the antigen binding domain is a T cell receptor (TCR), or a fragment thereof, for example, a single chain TCR (scTCR). In certain instances, the antigen binding domain is a bi- or multi-specific molecule (e.g., a multispecific antibody molecule). In some instances, the antigen binding domain recognizes one or more particular target molecule(s) of interest. A target molecule of interest may be, for example, associated with a disease or the development thereof.

In some instances, scFvs can be prepared according to method known in the art (see, for example, Bird et al., (1988) Science 242:423-426 and Huston et al., (1988) Proc. Natl. Acad. Sci. USA 85:5879-5883). ScFv molecules can be produced by linking VH and VL regions together using flexible polypeptide linkers. The scFv molecules comprise a linker (e.g., a Ser-Gly linker) with an optimized length and/or amino acid composition. The linker length can greatly affect how the variable regions of a scFv fold and interact. In fact, if a short polypeptide linker is employed (e.g., between 5-10 amino acids) intrachain folding is prevented. Interchain folding is also required to bring the two variable regions together to form a functional epitope binding site. For examples of linker orientation and size see, e.g., Hollinger et al. 1993 Proc Natl Acad. Sci. U.S.A. 90:6444-6448, U.S. Patent Application Publication Nos. 2005/0100543, 2005/0175606, 2007/0014794, and PCT publication Nos. WO2006/020258 and WO2007/024715, is incorporated herein by reference.

An scFv can comprise a linker of at least 1, 2, 3, 4, 5, 6, 7, 8, 9, 10, 11, 12, 13, 14, 15, 16, 17, 18, 19, 20, 25, 30, 35, 40, 45, 50, or more amino acid residues between its VL and VH regions. The linker sequence may comprise any naturally occurring amino acid. In some embodiments, the linker sequence comprises amino acids glycine and serine. In another embodiment, the linker sequence comprises sets of glycine and serine repeats such as (Gly$_4$Ser)n, where n is a positive integer equal to or greater than 1 (SEQ ID NO: 22). In one embodiment, the linker can be (Gly$_4$Ser)$_4$ (SEQ ID NO: 29) or (Gly$_4$Ser)$_3$ (SEQ ID NO: 30). Variation in the linker length may retain or enhance activity, giving rise to superior efficacy in activity studies.

In another aspect, the antigen binding domain is a T cell receptor ("TCR"), or a fragment thereof, for example, a single chain TCR (scTCR). Methods to make such TCRs are known in the art. See, e.g., Willemsen R A et al, Gene Therapy 7: 1369-1377 (2000); Zhang T et al, Cancer Gene Ther 11: 487-496 (2004); Aggen et al, Gene Ther. 19(4): 365-74 (2012) (references are incorporated herein by its entirety). For example, scTCR can be engineered that contains the Vα and Vβ genes from a T cell clone linked by a linker (e.g., a flexible peptide). This approach is very useful to cancer associated target that itself is intracellar, however, a fragment of such antigen (peptide) is presented on the surface of the cancer cells by MHC.

In certain embodiments, the encoded antigen binding domain has a binding affinity KD of $10^{-4}$ M to $10^{-8}$ M.

In one embodiment, the encoded CAR molecule comprises an antigen binding domain that has a binding affinity KD of $10^{-4}$ M to $10^{-8}$ M, e.g., $10^{-5}$ M to $10^{-7}$ M, e.g., $10^{-6}$ M or $10^{-7}$ M, for the target antigen. In one embodiment, the antigen binding domain has a binding affinity that is at least five-fold, 10-fold, 20-fold, 30-fold, 50-fold, 100-fold or 1,000-fold less than a reference antibody, e.g., an antibody described herein. In one embodiment, the encoded antigen binding domain has a binding affinity at least 5-fold less than a reference antibody (e.g., an antibody from which the antigen binding domain is derived). In one aspect such antibody fragments are functional in that they provide a biological response that can include, but is not limited to, activation of an immune response, inhibition of signal-transduction origination from its target antigen, inhibition of kinase activity, and the like, as will be understood by a skilled artisan.

In one aspect, the antigen binding domain of the CAR is a scFv antibody fragment that is humanized compared to the murine sequence of the scFv from which it is derived.

In one aspect, the antigen binding domain of a CAR of the invention (e.g., a scFv) is encoded by a nucleic acid molecule whose sequence has been codon optimized for expression in a mammalian cell. In one aspect, entire CAR construct of the invention is encoded by a nucleic acid molecule whose entire sequence has been codon optimized for expression in a mammalian cell. Codon optimization refers to the discovery that the frequency of occurrence of synonymous codons (i.e., codons that code for the same amino acid) in coding DNA is biased in different species. Such codon degeneracy allows an identical polypeptide to be encoded by a variety of nucleotide sequences. A variety of codon optimization methods is known in the art, and include, e.g., methods disclosed in at least U.S. Pat. Nos. 5,786,464 and 6,114,148.

Specific Antigen Antibody Pairs

In one embodiment, an antigen binding domain against CD22 is an antigen binding portion, e.g., CDRs, of an antibody described in, e.g., Haso et al., Blood, 121(7): 1165-1174 (2013); Wayne et al., Clin Cancer Res 16(6): 1894-1903 (2010); Kato et al., Leuk Res 37(1):83-88 (2013); Creative BioMart (creativebiomart.net): MOM-18047-S(P).

In one embodiment, an antigen binding domain against CS-1 is an antigen binding portion, e.g., CDRs, of Elotuzumab (BMS), see e.g., Tai et al., 2008, Blood 112(4): 1329-37; Tai et al., 2007, Blood. 110(5):1656-63.

In one embodiment, an antigen binding domain against CLL-1 is an antigen binding portion, e.g., CDRs, of an antibody available from R&D, ebiosciences, Abcam, for example, PE-CLL1-hu Cat #353604 (BioLegend); and PE-CLL1 (CLEC12A) Cat #562566 (BD).

In one embodiment, an antigen binding domain against CD33 is an antigen binding portion, e.g., CDRs, of an antibody described in, e.g., Bross et al., Clin Cancer Res 7(6):1490-1496 (2001) (Gemtuzumab Ozogamicin, hP67.6), Caron et al., Cancer Res 52(24):6761-6767 (1992) (Lintuzumab, HuM195), Lapusan et al., Invest New Drugs 30(3):1121-1131 (2012) (AVE9633), Aigner et al., Leukemia 27(5): 1107-1115 (2013) (AMG330, CD33 BiTE), Dutour et al., Adv hematol 2012:683065 (2012), and Pizzitola et al., Leukemia doi:10.1038/Lue.2014.62 (2014).

In one embodiment, an antigen binding domain against GD2 is an antigen binding portion, e.g., CDRs, of an antibody described in, e.g., Mujoo et al., Cancer Res. 47(4)1098-1104 (1987); Cheung et al., Cancer Res 45(6): 2642-2649 (1985), Cheung et al., J Clin Oncol 5(9):1430-1440 (1987), Cheung et al., J Clin Oncol 16(9):3053-3060 (1998), Handgretinger et al., Cancer Immunol Immunother 35(3):199-204 (1992). In some embodiments, an antigen binding domain against GD2 is an antigen binding portion of an antibody selected from mAb 14.18, 14G2a, ch14.18, hu14.18, 3F8, hu3F8, 3G6, 8B6, 60C3, 10B8, ME36.1, and 8H9, see e.g., WO2012033885, WO2013040371, WO2013192294, WO2013061273, WO2013123061, WO2013074916, and WO201385552. In some embodiments, an antigen binding domain against GD2 is an antigen binding portion of an antibody described in US Publication No.: 20100150910 or PCT Publication No.: WO 2011160119.

In one embodiment, an antigen binding domain against BCMA is an antigen binding portion, e.g., CDRs, of an antibody described in, e.g., WO2012163805, WO200112812, and WO2003062401.

In one embodiment, an antigen binding domain against Tn antigen is an antigen binding portion, e.g., CDRs, of an antibody described in, e.g., U.S. Pat. No. 8,440,798, Brooks et al., PNAS 107(22):10056-10061 (2010), and Stone et al., OncoImmunology 1(6):863-873(2012).

In one embodiment, an antigen binding domain against PSMA is an antigen binding portion, e.g., CDRs, of an antibody described in, e.g., Parker et al., Protein Expr Purif 89(2):136-145 (2013), US 20110268656 (J591 ScFv); Frigerio et al, European J Cancer 49(9):2223-2232 (2013) (scFvD2B); WO 2006125481 (mAbs 3/A12, 3/E7 and 3/F11) and single chain antibody fragments (scFv A5 and D7).

In one embodiment, an antigen binding domain against ROR1 is an antigen binding portion, e.g., CDRs, of an antibody described in, e.g., Hudecek et al., Clin Cancer Res 19(12):3153-3164 (2013); WO 2011159847; and US20130101607.

In one embodiment, an antigen binding domain against FLT3 is an antigen binding portion, e.g., CDRs, of an antibody described in, e.g., WO2011076922, U.S. Pat. No. 5,777,084, EP0754230, US20090297529, and several commercial catalog antibodies (R&D, ebiosciences, Abcam).

In one embodiment, an antigen binding domain against TAG72 is an antigen binding portion, e.g., CDRs, of an antibody described in, e.g., Hombach et al., Gastroenterology 113(4):1163-1170 (1997); and Abcam ab691.

In one embodiment, an antigen binding domain against FAP is an antigen binding portion, e.g., CDRs, of an antibody described in, e.g., Ostermann et al., Clinical Cancer Research 14:4584-4592 (2008) (FAP5), US Pat. Publication No. 2009/0304718; sibrotuzumab (see e.g., Hofheinz et al., Oncology Research and Treatment 26(1), 2003); and Tran et al., J Exp Med 210(6):1125-1135 (2013).

In one embodiment, an antigen binding domain against CD38 is an antigen binding portion, e.g., CDRs, of daratumumab (see, e.g., Groen et al., Blood 116(21):1261-1262 (2010); MOR202 (see, e.g., U.S. Pat. No. 8,263,746); or antibodies described in U.S. Pat. No. 8,362,211.

In one embodiment, an antigen binding domain against CD44v6 is an antigen binding portion, e.g., CDRs, of an antibody described in, e.g., Casucci et al., Blood 122(20): 3461-3472 (2013).

In one embodiment, an antigen binding domain against CEA is an antigen binding portion, e.g., CDRs, of an antibody described in, e.g., Chmielewski et al., Gastoenterology 143(4):1095-1107 (2012).

In one embodiment, an antigen binding domain against EPCAM is an antigen binding portion, e.g., CDRS, of an antibody selected from MT110, EpCAM-CD3 bispecific Ab (see, e.g., clinicaltrials.gov/ct2/show/NCT00635596); Edrecolomab; 3622W94; ING-1; and adecatumumab (MT201).

In one embodiment, an antigen binding domain against PRSS21 is an antigen binding portion, e.g., CDRs, of an antibody described in U.S. Pat. No. 8,080,650.

In one embodiment, an antigen binding domain against B7H3 is an antigen binding portion, e.g., CDRs, of an antibody MGA271 (Macrogenics).

In one embodiment, an antigen binding domain against KIT is an antigen binding portion, e.g., CDRs, of an antibody described in, e.g., U.S. Pat. No. 7,915,391, US20120288506, and several commercial catalog antibodies.

In one embodiment, an antigen binding domain against IL-13Ra2 is an antigen binding portion, e.g., CDRs, of an antibody described in, e.g., WO2008/146911, WO2004087758, several commercial catalog antibodies, and WO2004087758.

In one embodiment, an antigen binding domain against CD30 is an antigen binding portion, e.g., CDRs, of an antibody described in, e.g., U.S. Pat. No. 7,090,843 B1, and EP0805871.

In one embodiment, an antigen binding domain against GD3 is an antigen binding portion, e.g., CDRs, of an antibody described in, e.g., U.S. Pat. Nos. 7,253,263; 8,207, 308; US 20120276046; EP1013761; WO2005035577; and U.S. Pat. No. 6,437,098.

In one embodiment, an antigen binding domain against CD171 is an antigen binding portion, e.g., CDRs, of an antibody described in, e.g., Hong et al., J Immunother 37(2):93-104 (2014).

In one embodiment, an antigen binding domain against IL-11 Ra is an antigen binding portion, e.g., CDRs, of an antibody available from Abcam (cat #ab55262) or Novus Biologicals (cat #EPR5446). In another embodiment, an antigen binding domain again IL-11 Ra is a peptide, see, e.g., Huang et al., Cancer Res 72(1):271-281 (2012).

In one embodiment, an antigen binding domain against PSCA is an antigen binding portion, e.g., CDRs, of an antibody described in, e.g., Morgenroth et al., Prostate 67(10):1121-1131 (2007) (scFv 7F5); Nejatollahi et al., J of Oncology 2013(2013), article ID 839831 (scFv C5-II); and US Pat Publication No. 20090311181.

In one embodiment, an antigen binding domain against VEGFR2 is an antigen binding portion, e.g., CDRs, of an antibody described in, e.g., Chinnasamy et al., J Clin Invest 120(11):3953-3968 (2010).

In one embodiment, an antigen binding domain against LewisY is an antigen binding portion, e.g., CDRs, of an antibody described in, e.g., Kelly et al., Cancer Biother Radiopharm 23(4):411-423 (2008) (hu3S193 Ab (scFvs)); Dolezal et al., Protein Engineering 16(1):47-56 (2003) (NC10 scFv).

In one embodiment, an antigen binding domain against CD24 is an antigen binding portion, e.g., CDRs, of an antibody described in, e.g., Maliar et al., Gastroenterology 143(5):1375-1384 (2012).

In one embodiment, an antigen binding domain against PDGFR-beta is an antigen binding portion, e.g., CDRs, of an antibody Abcam ab32570.

In one embodiment, an antigen binding domain against SSEA-4 is an antigen binding portion, e.g., CDRs, of antibody MC813 (Cell Signaling), or other commercially available antibodies.

In one embodiment, an antigen binding domain against CD20 is an antigen binding portion, e.g., CDRs, of the antibody Rituximab, Ofatumumab, Ocrelizumab, Veltuzumab, or GA101.

In one embodiment, an antigen binding domain against Folate receptor alpha is an antigen binding portion, e.g., CDRs, of the antibody IMGN853, or an antibody described in US20120009181; U.S. Pat. No. 4,851,332, LK26: U.S. Pat. No. 5,952,484.

In one embodiment, an antigen binding domain against ERBB2 (Her2/neu) is an antigen binding portion, e.g., CDRs, of the antibody trastuzumab, or pertuzumab.

In one embodiment, an antigen binding domain against MUC1 is an antigen binding portion, e.g., CDRs, of the antibody SAR566658.

In one embodiment, the antigen binding domain against EGFR is antigen binding portion, e.g., CDRs, of the antibody cetuximab, panitumumab, zalutumumab, nimotuzumab, or matuzumab.

In one embodiment, an antigen binding domain against NCAM is an antigen binding portion, e.g., CDRs, of the antibody clone 2-2B: MAB5324 (EMD Millipore)

In one embodiment, an antigen binding domain against Ephrin B2 is an antigen binding portion, e.g., CDRs, of an antibody described in, e.g., Abengozar et al., Blood 119(19): 4565-4576 (2012).

In one embodiment, an antigen binding domain against IGF-I receptor is an antigen binding portion, e.g., CDRs, of an antibody described in, e.g., U.S. Pat. No. 8,344,112 B2; EP2322550 A1; WO 2006/138315, or PCT/US2006/022995.

In one embodiment, an antigen binding domain against CAIX is an antigen binding portion, e.g., CDRs, of the antibody clone 303123 (R&D Systems).

In one embodiment, an antigen binding domain against LMP2 is an antigen binding portion, e.g., CDRs, of an antibody described in, e.g., U.S. Pat. No. 7,410,640, or US20050129701.

In one embodiment, an antigen binding domain against gp100 is an antigen binding portion, e.g., CDRs, of the antibody HMB45, NKIbetaB, or an antibody described in WO2013165940, or US20130295007

In one embodiment, an antigen binding domain against tyrosinase is an antigen binding portion, e.g., CDRs, of an antibody described in, e.g., U.S. Pat. No. 5,843,674; or US 19950504048.

In one embodiment, an antigen binding domain against EphA2 is an antigen binding portion, e.g., CDRs, of an antibody described in, e.g., Yu et al., Mol Ther 22(1):102-111 (2014).

In one embodiment, an antigen binding domain against GD3 is an antigen binding portion, e.g., CDRs, of an antibody described in, e.g., U.S. Pat. Nos. 7,253,263; 8,207,308; US 20120276046; EP1013761 A3; 20120276046; WO2005035577; or U.S. Pat. No. 6,437,098.

In one embodiment, an antigen binding domain against fucosyl GM1 is an antigen binding portion, e.g., CDRs, of an antibody described in, e.g., US20100297138; or WO2007/067992.

In one embodiment, an antigen binding domain against sLe is an antigen binding portion, e.g., CDRs, of the antibody G193 (for lewis Y), see Scott A M et al, Cancer Res 60: 3254-61 (2000), also as described in Neeson et al, J Immunol May 2013 190 (Meeting Abstract Supplement) 177.10.

In one embodiment, an antigen binding domain against GM3 is an antigen binding portion, e.g., CDRs, of the antibody CA 2523449 (mAb 14F7).

In one embodiment, an antigen binding domain against HMWMAA is an antigen binding portion, e.g., CDRs, of an antibody described in, e.g., Kmiecik et al., Oncoimmunology 3(1):e27185 (2014) (PMID: 24575382) (mAb9.2.27); U.S. Pat. No. 6,528,481; WO2010033866; or US 20140004124.

In one embodiment, an antigen binding domain against o-acetyl-GD2 is an antigen binding portion, e.g., CDRs, of the antibody 8B6.

In one embodiment, an antigen binding domain against TEM1/CD248 is an antigen binding portion, e.g., CDRs, of an antibody described in, e.g., Marty et al., Cancer Lett 235(2):298-308 (2006); Zhao et al., J Immunol Methods 363(2):221-232 (2011).

In one embodiment, an antigen binding domain against CLDN6 is an antigen binding portion, e.g., CDRs, of the antibody IMAB027 (Ganymed Pharmaceuticals), see e.g., clinicaltrial.gov/show/NCT02054351.

In one embodiment, an antigen binding domain against TSHR is an antigen binding portion, e.g., CDRs, of an antibody described in, e.g., U.S. Pat. Nos. 8,603,466; 8,501,415; or U.S. Pat. No. 8,309,693.

In one embodiment, an antigen binding domain against GPRC5D is an antigen binding portion, e.g., CDRs, of the antibody FAB6300A (R&D Systems); or LS-A4180 (Lifespan Biosciences).

In one embodiment, an antigen binding domain against CD97 is an antigen binding portion, e.g., CDRs, of an antibody described in, e.g., U.S. Pat. No. 6,846,911; de Groot et al., J Immunol 183(6):4127-4134 (2009); or an antibody from R&D:MAB3734.

In one embodiment, an antigen binding domain against ALK is an antigen binding portion, e.g., CDRs, of an antibody described in, e.g., Mino-Kenudson et al., Clin Cancer Res 16(5):1561-1571 (2010).

In one embodiment, an antigen binding domain against polysialic acid is an antigen binding portion, e.g., CDRs, of an antibody described in, e.g., Nagae et al., J Biol Chem 288(47):33784-33796 (2013)

In one embodiment, an antigen binding domain against PLAC1 is an antigen binding portion, e.g., CDRs, of an antibody described in, e.g., Ghods et al., Biotechnol Appl Biochem 2013 doi:10.1002/bab.1177.

In one embodiment, an antigen binding domain against GloboH is an antigen binding portion of the antibody VK9; or an antibody described in, e.g., Kudryashov V et al, Glycoconj J. 15(3):243-9 (1998), Lou et al., Proc Natl Acad Sci USA 111(7):2482-2487 (2014); MBr1: Bremer E-G et al. J Biol Chem 259:14773-14777 (1984).

In one embodiment, an antigen binding domain against NY-BR-1 is an antigen binding portion, e.g., CDRs of an antibody described in, e.g., Jager et al., Appl Immunohistochem Mol Morphol 15(1):77-83 (2007).

In one embodiment, an antigen binding domain against WT-1 is an antigen binding portion, e.g., CDRs, of an antibody described in, e.g., Dao et al., Sci Transl Med 5(176):176ra33 (2013); or WO2012/135854.

In one embodiment, an antigen binding domain against MAGE-A1 is an antigen binding portion, e.g., CDRs, of an antibody described in, e.g., Willemsen et al., J Immunol 174(12):7853-7858 (2005) (TCR-like scFv).

In one embodiment, an antigen binding domain against sperm protein 17 is an antigen binding portion, e.g., CDRs, of an antibody described in, e.g., Song et al., Target Oncol 2013 Aug. 14 (PMID: 23943313); Song et al., Med Oncol 29(4):2923-2931 (2012).

In one embodiment, an antigen binding domain against Tie 2 is an antigen binding portion, e.g., CDRs, of the antibody AB33 (Cell Signaling Technology).

In one embodiment, an antigen binding domain against MAD-CT-2 is an antigen binding portion, e.g., CDRs, of an antibody described in, e.g., PMID: 2450952; U.S. Pat. No. 7,635,753.

In one embodiment, an antigen binding domain against Fos-related antigen 1 is an antigen binding portion, e.g., CDRs, of the antibody 12F9 (Novus Biologicals).

In one embodiment, an antigen binding domain against MelanA/MART1 is an antigen binding portion, e.g., CDRs, of an antibody described in, EP2514766 A2; or U.S. Pat. No. 7,749,719.

In one embodiment, an antigen binding domain against sarcoma translocation breakpoints is an antigen binding portion, e.g., CDRs, of an antibody described in, e.g., Luo et al, EMBO Mol. Med. 4(6):453-461 (2012).

In one embodiment, an antigen binding domain against TRP-2 is an antigen binding portion, e.g., CDRs, of an antibody described in, e.g., Wang et al, J Exp Med. 184(6): 2207-16 (1996).

In one embodiment, an antigen binding domain against CYP1B1 is an antigen binding portion, e.g., CDRs, of an antibody described in, e.g., Maecker et al, Blood 102 (9): 3287-3294 (2003).

In one embodiment, an antigen binding domain against RAGE-1 is an antigen binding portion, e.g., CDRs, of the antibody MAB5328 (EMD Millipore).

In one embodiment, an antigen binding domain against human telomerase reverse transcriptase is an antigen binding portion, e.g., CDRs, of the antibody cat no: LS-B95-100 (Lifespan Biosciences)

In one embodiment, an antigen binding domain against intestinal carboxyl esterase is an antigen binding portion, e.g., CDRs, of the antibody 4F12: cat no: LS-B6190-50 (Lifespan Biosciences).

In one embodiment, an antigen binding domain against mut hsp70-2 is an antigen binding portion, e.g., CDRs, of the antibody Lifespan Biosciences: monoclonal: cat no: LS-C133261-100 (Lifespan Biosciences).

In one embodiment, an antigen binding domain against CD79a is an antigen binding portion, e.g., CDRs, of the antibody Anti-CD79a antibody [HM47/A9] (ab3121), available from Abcam; antibody CD79A Antibody #3351 available from Cell Signalling Technology; or antibody HPA017748-Anti-CD79A antibody produced in rabbit, available from Sigma Aldrich.

In one embodiment, an antigen binding domain against CD79b is an antigen binding portion, e.g., CDRs, of the antibody polatuzumab vedotin, anti-CD79b described in Dornan et al., "Therapeutic potential of an anti-CD79b antibody-drug conjugate, anti-CD79b-vc-MMAE, for the treatment of non-Hodgkin lymphoma" Blood. 2009 Sep. 24; 114(13):2721-9. doi: 10.1182/blood-2009-02-205500. Epub 2009 Jul. 24, or the bispecific antibody Anti-CD79b/CD3 described in "4507 Pre-Clinical Characterization of T Cell-Dependent Bispecific Antibody Anti-CD79b/CD3 As a Potential Therapy for B Cell Malignancies" Abstracts of 56th ASH Annual Meeting and Exposition, San Francisco, CA Dec. 6-9 2014.

In one embodiment, an antigen binding domain against CD72 is an antigen binding portion, e.g., CDRs, of the antibody J3-109 described in Myers, and Uckun, "An anti-CD72 immunotoxin against therapy-refractory B-lineage acute lymphoblastic leukemia." Leuk Lymphoma. 1995 June; 18(1-2):119-22, or anti-CD72 (10D6.8.1, mIgG1) described in Polson et al., "Antibody-Drug Conjugates for the Treatment of Non-Hodgkin's Lymphoma: Target and Linker-Drug Selection" Cancer Res Mar. 15, 2009 69; 2358.

In one embodiment, an antigen binding domain against LAIR1 is an antigen binding portion, e.g., CDRs, of the antibody ANT-301 LAIR1 antibody, available from ProSpec; or anti-human CD305 (LAIR1) Antibody, available from BioLegend.

In one embodiment, an antigen binding domain against FCAR is an antigen binding portion, e.g., CDRs, of the antibody CD89/FCARAntibody (Catalog #10414-H08H), available from Sino Biological Inc.

In one embodiment, an antigen binding domain against LILRA2 is an antigen binding portion, e.g., CDRs, of the antibody LILRA2 monoclonal antibody (M17), clone 3C7, available from Abnova, or Mouse Anti-LILRA2 antibody, Monoclonal (2D7), available from Lifespan Biosciences.

In one embodiment, an antigen binding domain against CD300LF is an antigen binding portion, e.g., CDRs, of the antibody Mouse Anti-CMRF35-like molecule 1 antibody, Monoclonal[UP-D2], available from BioLegend, or Rat Anti-CMRF35-like molecule 1 antibody, Monoclonal [234903], available from R&D Systems.

In one embodiment, an antigen binding domain against CLEC12A is an antigen binding portion, e.g., CDRs, of the antibody Bispecific T cell Engager (BiTE) scFv-antibody and ADC described in Noordhuis et al., "Targeting of CLEC12A In Acute Myeloid Leukemia by Antibody-Drug-Conjugates and Bispecific CLL-1×CD3 BiTE Antibody" 53rd ASH Annual Meeting and Exposition, Dec. 10-13, 2011, and MCLA-117 (Merus).

In one embodiment, an antigen binding domain against BST2 (also called CD317) is an antigen binding portion, e.g., CDRs, of the antibody Mouse Anti-CD317 antibody, Monoclonal[3H4], available from Antibodies-Online or Mouse Anti-CD317 antibody, Monoclonal[696739], available from R&D Systems.

In one embodiment, an antigen binding domain against EMR2 (also called CD312) is an antigen binding portion, e.g., CDRs, of the antibody Mouse Anti-CD312 antibody, Monoclonal[LS-B8033] available from Lifespan Biosciences, or Mouse Anti-CD312 antibody, Monoclonal [494025] available from R&D Systems.

In one embodiment, an antigen binding domain against LY75 is an antigen binding portion, e.g., CDRs, of the antibody Mouse Anti-Lymphocyte antigen 75 antibody, Monoclonal[HD30] available from EMD Millipore or Mouse Anti-Lymphocyte antigen 75 antibody, Monoclonal [A15797] available from Life Technologies.

In one embodiment, an antigen binding domain against GPC3 is an antigen binding portion, e.g., CDRs, of the antibody hGC33 described in Nakano K, Ishiguro T, Konishi H, et al. Generation of a humanized anti-glypican 3 antibody by CDR grafting and stability optimization. Anticancer Drugs. 2010 Nov.; 21(10):907-916, or MDX-1414, HN3, or YP7, all three of which are described in Feng et al., "Glypican-3 antibodies: a new therapeutic target for liver cancer." FEBS Lett. 2014 Jan. 21; 588(2):377-82.

In one embodiment, an antigen binding domain against FCRL5 is an antigen binding portion, e.g., CDRs, of the anti-FcRL5 antibody described in Elkins et al., "FcRL5 as a target of antibody-drug conjugates for the treatment of multiple myeloma" Mol Cancer Ther. 2012 October; 11(10): 2222-32.

In one embodiment, an antigen binding domain against IGLL1 is an antigen binding portion, e.g., CDRs, of the antibody Mouse Anti-Immunoglobulin lambda-like polypeptide 1 antibody, Monoclonal[AT1G4] available from Lifespan Biosciences, Mouse Anti-Immunoglobulin lambda-like polypeptide 1 antibody, Monoclonal[HSL11] available from BioLegend.

In one embodiment, the antigen binding domain comprises one, two three (e.g., all three) heavy chain CDRs, HC CDR1, HC CDR2 and HC CDR3, from an antibody listed above, and/or one, two, three (e.g., all three) light chain CDRs, LC CDR1, LC CDR2 and LC CDR3, from an antibody listed above. In one embodiment, the antigen binding domain comprises a heavy chain variable region and/or a variable light chain region of an antibody listed above.

In another aspect, the antigen binding domain comprises a humanized antibody or an antibody fragment. In some aspects, a non-human antibody is humanized, where specific sequences or regions of the antibody are modified to increase similarity to an antibody naturally produced in a human or fragment thereof. In one aspect, the antigen binding domain is humanized.

Bispecific CARs

In certain embodiments, the antigen binding domain is a bi- or multi-specific molecule (e.g., a multispecific antibody molecule). In an embodiment a multispecific antibody molecule is a bispecific antibody molecule. A bispecific antibody has specificity for no more than two antigens. A bispecific antibody molecule is characterized by a first immunoglobulin variable domain sequence which has binding specificity for a first epitope and a second immunoglobulin variable domain sequence that has binding specificity for a second epitope. In an embodiment the first and second epitopes are on the same antigen, e.g., the same protein (or subunit of a multimeric protein). In an embodiment the first and second epitopes overlap. In an embodiment the first and second epitopes do not overlap. In an embodiment the first and second epitopes are on different antigens, e.g., different proteins (or different subunits of a multimeric protein). In an embodiment a bispecific antibody molecule comprises a heavy chain variable domain sequence and a light chain variable domain sequence which have binding specificity for a first epitope and a heavy chain variable domain sequence and a light chain variable domain sequence which have binding specificity for a second epitope. In an embodiment a bispecific antibody molecule comprises a half antibody having binding specificity for a first epitope and a half antibody having binding specificity for a second epitope. In an embodiment a bispecific antibody molecule comprises a half antibody, or fragment thereof, having binding specificity for a first epitope and a half antibody, or fragment thereof, having binding specificity for a second epitope. In an embodiment a bispecific antibody molecule comprises a scFv, or fragment thereof, have binding specificity for a first epitope and a scFv, or fragment thereof, have binding specificity for a second epitope.

In certain embodiments, the antibody molecule is a multispecific (e.g., a bispecific or a trispecific) antibody molecule. Such molecules include bispecific fusion proteins, e.g., an expression construct containing two scFvs with a hydrophilic helical peptide linker between them and a full constant region, as described in, e.g., U.S. Pat. No. 5,637,481; minibody constructs with linked VL and VH chains further connected with peptide spacers to an antibody hinge region and CH3 region, which can be dimerized to form bispecific/multivalent molecules, as described in, e.g., U.S. Pat. No. 5,837,821; String of VH domains (or VL domains in family members) connected by peptide linkages with crosslinkable groups at the C-terminus futher associated with VL domains to form a series of FVs (or scFvs), as described in, e.g., U.S. Pat. No. 5,864,019; and single chain binding polypeptides with both a VH and a VL domain linked through a peptide linker are combined into multivalent structures through non-covalent or chemical crosslinking to form, e.g., homobivalent, heterobivalent, trivalent, and tetravalent structures using both scFV or diabody type format, as described in, e.g., U.S. Pat. No. 5,869,620. The contents of the above-referenced applications are incorporated herein by reference in their entireties.

Within each antibody or antibody fragment (e.g., scFv) of a bispecific antibody molecule, the VH can be upstream or downstream of the VL. In some embodiments, the upstream antibody or antibody fragment (e.g., scFv) is arranged with its VH ($VH_1$) upstream of its VL ($VL_1$) and the downstream antibody or antibody fragment (e.g., scFv) is arranged with its VL ($VL_2$) upstream of its VH ($VH_2$), such that the overall bispecific antibody molecule has the arrangement $VH_1$-$VL_1$-$VL_2$-$VH_2$. In other embodiments, the upstream antibody or antibody fragment (e.g., scFv) is arranged with its VL ($VL_1$) upstream of its VH ($VH_1$) and the downstream antibody or antibody fragment (e.g., scFv) is arranged with its VH ($VH_2$) upstream of its VL ($VL_2$), such that the overall bispecific antibody molecule has the arrangement $VL_1$-$VH_1$-$VH_2$-$VL_2$. Optionally, a linker is disposed between the two antibodies or antibody fragments (e.g., scFvs), e.g., between $VL_1$ and $VL_2$ if the construct is arranged as $VH_1$-$VL_1$-$VL_2$-$VH_2$, or between $VH_1$ and $VH_2$ if the construct is arranged as $VL_1$-$VH_1$-$VH_2$-$VL_2$. The linker may be a linker as described herein, e.g., a $(Gly_4$-Ser)n linker, wherein n is 1, 2, 3, 4, 5, or 6, preferably 4 (SEQ ID NO: 29). In general, the linker between the two scFvs should be long enough to avoid mispairing between the domains of the two scFvs. Optionally, a linker is disposed between the VL and VH of the first scFv. Optionally, a linker is disposed between the VL and VH of the second scFv. In constructs that have multiple linkers, any two or more of the linkers can be the same or different. Accordingly, in some embodiments, a bispecific CAR comprises VLs, VHs, and optionally one or more linkers in an arrangement as described herein.

Transmembrane Domain

A transmembrane domain of the CAR may be any polypeptide domain capable of traversing a phospholipid bilayer, so that one end of the domain is attached to, e.g., an extracellular antigen binding domain, and the other end is, e.g., attached to an intracellular signaling domain. A transmembrane domain can include one or more additional amino acids adjacent to the transmembrane region, e.g., one or more amino acids associated with the extracellular region of the protein from which the transmembrane was derived (e.g., 1, 2, 3, 4, 5, 6, 7, 8, 9, 10 up to 15 amino acids of the extracellular region) and/or one or more additional amino acids associated with the intracellular region of the protein from which the transmembrane protein is derived (e.g., 1, 2, 3, 4, 5, 6, 7, 8, 9, 10 up to 15 amino acids of the intracellular region). The transmembrane domain can be is associated with one of the other domains of the CAR. In some instances, the transmembrane domain can be selected or modified by amino acid substitution to avoid binding of such domains to the transmembrane domains of the same or different surface membrane proteins, e.g., to minimize interactions with other members of the receptor complex. In one aspect, the transmembrane domain is capable of homodimerization with another CAR on the surface of a CAR-expressing cell. In a different aspect, the amino acid sequence of the transmembrane domain may be modified or substituted so as to minimize interactions with the binding domains of the native binding partner present in the same CAR-expressing cell. A transmembrane domain of particular use in this invention may include at least the transmembrane region(s) of e.g., the alpha, beta or zeta chain of the T-cell receptor, CD28, CD27, CD3 epsilon, CD45, CD4, CD5, CD8, CD9, CD16, CD22, CD33, CD37, CD64, CD80, CD86, CD134, CD137, CD154. In some embodiments, a transmembrane domain may include at least the transmembrane region(s) of, e.g., KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), NKp44, NKp30, NKp46, CD160, CD19, IL2R beta, IL2R gamma, IL7R a, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11 b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKG2D, NKG2C.

In some instances, the transmembrane domain can be attached to the extracellular region of the CAR, e.g., the antigen binding domain of the CAR, via a hinge, e.g., a hinge from a human protein. For example, in one embodiment, the hinge can be a human Ig (immunoglobulin) hinge (e.g., an IgG4 hinge, an IgD hinge), a GS linker (e.g., a GS linker described herein), a KIR2DS2 hinge or a CD8a hinge. In one embodiment, the hinge or spacer comprises (e.g., consists of) the amino acid sequence of SEQ ID NO:4. In one aspect, the transmembrane domain comprises (e.g., consists of) a transmembrane domain of SEQ ID NO: 12.

In certain embodiments, the encoded transmembrane domain comprises an amino acid sequence of a CD8 transmembrane domain having at least one, two or three modifications but not more than 20, 10 or 5 modifications of an amino acid sequence of SEQ ID NO: 12, or a sequence with 95-99% identity to an amino acid sequence of SEQ ID NO: 12. In one embodiment, the encoded transmembrane domain comprises the sequence of SEQ ID NO: 12.

In other embodiments, the nucleic acid molecule encoding the CAR comprises a nucleotide sequence of a CD8 transmembrane domain, e.g., comprising the sequence of SEQ ID NO: 13, or a sequence with 95-99% identity thereof.

In certain embodiments, the encoded antigen binding domain is connected to the transmembrane domain by a hinge region. In one embodiment, the encoded hinge region comprises the amino acid sequence of a CD8 hinge, e.g., SEQ ID NO: 4; or the amino acid sequence of an IgG4 hinge, e.g., SEQ ID NO: 6, or a sequence with 95-99% identity to SEQ ID NO:4 or 6. In other embodiments, the nucleic acid sequence encoding the hinge region comprises a sequence of SEQ ID NO: 5 or SEQ ID NO: 7, corresponding to a CD8 hinge or an IgG4 hinge, respectively, or a sequence with 95-99% identity to SEQ ID NO:5 or 7.

In one aspect, the hinge or spacer comprises an IgG4 hinge. For example, in one embodiment, the hinge or spacer comprises a hinge of the amino acid sequence ESKY-GPPCPPCPAPEFLGGPSVFLFPPKPKDTLMISRTPE-VTCVVVDVSQEDPEVQFNWYVDGVEVHNA KTKPREEQFN-STYRVVSVLTVLHQDWLNGKEYKCKVSNK-GLPSSIEKTISKAKGQPREPQVYTLPPSQEE MTKNQVSLTCLVKGFYPSDIAVEWESNGQPEN-NYKTTPPVLDSDGSFFLYSRLTVDKSRWQEGNVFSCS VMHEALHNHYTQKSLSLSLGKM (SEQ ID NO:6). In some embodiments, the hinge or spacer comprises a hinge encoded by a nucleotide sequence of

```
                                           (SEQ ID NO: 7)
GAGAGCAAGTACGGCCCTCCCTGCCCCCCTTGCCCTGCCCCCGAGTTCCT

GGGCGGACCCAGCGTGTTCCTGTTCCCCCCCAAGCCCAAGGACACCCTGA

TGATCAGCCGGACCCCCGAGGTGACCTGTGTGGTGGTGGACGTGTCCCAG

GAGGACCCCGAGGTCCAGTTCAACTGGTACGTGGACGGCGTGGAGGTGCA

CAACGCCAAGACCAAGCCCCGGGAGGAGCAGTTCAATAGCACCTACCGGG

TGGTGTCCGTGCTGACCGTGCTGCACCAGGACTGGCTGAACGGCAAGGAA

TACAAGTGTAAGGTGTCCAACAAGGGCCTGCCCAGCAGCATCGAGAAAAC

CATCAGCAAGGCCAAGGGCCAGCCTCGGGAGCCCCAGGTGTACACCCTGC

CCCCTAGCCAAGAGGAGATGACCAAGAACCAGGTGTCCCTGACCTGCCTG

GTGAAGGGCTTCTACCCCAGCGACATCGCCGTGGAGTGGGAGAGCAACGG

CCAGCCCGAGAACAACTACAAGACCACCCCCCCTGTGCTGGACAGCGACG

GCAGCTTCTTCCTGTACAGCCGGCTGACCGTGGACAAGAGCCGGTGGCAG

GAGGGCAACGTCTTTAGCTGCTCCGTGATGCACGAGGCCCTGCACAACCA

CTACACCCAGAAGAGCCTGAGCCTGTCCCTGGGCAAGATG.
```

In one aspect, the hinge or spacer comprises an IgD hinge. For example, in one embodiment, the hinge or spacer comprises a hinge of the amino acid sequence RWPESPKAQASSVPTAQPQAEGSLAKATTAPATTRN-TGRGGEEKKKEKEKEEQEERETKTPECPSHTQ PLGVYLLTPAVQDLWLRDKATFTCFVVGSDLKDAHL-TWEVAGKVPTGGVEEGLLERHSNGSQSQHSRLT LPRSLWNAGTSVTCTLNHPSLPPQRLMAL-REPAAQAPVKLSLNLLASSDPPEAASWLLCE-VSGFSPPNIL LMWLEDQREVNTSGFAPARPPPQPG-STTFWAWSVLRVPAPPSPQPATYTCVVSHEDSRTL-p LNASRSLE VSYVTDH (SEQ ID NO:8). In some embodiments, the hinge or spacer comprises a hinge encoded by a nucleotide sequence of

```
                                           (SEQ ID NO: 9)
AGGTGGCCCGAAAGTCCCAAGGCCCAGGCATCTAGTGTTCCTACTGCACA

GCCCCAGGCAGAAGGCAGCCTAGCCAAAGCTACTACTGCACCTGCCACTA

CGCGCAATACTGGCCGTGGCGGGAGGAGAAGAAAAAGGAGAAAGAGAAA

GAAGAACAGGAAGAGAGGGAGACCAAGACCCCTGAATGTCCATCCCATAC

CCAGCCGCTGGGCGTCTATCTCTTGACTCCCGCAGTACAGGACTTGTGGC

TTAGAGATAAGGCCACCTTTACATGTTTCGTCGTGGGCTCTGACCTGAAG

GATGCCCATTTGACTTGGGAGGTTGCCGGAAAGGTACCCACAGGGGGGT

TGAGGAAGGGTTGCTGGAGCGCCATTCCAATGGCTCTCAGAGCCAGCACT

CAAGACTCACCCTTCCGAGATCCCTGTGGAACGCCGGGACCTCTGTCACA

TGTACTCTAAATCATCCTAGCCTGCCCCCACAGCGTCTGATGGCCCTTAG

AGAGCCAGCCGCCCAGGCACCAGTTAAGCTTAGCCTGAATCTGCTCGCCA
```

-continued

```
GTAGTGATCCCCCAGAGGCCGCCAGCTGGCTCTTATGCGAAGTGTCCGGC

TTTAGCCCGCCCAACATCTTGCTCATGTGGCTGGAGGACCAGCGAGAAGT

GAACACCAGCGGCTTCGCTCCAGCCCGGCCCCCACCCCAGCCGGGTTCTA

CCACATTCTGGGCCTGGAGTGTCTTAAGGGTCCCAGCACCACCTAGCCCC

CAGCCAGCCACATACACCTGTGTTGTGTCCCATGAAGATAGCAGGACCCT

GCTAAATGCTTCTAGGAGTCTGGAGGTTTCCTACGTGACTGACCATT.
```

In one aspect, the transmembrane domain may be recombinant, in which case it will comprise predominantly hydrophobic residues such as leucine and valine. In one aspect a triplet of phenylalanine, tryptophan and valine can be found at each end of a recombinant transmembrane domain.

Optionally, a short oligo- or polypeptide linker, between 2 and 10 amino acids in length may form the linkage between the transmembrane domain and the cytoplasmic region of the CAR. A glycine-serine doublet provides a particularly suitable linker. For example, in one aspect, the linker comprises the amino acid sequence of GGGGSGGGGS (SEQ ID NO: 10). In some embodiments, the linker is encoded by a nucleotide sequence of GGTGGCGGAGGTTCTGGAGGTGGAGGTTCC (SEQ ID NO: 11).

In one aspect, the hinge or spacer comprises a KIR2DS2 hinge.

Signaling Domains

A CAR may include one or more intracellular signaling domains, which may activate and/or inhibit one or more intracellular signaling pathways in response to binding of the extracellular antigen binding domain to a ligand. In some instances, the intracellular signaling domain may be capable of inducing an immune response. For example, the intracellular signaling domain of a CAR expressed by a T cell may induce activation of the T cell upon binding of the antigen binding domain to its cognate target molecule of interest.

In embodiments of the invention having an intracellular signaling domain, such a domain can contain, e.g., one or more of a primary signaling domain and/or a costimulatory signaling domain. In some embodiments, the intracellular signaling domain comprises a sequence encoding a primary signaling domain. In some embodiments, the intracellular signaling domain comprises a costimulatory signaling domain. In some embodiments, the intracellular signaling domain comprises a a primary signaling domain and a costimulatory signaling domain.

The intracellular signaling sequences within the cytoplasmic portion of the CAR of the invention may be linked to each other in a random or specified order. Optionally, a short oligo- or polypeptide linker, for example, between 2 and 10 amino acids (e.g., 2, 3, 4, 5, 6, 7, 8, 9, or 10 amino acids) in length may form the linkage between intracellular signaling sequences. In one embodiment, a glycine-serine doublet can be used as a suitable linker. In one embodiment, a single amino acid, e.g., an alanine, a glycine, can be used as a suitable linker.

In one aspect, the intracellular signaling domain is designed to comprise two or more, e.g., 2, 3, 4, 5, or more, costimulatory signaling domains. In an embodiment, the two or more, e.g., 2, 3, 4, 5, or more, costimulatory signaling domains, are separated by a linker molecule, e.g., a linker molecule described herein. In one embodiment, the intracellular signaling domain comprises two costimulatory signaling domains. In some embodiments, the linker molecule is a glycine residue. In some embodiments, the linker is an alanine residue.

Primary Signaling Domains

A primary signaling domain regulates primary activation of the TCR complex either in a stimulatory way, or in an inhibitory way. Primary intracellular signaling domains that act in a stimulatory manner may contain signaling motifs which are known as immunoreceptor tyrosine-based activation motifs or ITAMs.

Examples of ITAM containing primary intracellular signaling domains that are of particular use in the invention include those of CD3 zeta, common FcR gamma (FCER1G), Fc gamma RIIa, FcR beta (Fc Epsilon R1 b), CD3 gamma, CD3 delta, CD3 epsilon, CD79a, CD79b, DAP10, and DAP12. In one embodiment, a CAR of the invention comprises an intracellular signaling domain, e.g., a primary signaling domain of CD3-zeta.

In one embodiment, the encoded primary signaling domain comprises a functional signaling domain of CD3 zeta. The encoded CD3 zeta primary signaling domain can comprise an amino acid sequence having at least one, two or three modifications but not more than 20, 10 or 5 modifications of an amino acid sequence of SEQ ID NO: 18 or SEQ ID NO: 20, or a sequence with 95-99% identity to an amino acid sequence of SEQ ID NO: 18 or SEQ ID NO: 20. In some embodiments, the encoded primary signaling domain comprises a sequence of SEQ ID NO: 18 or SEQ ID NO: 20. In other embodiments, the nucleic acid sequence encoding the primary signaling domain comprises a sequence of SEQ ID NO: 19 or SEQ ID NO: 21, or a sequence with 95-99% identity thereof.

Costimulatory Signaling Domain

In some embodiments, the encoded intracellular signaling domain comprises a a costimulatory signaling domain. For example, the intracellular signaling domain can comprise a primary signaling domain and a costimulatory signaling domain. In some embodiments, the encoded costimulatory signaling domain comprises a functional signaling domain of a protein chosen from one or more of CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11 b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, or NKG2D.

In certain embodiments, the encoded costimulatory signaling domain comprises an amino acid sequence having at least one, two or three modifications but not more than 20, 10 or 5 modifications of an amino acid sequence of SEQ ID NO: 14 or SEQ ID NO: 16, or a sequence with 95-99% identity to an amino acid sequence of SEQ ID NO:14 or SEQ ID NO: 16. In one embodiment, the encoded costimulatory signaling domain comprises a sequence of SEQ ID NO: 14 or SEQ ID NO: 16. In other embodiments, the nucleic acid sequence encoding the costimulatory signaling domain comprises a sequence of SEQ ID NO: 15 or SEQ ID NO: 17, or a sequence with 95-99% identity thereof.

In other embodiments, the encoded intracellular domain comprises the sequence of SEQ ID NO: 14 or SEQ ID NO: 16, and the sequence of SEQ ID NO: 18 or SEQ ID NO: 20, wherein the sequences comprising the intracellular signaling domain are expressed in the same frame and as a single polypeptide chain.

In certain embodiments, the nucleic acid sequence encoding the intracellular signaling domain comprises a sequence of SEQ ID NO: 15 or SEQ ID NO: 17, or a sequence with 95-99% identity thereof, and a sequence of SEQ ID NO: 19 or SEQ ID NO: 21, or a sequence with 95-99% identity thereof.

In some embodiments, the nucleic acid molecule further encodes a leader sequence. In one embodiment, the leader sequence comprises the sequence of SEQ ID NO: 2.

In one aspect, the intracellular signaling domain is designed to comprise the signaling domain of CD3-zeta and the signaling domain of CD28. In one aspect, the intracellular signaling domain is designed to comprise the signaling domain of CD3-zeta and the signaling domain of 4-1BB. In one aspect, the signaling domain of 4-1BB is a signaling domain of SEQ ID NO: 14. In one aspect, the signaling domain of CD3-zeta is a signaling domain of SEQ ID NO: 18.

In one aspect, the intracellular signaling domain is designed to comprise the signaling domain of CD3-zeta and the signaling domain of CD27. In one aspect, the signaling domain of CD27 comprises an amino acid sequence of QRRKYRSNKGESPVEPAEPCRYSCPREEEGSTIP-IQEDYRKPEPACSP (SEQ ID NO: 16). In one aspect, the signaling domain of CD27 is encoded by a nucleic acid sequence of

```
                                            (SEQ ID NO: 17)
AGGAGTAAGAGGAGCAGGCTCCTGCACAGTGACTACATGAACATGACTC

CCCGCCGCCCCGGGCCCACCCGCAAGCATTACCAGCCCTATGCCCCACC

ACGCGACTTCGCAGCCTATCGCTCC.
```

Host Cells for CAR Expression

As noted above, in some aspects the invention pertains to a cell, e.g., an immune effector cell, (e.g., a population of cells, e.g., a population of immune effector cells) comprising a nucleic acid molecule, a CAR polypeptide molecule, or a vector as described herein.

In certain aspects of the present disclosure, immune effector cells, e.g., T cells, can be obtained from a unit of blood collected from a subject using any number of techniques known to the skilled artisan, such as Ficoll™ separation. In one preferred aspect, cells from the circulating blood of an individual are obtained by apheresis. The apheresis product typically contains lymphocytes, including T cells, monocytes, granulocytes, B cells, other nucleated white blood cells, red blood cells, and platelets. In one aspect, the cells collected by apheresis may be washed to remove the plasma fraction and, optionally, to place the cells in an appropriate buffer or media for subsequent processing steps. In one embodiment, the cells are washed with phosphate buffered saline (PBS). In an alternative embodiment, the wash solution lacks calcium and may lack magnesium or may lack many if not all divalent cations.

Initial activation steps in the absence of calcium can lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter Cyto-Mate, or the Haemonetics Cell Saver 5) according to the manufacturer's instructions. After washing, the cells may be resuspended in a variety of biocompatible buffers, such as, for example, Ca-free, Mg-free PBS, PlasmaLyte A, or other saline solution with or without buffer. Alternatively, the undesirable components of the apheresis sample may be removed and the cells directly resuspended in culture media.

It is recognized that the methods of the application can utilize culture media conditions comprising 5% or less, for example 2%, human AB serum, and employ known culture media conditions and compositions, for example those described in Smith et al., "Ex vivo expansion of human T cells for adoptive immunotherapy using the novel Xeno-free CTS Immune Cell Serum Replacement" *Clinical & Translational Immunology* (2015) 4, e31; doi:10.1038/cti.2014.31.

In one aspect, T cells are isolated from peripheral blood lymphocytes by lysing the red blood cells and depleting the monocytes, for example, by centrifugation through a PER-COLL™ gradient or by counterflow centrifugal elutriation.

The methods described herein can include, e.g., selection of a specific subpopulation of immune effector cells, e.g., T cells, that are a T regulatory cell-depleted population, CD25+ depleted cells, using, e.g., a negative selection technique, e.g., described herein. Preferably, the population of T regulatory depleted cells contains less than 30%, 25%, 20%, 15%, 10%, 5%, 4%, 3%, 2%, 1% of CD25+ cells.

In one embodiment, T regulatory cells, e.g., CD25+ T cells, are removed from the population using an anti-CD25 antibody, or fragment thereof, or a CD25-binding ligand, IL-2. In one embodiment, the anti-CD25 antibody, or fragment thereof, or CD25-binding ligand is conjugated to a substrate, e.g., a bead, or is otherwise coated on a substrate, e.g., a bead. In one embodiment, the anti-CD25 antibody, or fragment thereof, is conjugated to a substrate as described herein.

In one embodiment, the T regulatory cells, e.g., CD25+ T cells, are removed from the population using CD25 depletion reagent from Miltenyi™. In one embodiment, the ratio of cells to CD25 depletion reagent is 1e7 cells to 20 uL, or 1e7 cells to 15 uL, or 1e7 cells to 10 uL, or 1e7 cells to 5 uL, or 1e7 cells to 2.5 uL, or 1e7 cells to 1.25 uL. In one embodiment, e.g., for T regulatory cells, e.g., CD25+ depletion, greater than 500 million cells/ml is used. In a further aspect, a concentration of cells of 600, 700, 800, or 900 million cells/ml is used.

In one embodiment, the population of immune effector cells to be depleted includes about $6\times10^9$ CD25+ T cells. In other aspects, the population of immune effector cells to be depleted include about $1\times10^9$ to $1\times10^{10}$ CD25+ T cell, and any integer value in between. In one embodiment, the resulting population T regulatory depleted cells has $2\times10^9$ T regulatory cells, e.g., CD25+ cells, or less (e.g., $1\times10^9$, $5\times10^8$, $1\times10^8$, $5\times10^7$, $1\times10^7$, or less CD25+ cells).

In one embodiment, the T regulatory cells, e.g., CD25+ cells, are removed from the population using the CliniMAC system with a depletion tubing set, such as, e.g., tubing 162-01. In one embodiment, the CliniMAC system is run on a depletion setting such as, e.g., DEPLETION2.1.

Without wishing to be bound by a particular theory, decreasing the level of negative regulators of immune cells (e.g., decreasing the number of unwanted immune cells, e.g., $T_{REG}$ cells), in a subject prior to apheresis or during manufacturing of a CAR-expressing cell product can reduce the risk of subject relapse. For example, methods of depleting $T_{REG}$ cells are known in the art. Methods of decreasing $T_{REG}$ cells include, but are not limited to, cyclophosphamide, anti-GITR antibody (an anti-GITR antibody described herein), CD25-depletion, and combinations thereof.

In some embodiments, the manufacturing methods comprise reducing the number of (e.g., depleting) $T_{REG}$ cells prior to manufacturing of the CAR-expressing cell. For example, manufacturing methods comprise contacting the sample, e.g., the apheresis sample, with an anti-GITR antibody and/or an anti-CD25 antibody (or fragment thereof, or a CD25-binding ligand), e.g., to deplete $T_{REG}$ cells prior to manufacturing of the CAR-expressing cell (e.g., T cell, NK cell) product.

In an embodiment, a subject is pre-treated with one or more therapies that reduce $T_{REG}$ cells prior to collection of cells for CAR-expressing cell product manufacturing, thereby reducing the risk of subject relapse to CAR-expressing cell treatment. In an embodiment, methods of decreasing $T_{REG}$ cells include, but are not limited to, administration to the subject of one or more of cyclophosphamide, anti-GITR antibody, CD25-depletion, or a combination thereof. Administration of one or more of cyclophosphamide, anti-GITR antibody, CD25-depletion, or a combination thereof, can occur before, during or after an infusion of the CAR-expressing cell product.

In an embodiment, a subject is pre-treated with cyclophosphamide prior to collection of cells for CAR-expressing cell product manufacturing, thereby reducing the risk of subject relapse to CAR-expressing cell treatment. In an embodiment, a subject is pre-treated with an anti-GITR antibody prior to collection of cells for CAR-expressing cell product manufacturing, thereby reducing the risk of subject relapse to CAR-expressing cell treatment.

In one embodiment, the population of cells to be removed are neither the regulatory T cells or tumor cells, but cells that otherwise negatively affect the expansion and/or function of CART cells, e.g. cells expressing CD14, CD11b, CD33, CD15, or other markers expressed by potentially immune suppressive cells. In one embodiment, such cells are envisioned to be removed concurrently with regulatory T cells and/or tumor cells, or following said depletion, or in another order.

The methods described herein can include more than one selection step, e.g., more than one depletion step. Enrichment of a T cell population by negative selection can be accomplished, e.g., with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail can include antibodies to CD14, CD20, CD11 b, CD16, HLA-DR, and CD8.

The methods described herein can further include removing cells from the population which express a tumor antigen, e.g., a tumor antigen that does not comprise CD25, e.g., CD19, CD30, CD38, CD123, CD20, CD14 or CD11 b, to thereby provide a population of T regulatory depleted, e.g., CD25+ depleted, and tumor antigen depleted cells that are suitable for expression of a CAR, e.g., a CAR described herein. In one embodiment, tumor antigen expressing cells are removed simultaneously with the T regulatory, e.g., CD25+ cells. For example, an anti-CD25 antibody, or fragment thereof, and an anti-tumor antigen antibody, or fragment thereof, can be attached to the same substrate, e.g., bead, which can be used to remove the cells or an anti-CD25 antibody, or fragment thereof, or the anti-tumor antigen antibody, or fragment thereof, can be attached to separate beads, a mixture of which can be used to remove the cells. In other embodiments, the removal of T regulatory cells, e.g., CD25+ cells, and the removal of the tumor antigen expressing cells is sequential, and can occur, e.g., in either order.

Also provided are methods that include removing cells from the population which express a check point inhibitor, e.g., a check point inhibitor described herein, e.g., one or more of PD1+ cells, LAG3+ cells, and TIM3+ cells, to thereby provide a population of T regulatory depleted, e.g., CD25+ depleted cells, and check point inhibitor depleted cells, e.g., PD1+, LAG3+ and/or TIM3+ depleted cells. Exemplary check point inhibitors include B7-H1, B7-1, CD160, P1H, 2B4, PD1, TIM3, CEACAM (e.g., CEACAM-1, CEACAM-3 and/or CEACAM-5), LAG3, TIGIT, CTLA-4, BTLA and LAIR1. In one embodiment, check point inhibitor expressing cells are removed simultaneously with the T regulatory, e.g., CD25+ cells. For example, an anti-CD25 antibody, or fragment thereof, and an anti-check point inhibitor antibody, or fragment thereof, can be attached to the same bead which can be used to remove the cells, or an anti-CD25 antibody, or fragment thereof, and the anti-check point inhibitor antibody, or fragment there, can be attached to separate beads, a mixture of which can be used to remove the cells. In other embodiments, the removal of T regulatory cells, e.g., CD25+ cells, and the removal of the check point inhibitor expressing cells is sequential, and can occur, e.g., in either order.

Methods described herein can include a positive selection step. For example, T cells can isolated by incubation with anti-CD3/anti-CD28 (e.g., 3×28)-conjugated beads, such as DYNABEADS® M-450 CD3/CD28 T, for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another embodiment, the time period is 10 to 24 hours, e.g., 24 hours. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points.

In one embodiment, a T cell population can be selected that expresses one or more of IFN-γ, TNFα, IL-17A, IL-2, IL-3, IL-4, GM-CSF, IL-10, IL-13, granzyme B, and perforin, or other appropriate molecules, e.g., other cytokines. Methods for screening for cell expression can be determined, e.g., by the methods described in PCT Publication No.: WO 2013/126712.

For isolation of a desired population of cells by positive or negative selection, the concentration of cells and surface (e.g., particles such as beads) can be varied. In certain aspects, it may be desirable to significantly decrease the volume in which beads and cells are mixed together (e.g., increase the concentration of cells), to ensure maximum contact of cells and beads. For example, in one aspect, a concentration of 10 billion cells/ml, 9 billion/ml, 8 billion/ml, 7 billion/ml, 6 billion/ml, or 5 billion/ml is used. In one aspect, a concentration of 1 billion cells/ml is used. In yet one aspect, a concentration of cells from 75, 80, 85, 90, 95, or 100 million cells/ml is used. In further aspects, concentrations of 125 or 150 million cells/ml can be used.

Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (e.g., leukemic blood, tumor tissue, etc.). Such populations of cells may have therapeutic value and would be desirable to obtain. For example, using high concentration of cells allows more efficient selection of CD8+ T cells that normally have weaker CD28 expression.

In a related aspect, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4+ T cells express higher levels of CD28 and are more efficiently captured than CD8+ T cells in dilute concentrations. In one aspect, the concentration of cells used is $5\times10^6$/ml. In other aspects, the concentration used can be from about $1\times10^5$/ml to $1\times10^6$/ml, and any integer value in between.

In other aspects, the cells may be incubated on a rotator for varying lengths of time at varying speeds at either 2-10° C. or at room temperature.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In certain aspects, cryopreserved cells are thawed and washed as described herein and allowed to rest for one hour at room temperature prior to activation using the methods of the present invention.

Also contemplated in the context of the invention is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in immune effector cell therapy for any number of diseases or conditions that would benefit from immune effector cell therapy, such as those described herein. In one aspect a blood sample or an apheresis is taken from a generally healthy subject. In certain aspects, a blood sample or an apheresis is taken from a generally healthy subject who is at risk of developing a disease, but who has not yet developed a disease, and the cells of interest are isolated and frozen for later use. In certain aspects, the T cells may be expanded, frozen, and used at a later time. In certain aspects, samples are collected from a patient shortly after diagnosis of a particular disease as described herein but prior to any treatments. In a further aspect, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAM-PATH, anti-CD3 antibodies, cytoxan, fludarabine, cyclosporin, FK506, rapamycin, mycophenolic acid, steroids, FR901228, and irradiation.

In a further aspect of the present invention, T cells are obtained from a patient directly following treatment that leaves the subject with functional T cells. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in certain aspects, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

In one embodiment, the immune effector cells expressing a CAR molecule, e.g., a CAR molecule described herein, are obtained from a subject that has received a low, immune enhancing dose of an mTOR inhibitor. In an embodiment, the population of immune effector cells, e.g., T cells, to be engineered to express a CAR, are harvested after a sufficient time, or after sufficient dosing of the low, immune enhancing, dose of an mTOR inhibitor, such that the level of PD1 negative immune effector cells, e.g., T cells, or the ratio of PD1 negative immune effector cells, e.g., T cells/PD1 positive immune effector cells, e.g., T cells, in the subject or harvested from the subject has been, at least transiently, increased.

In other embodiments, population of immune effector cells, e.g., T cells, which have, or will be engineered to express a CAR, can be treated ex vivo by contact with an amount of an mTOR inhibitor that increases the number of PD1 negative immune effector cells, e.g., T cells or increases the ratio of PD1 negative immune effector cells, e.g., T cells/PD1 positive immune effector cells, e.g., T cells.

In one embodiment, a T cell population is diacylglycerol kinase (DGK)-deficient. DGK-deficient cells include cells that do not express DGK RNA or protein, or have reduced or inhibited DGK activity. DGK-deficient cells can be generated by genetic approaches, e.g., administering RNA-interfering agents, e.g., siRNA, shRNA, miRNA, to reduce or prevent DGK expression. Alternatively, DGK-deficient cells can be generated by treatment with DGK inhibitors described herein.

In one embodiment, a T cell population is Ikaros-deficient. Ikaros-deficient cells include cells that do not express Ikaros RNA or protein, or have reduced or inhibited Ikaros activity, Ikaros-deficient cells can be generated by genetic approaches, e.g., administering RNA-interfering agents, e.g., siRNA, shRNA, miRNA, to reduce or prevent Ikaros expression. Alternatively, Ikaros-deficient cells can be generated by treatment with Ikaros inhibitors, e.g., lenalidomide.

In embodiments, a T cell population is DGK-deficient and Ikaros-deficient, e.g., does not express DGK and Ikaros, or has reduced or inhibited DGK and Ikaros activity. Such DGK and Ikaros-deficient cells can be generated by any of the methods described herein.

In an embodiment, the NK cells are obtained from the subject. In another embodiment, the NK cells are an NK cell line, e.g., NK-92 cell line (Conkwest).

Additional Expressed Agents

In another embodiment, a CAR-expressing immune effector cell described herein can further express another agent, e.g., an agent which enhances the activity of a CAR-expressing cell. For example, in one embodiment, the agent can be an agent which inhibits an inhibitory molecule. Examples of inhibitory molecules include PD-1, PD-L1, CTLA-4, TIM-3, CEACAM (e.g., CEACAM-1, CEACAM-3 and/or CEACAM-5), LAG-3, VISTA, BTLA, TIGIT, LAIR1, CD160, 2B4 and TGFR beta, e.g., as described herein. In one embodiment, the agent that inhibits an inhibitory molecule comprises a first polypeptide, e.g., an inhibitory molecule, associated with a second polypeptide that provides a positive signal to the cell, e.g., an intracellular signaling domain described herein. In one embodiment, the agent comprises a first polypeptide, e.g., of an inhibitory molecule such as PD-1, PD-L1, CTLA-4, TIM-3, CEACAM (e.g., CEACAM-1, CEACAM-3 and/or CEACAM-5), LAG-3, VISTA, BTLA, TIGIT, LAIR1, CD160, 2B4 or TGFR beta, or a fragment of any of these, and a second polypeptide which is an intracellular signaling domain described herein (e.g., comprising a costimulatory domain (e.g., 41BB, CD27 or CD28, e.g., as described herein) and/or a primary signaling domain (e.g., a CD3 zeta signaling domain described herein). In one embodiment, the agent comprises a first polypeptide of PD-1 or a fragment thereof, and a second polypeptide of an intracellular signaling domain described herein (e.g., a CD28, CD27, OX40 or 4-IBB signaling domain described herein and/or a CD3 zeta signaling domain described herein).

In one embodiment, the CAR-expressing immune effector cell described herein can further comprise a second CAR, e.g., a second CAR that includes a different antigen binding domain, e.g., to the same target (e.g., a target described above) or a different target. In one embodiment, the second CAR includes an antigen binding domain to a target expressed on the same cancer cell type as the target of the first CAR. In one embodiment, the CAR-expressing immune effector cell comprises a first CAR that targets a first antigen and includes an intracellular signaling domain having a costimulatory signaling domain but not a primary signaling domain, and a second CAR that targets a second, different antigen and includes an intracellular signaling domain having a primary signaling domain but not a costimulatory signaling domain.

While not wishing to be bound by theory, placement of a costimulatory signaling domain, e.g., 4-1BB, CD28, CD27 or OX-40, onto the first CAR, and the primary signaling domain, e.g., CD3 zeta, on the second CAR can limit the CAR activity to cells where both targets are expressed. In one embodiment, the CAR expressing immune effector cell comprises a first CAR that includes an antigen binding domain that targets, e.g., a target described above, a transmembrane domain and a costimulatory domain and a second CAR that targets an antigen other than antigen targeted by the first CAR (e.g., an antigen expressed on the same cancer cell type as the first target) and includes an antigen binding domain, a transmembrane domain and a primary signaling domain. In another embodiment, the CAR expressing immune effector cell comprises a first CAR that includes an antigen binding domain that targets, e.g., a target described above, a transmembrane domain and a primary signaling domain and a second CAR that targets an antigen other than antigen targeted by the first CAR (e.g., an antigen expressed on the same cancer cell type as the first target) and includes an antigen binding domain to the antigen, a transmembrane domain and a costimulatory signaling domain.

In one embodiment, the CAR-expressing immune effector cell comprises a CAR described herein, e.g., a CAR to a target described above, and an inhibitory CAR. In one embodiment, the inhibitory CAR comprises an antigen binding domain that binds an antigen found on normal cells but not cancer cells, e.g., normal cells that also express the target. In one embodiment, the inhibitory CAR comprises the antigen binding domain, a transmembrane domain and an intracellular domain of an inhibitory molecule. For example, the intracellular domain of the inhibitory CAR can be an intracellular domain of PD1, PD-L1, CTLA-4, TIM-3, CEACAM (e.g., CEACAM-1, CEACAM-3 and/or CEACAM-5), LAG-3, VISTA, BTLA, TIGIT, LAIR1, CD160, 2B4 or TGFR beta.

In one embodiment, an immune effector cell (e.g., T cell, NK cell) comprises a first CAR comprising an antigen binding domain that binds to a tumor antigen as described herein, and a second CAR comprising a PD1 extracellular domain or a fragment thereof.

In one embodiment, the cell further comprises an inhibitory molecule as described above.

In one embodiment, the second CAR in the cell is an inhibitory CAR, wherein the inhibitory CAR comprises an antigen binding domain, a transmembrane domain, and an intracellular domain of an inhibitory molecule. The inhibitory molecule can be chosen from one or more of: PD1, PD-L1, CTLA-4, TIM-3, LAG-3, VISTA, BTLA, TIGIT, LAIR1, CD160, 2B4, TGFR beta, CEACAM-1, CEACAM-3, and CEACAM-5. In one embodiment, the second CAR molecule comprises the extracellular domain of PD1 or a fragment thereof.

In embodiments, the second CAR molecule in the cell further comprises an intracellular signaling domain comprising a primary signaling domain and/or an intracellular signaling domain.

In other embodiments, the intracellular signaling domain in the cell comprises a primary signaling domain comprising the functional domain of CD3 zeta and a costimulatory signaling domain comprising the functional domain of 4-1BB.

In one embodiment, the second CAR molecule in the cell comprises the amino acid sequence of SEQ ID NO: 26.

In certain embodiments, the antigen binding domain of the first CAR molecule comprises a scFv and the antigen binding domain of the second CAR molecule does not comprise a scFv. For example, the antigen binding domain of the first CAR molecule comprises a scFv and the antigen binding domain of the second CAR molecule comprises a camelid VHH domain.

Split CAR

In some embodiments, the CAR-expressing cell uses a split CAR. The split CAR approach is described in more detail in publications WO2014/055442 and WO2014/055657. Briefly, a split CAR system comprises a cell expressing a first CAR having a first antigen binding domain and a costimulatory domain (e.g., 41BB), and the cell also expresses a second CAR having a second antigen binding domain and an intracellular signaling domain (e.g., CD3 zeta). When the cell encounters the first antigen, the costimulatory domain is activated, and the cell proliferates. When the cell encounters the second antigen, the intracellular signaling domain is activated and cell-killing activity begins. Thus, the CAR-expressing cell is only fully activated in the presence of both antigens.

Multiple CAR Expression

In one aspect, the CAR-expressing cell described herein can further comprise a second CAR, e.g., a second CAR that includes a different antigen binding domain, e.g., to the same target or a different target (e.g., a target other than a cancer associated antigen described herein or a different cancer associated antigen described herein). In one embodiment, the second CAR includes an antigen binding domain to a target expressed the same cancer cell type as the cancer associated antigen. In one embodiment, the CAR-expressing cell comprises a first CAR that targets a first antigen and includes an intracellular signaling domain having a costimulatory signaling domain but not a primary signaling domain, and a second CAR that targets a second, different, antigen and includes an intracellular signaling domain having a primary signaling domain but not a costimulatory signaling domain. While not wishing to be bound by theory, placement of a costimulatory signaling domain, e.g., 4-1BB, CD28, CD27 or OX-40, onto the first CAR, and the primary signaling domain, e.g., CD3 zeta, on the second CAR can limit the CAR activity to cells where both targets are expressed. In one embodiment, the CAR expressing cell comprises a first cancer associated antigen CAR that includes an antigen binding domain that binds a target antigen described herein, a transmembrane domain and a costimulatory domain and a second CAR that targets a different target antigen (e.g., an antigen expressed on that same cancer cell type as the first target antigen) and includes an antigen binding domain, a transmembrane domain and a primary signaling domain. In another embodiment, the CAR expressing cell comprises a first CAR that includes an antigen binding domain that binds a target antigen described herein, a transmembrane domain and a primary signaling domain and a second CAR that targets an antigen other than the first target antigen (e.g., an antigen expressed on the same cancer cell type as the first target antigen) and includes an antigen binding domain to the antigen, a transmembrane domain and a costimulatory signaling domain.

In some embodiments, the claimed invention comprises a first and second CAR, wherein the antigen binding domain of one of said first CAR said second CAR does not comprise a variable light domain and a variable heavy domain. In some embodiments, the antigen binding domain of one of said first CAR said second CAR is an scFv, and the other is not an scFv. In some embodiments, the antigen binding domain of one of said first CAR said second CAR comprises a single VH domain, e.g., a camelid, shark, or lamprey single VH domain, or a single VH domain derived from a human or mouse sequence. In some embodiments, the antigen binding domain of one of said first CAR said second CAR comprises a nanobody. In some embodiments, the antigen binding domain of one of said first CAR said second CAR comprises a camelid VHH domain.

Telomerase Expression

While not wishing to be bound by any particular theory, in some embodiments, a therapeutic T cell has short term persistence in a patient, due to shortened telomeres in the T cell; accordingly, transfection with a telomerase gene can lengthen the telomeres of the T cell and improve persistence of the T cell in the patient. See Carl June, "Adoptive T cell therapy for cancer in the clinic", Journal of Clinical Investigation, 117:1466-1476 (2007). Thus, in an embodiment, an immune effector cell, e.g., a T cell, ectopically expresses a telomerase subunit, e.g., the catalytic subunit of telomerase, e.g., TERT, e.g., hTERT. In some aspects, this disclosure provides a method of producing a CAR-expressing cell, comprising contacting a cell with a nucleic acid encoding a telomerase subunit, e.g., the catalytic subunit of telomerase, e.g., TERT, e.g., hTERT. The cell may be contacted with the nucleic acid before, simultaneous with, or after being contacted with a construct encoding a CAR.

Expansion and Activation

Immune effector cells such as T cells may be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005, each of which is incorporated by reference in its entirety.

Generally, a population of immune effector cells e.g., T regulatory cell depleted cells, may be expanded by contact with a surface having attached thereto an agent that stimulates a CD3/TCR complex associated signal and a ligand that stimulates a costimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either CD4+ T cells or CD8+ T cells, an anti-CD3 antibody and an anti-CD28 antibody can be used. Examples of an anti-CD28 antibody include 9.3, B-T3, XR-CD28 (Diaclone, Besancon, France) can be used as can other methods commonly known in the art (Berg et al., Transplant Proc. 30(8):3975-3977, 1998; Haanen et al., J. Exp. Med. 190(9):13191328, 1999; Garland et al., J. Immunol Meth. 227(1-2):53-63, 1999).

In certain aspects, the primary stimulatory signal and the costimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one aspect, the agent providing the costimulatory signal is bound to a cell surface and the agent providing the primary activation signal is in solution or coupled to a surface. In certain aspects, both agents can be in solution. In one aspect, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In one aspect, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the costimulatory signal is an anti-CD28 antibody or antigen-binding fragment thereof; and both agents are co-immobilized to the same bead in equivalent molecular amounts. In one aspect, a 1:1 ratio of each antibody bound to the beads for CD4+ T cell expansion and T cell growth is used. In certain aspects of the present invention, a ratio of anti CD3:CD28 antibodies bound to the beads is used such that an increase in T cell expansion is observed as compared to the expansion observed using a ratio of 1:1. In one particular aspect an increase of from about 1 to about 3 fold is observed as compared to the expansion observed using a ratio of 1:1. In one aspect, the ratio of CD3:CD28 antibody bound to the beads ranges from 100:1 to 1:100 and all integer values there between. In one aspect, more anti-CD28 antibody is bound to the particles than anti-CD3 antibody, i.e., the ratio of CD3:CD28 is less than one. In certain aspects, the ratio of anti CD28 antibody to anti CD3 antibody bound to the beads is greater than 2:1. In one particular aspect, a 1:100 CD3:CD28 ratio of antibody bound to beads is used. In one aspect, a 1:75 CD3:CD28 ratio of antibody bound to beads is used. In a further aspect, a 1:50 CD3:CD28 ratio of antibody bound to beads is used. In one aspect, a 1:30 CD3:CD28 ratio of antibody bound to beads is used. In one preferred aspect, a 1:10 CD3:CD28 ratio of antibody bound to beads is used. In one aspect, a 1:3 CD3:CD28 ratio of antibody bound to the beads is used. In yet one aspect, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain aspects the ratio of cells to particles ranges from 1:100 to 100:1 and any integer values in-between and in further aspects the ratio comprises 1:9 to 9:1 and any integer values in between, can also be used to stimulate T cells. The ratio of anti-CD3- and anti-CD28-coupled particles to T cells that result in T cell stimulation can vary as noted above, however certain preferred values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T cell. In one aspect, a ratio of particles to cells of 1:1 or less is used. In one particular aspect, a preferred particle: cell ratio is 1:5. In further aspects, the ratio of particles to cells can be varied depending on the day of stimulation. For example, in one aspect, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular aspect, the ratio of particles to cells is 1:1 on the first day of stimulation and adjusted to 1:5 on the third and fifth days of stimulation. In one aspect, particles are added on a daily or every other day basis to a final ratio of 1:1 on the first day, and 1:5 on the third and fifth days of stimulation. In one aspect, the ratio of particles to cells is 2:1 on the first day of stimulation and adjusted to 1:10 on the third and fifth days of stimulation. In one aspect, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type. In one aspect, the most typical ratios for use are in the neighborhood of 1:1, 2:1 and 3:1 on the first day.

In further aspects, the cells, such as T cells, are combined with agent-coated beads, the beads and the cells are subsequently separated, and then the cells are cultured. In an alternative aspect, prior to culture, the agent-coated beads and cells are not separated but are cultured together. In a further aspect, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one aspect the cells (for example, $10^4$ to $10^9$ T cells) and beads (for example, DYNABEADS® M-450 CD3/CD28 T paramagnetic beads at a ratio of 1:1) are combined in a buffer, for example PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present invention. In certain aspects, it may be desirable to significantly decrease the volume in which particles and cells are mixed together (i.e., increase the concentration of cells), to ensure maximum contact of cells and particles. For example, in one aspect, a concentration of about 10 billion cells/ml, 9 billion/ml, 8 billion/ml, 7 billion/ml, 6 billion/ml, 5 billion/ml, or 2 billion cells/ml is used. In one aspect, greater than 100 million cells/ml is used. In a further aspect, a concentration of cells of 10, 15, 20, 25, 30, 35, 40, 45, or 50 million cells/ml is used. In yet one aspect, a concentration of cells from 75, 80, 85, 90, 95, or 100 million cells/ml is used. In further aspects, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain aspects. For example, using high concentration of cells allows more efficient selection of CD8+ T cells that normally have weaker CD28 expression.

In one embodiment, cells transduced with a nucleic acid encoding a CAR, e.g., a CAR described herein, are expanded, e.g., by a method described herein. In one embodiment, the cells are expanded in culture for a period of several hours (e.g., about 2, 3, 4, 5, 6, 7, 8, 9, 10, 15, 18, 21 hours) to about 14 days (e.g., 1, 2, 3, 4, 5, 6, 7, 8, 9, 10, 11, 12, 13 or 14 days). In one embodiment, the cells are expanded for a period of 4 to 9 days. In one embodiment, the cells are expanded for a period of 8 days or less, e.g., 7, 6 or 5 days. In one embodiment, the cells are expanded in culture for 5 days, and the resulting cells are more potent than the same cells expanded in culture for 9 days under the same culture conditions. Potency can be defined, e.g., by various T cell functions, e.g. proliferation, target cell killing, cytokine production, activation, migration, or combinations thereof. In one embodiment, the cells are expanded for 5 days show at least a one, two, three or four fold increase in cells doublings upon antigen stimulation as compared to the same cells expanded in culture for 9 days under the same culture conditions. In one embodiment, the cells are expanded in culture for 5 days, and the resulting cells exhibit higher proinflammatory cytokine production, e.g., IFN-γ and/or GM-CSF levels, as compared to the same cells expanded in culture for 9 days under the same culture conditions. In one embodiment, the cells expanded for 5 days show at least a one, two, three, four, five, ten fold or more increase in pg/ml of proinflammatory cytokine production, e.g., IFN-γ and/or GM-CSF levels, as compared to the same cells expanded in culture for 9 days under the same culture conditions.

Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

In one embodiment, the cells are expanded in an appropriate media (e.g., media described herein) that includes one or more interleukin that result in at least a 200-fold (e.g., 200-fold, 250-fold, 300-fold, 350-fold) increase in cells over a 14 day expansion period, e.g., as measured by a method described herein such as flow cytometry. In one embodiment, the cells are expanded in the presence of IL-15 and/or IL-7 (e.g., IL-15 and IL-7).

In embodiments, methods described herein, e.g., CAR-expressing cell manufacturing methods, comprise removing T regulatory cells, e.g., CD25+ T cells, from a cell population, e.g., using an anti-CD25 antibody, or fragment thereof, or a CD25-binding ligand, IL-2. Methods of removing T regulatory cells, e.g., CD25+ T cells, from a cell population are described herein. In embodiments, the methods, e.g., manufacturing methods, further comprise contacting a cell population (e.g., a cell population in which T regulatory cells, such as CD25+ T cells, have been depleted; or a cell population that has previously contacted an anti-CD25 antibody, fragment thereof, or CD25-binding ligand) with IL-15 and/or IL-7. For example, the cell population (e.g., that has previously contacted an anti-CD25 antibody, fragment thereof, or CD25-binding ligand) is expanded in the presence of IL-15 and/or IL-7.

In some embodiments a CAR-expressing cell described herein is contacted with a composition comprising a interleukin-15 (IL-15) polypeptide, a interleukin-15 receptor alpha (IL-15Ra) polypeptide, or a combination of both a IL-15 polypeptide and a IL-15Ra polypeptide e.g., hetIL-15, during the manufacturing of the CAR-expressing cell, e.g., ex vivo. In embodiments, a CAR-expressing cell described herein is contacted with a composition comprising a IL-15 polypeptide during the manufacturing of the CAR-expressing cell, e.g., ex vivo. In embodiments, a CAR-expressing cell described herein is contacted with a composition comprising a combination of both a IL-15 polypeptide and a IL-15 Ra polypeptide during the manufacturing of the CAR-expressing cell, e.g., ex vivo. In embodiments, a CAR-expressing cell described herein is contacted with a composition comprising hetIL-15 during the manufacturing of the CAR-expressing cell, e.g., ex vivo.

In one embodiment the CAR-expressing cell described herein is contacted with a composition comprising hetIL-15 during ex vivo expansion. In an embodiment, the CAR-expressing cell described herein is contacted with a composition comprising an IL-15 polypeptide during ex vivo expansion. In an embodiment, the CAR-expressing cell described herein is contacted with a composition comprising both an IL-15 polypeptide and an IL-15Ra polypeptide during ex vivo expansion. In one embodiment the contacting results in the survival and proliferation of a lymphocyte subpopulation, e.g., CD8+ T cells.

T cells that have been exposed to varied stimulation times may exhibit different characteristics. For example, typical blood or apheresed peripheral blood mononuclear cell products have a helper T cell population (TH, CD4+) that is greater than the cytotoxic or suppressor T cell population (TC, CD8+). Ex vivo expansion of T cells by stimulating CD3 and CD28 receptors produces a population of T cells that prior to about days 8-9 consists predominately of TH cells, while after about days 8-9, the population of T cells comprises an increasingly greater population of TC cells. Accordingly, depending on the purpose of treatment, infusing a subject with a T cell population comprising predominately of TH cells may be advantageous. Similarly, if an antigen-specific subset of TC cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

Once a CAR described herein is constructed, various assays can be used to evaluate the activity of the molecule, such as but not limited to, the ability to expand T cells following antigen stimulation, sustain T cell expansion in the absence of re-stimulation, and anti-cancer activities in appropriate in vitro and animal models. Assays to evaluate the effects of a cars of the present invention are described in further detail below Western blot analysis of CAR expression in primary T cells can be used to detect the presence of monomers and dimers. See, e.g., Milone et al., Molecular Therapy 17(8): 1453-1464 (2009). Very briefly, T cells (1:1 mixture of CD4+ and CD8+ T cells) expressing the CARs are expanded in vitro for more than 10 days followed by lysis and SDS-PAGE under reducing conditions. CARs containing the full length TCR-ζ cytoplasmic domain and the endogenous TCR-ζ chain are detected by western blotting using an antibody to the TCR-ζ chain. The same T cell subsets are used for SDS-PAGE analysis under non-reducing conditions to permit evaluation of covalent dimer formation.

In vitro expansion of CAR$^+$ T cells following antigen stimulation can be measured by flow cytometry. For example, a mixture of CD4$^+$ and CD8$^+$ T cells are stimulated with αCD3/αCD28 aAPCs followed by transduction with lentiviral vectors expressing GFP under the control of the promoters to be analyzed. Exemplary promoters include the CMV IE gene, EF-1α, ubiquitin C, or phosphoglycerokinase (PGK) promoters. GFP fluorescence is evaluated on day 6 of culture in the CD4$^+$ and/or CD8$^+$ T cell subsets by flow cytometry. See, e.g., Milone et al., Molecular Therapy 17(8): 1453-1464 (2009). Alternatively, a mixture of CD4$^+$ and CD8$^+$ T cells are stimulated with αCD3/αCD28 coated magnetic beads on day 0, and transduced with CAR on day 1 using a bicistronic lentiviral vector expressing CAR along with eGFP using a 2A ribosomal skipping sequence. Cultures are re-stimulated with either a cancer associated antigen as described herein$^+$ K562 cells (K562 expressing a cancer associated antigen as described herein), wild-type K562 cells (K562 wild type) or K562 cells expressing hCD32 and 4-1BBL in the presence of antiCD3 and anti-CD28 antibody (K562-BBL-3/28) following washing. Exogenous IL-2 is added to the cultures every other day at 100 IU/ml. GFP$^+$ T cells are enumerated by flow cytometry using bead-based counting. See, e.g., Milone et al., Molecular Therapy 17(8): 1453-1464 (2009).

Sustained CAR$^+$ T cell expansion in the absence of re-stimulation can also be measured. See, e.g., Milone et al., Molecular Therapy 17(8): 1453-1464 (2009). Briefly, mean T cell volume (fl) is measured on day 8 of culture using a Coulter Multisizer III particle counter, a Nexcelom Cellometer Vision or Millipore Scepter, following stimulation with αCD3/αCD28 coated magnetic beads on day 0, and transduction with the indicated CAR on day 1.

Animal models can also be used to measure a CART activity. For example, xenograft model using human a cancer associated antigen described herein-specific CAR$^+$ T cells to treat a primary human pre-B ALL in immunodeficient mice can be used. See, e.g., Milone et al., Molecular Therapy 17(8): 1453-1464 (2009). Very briefly, after establishment of ALL, mice are randomized as to treatment groups. Different numbers of a cancer associated antigen-specific CARengineered T cells are coinjected at a 1:1 ratio into NOD-SCID-γ$^{-/-}$ mice bearing B-ALL. The number of copies of a cancer associated antigen-specific CAR vector in spleen DNA from mice is evaluated at various times following T cell injection. Animals are assessed for leukemia at weekly intervals. Peripheral blood a cancer associate antigen as described herein$^+$ B-ALL blast cell counts are measured in mice that are injected with a cancer associated antigen described herein-ζ CAR$^+$ T cells or mock-transduced T cells. Survival curves for the groups are compared using the log-rank test. In addition, absolute peripheral blood CD4$^+$ and CD8$^+$ T cell counts 4 weeks following T cell injection in NOD-SCID-γ$^{-/-}$ mice can also be analyzed. Mice are injected with leukemic cells and 3 weeks later are injected with T cells engineered to express CAR by a bicistronic lentiviral vector that encodes the CAR linked to eGFP. T cells are normalized to 45-50% input GFP$^+$ T cells by mixing with mock-transduced cells prior to injection, and confirmed by flow cytometry. Animals are assessed for leukemia at 1-week intervals. Survival curves for the CAR$^+$ T cell groups are compared using the log-rank test.

Dose dependent CAR treatment response can be evaluated. See, e.g., Milone et al., Molecular Therapy 17(8): 1453-1464 (2009). For example, peripheral blood is obtained 35-70 days after establishing leukemia in mice injected on day 21 with CAR T cells, an equivalent number of mock-transduced T cells, or no T cells. Mice from each group are randomly bled for determination of peripheral blood a cancer associate antigen as described herein$^+$ ALL blast counts and then killed on days 35 and 49. The remaining animals are evaluated on days 57 and 70.

Assessment of cell proliferation and cytokine production has been previously described, e.g., at Milone et al., Molecular Therapy 17(8): 1453-1464 (2009). Briefly, assessment of CAR-mediated proliferation is performed in microtiter plates by mixing washed T cells with K562 cells expressing a cancer associated antigen described herein (K19) or CD32 and CD137 (KT32-BBL) for a final T-cell:K562 ratio of 2:1. K562 cells are irradiated with gamma-radiation prior to use. Anti-CD3 (clone OKT3) and anti-CD28 (clone 9.3) monoclonal antibodies are added to cultures with KT32-BBL cells to serve as a positive control for stimulating T-cell proliferation since these signals support long-term CD8$^+$ T cell expansion ex vivo. T cells are enumerated in cultures using CountBright™ fluorescent beads (Invitrogen, Carlsbad, CA) and flow cytometry as described by the manufacturer. CAR$^+$ T cells are identified by GFP expression using T cells that are engineered with eGFP-2A linked CAR-expressing lentiviral vectors. For CAR+ T cells not expressing GFP, the CAR+ T cells are detected with biotinylated recombinant a cancer associate antigen as described herein protein and a secondary avidin-PE conjugate. CD4+ and CD8$^+$ expression on T cells are also simultaneously detected with specific monoclonal antibodies (BD Biosciences). Cytokine measurements are performed on supernatants collected 24 hours following re-stimulation using the human TH1/TH2 cytokine cytometric bead array kit (BD Biosciences, San Diego, CA) according the manufacturer's instructions. Fluorescence is assessed using a FACScalibur flow cytometer, and data is analyzed according to the manufacturer's instructions.

Cytotoxicity can be assessed by a standard 51Cr-release assay. See, e.g., Milone et al., Molecular Therapy 17(8): 1453-1464 (2009). Briefly, target cells (K562 lines and primary pro-B-ALL cells) are loaded with 51Cr (as NaCrO4, New England Nuclear, Boston, MA) at 37° C. for 2 hours with frequent agitation, washed twice in complete RPMI and plated into microtiter plates. Effector T cells are mixed with target cells in the wells in complete RPMI at varying ratios of effector cell:target cell (E:T). Additional wells containing media only (spontaneous release, SR) or a 1% solution of triton-X 100 detergent (total release, TR) are also prepared. After 4 hours of incubation at 37° C., supernatant from each well is harvested. Released 51Cr is then measured using a gamma particle counter (Packard Instrument Co., Waltham, MA). Each condition is performed in at least triplicate, and the percentage of lysis is calculated using the formula: % Lysis=(ER−SR)/(TR−SR), where ER represents the average 51Cr released for each experimental condition.

Imaging technologies can be used to evaluate specific trafficking and proliferation of CARs in tumor-bearing animal models. Such assays have been described, for example, in Barrett et al., Human Gene Therapy 22:1575-1586 (2011). Briefly, NOD/SCID/γc$^{-/-}$ (NSG) mice are injected IV with Nalm-6 cells followed 7 days later with T cells 4 hour after electroporation with the CAR constructs. The T cells are stably transfected with a lentiviral construct to express firefly luciferase, and mice are imaged for bioluminescence.

Alternatively, therapeutic efficacy and specificity of a single injection of CAR+ T cells in Nalm-6 xenograft model can be measured as the following: NSG mice are injected with Nalm-6 transduced to stably express firefly luciferase, followed by a single tail-vein injection of T cells electroporated with cars of the present invention 7 days later. Animals are imaged at various time points post injection. For example, photon-density heat maps of firefly luciferasepositive leukemia in representative mice at day 5 (2 days before treatment) and day 8 (24 hr post CAR+ PBLs) can be generated.

Other assays, including those described in the Example section herein as well as those that are known in the art can also be used to evaluate the CARs described herein.

Methods of Treatment/Combination Therapies

In another aspect, the present invention provides a method comprising administering a CAR molecule, e.g., a CAR molecule described herein, or a cell comprising a nucleic acid encoding a CAR molecule, e.g., a CAR molecule described herein. In one embodiment, the subject has a disorder described herein, e.g., the subject has cancer, e.g., the subject has a cancer which expresses a target antigen described herein. In one embodiment, the subject is a human.

In another aspect, the invention pertains to a method of treating a subject having a disease associated with expression of a cancer associated antigen as described herein comprising administering to the subject an effective amount of a cell comprising a CAR molecule, e.g., a CAR molecule described herein.

In yet another aspect, the invention features a method of treating a subject having a disease associated with expression of a tumor antigen (e.g., an antigen described herein), comprising administering to the subject an effective amount of a cell, e.g., an immune effector cell (e.g., a population of immune effector cells) comprising a CAR molecule, wherein the CAR molecule comprises an antigen binding domain, a transmembrane domain, and an intracellular domain, said intracellular domain comprises a costimulatory domain and/or a primary signaling domain, wherein said antigen binding domain binds to the tumor antigen associated with the disease, e.g. a tumor antigen as described herein.

In a related aspect, the invention features a method of treating a subject having a disease associated with expression of a tumor antigen. The method comprises administering to the subject an effective amount of a cell, e.g., an immune effector cell (e.g., a population of immune effector cells) comprising a CAR molecule, in combination with an agent that increases the efficacy of the immune cell, wherein:
the agent that increases the efficacy of the immune cell is chosen from one or more of:
(i) a protein phosphatase inhibitor;
(ii) a kinase inhibitor;
(iii) a cytokine;
(iv) an inhibitor of an immune inhibitory molecule; or
(v) an agent that decreases the level or activity of a $T_{REG}$ cell.

In another aspect, the invention features a composition comprising an immune effector cell (e.g., a population of immune effector cells) comprising a CAR molecule (e.g., a CAR molecule as described herein) for use in the treatment of a subject having a disease associated with expression of a tumor antigen, e.g., a disorder as described herein.

In certain embodiments of any of the aforesaid methods or uses, the disease associated with a tumor antigen, e.g., a tumor antigen described herein, is selected from a proliferative disease such as a cancer or malignancy or a precancerous condition such as a myelodysplasia, a myelodysplastic syndrome or a preleukemia, or is a non-cancer related indication associated with expression of a tumor antigen described herein. In one embodiment, the disease is a cancer described herein, e.g., a cancer described herein as being associated with a target described herein. In one embodiment, the disease is a hematologic cancer. In one embodiment, the hematologic cancer is leukemia. In one embodiment, the cancer is selected from the group consisting of one or more acute leukemias including but not limited to B-cell acute lymphoid leukemia ("BALL"), T-cell acute lymphoid leukemia ("TALL"), acute lymphoid leukemia (ALL); one or more chronic leukemias including but not limited to chronic myelogenous leukemia (CML), chronic lymphocytic leukemia (CLL); additional hematologic cancers or hematologic conditions including, but not limited to B cell prolymphocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma, Marginal zone lymphoma, multiple myeloma, myelodysplasia and myelodysplastic syndrome, non-Hodgkin lymphoma, Hodgkin lymphoma, plasmablastic lymphoma, plasmacytoid dendritic cell neoplasm, Waldenstrom macroglobulinemia, and "preleukemia" which are a diverse collection of hematological conditions united by ineffective production (or dysplasia) of myeloid blood cells, and to disease associated with expression of a tumor antigen described herein include, but not limited to, atypical and/or non-classical cancers, malignancies, precancerous conditions or proliferative diseases expressing a tumor antigen as described herein; and any combination thereof. In another embodiment, the disease associated with a tumor antigen described herein is a solid tumor.

In certain embodiments, the methods or uses are carried out in combination with an agent that increases the efficacy of the immune effector cell, e.g., an agent as described herein.

In any of the aforesaid methods or uses, the disease associated with expression of the tumor antigen is selected from the group consisting of a proliferative disease, a precancerous condition, a cancer, and a non-cancer related indication associated with expression of the tumor antigen.

The cancer can be a hematologic cancer, e.g., a cancer chosen from one or more of chronic lymphocytic leukemia (CLL), acute leukemias, acute lymphoid leukemia (ALL), B-cell acute lymphoid leukemia (B-ALL), T-cell acute lymphoid leukemia (T-ALL), chronic myelogenous leukemia (CML), B cell prolymphocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma, marginal zone lymphoma, multiple myeloma, myelodysplasia and myelodysplastic syndrome, non-Hodgkin's lymphoma, Hodgkin's lymphoma, plasmablastic lymphoma, plasmacytoid dendritic cell neoplasm, Waldenstrom macroglobulinemia, or preleukemia.

The cancer can also be chosen from colon cancer, rectal cancer, renal-cell carcinoma, liver cancer, non-small cell carcinoma of the lung, cancer of the small intestine, cancer of the esophagus, melanoma, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the endocrine system, cancer of the thyroid gland, cancer of the parathyroid gland, cancer of the adrenal gland, sarcoma of soft tissue, cancer of the urethra, cancer of the penis, solid tumors of childhood, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers, combinations of said cancers, and metastatic lesions of said cancers.

In certain embodiments of the methods or uses described herein, the CAR molecule is administered in combination with an agent that increases the efficacy of the immune effector cell, e.g., one or more of a protein phosphatase inhibitor, a kinase inhibitor, a cytokine, an inhibitor of an immune inhibitory molecule; or an agent that decreases the level or activity of a $T_{REG}$ cell.

In certain embodiments of the methods or uses described herein, the protein phosphatase inhibitor is a SHP-1 inhibitor and/or an SHP-2 inhibitor.

In other embodiments of the methods or uses described herein, kinase inhibitor is chosen from one or more of a CDK4 inhibitor, a CDK4/6 inhibitor (e.g., palbociclib), a BTK inhibitor (e.g., ibrutinib or RN-486), an mTOR inhibitor (e.g., rapamycin or everolimus (RAD001)), an MNK inhibitor, or a dual PI3K/mTOR inhibitor. In one embodiment, the BTK inhibitor does not reduce or inhibit the kinase activity of interleukin-2-inducible kinase (ITK).

In other embodiments of the methods or uses described herein, the agent that inhibits the immune inhibitory molecule comprises an antibody or antibody fragment, an inhibitory nucleic acid, a clustered regularly interspaced short palindromic repeats (CRISPR), a transcription-activator like effector nuclease (TALEN), or a zinc finger endonuclease (ZFN) that inhibits the expression of the inhibitory molecule.

In other embodiments of the methods or uses described herein, the agent that decreases the level or activity of the $T_{REG}$ cells is chosen from cyclophosphamide, anti-GITR antibody, CD25-depletion, or a combination thereof.

In certain embodiments of the methods or uses described herein, the immune inhibitory molecule is selected from the group consisting of PD1, PD-L1, CTLA-4, TIM-3, LAG-3, VISTA, BTLA, TIGIT, LAIR1, CD160, 2B4, TGFR beta, CEACAM-1, CEACAM-3, and CEACAM-5.

In other embodiments, the agent that inhibits the inhibitory molecule comprises a first polypeptide comprising an inhibitory molecule or a fragment thereof and a second polypeptide that provides a positive signal to the cell, and wherein the first and second polypeptides are expressed on the CAR-containing immune cells, wherein (i) the first polypeptide comprises PD1, PD-L1, CTLA-4, TIM-3, LAG3, VISTA, BTLA, TIGIT, LAIR1, CD160, 2B4, TGFR beta, CEACAM-1, CEACAM-3, and CEACAM-5 or a fragment thereof; and/or (ii) the second polypeptide comprises an intracellular signaling domain comprising a primary signaling domain and/or a costimulatory signaling domain. In one embodiment, the primary signaling domain comprises a functional domain of CD3 zeta; and/or the costimulatory signaling domain comprises a functional domain of a protein selected from 41BB, CD27 and CD28.

In other embodiments, cytokine is chosen from IL-7, IL-15 or IL-21, or both.

In other embodiments, the immune effector cell comprising the CAR molecule and a second, e.g., any of the combination therapies disclosed herein (e.g., the agent that that increases the efficacy of the immune effector cell) are administered substantially simultaneously or sequentially.

In other embodiments, the immune cell comprising the CAR molecule is administered in combination with a molecule that targets GITR and/or modulates GITR function. In certain embodiments, the molecule targeting GITR and/or modulating GITR function is administered prior to the CAR-expressing cell or population of cells, or prior to apheresis.

In one embodiment, lymphocyte infusion, for example allogeneic lymphocyte infusion, is used in the treatment of the cancer, wherein the lymphocyte infusion comprises at least one CAR-expressing cell of the present invention. In one embodiment, autologous lymphocyte infusion is used in the treatment of the cancer, wherein the autologous lymphocyte infusion comprises at least one CAR-expressing cell described herein.

In one embodiment, the cell is a T cell and the T cell is diaglycerol kinase (DGK) deficient. In one embodiment, the cell is a T cell and the T cell is Ikaros deficient. In one embodiment, the cell is a T cell and the T cell is both DGK and Ikaros deficient.

In one embodiment, the method includes administering a cell expressing the CAR molecule, as described herein, in combination with an agent which enhances the activity of a CAR-expressing cell, wherein the agent is a cytokine, e.g., IL-7, IL-15, IL-18, IL-21, or a combination thereof. The cytokine can be delivered in combination with, e.g., simultaneously or shortly after, administration of the CAR-expressing cell. Alternatively, the cytokine can be delivered after a prolonged period of time after administration of the CAR-expressing cell, e.g., after assessment of the subject's response to the CAR-expressing cell. In one embodiment the cytokine is administered to the subject simultaneously (e.g., administered on the same day) with or shortly after administration (e.g., administered 1 day, 2 days, 3 days, 4 days, 5 days, 6 days, or 7 days after administration) of the cell or population of cells of any of claims 61-80. In other embodiments, the cytokine is administered to the subject after a prolonged period of time (e.g., e.g., at least 2 weeks, 3 weeks, 4 weeks, 6 weeks, 8 weeks, 10 weeks, or more) after administration of the cell or population of cells of any of claims 61-80, or after assessment of the subject's response to the cell.

In other embodiments, the cells expressing a CAR molecule are administered in combination with an agent that ameliorates one or more side effects associated with administration of a cell expressing a CAR molecule. Side effects associated with the CAR-expressing cell can be chosen from cytokine release syndrome (CRS) or hemophagocytic lymphohistiocytosis (HLH).

In embodiments of any of the aforeseaid methods or uses, the cells expressing the CAR molecule are administered in combination with an agent that treats the disease associated with expression of the tumor antigen, e.g., any of the second or third therapies disclosed herein. Additional exemplary combinations include one or more of the following.

In another embodiment, the cell expressing the CAR molecule, e.g., as described herein, can be administered in combination with another agent, e.g., a kinase inhibitor and/or checkpoint inhibitor described herein. In an embodiment, a cell expressing the CAR molecule can further express another agent, e.g., an agent which enhances the activity of a CAR-expressing cell.

For example, in one embodiment, the agent that enhances the activity of a CAR-expressing cell can be an agent which inhibits an inhibitory molecule (e.g., an immune inhibitor molecule). Examples of inhibitory molecules include PD1, PD-L1, CTLA-4, TIM-3, CEACAM (e.g., CEACAM-1, CEACAM-3 and/or CEACAM-5), LAG-3, VISTA, BTLA, TIGIT, LAIR1, CD160, 2B4 and TGFR beta.

In one embodiment, the agent that inhibits the inhibitory molecule is an inhibitory nucleic acid is a dsRNA, a siRNA, or a shRNA. In embodiments, the inhibitory nucleic acid is linked to the nucleic acid that encodes a component of the CAR molecule. For example, the inhibitory molecule can be expressed on the CAR-expressing cell.

In another embodiment, the agent which inhibits an inhibitory molecule, e.g., is a molecule described herein, e.g., an agent that comprises a first polypeptide, e.g., an inhibitory molecule, associated with a second polypeptide that provides a positive signal to the cell, e.g., an intracellular signaling domain described herein. In one embodiment, the agent comprises a first polypeptide, e.g., of an inhibitory molecule such as PD-1, PD-L1, CTLA-4, TIM-3, CEACAM (e.g., CEACAM-1, CEACAM-3 and/or CEACAM-5), LAG-3, VISTA, BTLA, TIGIT, LAIR1, CD160, 2B4 or TGFR beta, or a fragment of any of these (e.g., at least a portion of the extracellular domain of any of these), and a second polypeptide which is an intracellular signaling domain described herein (e.g., comprising a costimulatory domain (e.g., 41BB, CD27 or CD28, e.g., as described herein) and/or a primary signaling domain (e.g., a CD3 zeta signaling domain described herein). In one embodiment, the agent comprises a first polypeptide of PD1 or a fragment thereof (e.g., at least a portion of the extracellular domain of PD1), and a second polypeptide of an intracellular signaling domain described herein (e.g., a CD28 signaling domain described herein and/or a CD3 zeta signaling domain described herein).

In one embodiment, the CAR-expressing immune effector cell of the present invention, e.g., T cell or NK cell, is administered to a subject that has received a previous stem cell transplantation, e.g., autologous stem cell transplantation.

In one embodiment, the CAR-expressing immune effector cell of the present invention, e.g., T cell or NK cells, is administered to a subject that has received a previous dose of melphalan.

In one embodiment, the cell expressing a CAR molecule, e.g., a CAR molecule described herein, is administered in combination with an agent that increases the efficacy of a cell expressing a CAR molecule, e.g., an agent described herein.

In one embodiment, the cells expressing a CAR molecule, e.g., a CAR molecule described herein, are administered in combination with a low, immune enhancing dose of an mTOR inhibitor. While not wishing to be bound by theory, it is believed that treatment with a low, immune enhancing, dose (e.g., a dose that is insufficient to completely suppress the immune system but sufficient to improve immune function) is accompanied by a decrease in PD-1 positive T cells or an increase in PD-1 negative cells. PD-1 positive T cells, but not PD-1 negative T cells, can be exhausted by engagement with cells which express a PD-1 ligand, e.g., PD-L1 or PD-L2.

In an embodiment this approach can be used to optimize the performance of CAR cells described herein in the subject. While not wishing to be bound by theory, it is believed that, in an embodiment, the performance of endogenous, non-modified immune effector cells, e.g., T cells or NK cells, is improved. While not wishing to be bound by theory, it is believed that, in an embodiment, the performance of a target antigen CAR-expressing cell is improved. In other embodiments, cells, e.g., T cells or NK cells, which have, or will be engineered to express a CAR, can be treated ex vivo by contact with an amount of an mTOR inhibitor that increases the number of PD1 negative immune effector cells, e.g., T cells or increases the ratio of PD1 negative immune effector cells, e.g., T cells/PD1 positive immune effector cells, e.g., T cells.

In an embodiment, administration of a low, immune enhancing, dose of an mTOR inhibitor, e.g., an allosteric inhibitor, e.g., RAD001, or a catalytic inhibitor, is initiated prior to administration of an CAR expressing cell described herein, e.g., T cells or NK cells. In an embodiment, the CAR cells are administered after a sufficient time, or sufficient dosing, of an mTOR inhibitor, such that the level of PD1 negative immune effector cells, e.g., T cells or NK cells, or the ratio of PD1 negative immune effector cells, e.g., T cells/PD1 positive immune effector cells, e.g., T cells, has been, at least transiently, increased.

In an embodiment, the cell, e.g., T cell or NK cell, to be engineered to express a CAR, is harvested after a sufficient time, or after sufficient dosing of the low, immune enhancing, dose of an mTOR inhibitor, such that the level of PD1 negative immune effector cells, e.g., T cells, or the ratio of PD1 negative immune effector cells, e.g., T cells/PD1 positive immune effector cells, e.g., T cells, in the subject or harvested from the subject has been, at least transiently, increased.

In one embodiment, the cell expressing a CAR molecule, e.g., a CAR molecule described herein, is administered in combination with an agent that ameliorates one or more side effect associated with administration of a cell expressing a CAR molecule, e.g., an agent described herein.

In one embodiment, the cell expressing a CAR molecule, e.g., a CAR molecule described herein, is administered in combination with an agent that treats the disease associated with a cancer associated antigen as described herein, e.g., an agent described herein.

In one embodiment, a cell expressing two or more CAR molecules, e.g., as described herein, is administered to a subject in need thereof to treat cancer. In one embodiment, a population of cells including a CAR expressing cell, e.g., as described herein, is administered to a subject in need thereof to treat cancer.

In one embodiment, the cell expressing a CAR molecule, e.g., a CAR molecule described herein, is administered at a dose and/or dosing schedule described herein.

In one embodiment, the CAR molecule is introduced into immune effector cells (e.g., T cells, NK cells), e.g., using in vitro transcription, and the subject (e.g., human) receives an initial administration of cells comprising a CAR molecule, and one or more subsequent administrations of cells comprising a CAR molecule, wherein the one or more subsequent administrations are administered less than 15 days, e.g., 14, 13, 12, 11, 10, 9, 8, 7, 6, 5, 4, 3, or 2 days after the previous administration. In one embodiment, more than one administration of cells comprising a CAR molecule are administered to the subject (e.g., human) per week, e.g., 2, 3, or 4 administrations of cells comprising a CAR molecule are administered per week. In one embodiment, the subject (e.g., human subject) receives more than one administration of cells comprising a CAR molecule per week (e.g., 2, 3 or 4 administrations per week) (also referred to herein as a cycle), followed by a week of no administration of cells comprising a CAR molecule, and then one or more additional administration of cells comprising a CAR molecule (e.g., more than one administration of the cells comprising a CAR molecule per week) is administered to the subject. In another embodiment, the subject (e.g., human subject) receives more than one cycle of cells comprising a CAR molecule, and the time between each cycle is less than 10, 9, 8, 7, 6, 5, 4, or 3 days. In one embodiment, the cells comprising a CAR molecule are administered every other day for 3 administrations per week. In one embodiment, the cells comprising a CAR molecule are administered for at least two, three, four, five, six, seven, eight or more weeks.

In one embodiment, the cells expressing a CAR molecule, e.g., a CAR molecule described herein, are administered as a first line treatment for the disease, e.g., the cancer, e.g., the cancer described herein. In another embodiment, the cells expressing a CAR molecule, e.g., a CAR molecule described herein, are administered as a second, third, fourth line treatment for the disease, e.g., the cancer, e.g., the cancer described herein.

In one embodiment, a population of cells described herein is administered.

In another aspect, the invention pertains to the isolated nucleic acid molecule encoding a CAR of the invention, the isolated polypeptide molecule of a CAR of the invention, the vector comprising a CAR of the invention, and the cell comprising a CAR of the invention for use as a medicament.

In another aspect, the invention pertains to a the isolated nucleic acid molecule encoding a CAR of the invention, the isolated polypeptide molecule of a CAR of the invention, the vector comprising a CAR of the invention, and the cell comprising a CAR of the invention for use in the treatment of a disease expressing a cancer associated antigen as described herein.

In another aspect, the invention pertains to a cell expressing a CAR molecule described herein for use as a medicament in combination with a cytokine, e.g., IL-7, IL-15 and/or IL-21 as described herein. In another aspect, the invention pertains to a cytokine described herein for use as a medicament in combination with a cell expressing a CAR molecule described herein.

In another aspect, the invention pertains to a cell expressing a CAR molecule described herein for use as a medicament in combination with a kinase inhibitor and/or a checkpoint inhibitor as described herein. In another aspect, the invention pertains to a kinase inhibitor and/or a checkpoint inhibitor described herein for use as a medicament in combination with a cell expressing a CAR molecule described herein.

In another aspect, the invention pertains to a cell expressing a CAR molecule described herein for use in combination with a cytokine, e.g., IL-7, IL-15 and/or IL-21 as described herein, in the treatment of a disease expressing a tumor antigen targeted by the CAR. In another aspect, the invention pertains to a cytokine described herein for use in combination with a cell expressing a CAR molecule described herein, in the treatment of a disease expressing a tumor antigen targeted by the CAR.

In another aspect, the invention pertains to a cell expressing a CAR molecule described herein for use in combination with a kinase inhibitor and/or a checkpoint inhibitor as described herein, in the treatment of a disease expressing a tumor antigen targeted by the CAR. In another aspect, the invention pertains to a kinase inhibitor and/or a checkpoint inhibitor described herein for use in combination with a cell expressing a CAR molecule described herein, in the treatment of a disease expressing a tumor antigen targeted by the CAR.

In another aspect, the present invention provides a method comprising administering a CAR molecule, e.g., a CAR molecule described herein, or a cell comprising a nucleic acid encoding a CAR molecule, e.g., a CAR molecule described herein. In one embodiment, the subject has a disorder described herein, e.g., the subject has cancer, e.g., the subject has a cancer and has tumor-supporting cells which express a tumor-supporting antigen described herein. In one embodiment, the subject is a human.

In another aspect, the invention pertains to a method of treating a subject having a disease associated with expression of a tumor-supporting antigen as described herein comprising administering to the subject an effective amount of a cell comprising a CAR molecule, e.g., a CAR molecule described herein.

In yet another aspect, the invention features a method of treating a subject having a disease associated with expression of a tumor-supporting antigen, comprising administering to the subject an effective amount of a cell, e.g., an immune effector cell (e.g., a population of immune effector cells) comprising a CAR molecule, wherein the CAR molecule comprises an antigen binding domain, a transmembrane domain, and an intracellular domain, said intracellular domain comprises a costimulatory domain and/or a primary signaling domain, wherein said antigen binding domain binds to the tumor-supporting antigen associated with the disease, e.g. a tumor-supporting antigen as described herein.

In another aspect, the invention features a composition comprising an immune effector cell (e.g., a population of immune effector cells) comprising a CAR molecule (e.g., a CAR molecule as described herein) for use in the treatment of a subject having a disease associated with expression of a tumor-supporting antigen, e.g., a disorder as described herein.

In any of the aforesaid methods or uses, the disease associated with expression of the tumor-supporting antigen is selected from the group consisting of a proliferative disease, a precancerous condition, a cancer, and a non-cancer related indication associated with expression of the tumor-supporting antigen. In an embodiment, the disease associated with a tumor-supporting antigen described herein is a solid tumor.

In one embodiment of the methods or uses described herein, the CAR molecule is administered in combination with another agent. In one embodiment, the agent can be a kinase inhibitor, e.g., a CDK4/6 inhibitor, a BTK inhibitor, an mTOR inhibitor, a MNK inhibitor, or a dual PI3K/mTOR inhibitor, and combinations thereof. In one embodiment, the kinase inhibitor is a CDK4 inhibitor, e.g., a CDK4 inhibitor described herein, e.g., a CD4/6 inhibitor, such as, e.g., 6-Acetyl-8-cyclopentyl-5-methyl-2-(5-piperazin-1-yl-pyridin-2-ylamino)-8H-pyrido[2,3-d]pyrimidin-7-one, hydrochloride (also referred to as palbociclib or PD0332991). In one embodiment, the kinase inhibitor is a BTK inhibitor, e.g., a BTK inhibitor described herein, such as, e.g., ibrutinib. In one embodiment, the kinase inhibitor is an mTOR inhibitor, e.g., an mTOR inhibitor described herein, such as, e.g., rapamycin, a rapamycin analog, OSI-027. The mTOR inhibitor can be, e.g., an mTORC1 inhibitor and/or an mTORC2 inhibitor, e.g., an mTORC1 inhibitor and/or mTORC2 inhibitor described herein. In one embodiment, the kinase inhibitor is a MNK inhibitor, e.g., a MNK inhibitor described herein, such as, e.g., 4-amino-5-(4-fluoroanilino)-pyrazolo[3,4-d] pyrimidine. The MNK inhibitor can be, e.g., a MNK1a, MNK1b, MNK2a and/or MNK2b inhibitor. The dual PI3K/mTOR inhibitor can be, e.g., PF-04695102.

In one embodiment of the methods or uses described herein, the kinase inhibitor is a CDK4 inhibitor selected from aloisine A; flavopiridol or HMR-1275, 2-(2-chlorophenyl)-5,7-dihydroxy-8-[(3S,4R)-3-hydroxy-1-methyl-4-piperidinyl]-4-chromenone; crizotinib (PF-02341066; 2-(2-Chlorophenyl)-5,7-dihydroxy-8-[(2R,3S)-2-(hydroxymethyl)-1-methyl-3-pyrrolidinyl]-4H-1-benzopyran-4-one, hydrochloride (P276-00); 1-methyl-5-[[2-[5-(trifluoromethyl)-1H-imidazol-2-yl]-4-pyridinyl]oxy]-N-[4-(trifluoromethyl)phenyl]-1H-benzimidazol-2-amine (RAF265); indisulam (E7070); roscovitine (CYC202); palbociclib (PD0332991); dinaciclib (SCH727965); N-[5-[[(5-tert-butyloxazol-2-yl)methyl]thio]thiazol-2-yl]piperidine-4-carboxamide (BMS 387032); 4-[[9-chloro-7-(2,6-difluorophenyl)-5H-pyrimido[5,4-d][2]benzazepin-2-yl]amino]-benzoic acid (MLN8054); 5-[3-(4,6-difluoro-1H-benzimidazol-2-yl)-1H-indazol-5-yl]-N-ethyl-4-methyl-3-pyridinemethanamine (AG-024322); 4-(2,6-dichlorobenzoylamino)-1H-pyrazole-3-carboxylic acid N-(piperidin-4-yl)amide (AT7519); 4-[2-methyl-1-(1-methylethyl)-1H-imidazol-5-yl]-N-[4-(methylsulfonyl)phenyl]-2-pyrimidinamine (AZD5438); and XL281 (BMS908662).

In one embodiment of the methods or uses described herein, the kinase inhibitor is a CDK4 inhibitor, e.g., palbociclib (PD0332991), and the palbociclib is administered at a dose of about 50 mg, 60 mg, 70 mg, 75 mg, 80 mg, 90 mg, 100 mg, 105 mg, 110 mg, 115 mg, 120 mg, 125 mg, 130 mg, 135 mg (e.g., 75 mg, 100 mg or 125 mg) daily for a period of time, e.g., daily for 14-21 days of a 28 day cycle, or daily for 7-12 days of a 21 day cycle. In one embodiment, 1, 2, 3, 4, 5, 6, 7, 8, 9, 10, 11, 12 or more cycles of palbociclib are administered.

In one embodiment of the methods or uses described herein, the kinase inhibitor is a BTK inhibitor selected from ibrutinib (PCI-32765); GDC-0834; RN-486; CGI-560; CGI-1764; HM-71224; CC-292; ONO-4059; CNX-774; and LFM-A13. In one embodiment, the BTK inhibitor does not reduce or inhibit the kinase activity of interleukin-2-inducible kinase (ITK), and is selected from GDC-0834; RN-486; CGI-560; CGI-1764; HM-71224; CC-292; ONO-4059; CNX-774; and LFM-A13.

In one embodiment of the methods or uses described herein, the kinase inhibitor is a BTK inhibitor, e.g., ibrutinib (PCI-32765), and the ibrutinib is administered at a dose of about 250 mg, 300 mg, 350 mg, 400 mg, 420 mg, 440 mg, 460 mg, 480 mg, 500 mg, 520 mg, 540 mg, 560 mg, 580 mg, 600 mg (e.g., 250 mg, 420 mg or 560 mg) daily for a period of time, e.g., daily for 21 day cycle, or daily for 28 day cycle. In one embodiment, 1, 2, 3, 4, 5, 6, 7, 8, 9, 10, 11, 12 or more cycles of ibrutinib are administered.

In one embodiment of the methods or uses described herein, the kinase inhibitor is a BTK inhibitor that does not inhibit the kinase activity of ITK, e.g., RN-486, and RN-486 is administered at a dose of about 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg (e.g., 150 mg, 200 mg or 250 mg) daily for a period of time, e.g., daily a 28 day cycle. In one embodiment, 1, 2, 3, 4, 5, 6, 7, or more cycles of RN-486 are administered.

In one embodiment of the methods or uses described herein, the kinase inhibitor is an mTOR inhibitor selected from temsirolimus; ridaforolimus (1R,2R,4S)-4-[(2R)-2 [(1R,9S,12S,15R,16E,18R,19R,21R, 23S,24E,26E,28Z, 30S,32S,35R)-1,18-dihydroxy-19,30-dimethoxy-15,17,21, 23,29,35-hexamethyl-2,3,10,14,20-pentaoxo-11,36-dioxa-4-azatricyclo[30.3.1.0$^{4,9}$] hexatriaconta-16,24,26,28-tetraen-12-yl]propyl]-2-methoxycyclohexyl di methylphosphinate, also known as AP23573 and MK8669; everolimus (RAD001); rapamycin (AY22989); simapimod; (5-{2,4-bis[(3S)-3-methylmorpholin-4-yl]pyrido[2,3-d]pyrimidin-7-yl}-2-methoxyphenyl)methanol (AZD8055); 2-amino-8-[trans-4-(2-hydroxyethoxy)cyclohexyl]-6-(6-methoxy-3-pyridinyl)-4-methyl-pyrido[2,3-d]pyrimidin-7 (8H)-one (PF04691502); and N$^2$-[1,4-dioxo-4-[[4-(4-oxo-8-phenyl-4H-1-benzopyran-2-yl)morpholinium-4-yl]methoxy]butyl]-L-arginylglycyl-L-α-aspartylL-serine-, inner salt (SF1126); and XL765.

In one embodiment of the methods or uses described herein, the kinase inhibitor is an mTOR inhibitor, e.g., rapamycin, and the rapamycin is administered at a dose of about 3 mg, 4 mg, 5 mg, 6 mg, 7 mg, 8 mg, 9 mg, 10 mg (e.g., 6 mg) daily for a period of time, e.g., daily for 21 day cycle, or daily for 28 day cycle. In one embodiment, 1, 2, 3, 4, 5, 6, 7, 8, 9, 10, 11, 12 or more cycles of rapamycin are administered. In one embodiment, the kinase inhibitor is an mTOR inhibitor, e.g., everolimus and the everolimus is administered at a dose of about 2 mg, 2.5 mg, 3 mg, 4 mg, 5 mg, 6 mg, 7 mg, 8 mg, 9 mg, 10 mg, 11 mg, 12 mg, 13 mg, 14 mg, 15 mg (e.g., 10 mg) daily for a period of time, e.g., daily for 28 day cycle. In one embodiment, 1, 2, 3, 4, 5, 6, 7, 8, 9, 10, 11, 12 or more cycles of everolimus are administered.

In one embodiment of the methods or uses described herein, the kinase inhibitor is an MNK inhibitor selected from CGP052088; 4-amino-3-(p-fluorophenylamino)-pyrazolo[3,4-d] pyrimidine (CGP57380); cercosporamide; ETC-1780445-2; and 4-amino-5-(4-fluoroanilino)-pyrazolo[3,4-d] pyrimidine.

In one embodiment of the methods or uses described herein, the kinase inhibitor is a dual phosphatidylinositol 3-kinase (PI3K) and mTOR inhibitor selected from 2-Amino-8-[trans-4-(2-hydroxyethoxy)cyclohexyl]-6-(6-methoxy-3-pyridinyl)-4-methyl-pyrido[2,3-d]pyrimidin-7 (8H)-one (PF-04691502); N-[4-[[4-(Dimethylamino)-1-piperidinyl]carbonyl]phenyl]-N-[4-(4,6-di-4-morpholinyl-1,3,5-triazin-2-yl)phenyl]urea (PF-05212384, PKI-587); 2-Methyl-2-{4-[3-methyl-2-oxo-8-(quinolin-3-yl)-2,3-dihydro-1H-imidazo[4,5-c]quinolin-1-yl] phenyl}propanenitrile (BEZ-235); apitolisib (GDC-0980, RG7422); 2,4-Difluoro-N-{2-(methyloxy)-5-[4-(4-pyridazinyl)-6-quinolinyl]-3-pyridinyl}benzenesulfonamide (GSK2126458); 8-(6-methoxypyridin-3-yl)-3-methyl-1-(4-(piperazin-1-yl)-3-(trifluoromethyl)phenyl)-1H-imidazo[4,5-c]quinolin-2(3H)-one Maleic acid (NVP-BGT226); 3-[4-(4-Morpholinylpyrido[3',2':4,5]furo[3,2-d]pyrimidin-2-yl] phenol (PI-103); 5-(9-isopropyl-8-methyl-2-morpholino-9H-purin-6-yl)pyrimidin-2-amine (VS-5584, SB2343); and N-[2-[(3,5-Dimethoxyphenyl)amino]quinoxalin-3-yl]-4-[(4-methyl-3-methoxyphenyl)carbonyl]aminophenylsulfonamide (XL765).

In one embodiment of the methods or uses described herein, a CAR expressing immune effector cell described herein is administered to a subject in combination with a protein tyrosine phosphatase inhibitor, e.g., a protein tyrosine phosphatase inhibitor described herein. In one embodiment, the protein tyrosine phosphatase inhibitor is an SHP-1 inhibitor, e.g., an SHP-1 inhibitor described herein, such as, e.g., sodium stibogluconate. In one embodiment, the protein tyrosine phosphatase inhibitor is an SHP-2 inhibitor.

In one embodiment of the methods or uses described herein, the CAR molecule is administered in combination with another agent, and the agent is a cytokine. The cytokine can be, e.g., IL-7, IL-15, IL-21, or a combination thereof. In another embodiment, the CAR molecule is administered in combination with a checkpoint inhibitor, e.g., a checkpoint inhibitor described herein. For example, in one embodiment, the check point inhibitor inhibits an inhibitory molecule selected from PD-1, PD-L1, CTLA-4, TIM-3, CEACAM (e.g., CEACAM-1, CEACAM-3 and/or CEACAM-5), LAG-3, VISTA, BTLA, TIGIT, LAIR1, CD160, 2B4 and TGFR beta.

In one aspect, the CAR of the invention can be used to eradicate a normal cell that express a tumor antigen as described herein, thereby applicable for use as a cellular conditioning therapy prior to cell transplantation. In one aspect, the normal cell that expresses a tumor antigen as described herein is a normal stem cell and the cell transplantation is a stem cell transplantation.

Therapeutic Application

In another aspect, a method of treating a subject, e.g., reducing or ameliorating, a hyperproliferative condition or disorder (e.g., a cancer), e.g., solid tumor, a soft tissue tumor, or a metastatic lesion, in a subject is provided. As used herein, the term "cancer" is meant to include all types of cancerous growths or oncogenic processes, metastatic tissues or malignantly transformed cells, tissues, or organs, irrespective of histopathologic type or stage of invasiveness. Examples of solid tumors include malignancies, e.g., sarcomas, adenocarcinomas, and carcinomas, of the various organ systems, such as those affecting liver, lung, breast, lymphoid, gastrointestinal (e.g., colon), genitourinary tract (e.g., renal, urothelial cells), prostate and pharynx. Adenocarcinomas include malignancies such as most colon cancers, rectal cancer, renal-cell carcinoma, liver cancer, non-small cell carcinoma of the lung, cancer of the small intestine and cancer of the esophagus. In one embodiment, the cancer is a melanoma, e.g., an advanced stage melanoma. Metastatic lesions of the aforementioned cancers can also be treated or prevented using the methods and compositions of the invention. Examples of other cancers that can be treated include bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin Disease, non-Hodgkin lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. Treatment of metastatic cancers, e.g., metastatic cancers that express PD-L1 (Iwai et al. (2005) Int. Immunol. 17:133-144) can be effected using the antibody molecules described herein.

Exemplary cancers whose growth can be inhibited include cancers typically responsive to immunotherapy. Non-limiting examples of cancers for treatment include melanoma (e.g., metastatic malignant melanoma), renal cancer (e.g. clear cell carcinoma), prostate cancer (e.g. hormone refractory prostate adenocarcinoma), breast cancer, colon cancer and lung cancer (e.g. non-small cell lung cancer). Additionally, refractory or recurrent malignancies can be treated using the molecules described herein.

In one aspect, the invention pertains to a vector comprising a CAR operably linked to promoter for expression in mammalian immune effector cells (e.g., T cells, NK cells). In one aspect, the invention provides a recombinant immune effector cell expressing a CAR of the present invention for use in treating cancer expressing a cancer associate antigen as described herein. In one aspect, CAR-expressing cells of the invention is capable of contacting a tumor cell with at least one cancer associated antigen expressed on its surface such that the CAR-expressing cell targets the cancer cell and growth of the cancer is inhibited.

In one aspect, the invention pertains to a method of inhibiting growth of a cancer, comprising contacting the cancer cell with a CAR-expressing cell of the present invention such that the CART is activated in response to the antigen and targets the cancer cell, wherein the growth of the tumor is inhibited.

In one aspect, the invention pertains to a method of treating cancer in a subject. The method comprises administering to the subject CAR-expressing cell of the present invention such that the cancer is treated in the subject. In one aspect, the cancer associated with expression of a cancer associate antigen as described herein is a hematological cancer. In one aspect, the hematological cancer is a leukemia or a lymphoma. In one aspect, a cancer associated with expression of a cancer associate antigen as described herein includes cancers and malignancies including, but not limited to, e.g., one or more acute leukemias including but not limited to, e.g., B-cell acute Lymphoid Leukemia ("BALL"), T-cell acute Lymphoid Leukemia ("TALL"), acute lymphoid leukemia (ALL); one or more chronic leukemias including but not limited to, e.g., chronic myelogenous leukemia (CML), Chronic Lymphoid Leukemia (CLL). Additional cancers or hematologic conditions associated with expression of a cancer associate antigen as described herein include, but are not limited to, e.g., B cell prolymphocytic leukemia, blastic plasmacytoid dendritic cell neoplasm, Burkitt's lymphoma, diffuse large B cell lymphoma, Follicular lymphoma, Hairy cell leukemia, small cell- or a large cell-follicular lymphoma, malignant lymphoproliferative conditions, MALT lymphoma, mantle cell lymphoma, Marginal zone lymphoma, multiple myeloma, myelodysplasia and myelodysplastic syndrome, non-Hodgkin lymphoma, plasmablastic lymphoma, plasmacytoid dendritic cell neoplasm, Waldenstrom macroglobulinemia, and "preleukemia" which are a diverse collection of hematological conditions united by ineffective production (or dysplasia) of myeloid blood cells, and the like. Further a disease associated with a cancer associate antigen as described herein expression include, but not limited to, e.g., atypical and/or non-classical cancers, malignancies, precancerous conditions or proliferative diseases associated with expression of a cancer associate antigen as described herein.

In some embodiments, a cancer that can be treated with CAR-expressing cell of the present invention is multiple myeloma. Generally, myeloma cells are thought to be negative for a cancer associate antigen as described herein expression by flow cytometry. Thus, in some embodiments, a CD19 CAR, e.g., as described herein, may be used to target myeloma cells. In some embodiments, cars of the present invention therapy can be used in combination with one or more additional therapies, e.g., lenalidomide treatment.

The invention includes a type of cellular therapy where immune effector cells (e.g., T cells, NK cells) are genetically modified to express a chimeric antigen receptor (CAR) and the CAR-expressing T cell or NK cell is infused to a recipient in need thereof. The infused cell is able to kill tumor cells in the recipient. Unlike antibody therapies, CAR-modified immune effector cells (e.g., T cells, NK cells) are able to replicate in vivo resulting in long-term persistence that can lead to sustained tumor control. In various aspects, the immune effector cells (e.g., T cells, NK cells) administered to the patient, or their progeny, persist in the patient for at least four months, five months, six months, seven months, eight months, nine months, ten months, eleven months, twelve months, thirteen months, fourteen month, fifteen months, sixteen months, seventeen months, eighteen months, nineteen months, twenty months, twenty-one months, twenty-two months, twenty-three months, two years, three years, four years, or five years after administration of the T cell or NK cell to the patient.

The invention also includes a type of cellular therapy where immune effector cells (e.g., T cells, NK cells) are modified, e.g., by in vitro transcribed RNA, to transiently express a chimeric antigen receptor (CAR) and the CAR T cell or NK cell is infused to a recipient in need thereof. The infused cell is able to kill tumor cells in the recipient. Thus, in various aspects, the immune effector cells (e.g., T cells, NK cells) administered to the patient, is present for less than one month, e.g., three weeks, two weeks, one week, after administration of the T cell or NK cell to the patient.

Without wishing to be bound by any particular theory, the anti-tumor immunity response elicited by the CAR-modified immune effector cells (e.g., T cells, NK cells) may be an active or a passive immune response, or alternatively may be due to a direct vs indirect immune response. In one aspect, the CAR transduced immune effector cells (e.g., T cells, NK cells) exhibit specific proinflammatory cytokine secretion and potent cytolytic activity in response to human cancer cells expressing the a cancer associate antigen as described herein, resist soluble a cancer associate antigen as described herein inhibition, mediate bystander killing and mediate regression of an established human tumor. For example, antigen-less tumor cells within a heterogeneous field of a cancer associate antigen as described herein-expressing tumor may be susceptible to indirect destruction by a cancer associate antigen as described herein-redirected immune effector cells (e.g., T cells, NK cells) that have previously reacted against adjacent antigen-positive cancer cells.

In one aspect, the fully-human CAR-modified immune effector cells (e.g., T cells, NK cells) of the invention may be a type of vaccine for ex vivo immunization and/or in vivo therapy in a mammal. In one aspect, the mammal is a human.

With respect to ex vivo immunization, at least one of the following occurs in vitro prior to administering the cell into a mammal: i) expansion of the cells, ii) introducing a nucleic acid encoding a CAR to the cells or iii) cryopreservation of the cells.

Ex vivo procedures are well known in the art and are discussed more fully below. Briefly, cells are isolated from a mammal (e.g., a human) and genetically modified (i.e., transduced or transfected in vitro) with a vector expressing a CAR disclosed herein. The CAR-modified cell can be administered to a mammalian recipient to provide a therapeutic benefit. The mammalian recipient may be a human and the CAR-modified cell can be autologous with respect to the recipient. Alternatively, the cells can be allogeneic, syngeneic or xenogeneic with respect to the recipient.

The procedure for ex vivo expansion of hematopoietic stem and progenitor cells is described in U.S. Pat. No. 5,199,942, incorporated herein by reference, can be applied to the cells of the present invention. Other suitable methods are known in the art, therefore the present invention is not limited to any particular method of ex vivo expansion of the cells. Briefly, ex vivo culture and expansion of immune effector cells (e.g., T cells, NK cells) comprises: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells.

In addition to using a cell-based vaccine in terms of ex vivo immunization, the present invention also provides compositions and methods for in vivo immunization to elicit an immune response directed against an antigen in a patient.

Generally, the cells activated and expanded as described herein may be utilized in the treatment and prevention of diseases that arise in individuals who are immunocompromised. In particular, the CAR-modified immune effector cells (e.g., T cells, NK cells) of the invention are used in the treatment of diseases, disorders and conditions associated with expression of a cancer associate antigen as described herein. In certain aspects, the cells of the invention are used in the treatment of patients at risk for developing diseases, disorders and conditions associated with expression of a cancer associate antigen as described herein. Thus, the present invention provides methods for the treatment or prevention of diseases, disorders and conditions associated with expression of a cancer associate antigen as described herein comprising administering to a subject in need thereof, a therapeutically effective amount of the CAR-modified immune effector cells (e.g., T cells, NK cells) of the invention.

In one aspect the CAR-expressing cells of the inventions may be used to treat a proliferative disease such as a cancer or malignancy or is a precancerous condition such as a myelodysplasia, a myelodysplastic syndrome or a preleukemia. Further a disease associated with a cancer associate antigen as described herein expression include, but not limited to, e.g., atypical and/or non-classical cancers, malignancies, precancerous conditions or proliferative diseases expressing a cancer associated antigen as described herein. Non-cancer related indications associated with expression of a cancer associate antigen as described herein include, but are not limited to, e.g., autoimmune disease, (e.g., lupus), inflammatory disorders (allergy and asthma) and transplantation.

The CAR-modified immune effector cells (e.g., T cells, NK cells) of the present invention may be administered either alone, or as a pharmaceutical composition in combination with diluents and/or with other components such as IL-2 or other cytokines or cell populations.

Hematologic Cancer

Hematological cancer conditions are the types of cancer such as leukemia, lymphoma, and malignant lymphoproliferative conditions that affect blood, bone marrow and the lymphatic system.

Leukemia can be classified as acute leukemia and chronic leukemia. Acute leukemia can be further classified as acute myelogenous leukemia (AML) and acute lymphoid leukemia (ALL). Chronic leukemia includes chronic myelogenous leukemia (CML) and chronic lymphoid leukemia (CLL). Other related conditions include myelodysplastic syndromes (MDS, formerly known as "preleukemia") which are a diverse collection of hematological conditions united by ineffective production (or dysplasia) of myeloid blood cells and risk of transformation to AML.

Lymphoma is a group of blood cell tumors that develop from lymphocytes. Exemplary lymphomas include non-Hodgkin lymphoma and Hodgkin lymphoma.

The present invention also provides methods for inhibiting the proliferation or reducing a cancer associated antigen as described herein-expressing cell population, the methods comprising contacting a population of cells comprising a cancer associated antigen as described herein-expressing cell with a CAR-expressing T cell or NK cell of the invention that binds to the a cancer associate antigen as described herein-expressing cell. In a specific aspect, the present invention provides methods for inhibiting the proliferation or reducing the population of cancer cells expressing a cancer associated antigen as described herein, the methods comprising contacting a cancer associate antigen as described herein-expressing cancer cell population with a CAR-expressing T cell or NK cell of the invention that binds to a cancer associated antigen as described herein-expressing cell. In one aspect, the present invention provides methods for inhibiting the proliferation or reducing the population of cancer cells expressing a cancer associated antigen as described herein, the methods comprising contacting a cancer associated antigen as described herein-expressing cancer cell population with a CAR-expressing T cell or NK cell of the invention that binds to a cancer associated antigen as described herein-expressing cell. In certain aspects, a CAR-expressing T cell or NK cell of the invention reduces the quantity, number, amount or percentage of cells and/or cancer cells by at least 25%, at least 30%, at least 40%, at least 50%, at least 65%, at least 75%, at least 85%, at least 95%, or at least 99% in a subject with or animal model for myeloid leukemia or another cancer associated with a cancer associated antigen as described herein-expressing cells relative to a negative control. In one aspect, the subject is a human.

The present invention also provides methods for preventing, treating and/or managing a disease associated with a cancer associated antigen as described herein-expressing cells (e.g., a hematologic cancer or atypical cancer expressing a cancer associated antigen as described herein), the methods comprising administering to a subject in need a CAR T cell or NK cell of the invention that binds to a cancer associated antigen as described herein-expressing cell. In one aspect, the subject is a human. Non-limiting examples of disorders associated with a cancer associated antigen as described herein-expressing cells include autoimmune disorders (such as lupus), inflammatory disorders (such as allergies and asthma) and cancers (such as hematological cancers or atypical cancers expressing a cancer associated antigen as described herein).

The present invention also provides methods for preventing, treating and/or managing a disease associated with a cancer associated antigen as described herein-expressing cells, the methods comprising administering to a subject in need a CAR T cell or NK cell of the invention that binds to a cancer associated antigen as described herein-expressing cell. In one aspect, the subject is a human.

The present invention provides methods for preventing relapse of cancer associated with a cancer associated antigen as described herein-expressing cells, the methods comprising administering to a subject in need thereof a CAR T cell or NK cell of the invention that binds to a cancer associated antigen as described herein-expressing cell. In one aspect, the methods comprise administering to the subject in need thereof an effective amount of a CAR-expressing T cell or NK cell described herein that binds to a cancer associated antigen as described herein-expressing cell in combination with an effective amount of another therapy.

Pharmaceutical Compositions and Treatments

Pharmaceutical compositions of the present invention may comprise a CAR-expressing cell, e.g., a plurality of CAR-expressing cells, as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are in one aspect formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

In one embodiment, the pharmaceutical composition is substantially free of, e.g., there are no detectable levels of a contaminant, e.g., selected from the group consisting of endotoxin, mycoplasma, replication competent lentivirus (RCL), p24, VSV-G nucleic acid, HIV gag, residual anti-CD3/anti-CD28 coated beads, mouse antibodies, pooled human serum, bovine serum albumin, bovine serum, culture media components, vector packaging cell or plasmid components, a bacterium and a fungus. In one embodiment, the bacterium is at least one selected from the group consisting of *Alcaligenes faecalis, Candida albicans, Escherichia coli, Haemophilus influenza, Neisseria meningitides, Pseudomonas aeruginosa, Staphylococcus aureus, Streptococcus pneumonia*, and *Streptococcus pyogenes* group A.

When "an immunologically effective amount," "an anti-tumor effective amount," "a tumor-inhibiting effective amount," or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the immune effector cells (e.g., T cells, NK cells) described herein may be administered at a dosage of $10^4$ to $10^9$ cells/kg body weight, in some instances $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988).

In certain aspects, it may be desired to administer activated immune effector cells (e.g., T cells, NK cells) to a subject and then subsequently redraw blood (or have an apheresis performed), activate immune effector cells (e.g., T cells, NK cells) therefrom according to the present invention, and reinfuse the patient with these activated and expanded immune effector cells (e.g., T cells, NK cells). This process can be carried out multiple times every few weeks. In certain aspects, immune effector cells (e.g., T cells, NK cells) can be activated from blood draws of from 10 cc to 400 cc. In certain aspects, immune effector cells (e.g., T cells, NK cells) are activated from blood draws of 20 cc, 30 cc, 40 cc, 50 cc, 60 cc, 70 cc, 80 cc, 90 cc, or 100 cc.

The administration of the subject compositions may be carried out in any convenient manner, including by aerosol inhalation, injection, ingestion, transfusion, implantation or transplantation. The compositions described herein may be administered to a patient trans arterially, subcutaneously, intradermally, intratumorally, intranodally, intramedullary, intramuscularly, by intravenous (i.v.) injection, or intraperitoneally. In one aspect, the T cell compositions of the present invention are administered to a patient by intradermal or subcutaneous injection. In one aspect, the T cell compositions of the present invention are administered by i.v. injection. The compositions of immune effector cells (e.g., T cells, NK cells) may be injected directly into a tumor, lymph node, or site of infection.

In a particular exemplary aspect, subjects may undergo leukapheresis, wherein leukocytes are collected, enriched, or depleted ex vivo to select and/or isolate the cells of interest, e.g., T cells. These T cell isolates may be expanded by methods known in the art and treated such that one or more CAR constructs of the invention may be introduced, thereby creating a CAR T cell of the invention. Subjects in need thereof may subsequently undergo standard treatment with high dose chemotherapy followed by peripheral blood stem cell transplantation. In certain aspects, following or concurrent with the transplant, subjects receive an infusion of the expanded CAR T cells of the present invention. In an additional aspect, expanded cells are administered before or following surgery.

The dosage of the above treatments to be administered to a patient will vary with the precise nature of the condition being treated and the recipient of the treatment. The scaling of dosages for human administration can be performed according to art-accepted practices. The dose for CAM-PATH, for example, will generally be in the range 1 to about 100 mg for an adult patient, usually administered daily for a period between 1 and 30 days. The preferred daily dose is 1 to 10 mg per day although in some instances larger doses of up to 40 mg per day may be used (described in U.S. Pat. No. 6,120,766).

In one embodiment, the CAR is introduced into immune effector cells (e.g., T cells, NK cells), e.g., using in vitro transcription, and the subject (e.g., human) receives an initial administration of CAR immune effector cells (e.g., T cells, NK cells) of the invention, and one or more subsequent administrations of the CAR immune effector cells (e.g., T cells, NK cells) of the invention, wherein the one or more subsequent administrations are administered less than 15 days, e.g., 14, 13, 12, 11, 10, 9, 8, 7, 6, 5, 4, 3, or 2 days after the previous administration. In one embodiment, more than one administration of the CAR immune effector cells (e.g., T cells, NK cells) of the invention are administered to the subject (e.g., human) per week, e.g., 2, 3, or 4 administrations of the CAR immune effector cells (e.g., T cells, NK cells) of the invention are administered per week. In one embodiment, the subject (e.g., human subject) receives more than one administration of the CAR immune effector cells (e.g., T cells, NK cells) per week (e.g., 2, 3 or 4 administrations per week) (also referred to herein as a cycle), followed by a week of no CAR immune effector cells (e.g., T cells, NK cells) administrations, and then one or more additional administration of the CAR immune effector cells (e.g., T cells, NK cells) (e.g., more than one administration of the CAR immune effector cells (e.g., T cells, NK cells) per week) is administered to the subject. In another embodiment, the subject (e.g., human subject) receives more than one cycle of CAR immune effector cells (e.g., T cells, NK cells), and the time between each cycle is less than 10, 9, 8, 7, 6, 5, 4, or 3 days. In one embodiment, the CAR immune effector cells (e.g., T cells, NK cells) are administered every other day for 3 administrations per week. In one embodiment, the CAR immune effector cells (e.g., T cells, NK cells) of the invention are administered for at least two, three, four, five, six, seven, eight or more weeks.

In one aspect, CAR-expressing cells of the present inventions are generated using lentiviral viral vectors, such as lentivirus. Cells, e.g., CARTs, generated that way will have stable CAR expression.

In one aspect, CAR-expressing cells, e.g., CARTs, are generated using a viral vector such as a gammaretroviral vector, e.g., a gammaretroviral vector described herein. CARTs generated using these vectors can have stable CAR expression.

In one aspect, CARTs transiently express CAR vectors for 4, 5, 6, 7, 8, 9, 10, 11, 12, 13, 14, 15 days after transduction. Transient expression of CARs can be effected by RNA CAR vector delivery. In one aspect, the CAR RNA is transduced into the T cell by electroporation.

A potential issue that can arise in patients being treated using transiently expressing CAR immune effector cells (e.g., T cells, NK cells) (particularly with murine scFv bearing CARTs) is anaphylaxis after multiple treatments.

Without being bound by this theory, it is believed that such an anaphylactic response might be caused by a patient developing humoral anti-CAR response, i.e., anti-CAR antibodies having an anti-IgE isotype. It is thought that a patient's antibody producing cells undergo a class switch from IgG isotype (that does not cause anaphylaxis) to IgE isotype when there is a ten to fourteen day break in exposure to antigen.

If a patient is at high risk of generating an anti-CAR antibody response during the course of transient CAR therapy (such as those generated by RNA transductions), CART infusion breaks should not last more than ten to fourteen days.

Methods of Making CAR-Expressing Cells

In another aspect, the invention pertains to a method of making a cell (e.g., an immune effector cell or population thereof) comprising introducing into (e.g., transducing) a cell, e.g., a T cell or a NK cell described herein, with a vector of comprising a nucleic acid encoding a CAR, e.g., a CAR described herein; or a nucleic acid encoding a CAR molecule e.g., a CAR described herein.

The cell in the methods is an immune effector cell (e.g., aT cell or a NK cell, or a combination thereof). In some embodiments, the cell in the methods is diaglycerol kinase (DGK) and/or Ikaros deficient.

In some embodiment, the introducing the nucleic acid molecule encoding a CAR comprises transducing a vector comprising the nucleic acid molecule encoding a CAR, or transfecting the nucleic acid molecule encoding a CAR, wherein the nucleic acid molecule is an in vitro transcribed RNA.

In some embodiments, the method further comprises:
  a. providing a population of immune effector cells (e.g., T cells or NK cells); and
  b. removing T regulatory cells from the population, thereby providing a population of T regulatory-depleted cells;

wherein steps a) and b) are performed prior to introducing the nucleic acid encoding the CAR to the population.

In embodiments of the methods, the T regulatory cells comprise CD25+ T cells, and are removed from the cell population using an anti-CD25 antibody, or fragment thereof. The anti-CD25 antibody, or fragment thereof, can be conjugated to a substrate, e.g., a bead.

In other embodiments, the population of T regulatory-depleted cells provided from step (b) contains less than 30%, 25%, 20%, 15%, 10%, 5%, 4%, 3%, 2%, 1% of CD25+ cells.

In yet other embodiments, the method further comprises removing cells from the population which express a tumor antigen that does not comprise CD25 to provide a population of T regulatory-depleted and tumor antigen depleted cells prior to introducing the nucleic acid encoding a CAR to the population. The tumor antigen can be selected from CD19, CD30, CD38, CD123, CD20, CD14 or CD11b, or a combination thereof.

In other embodiments, the method further comprises removing cells from the population which express a checkpoint inhibitor, to provide a population of T regulatory-depleted and inhibitory molecule depleted cells prior to introducing the nucleic acid encoding a CAR to the population. The checkpoint inhibitor can be chosen from PD-1, LAG-3, TIM3, B7-H1, CD160, P1H, 2B4, CEACAM (e.g., CEACAM-1, CEACAM-3, and/or CEACAM-5), TIGIT, CTLA-4, BTLA, and LAIR1.

Further embodiments disclosed herein encompass providing a population of immune effector cells. The population of immune effector cells provided can be selected based upon the expression of one or more of CD3, CD28, CD4, CD8, CD45RA, and/or CD45RO. In certain embodiments, the population of immune effector cells provided are CD3+ and/or CD28+.

In certain embodiments of the method, the method further comprises expanding the population of cells after the nucleic acid molecule encoding a CAR has been introduced.

In embodiments, the population of cells is expanded for a period of 8 days or less.

In certain embodiments, the population of cells is expanded in culture for 5 days, and the resulting cells are more potent than the same cells expanded in culture for 9 days under the same culture conditions.

In other embodiments, the population of cells is expanded in culture for 5 days show at least a one, two, three or four fold increase in cell doublings upon antigen stimulation as compared to the same cells expanded in culture for 9 days under the same culture conditions.

In yet other embodiments, the population of cells is expanded in culture for 5 days, and the resulting cells exhibit higher proinflammatory IFN-γ and/or GM-CSF levels, as compared to the same cells expanded in culture for 9 days under the same culture conditions.

In other embodiments, the population of cells is expanded by culturing the cells in the presence of an agent that stimulates a CD3/TCR complex associated signal and/or a ligand that stimulates a costimulatory molecule on the surface of the cells. The agent can be a bead conjugated with anti-CD3 antibody, or a fragment thereof, and/or anti-CD28 antibody, or a fragment thereof.

In other embodiments, the population of cells is expanded in an appropriate media that includes one or more interleukin that result in at least a 200-fold, 250-fold, 300-fold, or 350-fold increase in cells over a 14 day expansion period, as measured by flow cytometry.

In other embodiments, the population of cells is expanded in the presence IL-15 and/or IL-7. In certain embodiments, the method further includes cryopreserving the population of the cells after the appropriate expansion period.

In yet other embodiments, the method of making disclosed herein further comprises contacting the population of immune effector cells with a nucleic acid encoding a telomerase subunit, e.g., hTERT. The the nucleic acid encoding the telomerase subunit can be DNA.

The present invention also provides a method of generating a population of RNA-engineered cells, e.g., cells described herein, e.g., immune effector cells (e.g., T cells, NK cells), transiently expressing exogenous RNA. The method comprises introducing an in vitro transcribed RNA or synthetic RNA into a cell, where the RNA comprises a nucleic acid encoding a CAR molecule described herein.

In another aspect, the invention pertains to a method of providing an anti-tumor immunity in a subject comprising administering to the subject an effective amount of a cell comprising a CAR molecule, e.g., a cell expressing a CAR molecule described herein. In one embodiment, the cell is an autologous T cell or NK cell. In one embodiment, the cell is an allogeneic T cell or NK cell. In one embodiment, the subject is a human.

In one aspect, the invention includes a population of autologous cells that are transfected or transduced with a vector comprising a nucleic acid molecule encoding a CAR molecule, e.g., as described herein. In one embodiment, the vector is a retroviral vector. In one embodiment, the vector is a self-inactivating lentiviral vector as described elsewhere herein. In one embodiment, the vector is delivered (e.g., by transfecting or electroporating) to a cell, e.g., a T cell or a NK cell, wherein the vector comprises a nucleic acid molecule encoding a CAR of the present invention as described herein, which is transcribed as an mRNA molecule, and the CARs of the present invention is translated from the RNA molecule and expressed on the surface of the cell.

In another aspect, the present invention provides a population of CAR-expressing cells, e.g., CAR-expressing immune effector cells (e.g., T cells or NK cells). In some embodiments, the population of CAR-expressing cells comprises a mixture of cells expressing different CARs. For example, in one embodiment, the population of CAR-expressing immune effector cells (e.g., T cells or NK cells) can include a first cell expressing a CAR having an antigen binding domain that binds to a first tumor antigen as described herein, and a second cell expressing a CAR having a different antigen binding domain that binds to a second tumor antigen as described herein. As another example, the population of CAR-expressing cells can include a first cell expressing a CAR that includes an antigen binding domain that binds to a tumor antigen as described herein, and a second cell expressing a CAR that includes an antigen binding domain to a target other than a tumor antigen as described herein. In one embodiment, the population of CAR-expressing cells includes, e.g., a first cell expressing a CAR that includes a primary intracellular signaling domain, and a second cell expressing a CAR that includes a secondary signaling domain, e.g., a costimulatory signaling domain.

In another aspect, the present invention provides a population of cells wherein at least one cell in the population expresses a CAR having an antigen binding domain that binds to a tumor antigen as described herein, and a second cell expressing another agent, e.g., an agent which enhances the activity of a CAR-expressing cell. For example, in one embodiment, the agent can be an agent which inhibits an inhibitory molecule. Examples of inhibitory molecules include PD-1, PD-L1, CTLA-4, TIM-3, CEACAM (e.g., CEACAM-1, CEACAM-3 and/or CEACAM-5), LAG-3, VISTA, BTLA, TIGIT, LAIR1, CD160, 2B4 and TGFR beta. In one embodiment, the agent which inhibits an inhibitory molecule, e.g., is a molecule described herein, e.g., an agent that comprises a first polypeptide, e.g., an inhibitory molecule, associated with a second polypeptide that provides a positive signal to the cell, e.g., an intracellular signaling domain described herein. In one embodiment, the agent comprises a first polypeptide, e.g., of an inhibitory molecule such as PD-1, LAG-3, CTLA-4, CD160, BTLA, LAIR1, TIM-3, CEACAM (e.g., CEACAM-1, CEACAM-3 and/or CEACAM-5), 2B4 and TIGIT, or a fragment of any of these, and a second polypeptide which is an intracellular signaling domain described herein (e.g., comprising a costimulatory domain (e.g., 41BB, CD27 or CD28, e.g., as described herein) and/or a primary signaling domain (e.g., a CD3 zeta signaling domain described herein). In one embodiment, the agent comprises a first polypeptide of PD-1 or a fragment thereof, and a second polypeptide of an intracellular signaling domain described herein (e.g., a CD28, CD27, OX40 or 4-IBB signaling domain described herein and/or a CD3 zeta signaling domain described herein).

In one embodiment, the nucleic acid molecule encoding a CAR of the present invention molecule, e.g., as described herein, is expressed as an mRNA molecule. In one embodiment, the genetically modified CAR of the present invention-expressing cells, e.g., immune effector cells (e.g., T cells, NK cells), can be generated by transfecting or electroporating an RNA molecule encoding the desired CARs (e.g., without a vector sequence) into the cell. In one embodiment, a CAR of the present invention molecule is translated from the RNA molecule once it is incorporated and expressed on the surface of the recombinant cell.

A method for generating mRNA for use in transfection involves in vitro transcription (IVT) of a template with specially designed primers, followed by polyA addition, to produce a construct containing 3' and 5' untranslated sequence ("UTR") (e.g., a 3' and/or 5' UTR described herein), a 5' cap (e.g., a 5' cap described herein) and/or Internal Ribosome Entry Site (IRES) (e.g., an IRES described herein), the nucleic acid to be expressed, and a polyA tail, typically 50-2000 bases in length. RNA so produced can efficiently transfect different kinds of cells. In one embodiment, the template includes sequences for the CAR. In an embodiment, an RNA CAR vector is transduced into a cell, e.g., a T cell or a NK cell, by electroporation.

Sequences of some examples of various components of CARs of the instant invention is listed in Table 1, where aa stands for amino acids, and na stands for nucleic acids that encode the corresponding peptide.

TABLE 1

Sequences of various components of CAR (aa-amino acids, na-nucleic acids that encodes the corresponding protein)

| SEQ ID NO | description | Sequence | Corresp. To huCD19 |
|---|---|---|---|
| 1 | EF-1 promoter | CGTGAGGCTCCGGTGCCCGTCAGTGGGCAGAGCGCACATCGCCCACAGTCCCCGAGAA GTTGGGGGGAGGGGTCGGCAATTGAACCGGTGCCTAGAGAAGGTGGCGCGGGGTAAAC TGGGAAAGTGATGTCGTGTACTGGCTCCGCCTTTTTCCCGAGGGTGGGGGAGAACCGT ATATAAGTGCAGTAGTCGCCGTGAACGTTCTTTTTCGCAACGGGTTTGCCGCCAGAAC ACAGGTAAGTGCCGTGTGTGGTTCCCGCGGGCCTGGCCTCTTTACGGGTTATGGCCCT TGCGTGCCTTGAATTACTTCCACCTGGCTGCAGTACGTGATTCTTGATCCCGAGCTTC GGGTTGGAAGTGGGTGGGAGAGTTCGAGGCCTTGCGCTTAAGGAGCCCCTTCGCCTCG TGCTTGAGTTGAGGCCTGGCCTGGGCGCTGGGGCCGCCGCGTGCGAATCTGGTGGCAC CTTCGCGCCTGTCTCGCTGCTTTCGATAAGTCTCTAGCCATTTAAAATTTTTGATGAC CTGCTGCGACGCTTTTTTTCTGGCAAGATAGTCTTGTAAATGCGGGCCAAGATCTGCA CACTGGTATTTCGGTTTTTTGGGGCCGCGGGCGGCGACGGGGCCCGTGCGTCCCAGCGC ACATGTTCGGCGAGGCGGGCCTGCGAGCGCGGCCACCGAGAATCGGACGGGGGTAGT CTCAAGCTGGCCGGCCTGCTCTGGTGCCTGGCCTCGCGCCGCGTGTATCGCCCCGCC CTGGGCGGCAAGGCTGGCCCGGTCGGCACCAGTTGCGTGAGCGGAAAGATGGCCGCTT CCCGGCCCTGCTGCAGGGAGCTCAAAATGGAGGACGCGGCGCTCGGGAGAGCGGGCGG GTGAGTCACCCACACAAAGGAAAAGGGCCTTTCCGTCCTCAGCCGTCGCTTCATGTGA CTCCACGGAGTACCGGGCGCCGTCCAGGCACCTCGATTAGTTCTCGAGCTTTTGGAGT ACGTCGTCTTTAGGTTGGGGGGAGGGGTTTTATGCGATGGAGTTTCCCCACACTGAGT GGGTGGAGACTGAAGTTAGGCCAGCTTGGCACTTGATGTAATTCTCCTTGGAATTTGC CCTTTTTGAGTTTGGATCTTGGTTCATTCTCAAGCCTCAGACAGTGGTTCAAAGTTTT TTTCTTCCATTTCAGGTGTCGTGA | 100 |
| 2 | Leader (aa) | MALPVTALLLPLALLLHAARP | 13 |
| 3 | Leader (na) | ATGGCCCTGCCTGTGACAGCCCTGCTGCTGCCTCTGGCTCTGCTGCTGCATGCCGCTA GACCC | 54 |
| 4 | CD 8 hinge (aa) | TTTPAPRPPTPAPTIASQPLSLRPEACRPAAGGAVHTRGLDFACD | 14 |
| 5 | CD8 hinge (na) | ACCACGACGCCAGCGCCGCGACCACCAACACCGGCGCCCACCATCGCGTCGCAGCCCC TGTCCCTGCGCCCAGAGGCGTGCCGGCCAGCGGCGGGGGGCGCAGTGCACACGAGGGG GCTGGACTTCGCCTGTGAT | 55 |
| 6 | Ig4 hinge (aa) | ESKYGPPCPPCPAPEFLGGPSVFLFPPKPKDTLMISRTPEVTCVVVDVSQEDPEVQFN WYVDGVEVHNAKTKPREEQFNSTYRVVSVLTVLHQDWLNGKEYKCKVSNKGLPSSIEK TISKAKGQPREPQVYTLPPSQEEMTKNQVSLTCLVKGFYPSDIAVEWESNGQPENNYK TTPPVLDSDGSFFLYSRLTVDKSRWQEGNVFSCSVMHEALHNHYTQKSLSLSLGKM | 102 |

TABLE 1-continued

Sequences of various components of CAR (aa-amino acids, na-nucleic acids that encodes the corresponding protein)

| SEQ ID NO | description | Sequence | Corresp. To huCD19 |
|---|---|---|---|
| 7 | Ig4 hinge (na) | GAGAGCAAGTACGGCCCTCCCTGCCCCCCTTGCCCTGCCCCCGAGTTCCTGGGCGGAC CCAGCGTGTTCCTGTTCCCCCCCAAGCCCAAGGACACCCTGATGATCAGCCGGACCCC CGAGGTGACCTGTGTGGTGGTGGACGTGTCCCAGGAGGACCCCGAGGTCCAGTTCAAC TGGTACGTGGACGGCGTGGAGGTGCACAACGCCAAGACCAAGCCCCGGGAGGAGCAGT TCAATAGCACCTACCGGGTGGTGTCCGTGCTGACCGTGCTGCACCAGGACTGGCTGAA CGGCAAGGAATACAAGTGTAAGGTGTCCAACAAGGGCCTGCCCAGCAGCATCGAGAAA ACCATCAGCAAGGCCAAGGGCCAGCCTCGGGAGCCCCAGGTGTACACCCTGCCCCCTA GCCAAGAGGAGATGACCAAGAACCAGGTGTCCCTGACCTGCCTGGTGAAGGGCTTCTA CCCCAGCGACATCGCCGTGGAGTGGGAGAGCAACGGCCAGCCCGAGAACAACTACAAG ACCACCCCCCCTGTGCTGGACAGCGACGGCAGCTTCTTCCTGTACAGCCGGCTGACCG TGGACAAGAGCCGGTGGCAGGAGGGCAACGTCTTTAGCTGCTCCGTGATGCACGAGGC CCTGCACAACCACTACACCCAGAAGAGCCTGAGCCTGTCCCTGGGCAAGATG | 103 |
| 8 | IgD hinge (aa) | RWPESPKAQASSVPTAQPQAEGSLAKATTAPATTRNTGRGGEEKKKEKEKEEQEERET KTPECPSHTQPLGVYLLTPAVQDLWLRDKATFTCFVVGSDLKDAHLTWEVAGKVPTGG VEEGLLERHSNGSQSQHSRLTLPRSLWNAGTSVTCTLNHPSLPPQRLMALREPAAQAP VKLSLNLLASSDPPEAASWLLCEVSGFSPPNILLMWLEDQREVNTSGFAPARPPPQPG STTFWAWSVLRVPAPPSPQPATYTCVVSHEDSRTLLNASRSLEVSYVTDH | 47 |
| 9 | IgD hinge (na) | AGGTGGCCCGAAAGTCCCAAGGCCCAGGCATCTAGTGTTCCTACTGCACAGCCCCAGG CAGAAGGCAGCCTAGCCAAAGCTACTACTGCACCTGCCACTACGCGCAATACTGGCCG TGGCGGGGAGGAGAAGAAAAAGGAGAAAGAGAAAGAAGAACAGGAAGAGGGGAGACC AAGACCCCTGAATGTCCATCCCATACCCAGCCGCTGGGCGTCTATCTCTTGACTCCCG CAGTACAGGACTTGTGGCTTAGAGATAAGGCCACCTTTACATGTTTCGTCGTGGGCTC TGACCTGAAGGATGCCCATTTGACTTGGGAGGTTGCCGGAAAGGTACCCACAGGGGGG GTTGAGGAAGGGTTGCTGGAGCGCCATTCCAATGGCTCTCAGAGCCAGCACTCAAGAC TCACCCTTCCGAGATCCCTGTGGAACGCCGGGACCTCTGTCACATGTACTCTAAATCA TCCTAGCCTGCCCCCACAGCGTCTGATGGCCCTTAGAGAGCCAGCCGCCCAGGCACCA GTTAAGCTTAGCCTGAATCTGCTCGCCAGTAGTGATCCCCAGAGGCCGCCAGCTGGC TCTTATGCGAAGTGTCCGGCTTTAGCCCGCCCAACATCTTGCTCATGTGGCTGGAGGA CCAGCGAGAAGTGAACACCAGCGGCTTCGCTCCAGCCCGGCCCCCACCCCAGCCGGGT TCTACCACATTCTGGGCCTGGAGTGTCTTAAGGGTCCCAGCACCACCTAGCCCCCAGC CAGCCACATACACCTGTGTTGTGTCCCATGAAGATAGCAGGACCCTGCTAAATGCTTC TAGGAGTCTGGAGGTTTCCTACGTGACTGACCATTGGGGSGGGGS | 48 |
| 10 | GS hinge/linker (aa) | GGGGSGGGGS | 49 |
| 11 | GS hinge/linker (na) | GGTGGCGGAGGTTCTGGAGGTGGAGGTTCC | 50 |
| 12 | CD8TM (aa) | IYIWAPLAGTCGVLLLSLVITLYC | 15 |
| 13 | CD8 TM (na) | ATCTACATCTGGGCGCCCTTGGCCGGGACTTGTGGGGTCCTTCTCCTGTCACTGGTTA TCACCCTTTACTGC | 56 |
| 14 | 4-1BB intracellular domain (aa) | KRGRKKLLYIFKQPFMRPVQTTQEEDGCSCRFPEEEEGGCEL | 16 |
| 15 | 4-1BB intracellular domain (na) | AAACGGGGCAGAAAGAAACTCCTGTATATATTCAAACAACCATTTATGAGACCAGTAC AAACTACTCAAGAGGAAGATGGCTGTAGCTGCCGATTTCCAGAAGAAGAAGAAGGAGG ATGTGAACTG | 60 |
| 16 | CD27 (aa) | QRRKYRSNKGESPVEPAEPCRYSCPREEEGSTIPIQEDYRKPEPACSP | 51 |
| 17 | CD27 (na) | AGGAGTAAGAGGAGCAGGCTCCTGCACAGTGACTACATGAACATGACTCCCCGCCGCC CCGGGCCCACCCGCAAGCATTACCAGCCCTATGCCCCACCACGCGACTTCGCAGCCTA TCGCTCC | 52 |
| 18 | CD3-zeta (aa) | RVKFSRSADAPAYKQGQNQLYNELNLGRREEYDVLDKRRGRDPEMGGKPRRKNPQEGL YNELQKDKMAEAYSEIGMKGERRRGKGHDGLYQGLSTATKDTYDALHMQALPPR | 17 |
| 19 | CD3-zeta (na) | AGAGTGAAGTTCAGCAGGAGCGCAGACGCCCCCGCGTACAAGCAGGGCCAGAACCAGC TCTATAACGAGCTCAATCTAGGACGAAGAGAGGAGTACGATGTTTTGGACAAGAGACG TGGCCGGGACCCTGAGATGGGGGGAAAGCCGAGAAGGAAGAACCCTCAGGAAGGCCTG TACAATGAACTGCAGAAAGATAAGATGGCGGAGGCCTACAGTGAGATTGGGATGAAAG GCGAGCGCCGGAGGGGCAAGGGGCACGATGGCCTTTACCAGGGTCTCAGTACAGCCAC CAAGGACACCTACGACGCCCTTCACATGCAGGCCCTGCCCCCTCGC | 101 |

TABLE 1-continued

Sequences of various components of CAR (aa-amino acids, na-nucleic acids that encodes the corresponding protein)

| SEQ ID NO | description | Sequence | Corresp. To huCD19 |
|---|---|---|---|
| 20 | CD3-zeta (aa) | RVKFSRSADAPAYQQGQNQLYNELNLGRREEYDVLDKRRGRDPEMGGKPRRKNPQEGL YNELQKDKMAEAYSEIGMKGERRRGKGHDGLYQGLSTATKDTYDALHMQALPPR | 43 |
| 21 | CD3-zeta (na) | AGAGTGAAGTTCAGCAGGAGCGCAGACGCCCCCGCGTACCAGCAGGGCCAGAACCAGC TCTATAACGAGCTCAATCTAGGACGAAGAGAGGAGTACGATGTTTTGGACAAGAGACG TGGCCGGGACCCTGAGATGGGGGGAAAGCCGAGAAGGAAGAACCCTCAGGAAGGCCTG TACAATGAACTGCAGAAAGATAAGATGGCGGAGGCCTACAGTGAGATTGGGATGAAAG GCGAGCGCCGGAGGGGCAAGGGCACGATGGCCTTTACCAGGGTCTCAGTACAGCCAC CAAGGACACCTACGACGCCCTTCACATGCAGGCCCTGCCCCCTCGC | 44 |
| 22 | linker | GGGGS | 18 |
| 23 | linker | GGTGGCGGAGGTTCTGGAGGTGGAGGTTCC | 50 |
| 24 | PD-1 extracellular domain (aa) | pgwfldspdrpwnpptfspallvvtegdnatftcsfsntsesfvlnwyrmspsnqtdk laafpedrsqpgqdcrfrvtqlpngrdfhmsvvrarrndsgtylcgaislapkaqike slraelrvterraevptahpspsprpagqfqtlv | |
| 25 | PD-1 extracellular domain (na) | cccggatggtttctggactctccggatcgcccgtggaatcccccaaccttctcaccgg cactcttggttgtgactgagggcgataatgcgaccttcacgtgctcgttctccaacac ctccgaatcattcgtgctgaactggtaccgcatgagcccgtcaaaccagaccgacaag ctcgccgcgtttccggaagatcggtcgcaaccgggacaggattgtcggttccgcgtga ctcaactgccgaatggcagagacttccacatgagcgtggtccgcgctaggcgaaacga ctccgggacctacctgtgcggagccatctcgctggcgcctaaggcccaaatcaaagag agcttgagggccgaactgagagtgaccgagcgcagagctgaggtgccaactgcacatc catccccatcgcctcggcctgcggggcagtttcagaccctggtc | |
| 26 | PD-1 CAR (aa) with signal | malpvtalllplalllhaarppgwfldspdrpwnpptfspallvvtegdnatftcsfs ntsesfvlnwyrmspsnqtdklaafpedrsqpgqdcrfrvtqlpngrdfhmsvvrarr ndsgtylcgaislapkaqikeslraelryterraevptahpspsprpagqfqtivttt paprrpptpaptiasqplslrpeacrpaaggavhtrgldfacdiyiwaplagtcgvlll slvitlyckrgrkkllyifkqpfmrpvqttqeedgcscrfpeeeeggcelrvkfsrsa dapaykqggnqlynelnlgrreeydvldkrrgrdpemggkprrknpqeglynelqkdk maeayseigmkgerrrgkghdglyqglstatkdtydalhmqalppr | |
| 27 | PD-1 CAR (na) | atggcccccctgtcactgccctgcttctcccctcgcactcctgctccacgccgcta gaccaccggatggtttctggactctccggatcgcccgtggaatcccccaaccttctc accggcactcttggttgtgactgagggcgataatgcgaccttcacgtgctcgttctcc aacacctccgaatcattcgtgctgaactggtaccgcatgagcccgtcaaaccagacca caagctcgccgcgtttccggaagatcggtcgcaaccgggacaggattgtcggttccg cgtgactcaactgccgaatggcagagacttccacatgagcgtggtccgcgctaggcga aacgactccgggacctacctgtgcggagccatctcgctggcgcctaaggcccaaatca aagagagcttgagggccgaactgagagtgaccgagcgcagagctgaggtgccaactgc acatccatccccatcgcctcggcctgcggggcagtttcagaccctggtcacgaccact ccggcgccgcgcccaccgactccggcccccaactatcgcgagccagcccctgtcgctga ggccggaagcatgccgccctgccgccgaggtgctgtgcatacccggggattggactt cgcatgcgacatctacatttgggctcctctcgccggaacttgtgggcgtgctccttctg tccctggtcatcaccctgtactgcaagcggggtcggaaaaagcttctgtacatttca agcagcccttcatgaggcccgtgcaaaccacccaggaggaggacggttgctcctgccg gttccccgaagaggaagaaggaggttgcgagctgcgcgtgaagttctcccggagcgcc gacgccccgcctataagcagggccagaaccagctgtacaacgaactgaacctgggac ggcgggaagagtacgatgtgctggacaagcggcggcggccgggaccccgaaatgggcgg gaagcctagaagaaagaaccctcaggaaggcctgtataacgagctgcagaaggacaag atggccgaggcctactccgaaattgggatgaagggagagcggcggaggggaaggggc acgacggcctgtaccaaggactgtccaccgccaccaaggacacatacgatgccctgca catgcaggcccttccccctcgc | |
| 28 | linker | (Gly-Gly-Gly-Ser)n, where n = 1-10 | 105 |
| 29 | linker | (Gly4 Ser)4 | 106 |
| 30 | linker | (Gly4 Ser)3 | 107 |
| 31 | linker | (Gly3Ser) | 108 |
| 32 | PD1CAR (aa) | <u>pqwfldspdrpwnpptfspallvvtegdnatftcsfsntsesfvlnwyrmspsnqtdk laafpedrsqpqdcrfrvtqlpnordfhmsvvrarrndsotylcgaislapkaqike slraelrvterraevptahpspsprpagqfqtlvtttpaprrpptpaptiasqplslrp eacrpaaggavhtrgldfacdiyiwaplagtcgvlllslvitlyckrgrkkllyifkq pfmrpvqttqeedgcscrfpeeeeggcelrvkfsrsadapaykqggnqlynelnlgrr eeydvldkrrgrdpemggkprrknpqeglynelqkdkmaeayseigmkgerrrgkghd glyqglstatkdtydalhmqalppr</u> | |

TABLE 1-continued

Sequences of various components of CAR (aa-amino acids, na-nucleic acids that encodes the corresponding protein)

| SEQ ID NO | description | Sequence | Corresp. To huCD19 |
|---|---|---|---|
| 33 | CD19 CAR (aa) murine | MALPVTALLLPLALLLHAARPDIQMTQTTSSLSASLGDRVTISCRASQDISKYLNWYQ QKPDGTVKLLIYHTSRLHSGVPSRFSGSGSGTDYSLTISNLEQEDIATYFCQQGNTLP YTFGGGTKLEITGGGGSGGGGSGGGGSEVKLQESGPGLVAPSQSLSVTCTVSGVSLPD YGVSWIRQPPRKGLEWLGVIWGSETTYYNSALKSRLTIIKDNSKSQVFLKMNSLQTDD TAIYYCAKHYYYGGSYAMDYWGQGTSVTVSSTTTPAPRPPTPAPTIASQPLSLRPEAC RPAAGGAVHTRGLDFACDIYIWAPLAGTCGVLLLSLVITLYCKRGRKKLLYIFKQPFM RPVQTTQEEDGCSCRFPEEEEGGCELRVKFSRSADAPAYKQGQNQLYNELNLGRREEY DVLDKRRGRDPEMGGKPRRKNPQEGLYNELQKDKMAEAYSEIGMKGERRRGKGHDGLY QGLSTATKDTYDALHMQALPPR | |
| 34 | CD19 CAR (na) murine | atggccttaccagtgaccgccttgctcctgccgctggccttgctgctccacgccgcca ggccggacatccagatgacacagactacatcctccctgtctgcctctctgggagacag agtcaccatcagttgcagggcaagtcaggacattagtaaatatttaaattggtatcag cagaaaccagatggaactgttaaactcctgatctaccatacatcaagattacactcag gagtcccatcaaggttcagtggcagtgggtctggaacagattattctctcaccattag caacctggagcaagaagatattgccacttacttttgccaacagggtaatacgcttccg tacacgttcggaggggggaccaagctggagatcacaggtggcggtggctcggcggtg gtgggtcgggtggcggcggatctgaggtgaaactgcaggagtcaggacctggcctggt ggcgccctcacagagcctgtccgtcacatgcactgtctcaggggtctcattacccgac tatggtgtaagctggattcgccagcctccacgaaagggtctggagtggctgggagtaa tatgggtagtgaaaccacatactataattcagctctcaaatccagactgaccatcat caaggacaactccaagagccaagttttcttaaaaatgaacagtctgcaaactgatgac acagcctatttactactgtgccaaacattattactacggtggtagctatgctatggact actggggccaaggaacctcagtcaccgtctcctcaaccacgacgccagcgccgcgacc accaacaccggcgccaccatcgcgtcgcagccctgtccctgcgcccagaggcgtgc cggccagcggcggggcgcagtgcacacgagggggctggacttcgcctgtgatatct acatctgggcgcccttggccgggacttgtgggtccttctcctgtcactggttatcac cctttactgcaaacggggcagaaagaaactcctgtatatattcaaacaaccatttatg agaccagtacaaactactcaagaggaagatggctgtagctgccgatttccagaagaag aagaaggaggatgtgaactgagagtgaagttcagcaggagcgcagacgcccccgcgta caagcagggcagaaccagctctataacgagctcaatctaggacgaagagaggagtac gatgttttggacaagagacgtggccgggaccctgagatgggggaaagccgagaagga agaaccctcaggaaggcctgtacaatgaactgcagaaagataagatggcggaggccta cagtgagattgggatgaaaggcgagcgccggaggggcaaggggcacgatggcctttac cagggtctcagtacagccaccaaggacacctacgacgcccttcacatgcaggccctgc cccctcgct | |
| 35 | CD19 CAR (aa) human | MALPVTALLLPLALLLHAARPEIVMTQSPATLSLSPGERATLSCRASQDISKYLNWYQ QKPGQAPRLLIYHTSRLHSGIPARFSGSGSGTDYTLTISSLQPEDFAVYFCQQGNTLP YTFGQGTKLEIKGGGGSGGGGSGGGGSQVQLQESGPGLVKPSETLSLTCTVSGVSLPD YGVSWIRQPPGKGLEWIGVIWGSETTYYQSSLKSRVTISKDNSKNQVSLKLSSVTAAD TAVYYCAKHYYYGGSYAMDYWGQGTLVTVSSTTTPAPRPPTPAPTIASQPLSLRPEAC RPAAGGAVHTRGLDFACDIYIWAPLAGTCGVLLLSLVITLYCKRGRKKLLYIFKQPFM RPVQTTQEEDGCSCRFPEEEEGGCELRVKFSRSADAPAYKQGQNQLYNELNLGRREEY DVLDKRRGRDPEMGGKPRRKNPQEGLYNELQKDKMAEAYSEIGMKGERRRGKGHDGLY QGLSTATKDTYDALHMQALPPR | |
| 36 | CD19 CAR (na) human | atggccctccctgtcaccgccctgctgcttccgctggctcttctgctccacgccgctc ggcccgaaattgtgatgacccagtcacccgccactcttagcctttcacccggtgagcg cgcaaccctgtcttgcagagcctcccaagacatctcaaaatacctcaattggtatcaa cagaagcccggacaggctcctcgccttctgatctaccacaccagccggctccattctg gaatccctgccaggttcagcggtagcggatctgggaccgactcacccctcactatcag ctcactgcagccagaggacttcgctgtctatttctgtcagcaagggaacaccctgccc tacaccttggacagggcaccaagctcgagattaaaggtggaggtggcagcggaggag gtgggtccggcggtggaggaagccaggtccaactccaagaaagcggaccgggtcttgt gaagccatcagaaactctttcactgacttgtactgtgagcggagtgtctctcccgat tacggggtgtcttggatcagacagccaccggggaagggtctggaatggattggagtga tttgggggctctgagactactactaccaatcatccctcaagtcacgcgtcaccatctc aaaggacaactctaagaatcaggtgtcactgaaactgtcatctgtgaccgcagccgac accgccgtgtactattgcgctaagcattactattatggcgggagctacgcaatggatt actggggacagggtactctggtcaccgtgtccagcaccactaccccagcaccgaggcc acccaccccggcctctaccatcgcctccagcctctgtcctgcgtccggaggcatgt agacccgcagctggtggggcgtgcatacccggggtcttgacttcgcctgcgatatct acatttgggcccctctggctggtacttgcggggtcctgctgctctttcactcgtgatcac tctttactgtaagcgcggtcggaagaagctgctgtacatctttaagcaacccttcatg aggcctgtgcagactactcaagaggaggacggctgttcatgccggttcccagaggagg aggaaggcggctgcgaactcgcgtgaaattcagccgcagcgcagatgctccagccta caagcaggggcagaaccagctctacaacgaactcaatcttggtcggagagaggagtac | |

TABLE 1-continued

Sequences of various components of CAR (aa-amino acids, na-nucleic acids that encodes the corresponding protein)

| SEQ ID NO | description | Sequence | Corresp. To huCD19 |
|---|---|---|---|
| | | gacgtgctggacaagcggagaggacgggacccagaaatgggcgggaagccgcgcagaa agaatccccaagagggcctgtacaacgagctccaaaaggataagatggcagaagccta tagcgagattggtatgaaaggggaacgcagaagaggcaaaggccacgacggactgtac cagggactcagcaccgccaccaaggacacctatgacgctcttcacatgcaggccctgc cgcctcgg | |

TABLE 2

Antigen Binding domains that bind B cell antigens

| B cell antigen | Name | Amino Acid Sequence | SEQ ID NO: |
|---|---|---|---|
| CD19 | huscF v1 | EIVMTQSPATLSLSPGERATLSCRASQDISKYLNWYQQKPGQAPRLLIYH TSRLHSGIPARFSGSGSGTDYTLTISSLQPEDFAVYFCQQGNTLPYTFGQ GTKLEIKGGGGSGGGGSGGGGSQVQLQESGPGLVKPSETLSLTCTVSGVS LPDYGVSWIRQPPGKGLEWIGVIWGSETTYYSSSLKSRVTISKDNSKNQV SLKLSSVTAADTAVYYCAKHYYYGGSYAMDYWGQGTLVTVSS | 37 |
| CD19 | huscF v2 | EIVMTQSPATLSLSPGERATLSCRASQDISKYLNWYQQKPGQAPRLLIYH TSRLHSGIPARFSGSGSGTDYTLTISSLQPEDFAVYFCQQGNTLPYTFGQ GTKLEIKGGGGSGGGGSGGGGSQVQLQESGPGLVKPSETLSLTCTVSGVS LPDYGVSWIRQPPGKGLEWIGVIWGSETTYYQSSLKSRVTISKDNSKNQV SLKLSSVTAADTAVYYCAKHYYYGGSYAMDYWGQGTLVTVSS | 38 |
| CD19 | huscF v3 | QVQLQESGPGLVKPSETLSLTCTVSGVSLPDYGVSWIRQPPGKGLEWIGV IWGSETTYYSSSLKSRVTISKDNSKNQVSLKLSSVTAADTAVYYCAKHYY YGGSYAMDYWGQGTLVTVSSGGGGSGGGGSGGGGSEIVMTQSPATLSLSP GERATLSCRASQDISKYLNWYQQKPGQAPRLLIYHTSRLHSGIPARFSGS GSGTDYTLTISSLQPEDFAVYFCQQGNTLPYTFGQGTKLEIK | 39 |
| CD19 | huscF v4 | QVQLQESGPGLVKPSETLSLTCTVSGVSLPDYGVSWIRQPPGKGLEWIGV IWGSETTYYQSSLKSRVTISKDNSKNQVSLKLSSVTAADTAVYYCAKHYY YGGSYAMDYWGQGTLVTVSSGGGGSGGGGSGGGGSEIVMTQSPATLSLSP GERATLSCRASQDISKYLNWYQQKPGQAPRLLIYHTSRLHSGIPARFSGS GSGTDYTLTISSLQPEDFAVYFCQQGNTLPYTFGQGTKLEIK | 40 |
| CD19 | huscF v5 | EIVMTQSPATLSLSPGERATLSCRASQDISKYLNWYQQKPGQAPRLLIYH TSRLHSGIPARFSGSGSGTDYTLTISSLQPEDFAVYFCQQGNTLPYTFGQ GTKLEIKGGGGSGGGGSGGGGSGGGGSQVQLQESGPGLVKPSETLSLTCT VSGVSLPDYGVSWIRQPPGKGLEWIGVIWGSETTYYSSSLKSRVTISKDN SKNQVSLKLSSVTAADTAVYYCAKHYYYGGSYAMDYWGQGTLVTVSS | 41 |
| CD19 | huscF v6 | EIVMTQSPATLSLSPGERATLSCRASQDISKYLNWYQQKPGQAPRLLIYH TSRLHSGIPARFSGSGSGTDYTLTISSLQPEDFAVYFCQQGNTLPYTFGQ GTKLEIKGGGGSGGGGSGGGGSGGGGSQVQLQESGPGLVKPSETLSLTCT VSGVSLPDYGVSWIRQPPGKGLEWIGVIWGSETTYYQSSLKSRVTISKDN SKNQVSLKLSSVTAADTAVYYCAKHYYYGGSYAMDYWGQGTLVTVSS | 42 |
| CD19 | huscF v7 | QVQLQESGPGLVKPSETLSLTCTVSGVSLPDYGVSWIRQPPGKGLEWIGV IWGSETTYYSSSLKSRVTISKDNSKNQVSLKLSSVTAADTAVYYCAKHYY YGGSYAMDYWGQGTLVTVSSGGGGSGGGGSGGGGSGGGGSEIVMTQSPAT LSLSPGERATLSCRASQDISKYLNWYQQKPGQAPRLLIYHTSRLHSGIPA RFSGSGSGTDYTLTISSLQPEDFAVYFCQQGNTLPYTFGQGTKLEIK | 43 |
| CD19 | huscF v8 | QVQLQESGPGLVKPSETLSLTCTVSGVSLPDYGVSWIRQPPGKGLEWIGV IWGSETTYYQSSLKSRVTISKDNSKNQVSLKLSSVTAADTAVYYCAKHYY YGGSYAMDYWGQGTLVTVSSGGGGSGGGGSGGGGSGGGGSEIVMTQSPAT LSLSPGERATLSCRASQDISKYLNWYQQKPGQAPRLLIYHTSRLHSGIPA RFSGSGSGTDYTLTISSLQPEDFAVYFCQQGNTLPYTFGQGTKLEIK | 44 |
| CD19 | huscF v9 | EIVMTQSPATLSLSPGERATLSCRASQDISKYLNWYQQKPGQAPRLLIYH TSRLHSGIPARFSGSGSGTDYTLTISSLQPEDFAVYFCQQGNTLPYTFGQ GTKLEIKGGGGSGGGGSGGGGSGGGGSQVQLQESGPGLVKPSETLSLTCT VSGVSLPDYGVSWIRQPPGKGLEWIGVIWGSETTYYNSSLKSRVTISKDN SKNQVSLKLSSVTAADTAVYYCAKHYYYGGSYAMDYWGQGTLVTVSS | 45 |

TABLE 2-continued

Antigen Binding domains that bind B cell antigens

| B cell antigen | Name | Amino Acid Sequence | SEQ ID NO: |
|---|---|---|---|
| CD19 | Hu scFv10 | QVQLQESGPGLVKPSETLSLTCTVSGVSLPDYGVSWIRQPPGKGLEWIGV IWGSETTYYNSSLKSRVTISKDNSKNQVSLKLSSVTAADTAVYYCAKHYY YGGSYAMDYWGQGTLVTVSSGGGGSGGGGSGGGGSGGGGSEIVMTQSPAT LSLSPGERATLSCRASQDISKYLNWYQQKPGQAPRLLIYHTSRLHSGIPA RFSGSGSGTDYTLTISSLQPEDFAVYFCQQGNTLPYTFGQGTKLEIK | 46 |
| CD19 | Hu scFv11 | EIVMTQSPATLSLSPGERATLSCRASQDISKYLNWYQQKPGQAPRLLIYH TSRLHSGIPARFSGSGSGTDYTLTISSLQPEDFAVYFCQQGNTLPYTFGQ GTKLEIKGGGGSGGGGSGGGGSQVQLQESGPGLVKPSETLSLTCTVSGVS LPDYGVSWIRQPPGKGLEWIGVIWGSETTYYNSSLKSRVTISKDNSKNQV SLKLSSVTAADTAVYYCAKHYYYGGSYAMDYWGQGTLVTVSS | 47 |
| CD19 | Hu scFv12 | QVQLQESGPGLVKPSETLSLTCTVSGVSLPDYGVSWIRQPPGKGLEWIGV IWGSETTYYNSSLKSRVTISKDNSKNQVSLKLSSVTAADTAVYYCAKHYY YGGSYAMDYWGQGTLVTVSSGGGGSGGGGSGGGGSEIVMTQSPATLSLSP GERATLSCRASQDISKYLNWYQQKPGQAPRLLIYHTSRLHSGIPARFSGS GSGTDYTLTISSLQPEDFAVYFCQQGNTLPYTFGQGTKLEIK | 48 |
| CD19 | muCT L019 | DIQMTQTTSSLSASLGDRVTISCRASQDISKYLNWYQQKPDGTVKLLIYH TSRLHSGVPSRFSGSGSGTDYSLTISNLEQEDIATYFCQQGNTLPYTFGG GTKLEITGGGGSGGGGSGGGGSEVKLQESGPGLVAPSQSLSVTCTVSGVS LPDYGVSWIRQPPRKGLEWLGVIWGSETTYYNSALKSRLTIIKDNSKSQV FLKMNSLQTDDTAIYYCAKHYYYGGSYAMDYWGQGTSVTVSS | 49 |

The following examples are intended to illustrate, rather than limit, the invention.

EXAMPLES

Example 1. Generation of the pCINS Vector

Figure 2:
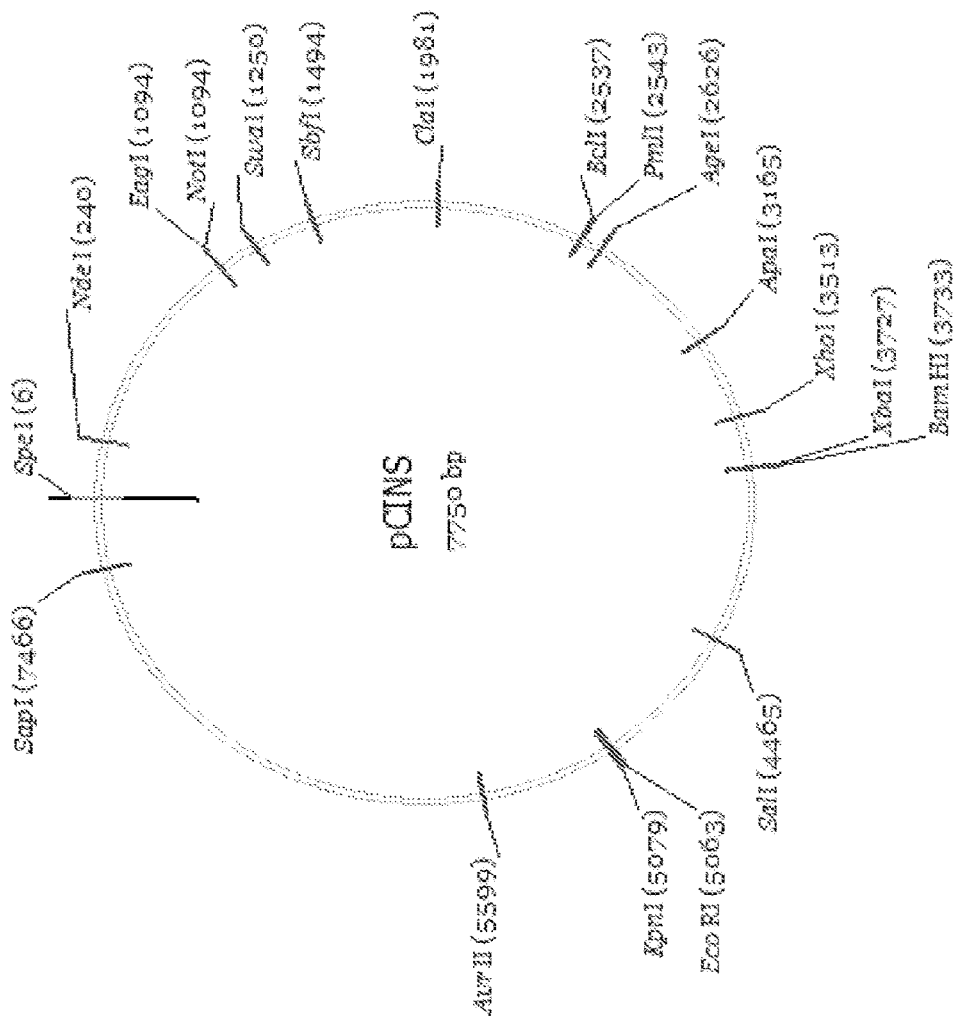
FIG. 2 is a schematic showing the restriction map of the pCINS lentiviral transfer vector, including the location of each restriction site within the vector sequence.
Figure 3:
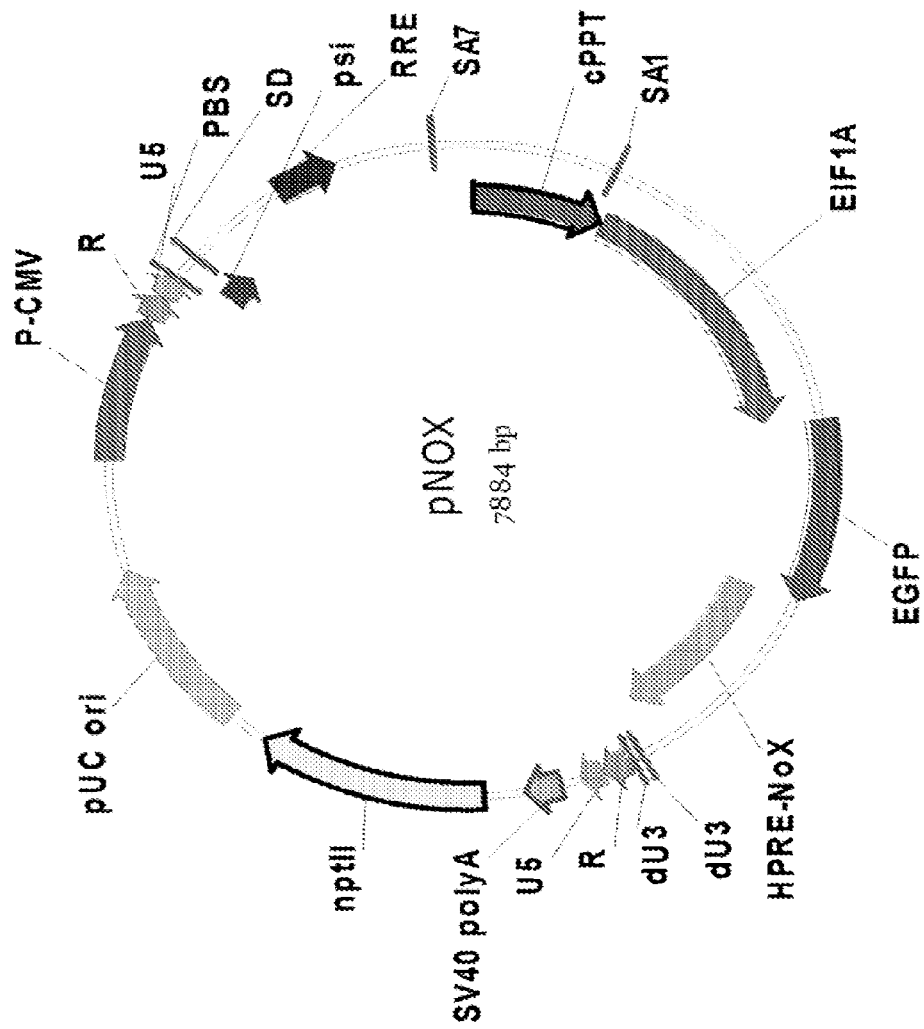
FIG. 3 is a schematic showing the feature map of the pNOX lentiviral transfer vector. P-CMV=cytomegalovirus (CMV) promoter; R=LTR R region, U5=LTR U5 region, PBS=primer binding site; SD=major splice donor site; psi=packaging signal; RRE=Rev-response element; SA7=splice acceptor site; cPPT=central polypurine tract; SA1=splice acceptor site; EF1A=human EF1alpha promoter; EGFP=GFP reporter open reading frame (ORF); HPRE-NoX=hepatitis B post-transcriptional regulatory element, without ORF encoding X protein; dU3=truncated LTR U3 region; SV40 polyA=SV40 polyadenylation sequence; nptII=kanamycin resistance gene; pUC ori=origin of replication from pUC.
Figure 4:
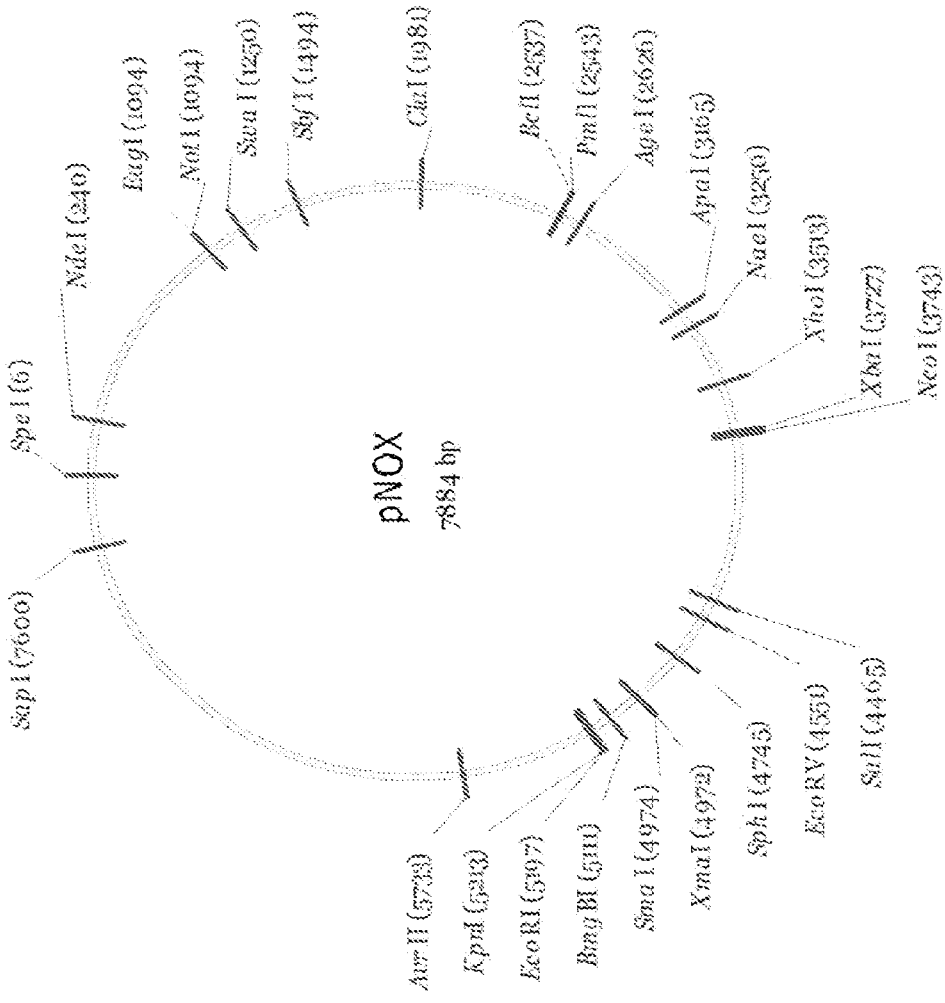
FIG. 4 is a schematic showing the restriction map of the pNOX lentiviral transfer vector, including the location of each restriction site within the vector sequence.

The parental lentiviral transfer vector pRRL.SIN.cPPT.EF1a.EGFP.WPRE was synthesized de novo by DNA2.0 using sequences derived from the backbone of pRRL.SIN vector made by Dull et al. (*J. Virol.* 72: 8463-8471, 1998; incorporated herein by reference). A feature map of pCINS is set forth in FIG. 1, while a restriction map of the vector is set forth in FIG. 2.

In generating the pCINS vector, the following modifications were made to the parental vector:
1. 5' cis elements were replaced with the corresponding natural sequence from HIV-1 isolate NL4-3. The replaced 5' cis elements included: packaging signal (psi), partial gag sequence adjacent to psi, Rev-response element (RRE) and the partial env sequence surrounding it, and a central polypurine tract (cPPT) sequence from pol.
2. The SV40 and f1 origins of replication were removed as redundant to decrease plasmid size.
3. Several restriction sites were introduced between the cis elements to facilitate DNA engineering.
4. The INS1 inhibitory sequence in gag, which restricts nuclear export of unspliced viral RNA (*J. Virol.* 71(7): 4892-4903, 1997; *J. Virol.* 66(12):7176-7182, 1992; each of which is incorporated herein by reference), was mutated, thereby reducing restriction of nuclear export of viral RNA(s) encoded by the vector.
5. Part of the gag sequence, after nucleotide 168, which contains inhibitory sequences INS2, INS3, and INS4 (*J. Virol.* 68(6):3784-3793, 1994; incorporated herein by reference), was removed.
6. The RSV promoter was replaced with a CMV promoter, since both RSV and CMV promoter can be used for SIN LV expression (*Science* 272(5259):263-267, 1996; *J. Virol.* 72(11):8463-8471, 1998; each of which is incorporated herein by reference).

The pCINS-EGFP sequence is set forth below and is detailed in Table 3. EGFP sequences can optionally be replaced with sequences of another transgene (e.g., a gene encoding a CAR), if desired, using standard methods in the art.

pCINS-EGFP sequence (SEQ ID NO: 50)

gcagactagtaagcttagtaatcaattacggggtcattagttcatagcccatatatggagttccgcgtta cataacttacggtaaatggcccgcctggctgaccgcccaacgacccccgcccattgacgtcaataatgac gtatgttcccatagtaacgccaatagggactttccattgacgtcaatgggtggagtatttacggtaaact gcccacttggcagtacatcaagtgtatcatatgccaagtacgccccctattgacgtcaatgacggtaaat ggcccgcctggcattatgcccagtacatgaccttatgggactttcctacttggcagtacatctacgtatt agtcatcgctattaccatgctgatgcggttttggcagtacatcaatgggcgtggatagcggtttgactca cggggatttccaagtctccaccccattgacgtcaatgggagtttgttttggcaccaaaatcaacgggact ttccaaaatgtcgtaacaactccgccccattgacgcaaatgggcggtaggcgtgtacggtgggaggtcta -continued

```
tataagcagagctggtttagtgaaccggggtctctctggttagaccagatctgagcctgggagctctctg gctaactagggaacccactgcttaagcctcaataaagcttgccttgagtgcttcaagtagtgtgtgcccg tctgttgtgtgactctggtaactagagatccctcagacccttttagtcagtgtggaaaatctctagcagt ggcgcccgaacagggacttgaaagcgaaagtaaagccagaggagatctctcgacgcaggactcggcttgc tgaagcgcgcacggcaagaggcgaggggcggcgactggtgagtacgccaaaaattttgactagcggaggc tagaaggagagagatgggtgcgagagcgtcggtattaagcggggagaattagataaatgggaaaaaatt cggtaataaggccaggggaaagaagaagtacaagctaaagcacatcgtatgggcaagcagggagctaga acgattcgcagttaatcctggccttttagagacatcagaaggcggccgctgatcttcagacctggaggag gcgatatgagggacaattggagaagtgaattatataaatataaagtagtaaaaattgaaccattaggagt agcacccaccaaggcaaagagaagagtggtgcagagagaaaaaagagcagtgggaatttaaataggagct ttgttccttgggttcttgggagcagcaggaagcactatgggcgcagcgtcaatgacgctgacggtacagg ccagacaattattgtctgatatagtgcagcagcagaacaatttgctgagggctattgaggcgcaacagca tctgttgcaactcacagtctggggcatcaaacagctccaggcaagaatcctggctgtggaaagatatccta aaggatcaacagctcctcctgcaggggatttggggttgctctggaaaactcatttgcaccactgctgtgc cttggaatgctagttggagtaataaatctctggaacagatttggaataacatgacctggatggagtggga cagagaaattaacaattacacaagcttaatacactccttaattgaagaatcgcaaaaccagcaagaaaag aatgaacaagaattattggaattagataaatgggcaagtttgtggaattggtttaacataacaaattggc tgtggtatataaaattattcataatgatagtaggaggcttggtaggtttaagaatagttttgctgtact ttctatagtgaatagagttaggcagggatattcaccattatcgtttcagacccacctcccaatcccgagg ggacccgacaggcccgaaggaatagaagaagaaggtggagagagagacagagacagatccattcgattag tgaacggatctcgacggtatcgattagactgtagcccaggaatatggcagctagattgtacacatttaga aggaaaagttatcttggtagcagttcatgtagccagtggatatatagaagcagaagtaattccagcagag acagggcaagaaacagcatacttcctcttaaaattagcaggaagatggccagtaaaaacagtacatacag acaatggcagcaatttcaccagtactacagttaaggccgcctgttggtgggcggggatcaagcaggaatt tggcattccctacaatccccaaagtcaaggagtaatagaatctatgaataaagaattaagagaaattata ggacaggtaagagatcaggctgaacatcttaagacagcagtacaaatggcagtattcatccacaattta aaagaaaaggggggattggggggtacagtgcaggggaaagaatagtagacataatagcaacagacataca aactaaagaattacaaaaacaaattacaaaaattcaaaattttcgggtttattacagggacagcagagat ccagtttggctgcattgatcacgtgaggctccggtgcccgtcagtgggcagagcgcacatcgcccacagt ccccgagaagttgggggggaggggtcggcaattgaaccggtgcctagagaaggtggcgcggggtaaactgg gaaagtgatgtcgtgtactggctccgccttttccccgagggtgggggagaaccgtatataagtgcagtag tcgccgtgaacgttctttttcgcaacgggtttgccgccagaacacaggtaagtgccgtgtgtggttcccg cgggcctggcctctttacggggttatggcccttgcgtgccttgaattacttccacctggctgcagtacgtg attcttgatcccgagcttcgggttggaagtgggtgggagagttcgaggccttgcgcttaaggagccccctt cgcctcgtgcttgagttgaggcctggcctgggcgctgggccgccgcgtgcgaatctggtggcaccttcg cgcctgtctcgctgctttcgataagtctctagccatttaaaattttttgatgacctgctgcgacgcttttt ttctggcaagatagtcttgtaaatgcgggccaagatctgcacactggtatttcggttttttggggccgcgg gcggcgacggggcccgtgcgtcccagcgcacatgttcggcgaggcggggcctgcgagcgcggccaccgag aatcggacggggtagtctcaagctggccggcctgctctggtgcctggcctcgcgccgccgtgtatcgcc ccgccctgggcggcaaggctggcccggtcggcaccagttgcgtgagcggaaagatggccgcttcccggcc
```

-continued

```
ctgctgcagggagctcaaaatggaggacgcggcgctcgggagagcgggcgggtgagtcacccacacaaag gaaaagggcctttccgtcctcagccgtcgcttcatgtgactccactgagtaccgggcgccgtccaggcac ctcgattagttctcgagcttttggagtacgtcgtctttaggttgggggagggttttatgcgatggagt ttccccacactgagtgggtggagactgaagttaggccagcttggcacttgatgtaattctccttggaatt tgccctttttgagtttggatcttggttcattctcaagcctcagacagtggttcaaagttttttcttcca tttcaggtgtcgtgatctagaggatccgccaccatggtgagcaagggcgaggagctgttcaccggggtgg tgcccatcctggtcgagctggacggcgacgtaaacggccacaagttcagcgtgtccggcgagggcgaggg cgatgccacctacggcaagctgaccctgaagttcatctgcaccaccggcaagctgcccgtgcctggccc accctcgtgaccaccctgacctacggcgtgcagtgcttcagccgctaccccgaccacatgaagcagcacg acttcttcaagtccgccatgcccgaaggctacgtccaggagcgcaccatcttcttcaaggacgacggcaa ctacaagacccgcgccgaggtgaagttcgagggcgacaccctggtgaaccgcatcgagctgaagggcatc gacttcaaggaggacggcaacatcctggggcacaagctggagtacaactacaacagccacaacgtctata tcatggccgacaagcagaagaacggcatcaaggtgaacttcaagatccgccacaacatcgaggacggcag cgtgcagctcgccgaccactaccagcagaacacccccatcggcgacggccccgtgctgctgcccgacaac cactacctgagcacccagtccgccctgagcaaagaccccaacgagaagcgcgatcacatggtcctgctgg agttcgtgaccgccgcgggatcactctcggcatggacgagctgtacaagtaagtcgacaatcaacctct ggattacaaaatttgtgaaagattgactggtattcttaactatgttgctccttttacgctatgtggatac gctgctttaatgcctttgtatcatgctattgcttcccgtatggctttcattttctcctccttgtataaat cctggttgctgtctctttatgaggagttgtggcccgttgtcaggcaacgtggcgtggtgtgcactgtgtt tgctgacgcaaccccactggttgggcattgccaccacctgtcagctcctttccgggactttcgctttc cccctcctattgccacggcggaactcatcgccgcctgccttgccgctgctggacagggctcggctgt tgggcactgacaattccgtggtgttgtcggggaagctgacgtcctttccatggctgctcgcctgtgttgc cacctggattctgcgcgggacgtccttctgctacgtcccttcggccctcaatccagcggaccttccttcc cgcggcctgctgccggctctgcggcctcttccgcgtcttcgccttcgccctcagacgagtcggatctccc tttgggccgcctccccgcctggaattcgagctcggtacctttaagaccaatgacttacaaggcagctgta gatcttagccacttttaaaagaaaaggggggactggaagggctaattcactcccaacgaagacaagatc tgctttttgcttgtactgggtctctctggttagaccagatctgagcctgggagctctctggctaactagg gaacccactgcttaagcctcaataaagcttgccttgagtgcttcaagtagtgtgtgcccgtctgttgtgt gactctggtaactagagatccctcagacccttttagtcagtgtggaaaatctctagcagtagtagttcat gtcatcttattattcagtatttataacttgcaaagaaatgaatatcagagagtgagaggaacttgtttat tgcagcttataatggttacaaataaagcaatagcatcacaaatttcacaaataaagcattttttcactg cattctagttgtggtttgtccaaactcatcaatgtatcttatcatgtctggctctagctatcccgcccct aggcaccggggaaatgtgcgcggaaccccctatttgtttattttctaaatacattcaaatatgtatccgc tcatgagacaataaccctgataaatgcttcaataatattgaaaaaggaagagtatgagccatattcaacg ggaaacgtcgaggccgcgattaaattccaacatggatgctgatttatatgggtataaatgggctcgcgat aatgtcgggcaatcaggtgcgacaatctatcgcttgtatgggaagcccgatgcgccagagttgtttctga aacatggcaaaggtagcgttgccaatgatgttacagatgagatggtcagactaaactggctgacggaatt tatgccacttccgaccatcaagcattttatccgtactcctgatgatgcatggttactcaccactgcgatc cccggaaaaacagcgttccaggtattagaagaatatcctgattcaggtgaaaatattgttgatgcgctgg cagtgttcctgcgccggttgcactcgattcctgtttgtaattgtccttttaacagcgatcgcgtatttcg cctcgctcaggcgcaatcacgaatgaataacggtttggttgatgcgagtgattttgatgacgagcgtaat
```

-continued

```
ggctggcctgttgaacaagtctggaaagaaatgcataaacttttgccattctcaccggattcagtcgtca ctcatggtgatttctcacttgataaccttattttttgacgaggggaaattaataggttgtattgatgttgg acgagtcggaatcgcagaccgataccaggatcttgccatcctatggaactgcctcggtgagttttctcct tcattacagaaacggcttttcaaaaatatggtattgataatcctgatatgaataaattgcagtttcatt tgatgctcgatgagttttctaactgtcagaccaagtttactcatatatactttagattgatttaaaact tcattttaatttaaaaggatctaggtgaagatcctttttgataatctcatgaccaaaatcccttaacgt gagttttcgttccactgagcgtcagacccgtagaaaagatcaaaggatcttcttgagatcctttttttc tgcgcgtaatctgctgcttgcaaacaaaaaaaccaccgctaccagcggtggtttgtttgccggatcaaga gctaccaactcttttccgaaggtaactggcttcagcagagcgcagataccaaatactgttcttctagtg tagccgtagttaggccaccacttcaagaactctgtagcaccgcctacatacctcgctctgctaatcctgt taccagtggctgctgccagtggcgataagtcgtgtcttaccgggttggactcaagacgatagttaccgga taaggcgcagcggtcgggctgaacggggggttcgtgcacacagcccagcttggagcgaacgacctacacc gaactgagatacctacagcgtgagctatgagaaagcgccacgcttcccgaagggagaaaggcggacaggt atccggtaagcggcagggtcggaacaggagagcgcacgagggagcttccaggggaaacgcctggtatct ttatagtcctgtcgggtttcgccacctctgacttgagcgtcgatttttgtgatgctcgtcagggggcgg agcctatggaaaaacgccagcaacgcggcctttttacggttcctggcctttttgctggccttttgctcaca tgttctttcctgcgttatcccctgattctgtggataaccgtattaccgcctttgagtgagctgataccgc tcgccgcagccgaacgaccgagcgcagcgagtcagtgagcgaggaagcggaagagcgcccaatacgcaaa ccgcctctccccgcgcgttggccgattcattaatgcagctggcacgacaggtttcccgactggaaagcgg gcagtgagcgcaacgcaattaatgtgagttagctcactcattaggcaccccaggctttacactttatgct tccggctcgtatgttgtgtggaattgtgagcggataacaatttcacacaggaaacagctatgaccatgat tacgccaagcgcgcaattaaccctcactaaagggaacaaaagctggagct
```

Example 2. Generation of the pNOX Vector

The pCINS vector generated in Example 1 was further modified to produce the pNOX vector. In particular, the post-transcriptional regulatory element (PRE) of woodchuck hepatitis virus (WPRE) present in pCINS was replaced with a PRE from hepatitis B virus (HPRE), which includes the natural sequence of hepatitis B virus isolate bba6, complete genome (GenBank: KP341007.1). WPRE was present in the parental vector to ensure efficient expression of the transgene. However, WPRE contains an X protein-coding sequence. The presence of the X protein ORF in WPRE may pose safety issues for integrating lentiviral vectors. For example, X protein has been implicated in the generation of liver cancers (*Gene Ther.* 12(1):3-4, 2005; incorporated herein by reference). In the pNOX vector, a point mutation was introduced in the start codon (ATG→AGG) of the X protein. As a result, the recombinant HPRE contains no X protein ORF. A feature map of pNOX is set forth in FIG. 13, while a restriction map of the vector is set forth in FIG. 14.

The pNOX-EGFP sequence is set forth below and is detailed in Table 4. EGFP sequences can optionally be replaced with sequences of another transgene (e.g., a gene encoding a CAR), if desired, using standard methods in the art.

pNOX-EGFP sequence
(SEQ ID NO: 51)

```
gcagactagtaagcttagtaatcaattacggggtcattagttcatagcccatatatggagttccgcgtta cataacttacggtaaatggcccgcctggctgaccgcccaacgacccccgcccattgacgtcaataatgac gtatgttcccatagtaacgccaatagggactttccattgacgtcaatgggtggagtatttacggtaaact gcccacttggcagtacatcaagtgtatcatatgccaagtacgccccctattgacgtcaatgacggtaaat ggcccgcctggcattatgcccagtacatgaccttatgggactttcctacttggcagtacatctacgtatt agtcatcgctattaccatgctgatgcggttttggcagtacatcaatgggcgtggatagcggtttgactca cggggatttccaagtctccaccccattgacgtcaatgggagtttgttttggcaccaaaatcaacgggact ttccaaaatgtcgtaacaactccgccccattgacgcaaatgggcggtaggcgtgtacggtgggaggtcta
```

-continued tataagcagagctggtttagtgaaccggggtctctctggttagaccagatctgagcctgggagctctctg gctaactagggaacccactgcttaagcctcaataaagcttgccttgagtgcttcaagtagtgtgtgcccg tctgttgtgtgactctggtaactagagatccctcagacccttttagtcagtgtggaaaatctctagcagt ggcgcccgaacagggacttgaaagcgaaagtaaagccagaggagatctctcgacgcaggactcggcttgc tgaagcgcgcacggcaagaggcgaggggcggcgactggtgagtacgccaaaaattttgactagcggaggc tagaaggagagagatgggtgcgagagcgtcggtattaagcggggagaattagataaatgggaaaaaatt cggtaataaggccaggggaaagaagaagtacaagctaaagcacatcgtatgggcaagcagggagctaga acgattcgcagttaatcctggccttttagagacatcagaaggcggccgctgatcttcagacctggaggag gcgatatgagggacaattggagaagtgaattatataaatataaagtagtaaaaattgaaccattaggagt agcacccaccaaggcaaagagaagagtggtgcagagagaaaaaagagcagtgggaatttaaataggagct ttgttccttgggttcttgggagcagcaggaagcactatgggcgcagcgtcaatgacgctgacggtacagg ccagacaattattgtctgatatagtgcagcagcagaacaatttgctgagggctattgaggcgcaacagca tctgttgcaactcacagtctggggcatcaaacagctccaggcaagaatcctggctgtggaaagataccta aaggatcaacagctcctcctgcaggggatttggggttgctctggaaaactcatttgcaccactgctgtgc cttggaatgctagttggagtaataaatctctggaacagatttggaataacatgacctggatggagtggga cagagaaattaacaattacacaagcttaatacactccttaattgaagaatcgcaaaaccagcaagaaaag aatgaacaagaattattggaattagataaatgggcaagtttgtggaattggtttaacataacaaattggc tgtggtatataaaattattcataatgatagtaggaggcttggtaggtttaagaatagttttgctgtact ttctatagtgaatagagttaggcagggatattcaccattatcgtttcagacccacctcccaatcccgagg ggacccgacaggcccgaaggaatagaagaagaaggtggagagagagacagagacagatccattcgattag tgaacggatctcgacggtatcgattagactgtagcccaggaatatggcagctagattgtacacatttaga aggaaaagttatcttggtagcagttcatgtagccagtggatatatagaagcagaagtaattccagcagag acagggcaagaaacagcatacttcctcttaaaattagcaggaagatggccagtaaaaacagtacatacag acaatggcagcaatttcaccagtactacagttaaggccgcctgttggtgggcggggatcaagcaggaatt tggcattccctacaatccccaaagtcaaggagtaatagaatctatgaataaagaattaaagaaaattata ggacaggtaagagatcaggctgaacatcttaagacagcagtacaaatggcagtattcatccacaatttta aaagaaaaggggggggattggggggtacagtgcaggggaaagaatagtagacataatagcaacagacataca aactaaagaattacaaaaacaaattacaaaaattcaaaattttcgggtttattacagggacagcagagat ccagtttggctgcattgatcacgtgaggctccggtgcccgtcagtgggcagagcgcacatcgcccacagt ccccgagaagttgggggggaggggtcggcaattgaaccggtgcctagagaaggtggcgcggggtaaactgg gaaagtgatgtcgtgtactggctccgccttttccccgagggtgggggagaaccgtatataagtgcagtag tcgccgtgaacgttctttttcgcaacgggtttgccgccagaacacaggtaagtgccgtgtgtggttcccg cgggcctggcctctttacggttatggcccttgcgtgccttgaattacttccacctggctgcagtacgtg attcttgatcccgagcttcgggttggaagtgggtgggagagttcgaggccttgcgcttaaggagcccctt cgcctcgtgcttgagttgaggcctggcctgggcgctgggccgccgcgtgcgaatctggtggcaccttcg cgcctgtctcgctgctttcgataagtctctagccatttaaaattttttgatgacctgctgcgacgctttt ttctggcaagatagtctttgtaaatgcgggccaagatctgcacactggtatttcggttttttggggccgcgg gcggcgacggggcccgtgcgtcccagcgcacatgttcggcgaggcggggcctgcgagcgcggccaccgag aatcggacgggggtagtctcaagctggccggcctgctctggtgcctggcctcgcgccgccgtgtatcgcc ccgccctgggcggcaaggctggcccggtcggcaccagttgcgtgagcggaaagatggccgcttcccggcc -continued

```
ctgctgcagggagctcaaaatggaggacgcggcgctcgggagagcgggcgggtgagtcacccacacaaag gaaaagggcctttccgtcctcagccgtcgcttcatgtgactccactgagtaccgggcgccgtccaggcac ctcgattagttctcgagcttttggagtacgtcgtctttaggttgggggaggggttttatgcgatggagt ttccccacactgagtgggtggagactgaagttaggccagcttggcacttgatgtaattctccttggaatt tgcccttttgagtttggatcttggttcattctcaagcctcagacagtggttcaaagttttttttcttcca tttcaggtgtcgtgatctagaggatccgccaccatggtgagcaagggcgaggagctgttcaccggggtgg tgcccatcctggtcgagctggacggcgactaaacggccacaagttcagcgtgtccggcgagggcgaggg cgatgccacctacggcaagctgaccctgaagttcatctgcaccaccggcaagctgcccgtgcctggccc accctcgtgaccacccctgacctacggcgtgcagtgcttcagccgctaccccgaccacatgaagcagcacg acttcttcaagtccgccatgcccgaaggctacgtccaggagcgcaccatcttcttcaaggacgacggcaa ctacaagacccgcgccgaggtgaagttcgagggcgacaccctggtgaaccgcatcgagctgaagggcatc gacttcaaggaggacggcaacatcctggggcacaagctggagtacaactacaacagccacaacgtctata tcatggccgacaagcagaagaacggcatcaaggtgaacttcaagatccgccacaacatcgaggacggcag cgtgcagctcgccgaccactaccagcagaacaccccatcggcgacggccccgtgctgctgcccgacaac cactacctgagcacccagtccgccctgagcaaagaccccaacgagaagcgcgatcacatggtcctgctgg agttcgtgaccgccgcgggatcactctcggcatggacgagctgtacaagtaagtcgactaaacaggcct attgattggaaagtatgtcaacgaattgtgggtcttttggggtttgctgccccttttacgcaatgtggat atcctgctttaatgcctttatatgcatgtatacaagcaaaacaggcttttactttctcgccaacttacaa ggcctttctaagtaaacagtatctgaccctttaccccgttgctcggcaacggcctggtctgtgccaagtg tttgctgacgcaaccccactggttggggcttggccataggccatcagcgcatgcgtggaacctttgtgt ctcctctgccgatccatactgcggaactcctagccgcttgttttgctcgcagcaggtctggagcgaaact catcgggactgacaattctgtcgtgctctcccgcaagtatacatcgtttccagggctgctaggctgtgct gccaactggatcctgcgcgggacgtcctttgtttacgtcccgtcggcgctgaatcccgcggacgacccct cccggggccgcttggggctctaccgcccgcttctccgtctgccgtaccgaccgaccacggggcgcacctc tctttacgcggactccccgtctgtgccttctcatctgccggaccgtgtgcacttcgcttcacctctgcac gtcgcatggagaccaccgtgaacgcccaccggaacctgcccaaggtcttgcataagaggactcttggact ttcagcaatgtcaacgaattcgagctcggtacctttaagaccaatgacttacaaggcagctgtagatctt agccacttttttaaaagaaaaggggggactggaagggctaattcactcccaacgaagacaagatctgctttt ttgcttgtactgggtctctctggttagaccagatctgagcctgggagctctctggctaactagggaaccc actgcttaagcctcaataaagcttgccttgagtgcttcaagtagtgtgtgcccgtctgttgtgtgactct ggtaactagagatccctcagacccttttagtcagtgtggaaaatctctagcagtagtagttcatgtcatc ttattattcagtatttataacttgcaaagaaatgaatatcagagagtgagaggaacttgtttattgcagc ttataatggttacaaataaagcaatagcatcacaaatttcacaaataaagcatttttttcactgcattct agttgtggtttgtccaaactcatcaatgtatcttatcatgtctggctctagctatcccgcccctaggcac cggggaaatgtgcgcggaacccctatttgtttatttttctaaatacattcaaatatgtatccgctcatga gacaataacctgataaatgcttcaataatattgaaaaaggaagagtatgagccatattcaacgggaaac gtcgaggccgcgattaaattccaacatggatgctgatttatatgggtataaatgggctcgcgataatgtc gggcaatcaggtgcgacaatctatcgcttgtatgggaagcccgatgcgccagagttgtttctgaaacatg gcaaaggtagcgttgccaatgatgttacagatgagatggtcagactaaactggctgacggaatttatgcc acttccgaccatcaagcattttatccgtactcctgatgatgcatggttactcaccactgcgatcccggga aaaacagcgttccaggtattagaagaatatcctgattcaggtgaaaatattgttgatgcgctggcagtgt
```

-continued

```
tcctgcgccggttgcactcgattcctgtttgtaattgtccttttaacagcgatcgcgtatttcgcctcgc tcaggcgcaatcacgaatgaataacggtttggttgatgcgagtgattttgatgacgagcgtaatggctgg cctgttgaacaagtctggaaagaaatgcataaacttttgccattctcaccggattcagtcgtcactcatg gtgatttctcacttgataaccttattttttgacgagggaaattaataggttgtattgatgttggacgagt cggaatcgcagaccgataccaggatcttgccatcctatggaactgcctcggtgagttttctccttcatta cagaaacggcttttcaaaaatatggtattgataatcctgatatgaataaattgcagtttcatttgatgc tcgatgagttttctaactgtcagaccaagtttactcatatatactttagattgatttaaaacttcattt ttaatttaaaaggatctaggtgaagatcctttttgataatctcatgaccaaaatcccttaacgtgagttt tcgttccactgagcgtcagacccgtagaaaagatcaaaggatcttcttgagatcctttttttctgcgcg taatctgctgcttgcaaacaaaaaaaccaccgctaccagcggtggtttgtttgccggatcaagagctacc aactcttttccgaaggtaactggcttcagcagagcgcagataccaaatactgttcttctagtgtagccg tagttaggccaccacttcaagaactctgtagcaccgcctacatacctcgctctgctaatcctgttaccag tggctgctgccagtggcgataagtcgtgtcttaccgggttggactcaagacgatagttaccggataaggc gcagcggtcgggctgaacggggggttcgtgcacacagcccagcttggagcgaacgacctacaccgaactg agatacctacagcgtgagctatgagaaagcgccacgcttcccgaagggagaaaggcggacaggtatccgg taagcggcagggtcggaacaggagagcgcacgagggagcttccaggggaaacgcctggtatctttatag tcctgtcgggtttcgccacctctgacttgagcgtcgatttttgtgatgctcgtcaggggggcggagccta tggaaaaacgccagcaacgcggcctttttacggttcctggccttttgctggccttttgctcacatgttct ttcctgcgttatcccctgattctgtggataaccgtattaccgcctttgagtgagctgataccgctcgccg cagccgaacgaccgagcgcagcgagtcagtgagcgaggaagcggaagagcgcccaatacgcaaaccgcct ctccccgcgcgttggccgattcattaatgcagctggcacgacaggtttcccgactggaaagcgggcagtg agcgcaacgcaattaatgtgagttagctcactcattaggcaccccaggctttacactttatgcttccggc tcgtatgttgtgtggaattgtgagcggataacaatttcacacaggaaacagctatgaccatgattacgcc aagcgcgcaattaaccctcactaaagggaacaaaagctggagct
```

Example 3. Viral Titers Generated Using the pCINS and pNOX Vectors

To determine the efficacy of the pCINS and pNOX lentiviral transfer vectors, a series of experiments was performed, in which one of the transfer vectors was introduced into cells using transient transfection of packaging cells. Briefly, Expi293™ cells (ThermoFischer) were grown in 5 ml of Freestyle (FS) medium at concentration 5 min/ml at 200 rpm, 37° C. and 8% $CO_2$, 80% humidity. Transfection was performed using PEIPro Transfer Reagent (PolyPlus) using 3 μg pNVS-MDLgp-RRE, 3 μg pNVS RSV Rev-Kan, 0.75 μg pNVS-MDG-VSVG-Kan, and 6 μg transfer vector (pCINS or pNOX). Viral supernatants were collected 48 hours after transfection and subjected to titer analysis (i.e., measurement of infectious titer).

In 293T cells, the pCINS plasmid transfer vector generated a viral titer approximately five times higher than that generated by the parental vector (FIG. 5A). Titer was evaluated based on percentage of GFP-positive cells. This unexpectedly strong viral production may be due to higher quantities of lentiviral genomic RNA generated by CMV promoter-mediated transcription in packaging cells (measured by qRT-PCR) and more efficient export of unspliced LV RNA from nucleus due to the absence of nuclear retention.

The pNOX transfer vector was able to generate similar or higher vector titers compared to pCINS (FIG. 5B-5D). Infectious titers were measured by GFP expression in transduced 293T cells, Jurkat T cells, and primary human T cells. In particular, pNOX generated similar levels of GFP expression to pCINS in 293T cells (FIG. 5B) and in primary human T cells (FIG. 5D), but actually yielded substantially greater quantities of GFP-expressing Jurkat cells relative to pCINS (FIG. 5C).

The level of transgene expression after genomic integration of elements from a lentiviral transfer vector was also examined. T cells were infected with viruses produced using the pNOX or pCINS transfer vectors, such that viral elements were integrated into the T cell genomes. The HPRE-containing lentiviral vector, pNOX, resulted in similar levels of transgene expressed compared to the WPRE-containing lentiviral vector, pCINS (FIG. 5 E). These results were surprising based on previous reports that WPRE (in pCINS) is more potent than HPRE (see, e.g., *J. Virol.* 72: 5085-5092, 1998; *Gene Therapy* 14, 1298-1304, 2007; each of which is incorporated herein by reference).

The invention includes the pCINS vector, as well as related vectors that include portions of the pCINS vector and/or sequences that share identity (e.g., at least 90%, 95%, 96%, 97%, 98%, 99%, or 100% identity with pCINS) with one or more sequences of pCINS. Sequences that may be included in such related vectors include all pCINS sequences, or subsets including, e.g., various combinations of the viral promoter (i.e., the promoter driving expression of the viral proteins), partial gag (e.g., lacking INS2, 3, and 4, and/or including an INS1 mutation as described herein), partial env, RRE, cPPT, subgenomic promoter (e.g., EF1alpha promoter, optionally including constitutive splice donor and splice acceptor sites as described herein), and PRE (optionally with an X protein inactivating mutation, as described herein) (these sequences each optionally have the sequence identities noted above). Such vectors may include a transgene (e.g., a gene encoding a CAR or EGFP, as described herein).

TABLE 3 pCINS Features

| Feature | Nucleic Acid Sequence | SEQ ID NO |
|---|---|---|
| CMV promoter | GTAATCAATTACGGGGTCATTAGTTCATAGCCCATATATGGAGTTCCGCGTTACA TAACTTACGGTAAATGGCCCGCCTGGCTGACCGCCCAACGACCCCCGCCCATTGA CGTCAATAATGACGTATGTTCCCATAGTAACGCCAATAGGGACTTTCCATTGACG TCAATGGGTGGAGTATTTACGGTAAACTGCCCACTTGGCAGTACATCAAGTGTAT CATATGCCAAGTACGCCCCCTATTGACGTCAATGACGGTAAATGGCCCGCCTGGC ATTATGCCCAGTACATGACCTTATGGGACTTTCCTACTTGGCAGTACATCTACGT ATTAGTCATCGCTATTACCATGCTGATGCGGTTTTGGCAGTACATCAATGGGCGT GGATAGCGGTTTGACTCACGGGGATTTCCAAGTCTCCACCCCATTGACGTCAATG GGAGTTTGTTTTGGCACCAAAATCAACGGGACTTTCCAAAATGTCGTAACAACTC CGCCCCATTGACGCAAATGGGCGGTAGGCGTGTACGGTGGGAGGTCTATATAAGC AGAGCTGGTTTAGTGAACCG | 52 |
| R | GGGTCTCTCTGGTTAGACCAGATCTGAGCCTGGGAGCTCTCTGGCTAACTAGGGA ACCCACTGCTTAAGCCTCAATAAAGCTTGCCTTGAGTGCTTC | 53 |
| U5 | AAGTAGTGTGTGCCCGTCTGTTGTGTGACTCTGGTAACTAGAGATCCCTCAGACC CTTTTAGTCAGTGTGGAAAATCTCTAGCAG | 54 |
| PBS | TGGCGCCCGAACAGGGAC | 55 |
| Packaging signal | TTGAAAGCGAAAGTAAAGCCAGAGGAGATCTCTCGACGCAGGACTCGGCTTGCTG AAGCGCGCACGGCAAGAGGCGAGGGGCGGCGACTGGTGAGTACGCCAAAAATTTT GACTAGCGGAGGCTAGAAGGAGAGAGATGGGTGCGAGAGCGTCGGTATTA | 56 |
| SD | ACTGGTGAGT (indicated in underlining in packaging signal sequence above) | 57 |
| Partial gag sequence (from NL4-3) with mutated INS signal | ATGGGTGCGAGAGCGTCGGTATTAAGCGGGGGAGAATTAGATAAATG GGAAAAAATTCGGTAATAAGGCCAGGGGGAAAGAAGAAGTACAAGCT AAAGCACATCGTATGGGCAAGCAGGGAGCTAGAACGATTCGCAGTTA ATCCTGGCCTTTTAGAGACATCAGAAG | 58 |
| NotI restriction site | *GCGGCCGC* | 59 |
| Partial env sequence | TGATCTTCAGACCTGGAGGAGGCGATATGAGGGACAATTGGAGAAGT GAATTATATAAATATAAAGTAGTAAAAATTGAACCATTAGGAGTAGCAC CCACCAAGGCAAAGAGAAGAGTGGTGCAGAGAGAAAAAAGAGCAGT GGGA | 60 |
| SwaI restriction site | *ATTTAAAT* | 61 |
| RRE | AGGAGCTTTGTTCCTTGGGTTCTTGGGAGCAGCAGGAAGCACTATGGGCGCAGCG TCAATGACGCTGACGGTACAGGCCAGACAATTATTGTCTGATATAGTGCAGCAGC AGAACAATTTGCTGAGGGCTATTGAGGCGCAACAGCATCTGTTGCAACTCACAGT CTGGGGCATCAAACAGCTCCAGGCAAGAATCCTGGCTGTGGAAAGATACCTAAAG GATCAACAGCTCCT | 62 |
| SbfI restriction site | *ATTTAAAT* | 63 |
| Partial env sequence containing splice acceptor SA7 | GGATTTGGGGTTGCTCTGGAAAACTCATTTGCACCACTGCTGTGCCT TGGAATGCTAGTTGGAGTAATAAATCTCTGGAACAGATTTGGAATAAC ATGACCTGGATGGAGTGGGACAGAGAAATTAACAATTACACAAGCTT AATACACTCCTTAATTGAAGAATCGCAAAACCAGCAAGAAAGAATGA ACAAGAATTATTGGAATTAGATAAATGGGCAAGTTTGTGGAATTGGTT TAACATAACAAATTGGCTGTGGTATATAAAATTATTCATAATGATAGTA GGAGGCTTGGTAGGTTTAAGAATAGTTTTTGCTGTACTTTCTATAGTG | 64 |

TABLE 3 -continued pCINS Features

| Feature | Nucleic Acid Sequence | SEQ ID NO |
|---|---|---|
| | AATAGAGTTAGGCAGGGATATTCACCATTATCGTTTCAGACCCACCT<br>CCCAATCCCGAGGGGACCCGACAGGCCCGAAGGAATAGAAGAAGAA<br>GGTGGAGAGAGAGACAGAGACAGATCCATTCGATTAGTGAACGGATC<br>TCGACGGT | |
| SA7 | AGTTAGGCAGGGATATTCACCATTATCGTTTCAGAC | 65 |
| ClaI restriction site | *ATCGAT* | 66 |
| cPPT | TAGACTGTAGCCCAGGAATATGGCAGCTAGATTGTACACATTTAGAAGGAAAAGT<br>TATCTTGGTAGCAGTTCATGTAGCCAGTGGATATATAGAAGCAGAAGTAATTCCA<br>GCAGAGACAGGGCAAGAAACAGCATACTTCCTCTTAAAATTAGCAGGAAGATGGC<br>CAGTAAAAACAGTACATACAGACAATGGCAGCAATTTCACCAGTACTACAGTTAA<br>GGCCGCCTGTTGGTGGGCGGGGATCAAGCAGGAATTTGGCATTCCCTACAATCCC<br>CAAAGTCAAGGAGTAATAGAATCTATGAATAAAGAATTAAAGAAAATTATAGGAC<br>AGGTAAGAGATCAGGCTGAACATCTTAAGACAGCAGTACAAATGGCAGTATTCAT<br>CCACAATTTTAAAAGAAAAGGGGGGATTGGGGGGTACAGTGCAGGGGAAAGAATA<br>GTAGACATAATAGCAACAGACATACAAACTAAAGAATTACAAAAACAAATTACAA<br>AAATTCAAAATTTTCGGGTTTATTACAGGGACAGCAGAGATCCAGTTTGGCT | 67 |
| SA1 | GTTTATTACAGGGACAGCAGAGATCCAGTTTGG<br>(indicated in underlining in cppt sequence above) | 68 |
| Blunted PstI restriction site | *CTGCAT* | 69 |
| BclI restriction site | *TGATCA* | 70 |
| EF1a promoter | CGTGAGGCTCCGGTGCCCGTCAGTGGGCAGAGCGCACATCGCCCACAGTCCCCGA<br>GAAGTTGGGGGGAGGGGTCGGCAATTGAACCGGTGCCTAGAGAAGGTGGCGCGGG<br>GTAAACTGGGAAAGTGATGTCGTGTACTGGCTCCGCCTTTTTCCCGAGGGTGGGG<br>GAGAACCGTATATAAGTGCAGTAGTCGCCGTGAACGTTCTTTTTCGCAACGGGTT<br>TGCCGCCAGAACACAGGTAAGTGCCGTGTGTGGTTCCCGCGGGCCTGGCCTCTTT<br>ACGGGTTATGGCCCTTGCGTGCCTTGAATTACTTCCACCTGGCTGCAGTACGTGA<br>TTCTTGATCCCGAGCTTCGGGTTGGAAGTGGGTGGGAGAGTTCGAGGCCTTGCGC<br>TTAAGGAGCCCCTTCGCCTCGTGCTTGAGTTGAGGCCTGGCCTGGGCGCTGGGGC<br>CGCCGCGTGCGAATCTGGTGGCACCTTCGCGCCTGTCTCGCTGCTTTCGATAAGT<br>CTCTAGCCATTTAAAATTTTTGATGACCTGCTGCGACGCTTTTTTTCTGGCAAGA<br>TAGTCTTGTAAATGCGGGCCAAGATCTGCACACTGGTATTTCGGTTTTTGGGGCC<br>GCGGGCGGCGACGGGGCCCGTGCGTCCCAGCGCACATGTTCGGCGAGGCGGGGCC<br>TGCGAGCGCGGCCACCGAGAATCGGACGGGGGTAGTCTCAAGCTGGCCGGCCTGC<br>TCTGGTGCCTGGCCTCGCGCCGCCGTGTATCGCCCCGCCCTGGGCGGCAAGGCTG<br>GCCCGGTCGGCACCAGTTGCGTGAGCGGAAAGATGGCCGCTTCCCGGCCCTGCTG<br>CAGGGAGCTCAAATGGAGGACGCGGCGCTCGGGAGAGCGGGCGGGTGAGTCACC<br>CACACAAAGGAAAAGGGCCTTTCCGTCCTCAGCCGTCGCTTCATGTGACTCCACT<br>GAGTACCGGGCGCCGTCCAGGCACCTCGATTAGTTCTCGAGCTTTTGGAGTACGT<br>CGTCTTTAGGTTGGGGGGAGGGGTTTTATGCGATGGAGTTTCCCCACACTGAGTG<br>GGTGGAGACTGAAGTTAGGCCAGCTTGGCACTTGATGTAATTCTCCTTGGAATTT<br>GCCCTTTTTGAGTTTGGATCTTGGTTCATTCTCAAGCCTCAGACAGTGGTTCAAA<br>GTTTTTTTCTTCCATTTCAGGTGTCGTGA | 71 |
| Constitutive splice donor (CD) | CAGAACACAGGTAAGTGCCG<br>(indicated by underlining in P-EF1a sequence above) | 72 |
| Constitutive splice acceptor (CA) | TCCATTTCAGGTGTCGTGA<br>(indicated by underlining in P-EF1a sequence above) | 73 |
| XbaI restriction site | *TCTAGA* | 74 |
| BamHI restriction site | *GGATCC* | 75 |

TABLE 3 -continued pCINS Features

| Feature | Nucleic Acid Sequence | SEQ ID NO |
|---|---|---|
| EGFP | ATGGTGAGCAAGGGCGAGGAGCTGTTCACCGGGGTGGTGCCCATCCTGGTCGAGC TGGACGGCGACGTAAACGGCCACAAGTTCAGCGTGTCCGGCGAGGGCGAGGGCGA TGCCACCTACGGCAAGCTGACCCTGAAGTTCATCTGCACCACCGGCAAGCTGCCC GTGCCCTGGCCCACCCTCGTGACCACCCTGACCTACGGCGTGCAGTGCTTCAGCC GCTACCCCGACCACATGAAGCAGCACGACTTCTTCAAGTCCGCCATGCCCGAAGG CTACGTCCAGGAGCGCACCATCTTCTTCAAGGACGACGGCAACTACAAGACCCGC GCCGAGGTGAAGTTCGAGGGCGACACCCTGGTGAACCGCATCGAGCTGAAGGGCA TCGACTTCAAGGAGGACGGCAACATCCTGGGGCACAAGCTGGAGTACAACTACAA CAGCCACAACGTCTATATCATGGCCGACAAGCAGAAGAACGGCATCAAGGTGAAC TTCAAGATCCGCCACAACATCGAGGACGGCAGCGTGCAGCTCGCCGACCACTACC AGCAGAACACCCCCATCGGCGACGGCCCCGTGCTGCTGCCCGACAACCACTACCT GAGCACCCAGTCCGCCCTGAGCAAAGACCCCAACGAGAAGCGCGATCACATGGTC CTGCTGGAGTTCGTGACCGCCGCCGGGATCACTCTCGGCATGGACGAGCTGTACA AGTAA | 76 |
| SalI restriction site | GTCGAC | 77 |
| WPRE | ATCAACCTCTGGATTACAAAATTTGTGAAAGATTGACTGGTATTCTTAACTATGT TGCTCCTTTTACGCTATGTGGATACGCTGCTTTAATGCCTTTGTATCATGCTATT GCTTCCCGTATGGCTTTCATTTTCTCCTCCTTGTATAAATCCTGGTTGCTGTCTC TTTATGAGGAGTTGTGGCCCGTTGTCAGGCAACGTGGCGTGGTGTGCACTGTGTT TGCTGACGCAACCCCCACTGGTTGGGGCATTGCCACCACCTGTCAGCTCCTTTCC GGGACTTTCGCTTTCCCCCTCCCTATTGCCACGGCGGAACTCATCGCCGCCTGCC TTGCCCGCTGCTGGACAGGGGCTCGGCTGTTGGGCACTGACAATTCCGTGGTGTT GTCGGGGAAGCTGACGTCCTTTCCATGGCTGCTCGCCTGTGTTGCCACCTGGATT CTGCGCGGGACGTCCTTCTGCTACGTCCCTTCGGCCCTCAATCCAGCGGACCTTC CTTCCCGCGGCCTGCTGCCGGCTCTGCGGCCTCTTCCGCGTCTTCGCCTTCGCCC TCAGACGAGTCGGATCTCCCTTTGGGCCGCCTCCCCGCCTG | 78 |
| EcoRI restriction site | *GAATTC* | 80 |
| SacI restriction site | *GAGCTC* | 81 |
| KpnI restriction site | *GGTACC* | 82 |
| Partial Nef sequence, containing PPT | CTTTAAGACCAATGACTTACAAGGCAGCTGTAGATCTTAGCCACTTTT TAAAAGAAAAGGGGGG | 83 |
| dU3 | ACTGGAAGGGCTAATTCACTCCCAACGAAGACAAGATCTGCTTTTTGC TTGTACT | 84 |
| R | GGGTCTCTCTGGTTAGACCAGATCTGAGCCTGGGAGCTCTCTGGCTAACTAGGGA ACCCACTGCTTAAGCCTCAATAAAGCTTGCCTTGAGTGCTTC | 85 |
| U5 | AAGTAGTGTGTGCCCGTCTGTTGTGTGACTCTGGTAACTAGAGATCCCTCAGACC CTTTTAGTCAGTGTGGAAAATCTCTAGCAG | 66 |
| SV40 polyA | AACTTGTTTATTGCAGCTTATAATGGTTACAAATAAAGCAATAGCATCACAAATT TCACAAATAAAGCATTTTTTTCACTGCATTCTAGTTGTGGTTTGTCCAAACTCAT CAATGTATCTTATCATGTC | 87 |
| nptlI | ATGAGCCATATTCAACGGGAAACGTCGAGGCCGCGATTAAATTCCAACATGGATG CTGATTTATATGGGTATAAATGGGCTCGCGATAATGTCGGGCAATCAGGTGCGAC AATCTATCGCTTGTATGGGAAGCCCGATGCGCCAGAGTTGTTTCTGAAACATGGC AAAGGTAGCGTTGCCAATGATGTTACAGATGAGATGGTCAGACTAAACTGGCTGA CGGAATTTATGCCACTTCCGACCATCAAGCATTTTATCCGTACTCCTGATGATGC ATGGTTACTCACCACTGCGATCCCCGGAAAAACAGCGTTCCAGGTATTAGAAGAA TATCCTGATTCAGGTGAAAATATTGTTGATGCGCTGGCAGTGTTCCTGCGCCGGT TGCACTCGATTCCTGTTTGTAATTGTCCTTTTAACAGCGATCGCGTATTTCGCCT CGCTCAGGCGCAATCACGAATGAATAACGGTTTGGTTGATGCGAGTGATTTTGAT GACGAGCGTAATGGCTGGCCTGTTGAACAAGTCTGGAAAGAAATGCATAAACTTT | 88 |

TABLE 3 -continued pCINS Features

| Feature | Nucleic Acid Sequence | SEQ ID NO |
|---|---|---|
|  | TGCCATTCTCACCGGATTCAGTCGTCACTCATGGTGATTTCTCACTTGATAACCT TATTTTTGACGAGGGGAAATTAATAGGTTGTATTGATGTTGGACGAGTCGGAATC GCAGACCGATACCAGGATCTTGCCATCCTATGGAACTGCCTCGGTGAGTTTTCTC CTTCATTACAGAAACGGCTTTTTCAAAAATATGGTATTGATAATCCTGATATGAA TAAATTGCAGTTTCATTTGATGCTCGATGAGTTTTTCTAA |  |
| pUC ori | AGATCAAAGGATCTTCTTGAGATCCTTTTTTTCTGCGCGTAATCTGCTGCTTGCA AACAAAAAAACCACCGCTACCAGCGGTGGTTTGTTTGCCGGATCAAGAGCTACCA ACTCTTTTTCCGAAGGTAACTGGCTTCAGCAGAGCGCAGATACCAAATACTGTTC TTCTAGTGTAGCCGTAGTTAGGCCACCACTTCAAGAACTCTGTAGCACCGCCTAC ATACCTCGCTCTGCTAATCCTGTTACCAGTGGCTGCTGCCAGTGGCGATAAGTCG TGTCTTACCGGGTTGGACTCAAGACGATAGTTACCGGATAAGGCGCAGCGGTCGG GCTGAACGGGGGGTTCGTGCACACAGCCCAGCTTGGAGCGAACGACCTACACCGA ACTGAGATACCTACAGCGTGAGCTATGAGAAAGCGCCACGCTTCCCGAAGGGAGA AAGGCGGACAGGTATCCGGTAAGCGGCAGGGTCGGAACAGGAGAGCGCACGAGGG AGCTTCCAGGGGGAAACGCCTGGTATCTTTATAGTCCTGTCGGGTTTCGCCACCT CTGACTTGAGCGTCGATTTTTGTGATGCTCGTCAGGGGGGCGGAGCCTATGGAAA AACGCCAGCAACGCG | 89 |

The invention includes the pNOX vector, as well as related vectors that include portions of the pNOX vector and/or sequences that share identity (e.g., at least 90%, 95%, 96%, 97%, 98%, 99%, or 100% identity with pNOX) with one or more sequences of pNOX. Sequences that may be included in such related vectors include all pNOX sequences, or subsets including, e.g., various combinations of the viral promoter (i.e., the promoter driving expression of the viral proteins), partial gag (e.g., lacking INS2, 3, and 4, and/or including an INS1 mutation as described herein), partial env, RRE, cPPT, subgenomic promoter (e.g., EF1alpha promoter, optionally including constitutive splice donor and splice acceptor sites as described herein), and PRE (optionally with an X protein inactivating mutation, as described herein) (these sequences each optionally have the sequence identities noted above). Such vectors may include a transgene (e.g., a gene encoding a CAR or EGFP, as described herein).

TABLE 4 pNOX Features

| Feature | Nucleic Acid Sequence | SEQ ID NO |
|---|---|---|
| CMV promoter | GTAATCAATTACGGGGTCATTAGTTCATAGCCCATATATGGAGTTCCGCGTTACA TAACTTACGGTAAATGGCCCGCCTGGCTGACCGCCCAACGACCCCCGCCCATTGA CGTCAATAATGACGTATGTTCCCATAGTAACGCCAATAGGGACTTTCCATTGACG TCAATGGGTGGAGTATTTACGGTAAACTGCCCACTTGGCAGTACATCAAGTGTAT CATATGCCAAGTACGCCCCCTATTGACGTCAATGACGGTAAATGGCCCGCCTGGC ATTATGCCCAGTACATGACCTTATGGGACTTTCCTACTTGGCAGTACATCTACGT ATTAGTCATCGCTATTACCATGCTGATGCGGTTTTGGCAGTACATCAATGGGCGT GGATAGCGGTTTGACTCACGGGGATTTCCAAGTCTCCACCCCATTGACGTCAATG GGAGTTTGTTTTGGCACCAAAATCAACGGGACTTTCCAAAATGTCGTAACAACTC CGCCCCATTGACGCAAATGGGCGGTAGGCGTGTACGGTGGGAGGTCTATATAAGC AGAGCTGGTTTAGTGAACCG | 52 |
| R | GGGTCTCTCTGGTTAGACCAGATCTGAGCCTGGGAGCTCTCTGGCTAACTAGGGA ACCCACTGCTTAAGCCTCAATAAAGCTTGCCTTGAGTGCTTC | 53 |
| U5 | AAGTAGTGTGTGCCCGTCTGTTGTGTGACTCTGGTAACTAGAGATCCCTCAGACC CTTTTAGTCAGTGTGGAAAATCTCTAGCAG | 54 |
| PBS | TGGCGCCCGAACAGGGAC | 55 |
| Packaging signal | TTGAAAGCGAAAGTAAAGCCAGAGGAGATCTCTCGACGCAGGACTCGGCTTGCTG AAGCGCGCACGGCAAGAGGCGAGGGGCGGCACTGGTGAGTACGCCAAAAATTTT GACTAGCGGAGGCTAGAAGGAGAGAGATGGGTGCGAGAGCGTCGGTATTA | 56 |
| SD | ACTGGTGAGT (indicated in underlining in packaging signal sequence above) | 57 |
| Partial gag sequence (from NL4-3) with mutated INS signal | ATGGGTGCGAGAGCGTCGGTATTAAGCGGGGGAGAATTAGATAAATGGGAAAAAA TTCGGTAATAAGGCCAGGGGGAAAGAAGAAGTACAAGCTAAAGCACATCGTATGG GCAAGCAGGGAGCTAGAACGATTCGCAGTTAATCCTGGCCTTTTAGAGACATCAG AAG | 58 |

TABLE 4 -continued pNOX Features

| Feature | Nucleic Acid Sequence | SEQ ID NO |
|---|---|---|
| NotI restriction site | GCGGCCGC | 59 |
| Partial env sequence | TGATCTTCAGACCTGGAGGAGGCGATATGAGGGACAATTGGAGAAGTGAATTATA TAAATATAAAGTAGTAAAAATTGAACCATTAGGAGTAGCACCCACCAAGGCAAAG AGAAGAGTGGTGCAGAGAGAAAAAAGAGCAGTGGGA | 60 |
| SwaI restriction site | ATTTAAAT | 61 |
| RRE | AGGAGCTTTGTTCCTTGGGTTCTTGGGAGCAGCAGGAAGCACTATGGGCGCAGCG TCAATGACGCTGACGGTACAGGCCAGACAATTATTGTCTGATATAGTGCAGCAGC AGAACAATTTGCTGAGGGCTATTGAGGCGCAACAGCATCTGTTCAACTCACAGT CTGGGGCATCAAACAGCTCCAGGCAAGAATCCTGGCTGTGGAAAGATACCTAAAG GATCAACAGCTCCT | 62 |
| SbfI restriction site | CCTGCAGG | 63 |
| Partial env sequence containing splice acceptor 5A7 | GGATTTGGGGTTGCTCTGGAAAACTCATTTGCACCACTGCTGTGCCT TGGAATGCTAGTTGGAGTAATAAATCTCTGGAACAGATTTGGAATAAC ATGACCTGGATGGAGTGGGACAGAGAAATTAACAATTACACAAGCTT AATACACTCCTTAATTGAAGAATCGCAAAACCAGCAAGAAAAGAATGA ACAAGAATTATTGGAATTAGATAAATGGGCAAGTTTGTGGAATTGGTT TAACATAACAAATTGGCTGTGGTATATAAAATTATTCATAATGATAGTA GGAGGCTTGGTAGGTTTAAGAATAGTTTTTGCTGTACTTTCTATAGTG AATAGAAGTTAGGCAGGGATATTCACCATTATCGTTTCAGACCCACCT CCCAATCCCGAGGGGACCCGACAGGCCCGAAGGAATAGAAGAAGAA GGTGGAGAGAGAGACAGAGACAGATCCATTCGATTAGTGAACGGATC TCGACGGT | 64 |
| SA7 | AGTTAGGCAGGGATATTCACCATTATCGTTTCAGAC | 65 |
| ClaI restriction site | ATCGAT | 66 |
| cPPT | TAGACTGTAGCCCAGGAATATGGCAGCTAGATTGTACACATTTAGAAGGAAAAGT TATCTTGGTAGCAGTTCATGTAGCCAGTGGATATATAGAAGCAGAAGTAATTCCA GCAGAGACAGGGCAAGAAACAGCATACTTCCTCTTAAAATTAGCAGGAAGATGGC CAGTAAAAACAGTACATACAGACAATGGCAGCAATTTCACCAGTACTACAGTTAA GGCCGCCTGTTGGTGGGCGGGATCAAGCAGGAATTTGGCATTCCCTACAATCCC CAAAGTCAAGGAGTAATAGAATCTATGAATAAAGAATTAAAGAAAATTATAGGAC AGGTAAGAGATCAGGCTGAACATCTTAAGACAGCAGTACAAATGGCAGTATTCAT CCACAATTTTAAAAGAAAAGGGGGGATTGGGGGGTACAGTGCAGGGGAAAGAATA GTAGACATAATAGCAACAGACATACAAACTAAAGAATTACAAAAACAAATTACAA AAATTCAAAATTTTCGGGTTTATTACAGGGACAGCAGAGATCCAGTTTGGCT | 67 |
| SA1 | GTTTATTACAGGGACAGCAGAGATCCAGTTTGG (indicated in underlining in cppt sequence above) | 68 |
| Blunted PstI restriction site | CTGCAT | 69 |
| BclI restriction site | TGATCA | 70 |
| EF1a promoter | CGTGAGGCTCCGGTGCCCGTCAGTGGGCAGAGCGCACATCGCCCACAGTCCCCGA GAAGTTGGGGGGAGGGGTCGGCAATTGAACCGGTGCCTAGAGAAGGTGGCGCGGG GTAAACTGGGAAAGTGATGTCGTGTACTGGCTCCGCCTTTTTCCCGAGGGTGGGG GAGAACCGTATATAAGTGCAGTAGTCGCCGTGAACGTTCTTTTTCGCAACGGGTT TGCCGCCAGAACACAGGTAAGTGCCGTGTGTGGTTCCCGCGGGCCTGGCCTCTTT ACGGGTTATGGCCCTTGCGTGCCTTGAATTACTTCCACCTGGCTGCAGTACGTGA TTCTTGATCCCGAGCTTCGGGTTGGAAGTGGGTGGGAGAGTTCGAGGCCTTGCGC TTAAGGAGCCCCTTCGCCTCGTGCTTGAGTTGAGGCCTGGCCTGGGCGCTGGGGC CGCCGCGTGCGAATCTGGTGGCACCTTCGCGCCTGTCTCGCTGCTTTCGATAAGT CTCTAGCCATTTAAAATTTTTGATGACCTGCTGCGACGCTTTTTTTCTGGCAAGA TAGTCTTGTAAATGCGGGCCAAGATCTGCACACTGGTATTTCGGTTTTTGGGGCC GCGGGCGGCGACGGGGCCCGTGCGTCCCAGCGCACATGTTCGGCGAGGCGGGGCC TGCGAGCGCGGCCACCGAGAATCGGACGGGGGTAGTCTCAAGCTGGCCGGCCTGC | 71 |

TABLE 4 -continued pNOX Features

| Feature | Nucleic Acid Sequence | SEQ ID NO |
|---|---|---|
| | TCTGGTGCCTGGCCTCGCGCCGCCGTGTATCGCCCCGCCCTGGGCGGCAAGGCTG<br>GCCCGGTCGGCACCAGTTGCGTGAGCGGAAAGATGGCCGCTTCCCGGCCCTGCTG<br>CAGGGGAGCTCAAAATGGAGGACGCGGCGCTCGGGAGAGCGGGCGGGTGAGTCACC<br>CACACAAAGGAAAAGGGCCTTTCCGTCCTCAGCCGTCGCTTCATGTGACTCCACT<br>GAGTACCGGGCGCCGTCCAGGCACCTCGATTAGTTCTCGAGCTTTTGGAGTACGT<br>CGTCTTTAGGTTGGGGGGAGGGGTTTTATGCGATGGAGTTTCCCCACACTGAGTG<br>GGTGGAGACTGAAGTTAGGCCAGCTTGGCACTTGATGTAATTCTCCTTGGAATTT<br>GCCCTTTTTGAGTTTGGATCTTGGTTCATTCTCAAGCCTCAGACAGTGGTTCAAA<br>GTTTTTTTCTTCCATTTCAGGTGTCGTGA | |
| Constitutive splice donor (CD) | CAGAACACAGGTAAGTGCCG<br>(indicated by underlining in P-EF1a sequence above) | 72 |
| Constitutive splice acceptor (CA) | TCCATTTCAGGTGTCGTGA<br>(indicated by underlining in P-EF1a sequence above) | 73 |
| XbaI restriction site | *TCTAGA* | 74 |
| BamHI restriction site | *GGATCC* | 75 |
| EGFP | ATGGTGAGCAAGGGCGAGGAGCTGTTCACCGGGGTGGTGCCCATCCTGGTCGAGC<br>TGGACGGCGACGTAAACGGCCACAAGTTCAGCGTGTCCGGCGAGGGCGAGGGCGA<br>TGCCACCTACGGCAAGCTGACCCTGAAGTTCATCTGCACCACCGGCAAGCTGCCC<br>GTGCCCTGGCCCACCCTCGTGACCACCCTGACCTACGGCGTGCAGTGCTTCAGCC<br>GCTACCCCGACCACATGAAGCAGCACGACTTCTTCAAGTCCGCCATGCCCGAAGG<br>CTACGTCCAGGAGCGCACCATCTTCTTCAAGGACGACGGCAACTACAAGACCCGC<br>GCCGAGGTGAAGTTCGAGGGCGACACCCTGGTGAACCGCATCGAGCTGAAGGGCA<br>TCGACTTCAAGGAGGACGGCAACATCCTGGGGCACAAGCTGGAGTACAACTACAA<br>CAGCCACAACGTCTATATCATGGCCGACAAGCAGAAGAACGGCATCAAGGTGAAC<br>TTCAAGATCCGCCACAACATCGAGGACGGCAGCGTGCAGCTCGCCGACCACTACC<br>AGCAGAACACCCCCATCGGCGACGGCCCCGTGCTGCTGCCCGACAACCACTACCT<br>GAGCACCCAGTCCGCCCTGAGCAAAGACCCCAACGAGAAGCGCGATCACATGGTC<br>CTGCTGGAGTTCGTGACCGCCGCCGGGATCACTCTCGGCATGGACGAGCTGTACA<br>AGTAA | 76 |
| SalI restriction site | GTCGAC | 77 |
| HPRE NoX | TAAACAGGCCTATTGATTGGAAAGTATGTCAACGAATTGTGGGTCTTTTGGGGTT<br>TGCTGCCCCTTTTACGCAATGTGGATATCCTGCTTTAATGCCTTTATATGCATGT<br>ATACAAGCAAAACAGGCTTTTACTTTCTCGCCAACTTACAAGGCCTTTCTAAGTA<br>AACAGTATCTGACCCTTTACCCCGTTGCTCGGCAACGGCCTGGTCTGTGCCAAGT<br>GTTTGCTGACGCAACCCCCACTGGTTGGGGCTTGGCCATAGGCCATCAGCGCATG<br>CGTGGAACCTTTGTGTCTCCTCTGCCGATCCATACTGCGGAACTCCTAGCCGCTT<br>GTTTTGCTCGCAGCAGGTCTGGAGCGAAACTCATCGGGACTGACAATTCTGTCGT<br>GCTCTCCCGCAAGTATACATCGTTTC<u>A</u>GGGCTGCTAGGCTGTGCTGCCAACTGG<br>ATCCTGCGCGGGACGTCCTTTGTTTAC<u>G</u>TCCCGTCGGCGCTGAATCCCGCGGACG<br>ACCCCTCCCGGGGCCGCTTGGGGCTCTACCGCCCGCTTCTCCGTCTGCCGTACCG<br>ACCGACCACGGGGCGCACCTCTCTTTACGCGGACTCCCCGTCGTGCCTTCTCAT<br>CTGCCGGACCGTGTGCACTTCGCTTCACCTCTGCACGTCGCATGGAGACCACCGT<br>GAACGCCCACCGGAACCTGCCCAAGGTCTTGCATAAGAGGACTCTTGGACTTTCA<br>GCAATGTCAAC<br>(underlined codon is mutated ATG/AGG codon of X protein ORF) | 79 |
| EcoRI restriction site | *GAATTC* | 80 |
| SacI restriction site | *GAGCTC* | 81 |
| KpnI restriction site | *GGTACC* | 82 |

TABLE 4 -continued pNOX Features

| Feature | Nucleic Acid Sequence | SEQ ID NO |
|---|---|---|
| Partial Nef sequence, containing PPT | CTTTAAGACCAATGACTTACAAGGCAGCTGTAGATCTTAGCCACTTTT TAAAAGAAAAGGGGGG | 83 |
| dU3 | ACTGGAAGGGCTAATTCACTCCCAACGAAGACAAGATCTGCTTTTTGC TTGTACT | 84 |
| R | GGGTCTCTCTGGTTAGACCAGATCTGAGCCTGGGAGCTCTCTGGCTAACTAGGGA ACCCACTGCTTAAGCCTCAATAAAGCTTGCCTTGAGTGCTTC | 85 |
| U5 | AAGTAGTGTGTGCCCGTCTGTTGTGTGACTCTGGTAACTAGAGATCCCTCAGACC CTTTTAGTCAGTGTGGAAAATCTCTAGCAG | 86 |
| SV40 polyA | AACTTGTTTATTGCAGCTTATAATGGTTACAAATAAAGCAATAGCATCACAAATT TCACAAATAAAGCATTTTTTTCACTGCATTCTAGTTGTGGTTTGTCCAAACTCAT CAATGTATCTTATCATGTC | 87 |
| nptII | ATGAGCCATATTCAACGGGAAACGTCGAGGCCGCGATTAAATTCCAACATGGATG CTGATTTATATGGGTATAAATGGGCTCGCGATAATGTCGGGCAATCAGGTGCGAC AATCTATCGCTTGTATGGGAAGCCCGATGCGCCAGAGTTGTTTCTGAAACATGGC AAAGGTAGCGTTGCCAATGATGTTACAGATGAGATGGTCAGACTAAACTGGCTGA CGGAATTTATGCCACTTCCGACCATCAAGCATTTTATCCGTACTCCTGATGATGC ATGGTTACTCACCACTGCGATCCCCGGAAAAACAGCGTTCCAGGTATTAGAAGAA TATCCTGATTCAGGTGAAAATATTGTTGATGCGCTGGCAGTGTTCCTGCGCCGGT TGCACTCGATTCCTGTTTGTAATTGTCCTTTTAACAGCGATCGCGTATTTCGCCT CGCTCAGGCGCAATCACGAATGAATAACGGTTTGGTTGATGCGAGTGATTTTGAT GACGAGCGTAATGGCTGGCCTGTTGAACAAGTCTGGAAAGAAATGCATAAACTTT TGCCATTCTCACCGGATTCAGTCGTCACTCATGGTGATTTCTCACTTGATAACCT TATTTTTGACGAGGGGAAATTAATAGGTTGTATTGATGTTGGACGAGTCGGAATC GCAGACCGATACCAGGATCTTGCCATCCTATGGAACTGCCTCGGTGAGTTTTCTC CTTCATTACAGAAACGGCTTTTTCAAAAATATGGTATTGATAATCCTGATATGAA TAAATTGCAGTTTCATTTGATGCTCGATGAGTTTTTCTAA | 88 |
| pUC on | AGATCAAAGGATCTTCTTGAGATCCTTTTTTTCTGCGCGTAATCTGCTGCTTGCA AACAAAAAAACCACCGCTACCAGCGGTGGTTTGTTTGCCGGATCAAGAGCTACCA ACTCTTTTTCCGAAGGTAACTGGCTTCAGCAGAGCGCAGATACCAAATACTGTTC TTCTAGTGTAGCCGTAGTTAGGCCACCACTTCAAGAACTCTGTAGCACCGCCTAC ATACCTCGCTCTGCTAATCCTGTTACCAGTGGCTGCTGCCAGTGGCGATAAGTCG TGTCTTACCGGGTTGGACTCAAGACGATAGTTACCGGATAAGGCGCAGCGGTCGG GCTGAACGGGGGGTTCGTGCACACAGCCCAGCTTGGAGCGAACGACCTACACCGA ACTGAGATACCTACAGCGTGAGCTATGAGAAAGCGCCACGCTTCCCGAAGGGAGA AAGGCGGACAGGTATCCGGTAAGCGGCAGGGTCGGAACAGGAGAGCGCACGAGGG AGCTTCCAGGGGGAAACGCCTGGTATCTTTATAGTCCTGTCGGGTTTCGCCACCT CTGACTTGAGCGTCGATTTTTGTGATGCTCGTCAGGGGGCGGAGCCTATGGAAA AACGCCAGCAACGCG | 89 |

Example 4. Generation of the pNLV Transfer Vector

Figure 13:
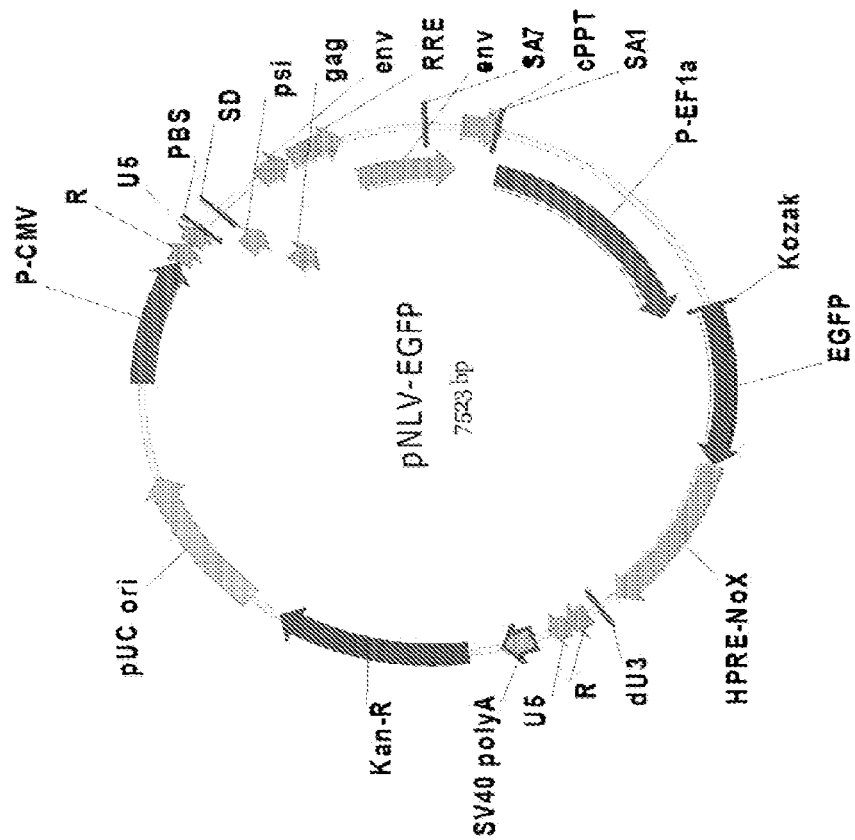
FIG. 13 is a schematic showing a feature map of the pNLV lentiviral transfer vector.
Figure 14:
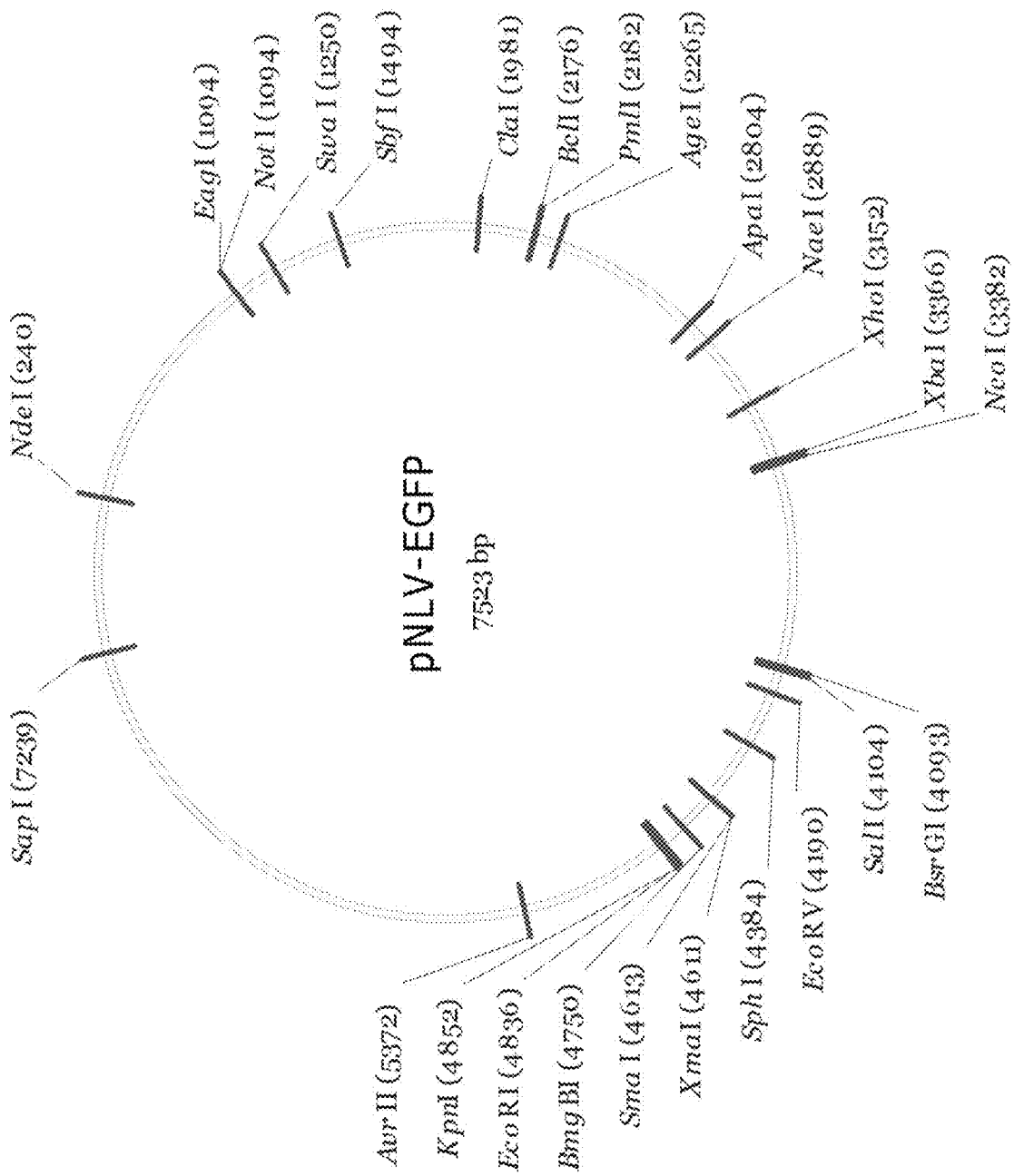
FIG. 14 is a schematic showing the restriction map of the pNLV lentiviral transfer vector, including the location of each restriction site within the vector sequence.

The pNOX vector generated in Example 2 was further modified to produce the pNLV vector. Feature and restriction maps of pNLV are shown in FIGS. 13 and 14, respectively. The cPPT element of pNOX was replaced with the cPPT sequence shown in SEQ ID NO:92. cPPT represents pol sequence position 2698-2850 (see SEQ ID NOs:92 and 93). A Kozak sequence is included immediately upstream of the gene encoding the transgene (e.g., EGFP, as shown in Table 5). Lastly, a wild-type EF1a promoter (P-EF1a) of SEQ ID NO: 95 was utilized. The pNLV vector has increased viral titer and an improved biosafety profile.

The sequence of the pNLV vector, and the sequences of the elements in the pNLV vector, are shown below. In some instances, the vector backbone and elements included in the pNLV vector, and portions thereof, may be used in any of the vectors described herein. Vector backbone sequences and functional elements may be inserted into another vector and/or replace portions of another vector according to cloning methods well known in the art.

The pNLV-EGFP sequence is set forth below and is detailed in Table 5. EGFP sequences can optionally be replaced with sequences of another transgene (e.g., a gene encoding a CAR), if desired, using standard methods in the art.

pNLV-EGFP sequence
(SEQ ID NO: 90)
GTAATCAATTACGGGGTCATTAGTTCATAGCCCATATATGGAGTTCCGCGTTACATAACTTACGGTAA

ATGGCCCGCCTGGCTGACCGCCCAACGACCCCCGCCCATTGACGTCAATAATGACGTATGTTCCCA

TAGTAACGCCAATAGGGACTTTCCATTGACGTCAATGGGTGGAGTATTTACGGTAAACTGCCCACTT

-continued

```
GGCAGTACATCAAGTGTATCATATGCCAAGTACGCCCCCTATTGACGTCAATGACGGTAAATGGCCC

GCCTGGCATTATGCCCAGTACATGACCTTATGGGACTTTCCTACTTGGCAGTACATCTACGTATTAGT

CATCGCTATTACCATGCTGATGCGGTTTTGGCAGTACATCAATGGGCGTGGATAGCGGTTTGACTCA

CGGGGATTTCCAAGTCTCCACCCCATTGACGTCAATGGGAGTTTGTTTTGGCACCAAAATCAACGGG

ACTTTCCAAAATGTCGTAACAACTCCGCCCCATTGACGCAAATGGGCGGTAGGCGTGTACGGTGGG

AGGTCTATATAAGCAGAGCTGGTTTAGTGAACCGGGGTCTCTCTGGTTAGACCAGATCTGAGCCTGG

GAGCTCTCTGGCTAACTAGGGAACCCACTGCTTAAGCCTCAATAAAGCTTGCCTTGAGTGCTTCAAG

TAGTGTGTGCCCGTCTGTTGTGTGACTCTGGTAACTAGAGATCCCTCAGACCCTTTTAGTCAGTGTG

GAAAATCTCTAGCAGTGGCGCCCGAACAGGGACTTGAAAGCGAAAGTAAAGCCAGAGGAGATCTCT

CGACGCAGGACTCGGCTTGCTGAAGCGCGCACGGCAAGAGGCGAGGGGCGGCGACTGGTGAGTA

CGCCAAAAATTTTGACTAGCGGAGGCTAGAAGGAGAGAGATGGGTGCGAGAGCGTCGGTATTAAGC

GGGGGAGAATTAGATAAATGGGAAAAAATTCGGTAATAAGGCCAGGGGGAAAGAAGAAGTACAAGC

TAAAGCACATCGTATGGGCAAGCAGGGAGCTAGAACGATTCGCAGTTAATCCTGGCCTTTTAGAGAC

ATCAGAAGGCGGCCGCTGATCTTCAGACCTGGAGGAGGCGATATGAGGGACAATTGGAGAAGTGAA

TTATATAAATATAAAGTAGTAAAAATTGAACCATTAGGAGTAGCACCCACCAAGGCAAAGAGAAGAGT

GGTGCAGAGAGAAAAAGAGCAGTGGGAATTTAAATAGGAGCTTTGTTCCTTGGGTTCTTGGGAGCA

GCAGGAAGCACTATGGGCGCAGCGTCAATGACGCTGACGGTACAGGCCAGACAATTATTGTCTGAT

ATAGTGCAGCAGCAGAACAATTTGCTGAGGGCTATTGAGGCGCAACAGCATCTGTTGCAACTCACAG

TCTGGGGCATCAAACAGCTCCAGGCAAGAATCCTGGCTGTGGAAAGATACCTAAAGGATCAACAGCT

CCTCCTGCAGGGGATTTGGGGTTGCTCTGGAAAACTCATTTGCACCACTGCTGTGCCTTGGAATGCT

AGTTGGAGTAATAAATCTCTGGAACAGATTTGGAATAACATGACCTGGATGGAGTGGGACAGAGAAA

TTAACAATTACACAAGCTTAATACACTCCTTAATTGAAGAATCGCAAAACCAGCAAGAAAAGAATGAA

CAAGAATTATTGGAATTAGATAAATGGGCAAGTTTGTGGAATTGGTTTAACATAACAAATTGGCTGTG

GTATATAAAATTATTCATAATGATAGTAGGAGGCTTGGTAGGTTTAAGAATAGTTTTTGCTGTACTTTC

TATAGTGAATAGAGTTAGGCAGGGATATTCACCATTATCGTTTCAGACCCACCTCCCAATCCCGAGG

GGACCCGACAGGCCCGAAGGAATAGAAGAAGAAGGTGGAGAGAGAGACAGAGACAGATCCATTCG

ATTAGTGAACGGATCTCGACGGTATCGATACTAGTACAAATGGCAGTATTCATCCACAATTTTAAAAG

AAAAGGGGGGATTGGGGGGTACAGTGCAGGGGAAAGAATAGTAGACATAATAGCAACAGACATACA

AACTAAAGAATTACAAAAACAAATTACAAAAATTCAAAATTTTCGGGTTTATTACAGGGACAGCAGAGA

TCCACTTTGGCTGCATTGATCACGTGAGGCTCCGGTGCCCGTCAGTGGGCAGAGCGCACATCGCCC

ACAGTCCCCGAGAAGTTGGGGGGAGGGGTCGGCAATTGAACCGGTGCCTAGAGAAGGTGGCGCGG

GGTAAACTGGGAAAGTGATGTCGTGTACTGGCTCCGCCTTTTTCCCGAGGGTGGGGGAGAACCGTA

TATAAGTGCAGTAGTCGCCGTGAACGTTCTTTTTCGCAACGGGTTTGCCGCCAGAACACAGGTAAGT

GCCGTGTGTGGTTCCCGCGGGCCTGGCCTCTTTACGGGTTATGGCCCTTGCGTGCCTTGAATTACT

TCCACCTGGCTGCAGTACGTGATTCTTGATCCCGAGCTTCGGGTTGGAAGTGGGTGGGAGAGTTCG

AGGCCTTGCGCTTAAGGAGCCCCTTCGCCTCGTGCTTGAGTTGAGGCCTGGCCTGGGCGCTGGGG

CCGCCGCGTGCGAATCTGGTGGCACCTTCGCGCCTGTCTCGCTGCTTTCGATAAGTCTCTAGCCATT

TAAAATTTTTGATGACCTGCTGCGACGCTTTTTTTCTGGCAAGATAGTCTTGTAAATGCGGGCCAAGA

TCTGCACACTGGTATTTCGGTTTTTGGGGCCGCGGGCGGCGACGGGCCCGTGCGTCCCAGCGCA

CATGTTCGGCGAGGCGGGGCCTGCGAGCGCGGCCACCGAGAATCGGACGGGGGTAGTCTCAAGC
```

-continued

```
TGGCCGGCCTGCTCTGGTGCCTGGCCTCGCGCCGCCGTGTATCGCCCCGCCCTGGGCGGCAAGG

CTGGCCCGGTCGGCACCAGTTGCGTGAGCGGAAAGATGGCCGCTTCCCGGCCCTGCTGCAGGGAG

CTCAAAATGGAGGACGCGGCGCTCGGGAGAGCGGGCGGGTGAGTCACCCACACAAAGGAAAAGGG

CCTTTCCGTCCTCAGCCGTCGCTTCATGTGACTCCACGGAGTACCGGGCGCCGTCCAGGCACCTCG

ATTAGTTCTCGAGCTTTTGGAGTACGTCGTCTTTAGGTTGGGGGGAGGGGTTTTATGCGATGGAGTT

TCCCCACACTGAGTGGGTGGAGACTGAAGTTAGGCCAGCTTGGCACTTGATGTAATTCTCCTTGGAA

TTTGCCCTTTTTGAGTTTGGATCTTGGTTCATTCTCAAGCCTCAGACAGTGGTTCAAAGTTTTTTTCTT

CCATTTCAGGTGTCGTGATCTAGAGGATCCGCCACCATGGTGAGCAAGGGCGAGGAGCTGTTCACC

GGGGTGGTGCCCATCCTGGTCGAGCTGGACGGCGACGTAAACGGCCACAAGTTCAGCGTGTCCGG

CGAGGGCGAGGGCGATGCCACCTACGGCAAGCTGACCCTGAAGTTCATCTGCACCACCGGCAAGC

TGCCCGTGCCCTGGCCCACCCTCGTGACCACCCTGACCTACGGCGTGCAGTGCTTCAGCCGCTACC

CCGACCACATGAAGCAGCACGACTTCTTCAAGTCCGCCATGCCCGAAGGCTACGTCCAGGAGCGCA

CCATCTTCTTCAAGGACGACGGCAACTACAAGACCCGCGCCGAGGTGAAGTTCGAGGGCGACACCC

TGGTGAACCGCATCGAGCTGAAGGGCATCGACTTCAAGGAGGACGGCAACATCCTGGGGCACAAG

CTGGAGTACAACTACAACAGCCACAACGTCTATATCATGGCCGACAAGCAGAAGAACGGCATCAAG

GTGAACTTCAAGATCCGCCACAACATCGAGGACGGCAGCGTGCAGCTCGCCGACCACTACCAGCAG

AACACCCCCATCGGCGACGGCCCCGTGCTGCTGCCCGACAACCACTACCTGAGCACCCAGTCCGC

CCTGAGCAAAGACCCCAACGAGAAGCGCGATCACATGGTCCTGCTGGAGTTCGTGACCGCCGCCG

GGATCACTCTCGGCATGGACGAGCTGTACAAGTAAGTCGACTAAACAGGCCTATTGATTGGAAAGTA

TGTCAACGAATTGTGGGTCTTTTGGGGTTTGCTGCCCCTTTTACGCAATGTGGATATCCTGCTTTAAT

GCCTTTATATGCATGTATACAAGCAAAACAGGCTTTTACTTTCTCGCCAACTTACAAGGCCTTTCTAA

GTAAACAGTATCTGACCCTTTACCCCGTTGCTCGGCAACGGCCTGGTCTGTGCCAAGTGTTTGCTGA

CGCAACCCCACTGGTTGGGGCTTGGCCATAGGCCATCAGCGCATGCGTGGAACCTTTGTGTCTCC

TCTGCCGATCCATACTGCGGAACTCCTAGCCGCTTGTTTTGCTCGCAGCAGGTCTGGAGCGAAACTC

ATCGGGACTGACAATTCTGTCGTGCTCTCCCGCAAGTATACATCGTTTCCAGGGCTGCTAGGCTGTG

CTGCCAACTGGATCCTGCGCGGGACGTCCTTTGTTTACGTCCCGTCGGCGCTGAATCCCGCGGACG

ACCCCTCCGGGGCCGCTTGGGGCTCTACCGCCCGCTTCTCCGTCTGCCGTACCGACCGACCACG

GGGCGCACCTCTCTTTACGCGGACTCCCCGTCTGTGCCTTCTCATCTGCCGGACCGTGTGCACTTC

GCTTCACCTCTGCACGTCGCATGGAGACCACCGTGAACGCCCACCGGAACCTGCCCAAGGTCTTGC

ATAAGAGGACTCTTGGACTTTCAGCAATGTCAACGAATTCGAGCTCGGTACCTTTAAGACCAATGACT

TACAAGGCAGCTGTAGATCTTAGCCACTTTTTAAAAGAAAAGGGGGGACTGGAAGGGCTAATTCACT

CCCAACGAAGACAAGATCTGCTTTTTGCTTGTACTGGGTCTCTCTGGTTAGACCAGATCTGAGCCTG

GGAGCTCTCTGGCTAACTAGGGAACCCACTGCTTAAGCCTCAATAAAGCTTGCCTTGAGTGCTTCAA

GTAGTGTGTGCCCGTCTGTTGTGTGACTCTGGTAACTAGAGATCCCTCAGACCCTTTTAGTCAGTGT

GGAAAATCTCTAGCAGTAGTAGTTCATGTCATCTTATTATTCAGTATTTATAACTTGCAAAGAAATGAA

TATCAGAGAGTGAGAGGAACTTGTTTATTGCAGCTTATAATGGTTACAAATAAAGCAATAGCATCACA

AATTTCACAAATAAAGCATTTTTTTCACTGCATTCTAGTTGTGGTTTGTCCAAACTCATCAATGTATCTT

ATCATGTCTGGCTCTAGCTATCCCGCCCCTAGGCACCGGGGAAATGTGCGCGGAACCCCTATTTGTT
```

-continued
```
TATTTTTCTAAATACATTCAAATATGTATCCGCTCATGAGACAATAACCCTGATAAATGCTTCAATAATA

TTGAAAAAGGAAGAGTATGAGCCATATTCAACGGGAAACGTCGAGGCCGCGATTAAATTCCAACATG

GATGCTGATTTATATGGGTATAAATGGGCTCGCGATAATGTCGGGCAATCAGGTGCGACAATCTATC

GCTTGTATGGGAAGCCCGATGCGCCAGAGTTGTTTCTGAAACATGGCAAAGGTAGCGTTGCCAATG

ATGTTACAGATGAGATGGTCAGACTAAACTGGCTGACGGAATTTATGCCACTTCCGACCATCAAGCA

TTTTATCCGTACTCCTGATGATGCATGGTTACTCACCACTGCGATCCCCGGAAAAACAGCGTTCCAG

GTATTAGAAGAATATCCTGATTCAGGTGAAAATATTGTTGATGCGCTGGCAGTGTTCCTGCGCCGGT

TGCACTCGATTCCTGTTTGTAATTGTCCTTTTAACAGCGATCGCGTATTTCGCCTCGCTCAGGCGCAA

TCACGAATGAATAACGGTTTGGTTGATGCGAGTGATTTTGATGACGAGCGTAATGGCTGGCCTGTTG

AACAAGTCTGGAAAGAAATGCATAAACTTTTGCCATTCTCACCGGATTCAGTCGTCACTCATGGTGAT

TTCTCACTTGATAACCTTATTTTTGACGAGGGGAAATTAATAGGTTGTATTGATGTTGGACGAGTCGG

AATCGCAGACCGATACCAGGATCTTGCCATCCTATGGAACTGCCTCGGTGAGTTTTCTCCTTCATTAC

AGAAACGGCTTTTTCAAAAATATGGTATTGATAATCCTGATATGAATAAATTGCAGTTTCATTTGATGC

TCGATGAGTTTTTCTAACTGTCAGACCAAGTTTACTCATATATACTTTAGATTGATTTAAAACTTCATTT

TTAATTTAAAAGGATCTAGGTGAAGATCCTTTTTGATAATCTCATGACCAAAATCCCTTAACGTGAGTT

TTCGTTCCACTGAGCGTCAGACCCCGTAGAAAAGATCAAAGGATCTTCTTGAGATCCTTTTTTTCTGC

GCGTAATCTGCTGCTTGCAAACAAAAAAACCACCGCTACCAGCGGTGGTTTGTTTGCCGGATCAAGA

GCTACCAACTCTTTTTCCGAAGGTAACTGGCTTCAGCAGAGCGCAGATACCAAATACTGTTCTTCTAG

TGTAGCCGTAGTTAGGCCACCACTTCAAGAACTCTGTAGCACCGCCTACATACCTCGCTCTGCTAAT

CCTGTTACCAGTGGCTGCTGCCAGTGGCGATAAGTCGTGTCTTACCGGGTTGGACTCAAGACGATA

GTTACCGGATAAGGCGCAGCGGTCGGGCTGAACGGGGGGTTCGTGCACACAGCCCAGCTTGGAGC

GAACGACCTACACCGAACTGAGATACCTACAGCGTGAGCTATGAGAAAGCGCCACGCTTCCCGAAG

GGAGAAAGGCGGACAGGTATCCGGTAAGCGGCAGGGTCGGAACAGGAGAGCGCACGAGGGAGCT

TCCAGGGGGAAACGCCTGGTATCTTTATAGTCCTGTCGGGTTTCGCCACCTCTGACTTGAGCGTCGA

TTTTTGTGATGCTCGTCAGGGGGGCGGAGCCTATGGAAAAACGCCAGCAACGCGGCCTTTTTACGG

TTCCTGGCCTTTTGCTGGCCTTTTGCTCACATGTTCTTTCCTGCGTTATCCCCTGATTCTGTGGATAA

CCGTATTACCGCCTTTGAGTGAGCTGATACCGCTCGCCGCAGCCGAACGACCGAGCGCAGCGAGTC

AGTGAGCGAGGAAGCGGAAGAGCGCCCAATACGCAAACCGCCTCTCCCCGCGCGTTGGCCGATTC

ATTAATGCAGCTGGCACGACAGGTTTCCCGACTGGAAAGCGGGCAGTGAGCGCAACGCAATTAATG

TGAGTTAGCTCACTCATTAGGCACCCCAGGCTTTACACTTTATGCTTCCGGCTCGTATGTTGTGTGGA

ATTGTGAGCGGATAACAATTTCACACAGGAAACAGCTATGACCATGATTACGCCAAGCGCGCAATTA

ACCCTCACTAAAGGGAACAAAAGCTGGAGCTGCAGACTAGTAAGCTTA
```

The functional elements present within the pNLV vector are shown in Table 4 below. Portions of the full pNLV sequence may include vector backbone sequences. Such vector backbone sequences may be used as and/or replace vector backbone sequences, or portions thereof, in any of the vectors described herein (e.g., pCINS, pNOX, and pNLV).

The invention includes the pNLV vector, as well as related vectors that include portions of the pNLV vector and/or sequences that share identity (e.g., at least 90%, 95%, 96%, 97%, 98%, 99%, or 100% identity with pNLV) with one or more sequences of pNLV. Sequences that may be included in such related vectors include all pNLV sequences, or subsets including, e.g., various combinations of the viral promoter (i.e., the promoter driving expression of the viral proteins), partial gag (e.g., lacking INS2, 3, and 4, and/or including an INS1 mutation as described herein), partial env, RRE, cPPT, subgenomic promoter (e.g., EF1alpha promoter, optionally including constitutive splice donor and splice acceptor sites as described herein), and PRE (optionally with an X protein inactivating mutation, as described herein) (these sequences each optionally have the sequence identities noted above). Such vectors may include a transgene (e.g., a gene encoding a CAR or EGFP, as described herein).

TABLE 5 pNLV features

| Feature | Nucleic Acid Sequence | Source | SEQ ID NO: |
|---|---|---|---|
| CMV promoter/ enhancer, P-CMV | GTAATCAATTACGGGGTCATTAGTTCATAGCCCATA TATGGAGTTCCGCGTTACATAACTTACGGTAAATG GCCCGCCTGGCTGACCGCCCAACGACCCCCGCCC ATTGACGTCAATAATGACGTATGTTCCCATAGTAAC GCCAATAGGGACTTTCCATTGACGTCAATGGGTGG AGTATTTACGGTAAACTGCCCACTTGGCAGTACAT CAAGTGTATCATATGCCAAGTACGCCCCCTATTGA CGTCAATGACGGTAAATGGCCCGCCTGGCATTATG CCCAGTACATGACCTTATGGGACTTTCCTACTTGG CAGTACATCTACGTATTAGTCATCGCTATTACCATG CTGATGCGGTTTTGGCAGTACATCAATGGGCGTGG ATAGCGGTTTGACTCACGGGGATTTCCAAGTCTCC ACCCCATTGACGTCAATGGGAGTTTGTTTTGGCAC CAAAATCAACGGGACTTTCCAAAATGTCGTAACAA CTCCGCCCCATTGACGCAAATGGGCGGTAGGCGT GTACGGTGGGAGGTCTATATAAGCAGAGCTGGTTT AGTGAACCG | GenBank: KT186368.1 | 52 |
| R | GGGTCTCTCTGGTTAGACCAGATCTGAGCCTGGG AGCTCTCTGGCTAACTAGGGAACCCACTGCTTAAG CCTCAATAAAGCTTGCCTTGAGTGCTTC | NL4-3 HIV-1 isolate GenBank: AF324493.1 | 53 |
| U5 | AAGTAGTGTGTGCCCGTCTGTTGTGTGACTCTGGT AACTAGAGATCCCTCAGACCCTTTTAGTCAGTGTG GAAAATCTCTAGCAG | NL4-3 HIV-1 isolate GenBank: AF324493.1 | 54 |
| PBS | TGGCGCCCGAACAGGGAC | NL4-3 HIV-1 isolate GenBank: AF324493.1 | 55 |
| Packaging signal, psi | TTGAAAGCGAAAGTAAAGCCAGAGGAGATCTCTCG ACGCAGGACTCGGCTTGCTGAAGCGCGCACGGCA AGAGGCGAGGGGCGGCGACTGGTGAGTACGCCA AAAATTTTGACTAGCGGAGGCTAGAAGGAGAGAGA TGGGTGCGAGAGCGTCGGTATTA | NL4-3 HIV-1 isolate GenBank: AF324493.1 | 56 |
| Major splice donor, SD | ACTGGTGAGT (indicated by underlining inside packaging signal sequence above) | | 57 |
| Partial gag sequence (from NL4-3) with mutated INS signal | ATGGGTGCGAGAGCGTCGGTATTAAGCGGGGGAG AATTAGATAAATGGGAAAAAATTCGGTAATAAGGC CAGGGGGAAAGAAGAAGTACAAGCTAAAGCACAT CGTATGGGCAAGCAGGGAGCTAGAACGATTCGCA GTTAATCCTGGCCTTTTAGAGACATCAGAAG | Modified sequence from NL4-3 HIV-1 isolate GenBank: AF324493.1 | 58 |
| NotI restriction site | *GCGGCCGC* | | 59 |
| Partial env sequence | TGATCTTCAGACCTGGAGGAGGCGATATGAGGGA CAATTGGAGAAGTGAATTATATAAATATAAAGTAGT AAAAATTGAACCATTAGGAGTAGCACCCACCAAGG CAAAGAGAAGAGTGGTGCAGAGAGAAAAAAGAGC AGTGGGA | NL4-3 HIV-1 isolate GenBank: AF324493.1 | 60 |
| Swat restriction site | *ATTTAAAT* | | 61 |
| RRE | AGGAGCTTTGTTCCTTGGGTTCTTGGGAGCAGCAG GAAGCACTATGGGCGCAGCGTCAATGACGCTGAC GGTACAGGCCAGACAATTATTGTCTGATATAGTGC AGCAGCAGAACAATTTGCTGAGGGCTATTGAGGC GCAACAGCATCTGTTGCAACTCACAGTCTGGGGCA TCAAACAGCTCCAGGCAAGAATCCTGGCTGTGGAA AGATACCTAAAGGATCAACAGCTCCT | NL4-3 HIV-1 isolate GenBank: AF324493.1 | 62 |

TABLE 5 -continued pNLV features

| Feature | Nucleic Acid Sequence | Source | SEQ ID NO: |
|---|---|---|---|
| SbfI restriction site | CCTGCAGG | | 63 |
| Partial env sequence containing splice acceptor 5A7 | GGATTTGGGGTTGCTCTGGAAAACTCATTTGCACC ACTGCTGTGCCTTGGAATGCTAGTTGGAGTAATAA ATCTCTGGAACAGATTTGGAATAACATGACCTGGA TGGAGTGGGACAGAGAAATTAACAATTACACAAGC TTAATACACTCCTTAATTGAAGAATCGCAAAACCAG CAAGAAAAGAATGAACAAGAATTATTGGAATTAGAT AAATGGGCAAGTTTGTGGAATTGGTTTAACATAACA AATTGGCTGTGGTATATAAAATTATTCATAATGATA GTAGGAGGCTTGGTAGGTTTAAGAATAGTTTTTGC TGTACTTTCTATAGTGAATAGAGTTAGGCAGGGAT ATTCACCATTATCGTTTCAGACCCACCTCCCAATC CCGAGGGGACCCGACAGGCCCGAAGGAATAGAAG AAGAAGGTGGAGAGAGAGACAGAGACAGATCCAT TCGATTAGTGAACGGATCTCGACGGT | NL4-3 HIV-1 isolate GenBank: AF324493.1 | 64 |
| SA7 | AGTTAGGCAGGGATATTCACCATTATCGTTTCAGA C (indicated by underlining inside env sequence above) | | 65 |
| ClaI restriction site | ATCGAT | | 66 |
| SpeI restriction site | ACTAGT | | 91 |
| Partial pol sequence containing cPPT and splice acceptor SA1 | AGTACAAATGGCAGTATTCATCCACAATTTTAAAAG AAAAGGGGGGATTGGGGGGTACAGTGCAGGGGAA AGAATAGTAGACATAATAGCAACAGACATACAAACT AAAGAATTACAAAAACAAATTACAAAAATTCAAAATT TTCGGGTTTATTACAGGGACAGCAGAGATCCACT TTGG<br>[alternatively:<br>ACAAATGGCAGTATTCATCCACAATTTTAAAAGAAA AGGGGGGATTGGGGGGTACAGTGCAGGGGAAAG AATAGTAGACATAATAGCAACAGACATACAAACTAA AGAATTACAAAAACAAATTACAAAAATTCAAAATTTT CGGGTTTATTACAGGGACAGCAGAGATCCACTTT GG] | HIV-1 isolate SF3 GenBank: KJ704796.1<br><br>[NL4-3 HIV-1 isolate GenBank: AF324493.1] | 92<br><br>93 |
| SA1 | GTTTATTACAGGGACAGCAGAGATCCACTTTGG (indicated by underlin- ing in cPPT sequence above) | NL4-3 HIV-1 isolate GenBank: AF324493.1 | 94 |
| Blunted PstI restriction site | CTGGAT | | 69 |
| BclI restriction site | TGATCA | | 70 |
| EF1alpha promoter | CGTGAGGCTCCGGTGCCCGTCAGTGGGCAGAGC GCACATCGCCCACAGTCCCCGAGAAGTTGGGGG AGGGGTCGGCAATTGAACCGGTGCCTAGAGAAGG TGGCGCGGGGTAAACTGGGAAAGTGATGTCGTGT ACTGGCTCCGCCTTTTTCCCGAGGGTGGGGGAGA ACCGTATATAAGTGCAGTAGTCGCCGTGAACGTTC TTTTTCGCAACGGGTTTGCCGCAGAACACAGGT AAGTGCCGTGTGTGGTTCCCGCGGGCCTGGCCTC TTTACGGGTTATGGCCCTTGCGTGCCTTGAATTAC TTCCACCTGGCTGCAGTACGTGATTCTTGATCCCG AGCTTCGGGTTGGAAGTGGGTGGGAGAGTTCGAG GCCTTGCGCTTAAGGAGCCCCTTCGCCTCGTGCTT GAGTTGAGGCCTGGCCTGGGCGCTGGGGCCGCC GCGTGCGAATCTGGTGGCACCTTCGCGCCTGTCT CGCTGCTTTCGATAAGTCTCTAGCCATTTAAAATTT TTGATGACCTGCTGCGACGCTTTTTTTCTGGCAAG | GenBank: HQ644134.1 | 95 |

TABLE 5 -continued pNLV features

| Feature | Nucleic Acid Sequence | Source | SEQ ID NO: |
|---|---|---|---|
| | ATAGTCTTGTAAATGCGGGCCAAGATCTGCACACT<br>GGTATTTCGGTTTTTGGGGCCGCGGGCGGCGACG<br>GGGCCCGTGCGTCCCAGCGCACATGTTCGGCGAG<br>GCGGGGCCTGCGAGCGCGGCCACCGAGAATCGG<br>ACGGGGGTAGTCTCAAGCTGGCCGGCCTGCTCTG<br>GTGCCTGGCCTCGCGCCGCCGTGTATCGCCCCGC<br>CCTGGGCGGCAAGGCTGGCCCGGTCGGCACCAG<br>TTGCGTGAGCGGAAAGATGGCCGCTTCCCGGCCC<br>TGCTGCAGGGAGCTCAAAATGGAGGACGCGGCGC<br>TCGGGAGAGCGGGCGGGTGAGTCACCCACACAAA<br>GGAAAAGGGCCTTTCCGTCCTCAGCCGTCGCTTCA<br>TGTGACTCCACGGAGTACCGGGCGCCGTCCAGGC<br>ACCTCGATTAGTTCTCGAGCTTTTGGAGTACGTCG<br>TCTTTAGGTTGGGGGGAGGGGTTTTATGCGATGGA<br>GTTTCCCCACACTGAGTGGGTGGAGACTGAAGTTA<br>GGCCAGCTTGGCACTTGATGTAATTCTCCTTGGAA<br>TTTGCCCTTTTTGAGTTTGGATCTTGGTTCATTCTC<br>AAGCCTCAGACAGTGGTTCAAAGTTTTTTTCTT<u>CCA</u><br><u>TTTCAGGTGTCGTGA</u> | | |
| Constitutive splice donor (CD) | CAGAACACAGGTAAGTGC<br>(indicated by underlining in P-EF1a sequence above) | | 72 |
| Constitutive splice acceptor (CA) | TCCATTTCAGGTGTCGTGA<br>(indicated by underlining in P-EF1a sequence above) | | 73 |
| XbaI restriction site | *TCTAGA* | | 74 |
| BamHI restriction site | *GGATCC* | | 75 |
| Kozak sequence | GCCACC | PMCID: PMC306349 | 96 |
| EGFP | ATGGTGAGCAAGGGCGAGGAGCTGTTCACCGGGG<br>TGGTGCCCATCCTGGTCGAGCTGGACGGCGACGT<br>AAACGGCCACAAGTTCAGCGTGTCCGGCGAGGGC<br>GAGGGCGATGCCACCTACGGCAAGCTGACCCTGA<br>AGTTCATCTGCACCACCGGCAAGCTGCCCGTGCC<br>CTGGCCCACCCTCGTGACCACCCTGACCTACGGC<br>GTGCAGTGCTTCAGCCGCTACCCCGACCACATGA<br>AGCAGCACGACTTCTTCAAGTCCGCCATGCCCGAA<br>GGCTACGTCCAGGAGCGCACCATCTTCTTCAAGGA<br>CGACGGCAACTACAAGACCCGCGCCGAGGTGAAG<br>TTCGAGGGCGACACCCTGGTGAACCGCATCGAGC<br>TGAAGGGCATCGACTTCAAGGAGGACGGCAACAT<br>CCTGGGGCACAAGCTGGAGTACAACTACAACAGC<br>CACAACGTCTATATCATGGCCGACAAGCAGAAGAA<br>CGGCATCAAGGTGAACTTCAAGATCCGCCACAACA<br>TCGAGGACGGCAGCGTGCAGCTCGCCGACCACTA<br>CCAGCAGAACACCCCCATCGGCGACGGCCCCGTG<br>CTGCTGCCCGACAACCACTACCTGAGCACCCAGT<br>CCGCCCTGAGCAAAGACCCCAACGAGAAGCGCGA<br>TCACATGGTCCTGCTGGAGTTCGTGACCGCCGCC<br>GGGATCACTCTCGGCATGGACGAGCTGTACAAGT<br>AA | GenBank: KJ697753.1 | 76 |
| SalI restriction site | GTCGAC | | 77 |
| Modified HPRE NoX | TAAACAGGCCTATTGATTGGAAAGTATGTCAACGA<br>ATTGTGGGTCTTTTGGGGTTTGCTGCCCCTTTTAC<br>GCAATGTGGATATCCTGCTTTAATGCCTTTATATGC<br>ATGTATACAAGCAAAACAGGCTTTTACTTTCTCGCC<br>AACTTACAAGGCCTTTCTAAGTAAACAGTATCTGAC<br>CCTTTACCCCGTTGCTCGGCAACGGCCTGGTCTGT<br>GCCAAGTGTTTGCTGACGCAACCCCCACTGGTTG<br>GGGCTTGGCCATAGGCCATCAGCGCATGCGTGGA | Hepatitis B virus isolate bba6, GenBank: KP341007.1 | 79 |

TABLE 5 -continued pNLV features

| Feature | Nucleic Acid Sequence | Source | SEQ ID NO: |
|---|---|---|---|
| | ACCTTTGTGTCTCCTCTGCCGATCCATACTGCGGA ACTCCTAGCCGCTTGTTTTGCTCGCAGCAGGTCTG GAGCGAAACTCATCGGGACTGACAATTCTGTCGTG CTCTCCCGCAAGTATACATCGTTTCC<u>AGG</u>GCTGCT AGGCTGTGCTGCCAACTGGATCCTG<u>CGC</u>GGGACG TCCTTTGTTTACGTCCCGTCGGCGCTGAATCCCGC GGACGACCCCTCCCGGGGCCGCTTGGGGCTCTAC CGCCCGCTTCTCCGTCTGCCGTACCGACCGACCA CGGGGCGCACCTCTCTTTACGCGGACTCCCCGTC TGTGCCTTCTCATCTGCCGGACCGTGTGCACTTCG CTTCACCTCTGCACGTCGCATGGAGACCACCGTGA ACGCCCACCGGAACCTGCCCAAGGTCTTGCATAA GAGGACTCTTGGACTTTCAGCAATGTCAAC (underlined codon is mutated ATG/AGG codon of X protein) | | |
| EcoRI restriction site | *GAATTC* | | 80 |
| SacI restriction site | *GAGCTC* | | 81 |
| KpnI restriction site | *GGTACC* | | 82 |
| Partial Nef sequence, containing PPT | CTTTAAGACCAATGACTTACAAGGCAGCTGTAGAT CTTAGCCACTTTTTAAAAGAAAAGGGGGG | NL4-3 HIV-1 isolate GenBank: AF324493.1 | 83 |
| dU3 | ACTGGAAGGGCTAATTCACTCCCAACGAAGACAAG ATCTGCTTTTTGCTTGTACT | NL4-3 HIV-1 isolate GenBank: AF324493.1 | 84 |
| R | GGGTCTCTCTGGTTAGACCAGATCTGAGCCTGGG AGCTCTCTGGCTAACTAGGGAACCCACTGCTTAAG CCTCAATAAAGCTTGCCTTGAGTGCTTC | NL4-3 HIV-1 isolate GenBank: AF324493.1 | 85 |
| U5 | AAGTAGTGTGTGCCCGTCTGTTGTGTGACTCTGGT AACTAGAGATCCCTCAGACCCTTTTAGTCAGTGTG GAAAATCTCTAGCAG | NL4-3 HIV-1 isolate GenBank: AF324493.1 | 86 |
| SV40 termination and polyadenylation signal | TAGTAGTTCATGTCATCTTATTATTCAGTATTTATAA CTTGCAAAGAAATGAATATCAGAGAGTGAGAGGAA CTTGTTTATTGCAGCTTATAATGGTTACAAATAAAG CAATAGCATCACAAATTTCACAAATAAAGCATTTTT TTCACTGCATTCTAGTTGTGGTTTGTCCAAACTCAT CAATGTATCTTATCATGTCTGGCTCTAGCTATCCCG CC | GenBank: KX757255.1 | 97 |
| Kan-R | ATGAGCCATATTCAACGGGAAACGTCGAGGCCGC GATTAAATTCCAACATGGATGCTGATTTATATGGGT ATAAATGGGCTCGCGATAATGTCGGGCAATCAGGT GCGACAATCTATCGCTTGTATGGGAAGCCCGATGC GCCAGAGTTGTTTCTGAAACATGGCAAAGGTAGCG TTGCCAATGATGTTACAGATGAGATGGTCAGACTA AACTGGCTGACGGAATTTATGCCACTTCCGACCAT CAAGCATTTTATCCGTACTCCTGATGATGCATGGTT ACTCACCACTGCGATCCCCGGAAAAACAGCGTTCC AGGTATTAGAAGAATATCCTGATTCAGGTGAAAATA TTGTTGATGCGCTGGCAGTGTTCCTGCGCCGGTTG CACTCGATTCCTGTTTGTAATTGTCCTTTTAACAGC GATCGCGTATTTCGCCTCGCTCAGGCGCAATCACG AATGAATAACGGTTTGGTTGATGCGAGTGATTTTG ATGACGAGCGTAATGGCTGGCCTGTTGAACAAGTC TGGAAAGAAATGCATAAACTTTTGCCATTCTCACCG GATTCAGTCGTCACTCATGGTGATTTCTCACTTGAT AACCTTATTTTTGACGAGGGGAAATTAATAGGTTGT ATTGATGTTGGACGAGTCGGAATCGCAGACCGATA | Synthesized by DNA2.0 | 88 |

TABLE 5 -continued pNLV features

| Feature | Nucleic Acid Sequence | Source | SEQ ID NO: |
|---|---|---|---|
| | CCAGGATCTTGCCATCCTATGGAACTGCCTCGGTG AGTTTTCTCCTTCATTACAGAAACGGCTTTTTCAAA AATATGGTATTGATAATCCTGATATGAATAAATTGC AGTTTCATTTGATGCTCGATGAGTTTTTCTAA | | |

Example 5. Optimization of Transfer Vectors for Lentiviral Production

Figure 6:
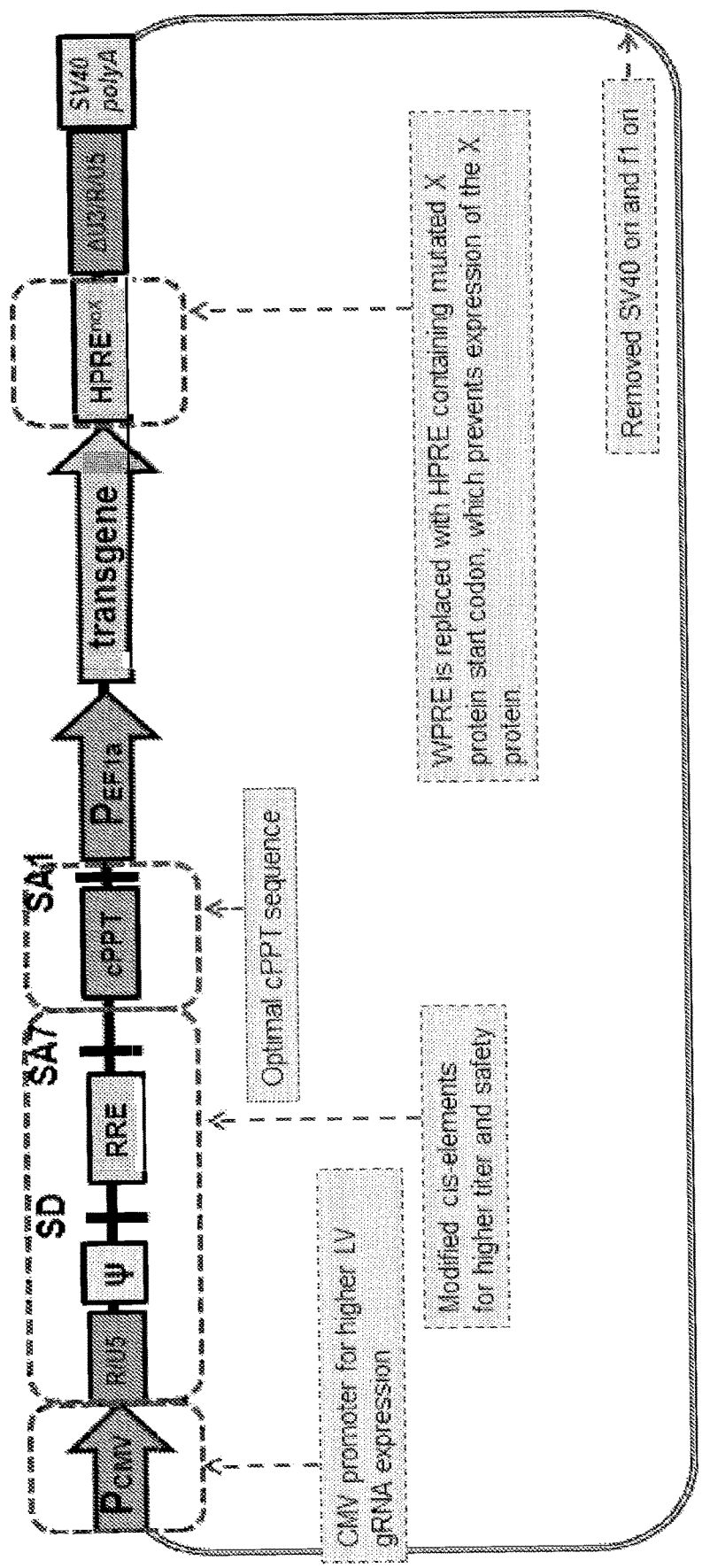
FIG. 6 is a schematic showing certain features that were modified in a strategy undertaken to optimize a lentiviral production system.

An improved lentiviral transfer vector system with greater viral titers, enhanced biosafety features, improved transduction efficiency, and durable transgene expression was developed. A number of cis-elements were re-engineered to generate a pNLV transfer vector backbone (FIG. 6). To determine the efficacy of the GFP-encoding pNLV lentiviral transfer vector compared to the GFP-encoding pCINS transfer vector, a series of experiments was performed, in which one of the transfer vectors was introduced into cells by transient transfection of packaging cells. Briefly, Expi293™ cells (Thermo Fisher) were grown in 5 ml of Freestyle (FS) medium at a concentration of 5 min/ml at 200 rpm, 3TC and 8% $CO_2$, 80% humidity. Transfections were performed using PEIPro Transfer Reagent (PolyPlus) using 3 µg pNVS-MDLgp-RRE, 3 µg pNVS 20 RSV Rev-Kan, 0.75 µg pNVS-MDG-VSVG-Kan, and 6 µg transfer plasmid. Viral supernatants were collected 48 hours after transfection and subjected to titer analysis (i.e., measurement of infectious titer).

The pNLV transfer vector generated a viral titer approximately two to three times higher than that generated by the control parental (i.e., before optimization) vector (FIG. 7 A). Physical titer was evaluated based on the viral RNA copy number (e.g., as measured by qRT-PCR), and the infectious titer was determined based on the infectious units determined by proviral integration titer assay (FIG. 7 B).

Next, the level of transgene expression was examined after genomic integration of elements from the pNLV vector compared to the pCINS transfer vector. T cells were infected with viruses produced using the pCINS or pNLV lentiviral vectors, such that viral elements were integrated into the T cell genomes. The pNLV vector was found to have a greater level of transgene expression (as measured by FACS) compared to pCINS (FIGS. 8A-8C).

Figures 9A, 9B, 9C, 9D, 9E:
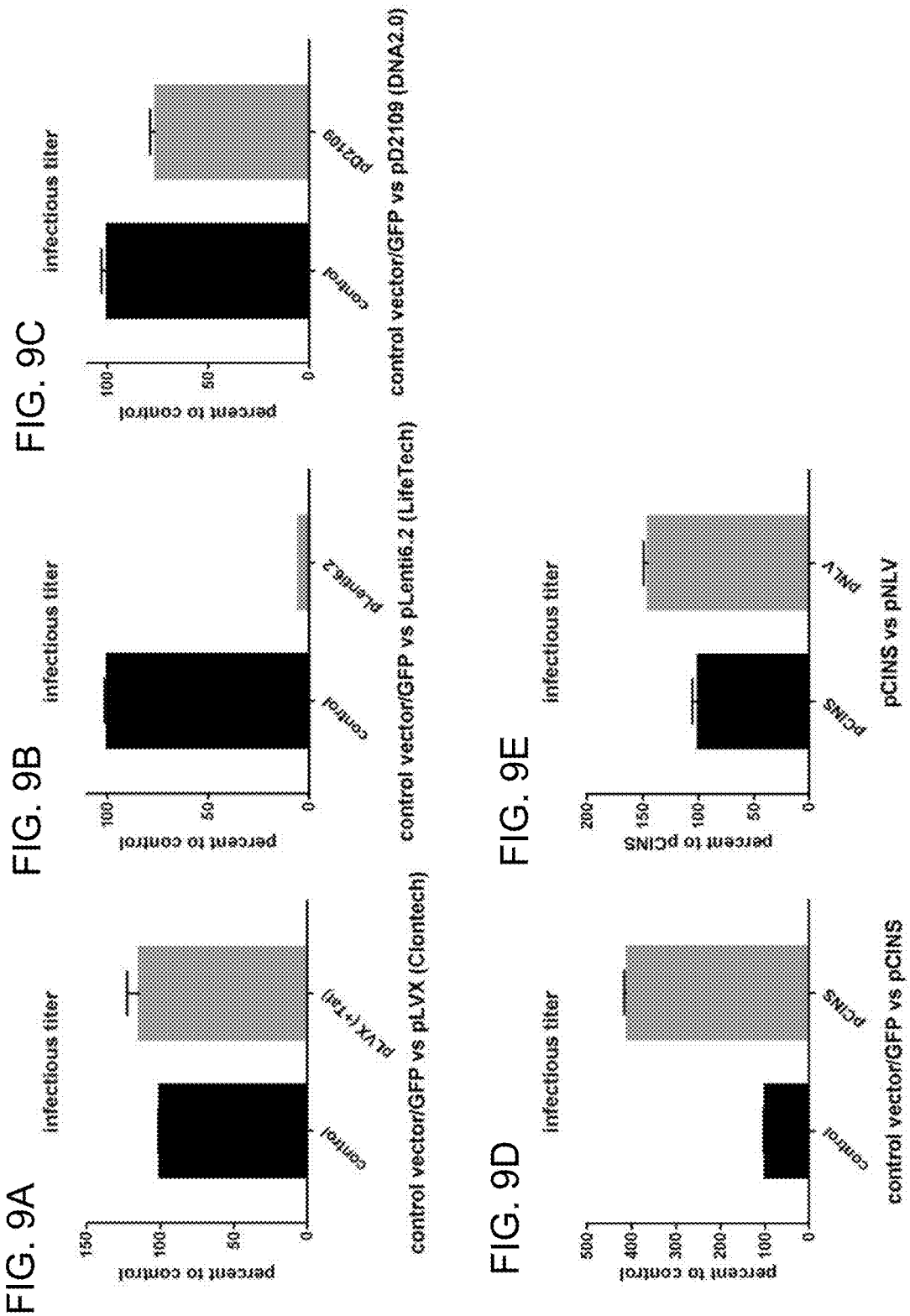
FIG. 9A-9E is a series of graphs comparing the viral titers of commercial transfer vectors to a control vector, which is GFP-encoding SIN transfer vector before optimization, and to the pCINS and pNLV transfer vectors.

The pNLV and pCINS vectors were also compared to several commercial transfer vectors with respect to their relative infectious titer. Each of the commercial vectors and the pCINS vector were separately compared to a GFP-encoding control (parental) vector, and the pCINS vector was further compared to pNLV. The pLVX (Clontech) transfer vector was transduced into 293T cells and was found to have a slightly higher viral titer than the control vector (FIG. 9A). The pLenti6.2 (Life Technologies) transfer vector was transduced into cells and was found to have a large decrease in viral titer compared to the control vector (FIG. 9B). The pD2109 (DNA2.0) transfer vector was transduced into cells and was found to have a small decrease in viral titer compared to the control vector (FIG. 9C). The pCINS transfer vector was transduced into cells and was found to have a substantially higher viral titer than the control vector (FIG. 9D). The pNLV transfer vector was also transduced into cells and was found to have a higher viral titer than the pCINS vector (FIG. 9E). These results indicate that viruses made using both the pCINS and pNLV are, overall, significantly more infectious than those made using commercially available lentiviral transfer vectors, with virus made using the pNLV vector exhibiting the highest viral titer.

To investigate the effects of splicing on infectious titer, a series of splice donor and splice acceptor sites were mutated for subsequent viral titer determination (FIG. 10A). The various splice donor and splice acceptor site mutants of the pCINS transfer vector were transfected into packaging cells and the viral titer was compared across the panel of mutants to a control transfer vector (FIG. 10B). All of the mutations led to a large decrease in viral titer, indicating that the presence of splice sites in the transfer vector backbone is required for maximum viral titer. These observations indicate that the presence of splice sites is important for lentiviral RNA nuclear export. Transport of genomic lentiviral RNA from the nucleus may require interaction with the spliceosome and Rev protein. High levels of Rev protein expressed from packaging vectors may ensure that full-size lentiviral RNA is protected from splicing and transported for packaging.

Lastly, the gag and env regions of the transfer vector backbone were removed in a series of newly engineered transfer vector constructs to determine the importance of the gag and env elements on infectious viral titer. Transfer vectors with 3' and 5' gag and env deletions (i.e., –gag3', –gag5', –env3', and –env5' mutants) were made (FIG. 11A) and each vector was then transduced into separate sets of cells. The viral titer was determined for each of the gag and/or env deletion mutants and compared to a control lentiviral transfer vector (FIG. 11B). It was found that the –env3' and –gag3'–env5' mutants exhibited a decrease in viral titer relative to the control vector, while the –env5' and –gag3' showed little difference in viral titer. These results indicate that the 3' gag and 5' env regions may be altered individually with only a slight effect on viral titer, but other gag and env truncations are detrimental to transfer vector efficacy.

Example 6. Sequence Differences Between pNLV and pRRLSIN

The pRRLSIN transfer vector was modified to generate the pNLV vector. These nucleotide substitutions and insertions were introduced to improve the efficacy and biosafety profile of the lentiviral transfer vector. In one example, the pNLV psi sequence has the following sequence differences compared to the pRRLSIN sequence (FIG. 12A): T771C, T784G, A785G, G788A, insertion of the polynucleotide sequence "GAG" (792-794), A798C, and G924A. pNLV has a partial gag sequence beginning at position 907 through position 1074. Additionally, pNLV has the following sequence differences in this region compared to pRRLSIN (FIG. 12B): insertion of the following nucleotides: A968 and A969 (resulting in a stop codon), as well as the following substitutions: G924A, A949C, A950G, G989A, G992A, C995T, G998A, C999T, G1004A, C1007T, C1010A, T1058G, and G1064A. pNLV also has a partial env sequence beginning at position 1083 through position 1228. In this region, pNLV has the following sequence difference compared to pRRLSIN (FIG. 12C): C1105A.

The pNLV RRE region has the following sequence differences compared to pRRLSIN (FIG. 12D): G1291C, A1332G, and A1414G. pNLV has a region of partial env (containing the major splice acceptor 7 site) beginning at position 1479 through position 1961. Additionally, pNLV has the following sequence differences in this partial env region compared to pRRLSIN (FIG. 12E): A1571C, T1575C, and T1866C.

pNLV has a cPPT region that begins at position 1971 through position 2118, and a partial pol sequence (containing the major splice acceptor 1 site) beginning at position 1974 through position 2151 (FIG. 12F). In some instances, the cPPT region includes a sequence of 178 nucleotides. In some instances, the partial gag, partial env, and/or partial pol sequences show reduced homology to wild-type viral sequences compared to the parent vector, thereby improving the biosafety profile. Additionally, pNLV has the following sequence differences insertions within the cPPT and partial pol regions compared to pRRLSIN: +A1971, +ACAAATGGCAG (1974-1984), +TTCATCC (1987-1993), +A1996, +A1997, and +CGGGTTTATTA-CAGGGACAGCAGAGATCCACTTTGG (2116-2151).

The above-described sequence differences between pNLV and pRLLSIN are each applicable to pCINS and pNOX, as compared to pRLLSIN, except for the cPPT region differences. The precise nucleotide positions of the differences between pCINS or pNOX, relative to pRLLSIN, can be identified by alignment of the relevant sequences provided herein.

Other Embodiments

All publications, patents, and patent applications mentioned in the above specification are hereby incorporated by reference to the same extent as if each individual publication, patent or patent application was specifically and individually indicated to be incorporated by reference in its entirety. Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

What is claimed is:

1. A lentiviral transfer vector comprising a heterologous nucleic acid sequence and being characterized by the following features:
   (a) comprising a promoter driving the expression of one or more viral sequences;
   (b) comprising a polynucleotide encoding a portion of a gag protein, wherein the polynucleotide comprises a mutated INS1 inhibitory sequence that reduces restriction of nuclear export of RNA relative to wild-type INS1, wherein the polynucleotide consists of 150-250 nucleotides; and
   (c) not comprising an SV40 origin of replication and/or an f1 origin of replication.

2. The lentiviral transfer vector of claim 1, comprising a two nucleotide insertion that results in frame shift and premature termination.

3. The lentiviral transfer vector of claim 1, further comprising a packaging signal (psi) or a cPPT sequence from pol.

4. The lentiviral transfer vector of claim 3, wherein the cPPT sequence comprises about 150-250 nucleotides and comprises splice acceptor SA1 sequence.

5. The lentiviral transfer vector of claim 1, further comprising one or more restriction sites positioned between elements of said vector.

6. The lentiviral transfer vector of claim 1, further comprising a post-transcriptional regulatory element (PRE) selected from:
   (a) a woodchuck hepatitis virus PRE (WPRE), which comprises a nucleic acid sequence having at least 95% identity to SEQ ID NO: 78; and
   (b) a hepatitis B virus isolate bba6 PRE (HPRE), which comprises a nucleic acid sequence having at least 95% identity to SEQ ID NO: 79.

7. The lentiviral transfer vector of claim 1, further comprising an EF1a promoter, wherein said EF1a promoter comprises a nucleic acid sequence having at least 95% identity to SEQ ID NO: 71 or SEQ ID NO: 95.

8. The lentiviral transfer vector of claim 1, wherein the lentiviral components of said lentiviral transfer vector originate from HIV-1.

9. The lentiviral transfer vector of claim 1, wherein said heterologous nucleic acid sequence is downstream of a Kozak sequence.

10. The lentiviral transfer vector of claim 1, wherein the sequence encoding said portion of said gag protein has less than 90% sequence identity to a corresponding region of gag protein encoded by pMDLgpRRE packaging plasmid.

11. The lentiviral transfer vector of claim 1, wherein said lentiviral transfer vector comprises:
   (i) a CMV promoter comprising a nucleic acid sequence having at least 95% identity to SEQ ID NO: 52,
   (ii) an LTR R region comprising a nucleic acid sequence having at least 95% identity to SEQ ID NO: 53,
   (iii) an LTR U5 region comprising a nucleic acid sequence having at least 95% identity to SEQ ID NO: 54,
   (iv) a primer binding site comprising a nucleic acid sequence having at least 95% identity to SEQ ID NO: 55,
   (v) a packaging signal comprising a nucleic acid sequence having at least 95% identity to SEQ ID NO: 56,
   (vi) a major splice donor site comprising the nucleic acid sequence of SEQ ID NO: 57, which is within said packaging signal,
   (vii) a partial gag sequence comprising a nucleic acid sequence having at least 95% identity to SEQ ID NO:58,
   (viii) a partial env sequence comprising a nucleic acid sequence having at least 95% identity to SEQ ID NO:60,
   (ix) a Rev-response element comprising a nucleic acid sequence having at least 95% identity to SEQ ID NO: 62,
   (x) a partial env sequence comprising a nucleic acid sequence having at least 95% identity to SEQ ID NO:64,
   (xi) a splice acceptor site comprising a nucleic acid sequence having at least 95% identity to SEQ ID NO: 65, which is within said partial env sequence of part (x),
   (xii) a central polypurine tract comprising a nucleic acid sequence having at least 95% identity to SEQ ID NO: 67, 92, or 93,
   (xiii) a splice acceptor site comprising a nucleic acid sequence having at least 95% identity to SEQ ID NO: 68 or 94, which is within said central polypurine tract,
   (xiv) an EF1alpha promoter having at least 95% sequence identity to SEQ ID NO: 71 or 95,
   (xv) a polynucleotide encoding an EGFP comprising a nucleic acid sequence having at least 95% identity to SEQ ID NO: 76 and/or a transgene sequence, (xvi) a PRE sequence comprising a nucleic acid sequence having at least 95% sequence identity to SEQ ID NO: 78 or 79, (xvii) a partial nef sequence comprising a nucleic acid sequence having at least 95% sequence identity to SEQ ID NO:83, (xviii) a dU3 sequence comprising a nucleic acid sequencing having at least 95% sequence identity to SEQ ID NO:84, (xix) an LTR R region comprising a nucleic acid sequence having at least 95% identity to SEQ ID NO: 85, and (xx) an LTR U5 region comprising a nucleic acid sequence having at least 95% identity to SEQ ID NO: 86.

12. The lentiviral transfer vector of claim 1, wherein expression of the heterologous sequence is under the control of a subgenomic promoter selected from the group consisting of a CMV promoter, an EF1 alpha promoter, and an RSV promoter.

13. The lentiviral transfer vector of claim 1, wherein said heterologous nucleic acid sequence encodes a protein, wherein said protein comprises a chimeric antigen receptor (CAR).

14. The lentiviral transfer vector of claim 13, wherein said CAR comprises, in a N-terminal to C-terminal direction, an antigen binding domain, a transmembrane domain, and one or more signaling domains.

15. The lentiviral transfer vector of claim 14, wherein said signaling domain comprises one or more primary signaling domains, wherein said signaling domains comprise one or more costimulatory signaling domains.

16. The lentiviral transfer vector of claim 15, wherein one of said one or more primary signaling domains comprises a CD3-zeta stimulatory domain, wherein one or more of said costimulatory signaling domains comprises an intracellular domain selected from a costimulatory protein selected from the group consisting of CD27, CD28, 4-1BB (CD137), OX40, GITR, CD30, CD40, ICOS, BAFFR, HVEM, ICAM-1, lymphocyte function-associated antigen-1 (LFA-1), CD2, CDS, CD7, CD287, LIGHT, NKG2C, NKG2D, SLAMF7, NKp80, NKp30, NKp44, NKp46, CD160, B7-H3, and a ligand that specifically binds with CD83.

17. The lentiviral transfer vector of claim 16, wherein said one or more of said costimulatory signaling domains comprises the 4-1BB (CD137) costimulatory domain, wherein one or more of said costimulatory domains comprises the CD28 costimulatory domain.

18. The lentiviral transfer vector of claim 14, wherein said antigen binding domain is an scFv.

19. The lentiviral transfer vector of claim 14, wherein said antigen binding domain binds to an antigen selected from the group consisting of CD19; CD123; CD22; CD30; CD171; CS-1; C-type lectin-like molecule-1, CD33; epidermal growth factor receptor variant III (EGFRvIII); ganglioside G2 (GD2); ganglioside GD3; TNF receptor family member B cell maturation (BCMA); Tn antigen ((Tn Ag) or (GalNAcα-Ser/Thr)); prostate-specific membrane antigen (PSMA); Receptor tyrosine kinase-like orphan receptor 1 (ROR1); Fms-Like Tyrosine Kinase 3 (FLT3); Tumor-associated glycoprotein 72 (TAG72); CD38; CD44v6; Carcinoembryonic antigen (CEA); Epithelial cell adhesion molecule (EPCAM); B7H3 (CD276); KIT (CD117); Interleukin-13 receptor subunit alpha-2; mesothelin; Interleukin 11 receptor alpha (IL-11 Ra); prostate stem cell antigen (PSCA); Protease Serine 21; vascular endothelial growth factor receptor 2 (VEGFR2); Lewis(Y) antigen; CD24; Platelet-derived growth factor receptor beta (PDGFR-beta); Stage-specific embryonic antigen-4 (SSEA-4); CD20; Folate receptor alpha; Receptor tyrosine-protein kinase ERBB2 (Her2/neu); Mucin 1, cell surface associated (MUC1); epidermal growth factor receptor (EGFR); neural cell adhesion molecule (NCAM); Prostase; prostatic acid phosphatase (PAP); elongation factor 2 mutated (ELF2M); Ephrin B2; fibroblast activation protein alpha (FAP); insulin-like growth factor 1 receptor (IGF-I receptor), carbonic anhydrase IX (CAIX); Proteasome (Prosome, Macropain) Subunit, Beta Type, 9 (LMP2); glycoprotein 100 (gp100); oncogene fusion protein consisting of breakpoint cluster region (BCR) and Abelson murine leukemia viral oncogene homolog 1 (Abl) (bcr-abl); tyrosinase; ephrin type-A receptor 2 (EphA2); Fucosyl GM1; sialyl Lewis adhesion molecule (sLe); ganglioside GM3; transglutaminase 5 (TGS5); high molecular weight-melanoma-associated antigen (HMWMAA); o-acetyl-GD2 ganglioside (OAcGD2); Folate receptor beta; tumor endothelial marker 1 (TEM1/CD248); tumor endothelial marker 7-related (TEM7R); claudin 6 (CLDN6); thyroid stimulating hormone receptor (TSHR); G protein-coupled receptor class C group 5, member D (GPRC5D); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (OR51 E2); TCR Gamma Alternate Reading Frame Protein (TARP); Wilms tumor protein (WT1); Cancer/testis antigen 1 (NY-ESO-1); Cancer/testis antigen 2 (LAGE-1a); Melanoma-associated antigen 1 (MAGE-A1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); melanoma cancer testis antigen-1 (MAD-CT-1); melanoma cancer testis antigen-2 (MAD-CT-2); Fos-related antigen 1; tumor protein p53 (p53); p53 mutant; prostein; surviving; telomerase; prostate carcinoma tumor antigen-1, melanoma antigen recognized by T cells 1; Rat sarcoma (Ras) mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin B1; v-myc avian myelocytomatosis viral oncogene neuroblastoma derived homolog (MYCN); Ras Homolog Family Member C (RhoC); Tyrosinase-related protein 2 (TRP-2); Cytochrome P450 1 B1 (CYP1B1); CCCTC-Binding Factor (Zinc Finger Protein)-Like, Squamous Cell Carcinoma Antigen Recognized By T Cells 3 (SART3); Paired box protein Pax-5 (PAX5); proacrosin binding protein sp32 (OY-TES1); lymphocyte-specific protein tyrosine kinase (LCK); A kinase anchor protein 4 (AKAP-4); synovial sarcoma, X breakpoint 2 (SSX2); Receptor for Advanced Glycation Endproducts (RAGE-1); renal ubiquitous 1 (RU1); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2); CD79a; CD79b; CD72; Leukocyte-associated immunoglobulin-like receptor 1 (LAIR1); Fc fragment of IgA receptor (FCAR or CD89); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); and immunoglobulin lambda-like polypeptide 1 (IGLL1).

20. The lentiviral transfer vector of claim 19, wherein said antigen binding domain binds to CD19, mesothelin, or CD123.

21. The lentiviral transfer vector of claim 13, wherein said CAR comprises an anti-CD19 antibody or a fragment thereof, a 4-1BB (CD137) transmembrane domain, and a CD3-zeta signaling domain.

22. A lentiviral transfer vector comprising, from 5' to 3', one or more of the following elements in operable association:
(a) a promoter to drive the expression of viral genes,
(b) a packaging signal (psi) comprising a major splice donor site (SD),
(c) a partial gag sequence consisting of 150-250 nucleotides,
(d) a partial env sequence consisting of a sequence having at least 95% sequence identity to SEQ ID NO: 60,
(e) a Rev-response element (RRE),
(f) a partial env sequence comprising splice acceptor site (SA7) and consisting of a sequence having at least 95% sequence identity to SEQ ID NO: 64,
(g) a central polypurine tract (cPPT) comprising a splice acceptor site (SA1),
(h) a subgenomic promoter,
(i) a gene encoding EGFP and/or a heterologous nucleic acid sequence, and
(j) a post-transcriptional regulatory element, which optionally comprises a woodchuck hepatitis virus PRE (WPRE) or a hepatitis B virus isolate bba6 PRE (HPRE).

23. A lentiviral transfer vector of claim 22 comprising, from 5' to 3', one or more of the following elements in operable association:
(a) a CMV promoter,
(b) an LTR R region,
(c) an LTR U5 region,
(d) a primer binding site (PBS),
(e) a packaging signal (psi) comprising a major splice donor site (SD),
(f) a partial gag sequence consisting of 150-250 nucleotides,
(g) a partial env sequence consisting of a sequence having at least 95% sequence identity to SEQ ID NO: 60,
(h) a Rev-response element (RRE),
(i) a partial env sequence comprising splice acceptor site (SA7) and consisting of a sequence having at least 95% sequence identity to SEQ ID NO: 64,
(j) a central polypurine tract (cPPT) comprising a splice acceptor site (SA1),
(k) an EF1a promoter,
(l) a gene encoding EGFP and/or a heterologous nucleic acid sequence,
(m) a post-transcriptional regulatory element, which optionally comprises a woodchuck hepatitis virus PRE (WPRE) or a hepatitis B virus isolate bba6 PRE (HPRE),
(n) an LTR R region,
(o) an LTR U5 region,
(p) an SV40 polyA tail,
(q) a kanamycin resistance gene (nptII), and
(r) a pUC origin of replication.

24. The lentiviral transfer vector of claim 22, wherein said heterologous nucleic acid sequence encodes a chimeric antigen receptor (CAR), which optionally comprises an anti-CD19 antibody or a fragment thereof, a 4-1BB (CD137) transmembrane domain, and a CD3-zeta signaling domain.

25. A host cell comprising the lentiviral transfer vector of claim 1, wherein:
(a) said host cell is a 293T cell, a Jurkat T cell, or a primary human T cell; and/or
(b) said host cell further comprises one or more lentiviral packaging vectors.

26. A composition comprising a lentiviral transfer vector of claim 1 and one or more packaging vectors.

27. A method of producing a lentivirus capable of expressing a heterologous nucleic acid sequence, said method comprising:
(a) introducing into a cell:
(i) the lentiviral transfer vector of claim 1, and
(ii) one or more lentiviral packaging vectors; and
(b) expressing viral proteins encoded by said lentiviral transfer vector and/or said packaging vector in said cell, thereby producing a lentivirus comprising the heterologous nucleic acid sequence of said lentiviral transfer vector,
wherein said cell is a 293T cell, a Jurkat T cell, or a primary human T cell.

* * * * *

SEQUENCE LISTING

<160> NUMBER OF SEQ ID NOS: 97

<210> SEQ ID NO 1
<211> LENGTH: 1184
<212> TYPE: DNA
<213> ORGANISM: Homo sapiens

<400> SEQUENCE: 1

```
cgtgaggctc cggtgcccgt cagtgggcag agcgcacatc gcccacagtc cccgagaagt      60
tggggggagg ggtcggcaat tgaaccggtg cctagagaag gtggcgcggg gtaaactggg     120
aaagtgatgt cgtgtactgg ctccgccttt ttcccgaggg tgggggagaa ccgtatataa     180
gtgcagtagt cgccgtgaac gttcttttc gcaacgggtt tgccgccaga acacaggtaa     240
gtgccgtgtg tggttcccgc gggcctggcc tctttacggg ttatggccct tgcgtgcctt     300
gaattacttc cacctggctg cagtacgtga ttcttgatcc cgagcttcgg gttggaagtg     360
ggtgggagag ttcgaggcct tgcgcttaag gagccccttc gcctcgtgct tgagttgagg     420
cctggcctgg gcgctgggc cgccgcgtgc gaatctggtg gcaccttcgc gcctgtctcg     480
ctgctttcga taagtctcta gccatttaaa attttgatg acctgctgcg acgctttttt      540
tctggcaaga tagtcttgta aatgcgggcc aagatctgca cactggtatt tcggttttg      600 gggccgcggg cggcgacggg gcccgtgcgt cccagcgcac atgttcggcg aggcgggcc      660 tgcgagcgcg gccaccgaga atcggacggg ggtagtctca agctggccgg cctgctctgg     720
tgcctggcct cgccgccgcg tgtatcgccc cgccctgggc ggcaaggctg gcccggtcgg     780
caccagttgc gtgagcggaa agatggccgc ttcccggccc tgctgcaggg agctcaaaat     840
```

```
ggaggacgcg gcgctcggga gagcgggcgg gtgagtcacc cacacaaagg aaaagggcct    900
ttccgtcctc agccgtcgct tcatgtgact ccacggagta ccgggcgccg tccaggcacc    960
tcgattagtt ctcgagcttt tggagtacgt cgtctttagg ttggggggag gggttttatg   1020
cgatggagtt tccccacact gagtgggtgg agactgaagt taggccagct tggcacttga   1080
tgtaattctc cttggaattt gcccttttg agtttggatc ttggttcatt ctcaagcctc    1140
agacagtggt tcaaagtttt tttcttccat ttcaggtgtc gtga                    1184
```

<210> SEQ ID NO 2
<211> LENGTH: 21
<212> TYPE: PRT
<213> ORGANISM: Homo sapiens

<400> SEQUENCE: 2

Met Ala Leu Pro Val Thr Ala Leu Leu Leu Pro Leu Ala Leu Leu Leu
1               5                   10                  15

His Ala Ala Arg Pro
            20

<210> SEQ ID NO 3
<211> LENGTH: 63
<212> TYPE: DNA
<213> ORGANISM: Homo sapiens

<400> SEQUENCE: 3

```
atggccctgc ctgtgacagc cctgctgctg cctctggctc tgctgctgca tgccgctaga    60
ccc                                                                   63
```

<210> SEQ ID NO 4
<211> LENGTH: 45
<212> TYPE: PRT
<213> ORGANISM: Homo sapiens

<400> SEQUENCE: 4

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 5
<211> LENGTH: 135
<212> TYPE: DNA
<213> ORGANISM: Homo sapiens

<400> SEQUENCE: 5

```
accacgacgc cagcgccgcg accaccaaca ccggcgccca ccatcgcgtc gcagcccctg    60
tccctgcgcc cagaggcgtg ccggccagcg gcggggggcg cagtgcacac gagggggctg   120
gacttcgcct gtgat                                                    135
```

<210> SEQ ID NO 6
<211> LENGTH: 230
<212> TYPE: PRT
<213> ORGANISM: Homo sapiens

<400> SEQUENCE: 6

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
210                 215                 220

Leu Ser Leu Gly Lys Met
225                 230

<210> SEQ ID NO 7
<211> LENGTH: 690
<212> TYPE: DNA
<213> ORGANISM: Homo sapiens

<400> SEQUENCE: 7
gagagcaagt acggccctcc ctgccccct tgccctgccc ccgagttcct gggcggaccc      60
agcgtgttcc tgttccccc caagcccaag gacaccctga tgatcagccg gacccccgag     120
gtgacctgtg tggtggtgga cgtgtcccag gaggacccg aggtccagtt caactggtac     180
gtggacggcg tggaggtgca caacgccaag accaagcccc gggaggagca gttcaatagc     240
acctaccggg tggtgtccgt gctgaccgtg ctgcaccagg actggctgaa cggcaaggaa     300
tacaagtgta aggtgtccaa caagggcctg cccagcagca tcgagaaaac catcagcaag     360
gccaagggcc agcctcggga gccccaggtg tacaccctgc ccctagcca agaggagatg     420 accaagaacc aggtgtccct gacctgcctg gtgaagggct tctacccag cgacatcgcc     480 gtggagtggg agagcaacgg ccagcccgag aacaactaca agaccacccc ccctgtgctg     540
gacagcgacg gcagcttctt cctgtacagc cggctgaccg tggacaagag ccggtggcag     600
gagggcaacg tctttagctg ctccgtgatg cacgaggccc tgcacaacca ctacacccag     660
aagagcctga gcctgtccct gggcaagatg                                       690

<210> SEQ ID NO 8
<211> LENGTH: 282
<212> TYPE: PRT

<213> ORGANISM: Homo sapiens

<400> SEQUENCE: 8

Arg Trp Pro Glu Ser Pro Lys Ala Gln Ala Ser Val Pro Thr Ala
1               5                   10                  15

Gln Pro Gln Ala Glu Gly Ser Leu Ala Lys Ala Thr Thr Ala Pro Ala
            20                  25                  30

Thr Thr Arg Asn Thr Gly Arg Gly Gly Glu Glu Lys Lys Lys Glu Lys
            35                  40                  45

Glu Lys Glu Glu Gln Glu Glu Arg Glu Thr Lys Thr Pro Glu Cys Pro
        50                  55                  60

Ser His Thr Gln Pro Leu Gly Val Tyr Leu Leu Thr Pro Ala Val Gln
65                  70                  75                  80

Asp Leu Trp Leu Arg Asp Lys Ala Thr Phe Thr Cys Phe Val Val Gly
                85                  90                  95

Ser Asp Leu Lys Asp Ala His Leu Thr Trp Glu Val Ala Gly Lys Val
            100                 105                 110

Pro Thr Gly Gly Val Glu Glu Gly Leu Leu Glu Arg His Ser Asn Gly
            115                 120                 125

Ser Gln Ser Gln His Ser Arg Leu Thr Leu Pro Arg Ser Leu Trp Asn
        130                 135                 140

Ala Gly Thr Ser Val Thr Cys Thr Leu Asn His Pro Ser Leu Pro Pro
145                 150                 155                 160

Gln Arg Leu Met Ala Leu Arg Glu Pro Ala Ala Gln Ala Pro Val Lys
                165                 170                 175

Leu Ser Leu Asn Leu Leu Ala Ser Ser Asp Pro Glu Ala Ala Ser
            180                 185                 190

Trp Leu Leu Cys Glu Val Ser Gly Phe Ser Pro Asn Ile Leu Leu
            195                 200                 205

Met Trp Leu Glu Asp Gln Arg Glu Val Asn Thr Ser Gly Phe Ala Pro
    210                 215                 220

Ala Arg Pro Pro Pro Gln Pro Gly Ser Thr Thr Phe Trp Ala Trp Ser
225                 230                 235                 240

Val Leu Arg Val Pro Ala Pro Pro Ser Pro Gln Pro Ala Thr Tyr Thr
                245                 250                 255

Cys Val Val Ser His Glu Asp Ser Arg Thr Leu Leu Asn Ala Ser Arg
            260                 265                 270

Ser Leu Glu Val Ser Tyr Val Thr Asp His
        275                 280

<210> SEQ ID NO 9
<211> LENGTH: 847
<212> TYPE: DNA
<213> ORGANISM: Homo sapiens

<400> SEQUENCE: 9
aggtggcccg aaagtcccaa ggcccaggca tctagtgttc ctactgcaca gccccaggca      60
gaaggcagcc tagccaaagc tactactgca cctgccacta cgcgcaatac tggccgtggc     120
ggggaggaga agaaaaagga gaaagagaaa gaagaacagg aagagaggga gaccaagacc     180
cctgaatgtc catcccatac ccagccgctg ggcgtctatc tcttgactcc cgcagtacag     240
gacttgtggc ttagagataa ggccaccttt acatgtttcg tcgtgggctc tgacctgaag     300
gatgcccatt tgacttggga ggttgccgga aaggtaccca caggggggt tgaggaaggg      360 ttgctggagc gccattccaa tggctctcag agccagcact caagactcac ccttccgaga     420

```
tccctgtgga acgccgggac ctctgtcaca tgtactctaa atcatcctag cctgccccca      480
cagcgtctga tggcccttag agagccagcc gcccaggcac cagttaagct tagcctgaat      540
ctgctcgcca gtagtgatcc cccagaggcc gccagctggc tcttatgcga agtgtccggc      600
tttagcccgc ccaacatctt gctcatgtgg ctggaggacc agcgagaagt gaacaccagc      660
ggcttcgctc cagcccggcc cccaccccag ccgggttcta ccacattctg ggcctggagt      720
gtcttaaggg tcccagcacc acctagcccc cagccagcca catacacctg tgttgtgtcc      780
catgaagata gcaggaccct gctaaatgct tctaggagtc tggaggtttc ctacgtgact      840
gaccatt                                                                847
```

<210> SEQ ID NO 10
<211> LENGTH: 10
<212> TYPE: PRT
<213> ORGANISM: Artificial Sequence
<220> FEATURE:
<223> OTHER INFORMATION: synthetic construct

<400> SEQUENCE: 10

Gly Gly Gly Gly Ser Gly Gly Gly Gly Ser
1               5                   10

<210> SEQ ID NO 11
<211> LENGTH: 30
<212> TYPE: DNA
<213> ORGANISM: Artificial Sequence
<220> FEATURE:
<223> OTHER INFORMATION: synthetic construct

<400> SEQUENCE: 11
ggtggcggag gttctggagg tggaggttcc                                        30

<210> SEQ ID NO 12
<211> LENGTH: 24
<212> TYPE: PRT
<213> ORGANISM: Homo sapiens

<400> SEQUENCE: 12

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 13
<211> LENGTH: 72
<212> TYPE: DNA
<213> ORGANISM: Homo sapiens

<400> SEQUENCE: 13
atctacatct gggcgccctt ggccgggact tgtggggtcc ttctcctgtc actggttatc      60
accctttact gc                                                           72

<210> SEQ ID NO 14
<211> LENGTH: 42
<212> TYPE: PRT
<213> ORGANISM: Homo sapiens

<400> SEQUENCE: 14

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 15
<211> LENGTH: 126
<212> TYPE: DNA
<213> ORGANISM: Homo sapiens

<400> SEQUENCE: 15
aaacggggca gaaagaaact cctgtatata ttcaaacaac catttatgag accagtacaa      60
actactcaag aggaagatgg ctgtagctgc cgatttccag aagaagaaga aggaggatgt     120
gaactg                                                               126

<210> SEQ ID NO 16
<211> LENGTH: 48
<212> TYPE: PRT
<213> ORGANISM: Homo sapiens

<400> SEQUENCE: 16

Gln Arg Arg Lys Tyr Arg Ser Asn Lys Gly Glu Ser Pro Val Glu Pro
1               5                   10                  15

Ala Glu Pro Cys Arg Tyr Ser Cys Pro Arg Glu Glu Glu Gly Ser Thr
            20                  25                  30

Ile Pro Ile Gln Glu Asp Tyr Arg Lys Pro Glu Pro Ala Cys Ser Pro
        35                  40                  45

<210> SEQ ID NO 17
<211> LENGTH: 123
<212> TYPE: DNA
<213> ORGANISM: Homo sapiens

<400> SEQUENCE: 17
aggagtaaga ggagcaggct cctgcacagt gactacatga acatgactcc ccgccgcccc     60
gggcccaccc gcaagcatta ccagccctat gccccaccac gcgacttcgc agcctatcgc    120
tcc                                                                  123

<210> SEQ ID NO 18
<211> LENGTH: 112
<212> TYPE: PRT
<213> ORGANISM: Homo sapiens

<400> SEQUENCE: 18

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 19
<211> LENGTH: 336
<212> TYPE: DNA
<213> ORGANISM: Homo sapiens

<400> SEQUENCE: 19

```
agagtgaagt tcagcaggag cgcagacgcc cccgcgtaca agcagggcca gaaccagctc    60
tataacgagc tcaatctagg acgaagagag gagtacgatg ttttggacaa gagacgtggc   120
cgggaccctg agatgggggg aaagccgaga aggaagaacc ctcaggaagg cctgtacaat   180
gaactgcaga aagataagat ggcggaggcc tacagtgaga ttgggatgaa aggcgagcgc   240
cggaggggca aggggcacga tggcctttac cagggtctca gtacagccac caaggacacc   300
tacgacgccc ttcacatgca ggccctgccc cctcgc                             336
```

<210> SEQ ID NO 20
<211> LENGTH: 112
<212> TYPE: PRT
<213> ORGANISM: Homo sapiens

<400> SEQUENCE: 20

Arg Val Lys Phe Ser Arg Ser Ala Asp Ala Pro Ala Tyr Gln Gln Gly
1               5                   10                  15
Gln Asn Gln Leu Tyr Asn Glu Leu Asn Leu Gly Arg Arg Glu Glu Tyr
            20                  25                  30
Asp Val Leu Asp Lys Arg Arg Gly Arg Asp Pro Glu Met Gly Gly Lys
        35                  40                  45
Pro Arg Arg Lys Asn Pro Gln Glu Gly Leu Tyr Asn Glu Leu Gln Lys
    50                  55                  60
Asp Lys Met Ala Glu Ala Tyr Ser Glu Ile Gly Met Lys Gly Glu Arg
65                  70                  75                  80
Arg Arg Gly Lys Gly His Asp Gly Leu Tyr Gln Gly Leu Ser Thr Ala
                85                  90                  95
Thr Lys Asp Thr Tyr Asp Ala Leu His Met Gln Ala Leu Pro Pro Arg
            100                 105                 110

<210> SEQ ID NO 21
<211> LENGTH: 336
<212> TYPE: DNA
<213> ORGANISM: Homo sapiens

<400> SEQUENCE: 21

```
agagtgaagt tcagcaggag cgcagacgcc cccgcgtacc agcagggcca gaaccagctc    60
tataacgagc tcaatctagg acgaagagag gagtacgatg ttttggacaa gagacgtggc   120
cgggaccctg agatgggggg aaagccgaga aggaagaacc ctcaggaagg cctgtacaat   180
gaactgcaga aagataagat ggcggaggcc tacagtgaga ttgggatgaa aggcgagcgc   240
cggaggggca aggggcacga tggcctttac cagggtctca gtacagccac caaggacacc   300
tacgacgccc ttcacatgca ggccctgccc cctcgc                             336
```

<210> SEQ ID NO 22
<211> LENGTH: 5
<212> TYPE: PRT
<213> ORGANISM: Artificial Sequence
<220> FEATURE:
<223> OTHER INFORMATION: synthetic construct

<400> SEQUENCE: 22

<210> SEQ ID NO 23
<211> LENGTH: 30
<212> TYPE: DNA
<213> ORGANISM: Artificial Sequence
<220> FEATURE:
<223> OTHER INFORMATION: synthetic construct

<400> SEQUENCE: 23

```
ggtggcggag gttctggagg tggaggttcc                                       30
```

<210> SEQ ID NO 24
<211> LENGTH: 150
<212> TYPE: PRT
<213> ORGANISM: Homo sapiens

<400> SEQUENCE: 24

```
Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150
```

<210> SEQ ID NO 25
<211> LENGTH: 450
<212> TYPE: DNA
<213> ORGANISM: Homo sapiens

<400> SEQUENCE: 25

```
cccggatggt ttctggactc tccggatcgc cgtggaatc ccccaacctt ctcaccggca      60
ctcttggttg tgactgaggg cgataatgcg accttcacgt gctcgttctc caacacctcc    120
gaatcattcg tgctgaactg gtaccgcatg agcccgtcaa accagaccga caagctcgcc    180
gcgtttccgg aagatcggtc gcaaccggga caggattgtc ggttccgcgt gactcaactg    240
ccgaatggca gagacttcca catgagcgtg gtccgcgcta ggcgaaacga ctccgggacc    300
tacctgtgcg gagccatctc gctggcgcct aaggcccaaa tcaaagagag cttgagggcc    360
gaactgagag tgaccgagcg cagagctgag gtgccaactg cacatccatc cccatcgcct    420
cggcctgcgg ggcagtttca gaccctggtc                                     450
```

```
<210> SEQ ID NO 26
<211> LENGTH: 394
<212> TYPE: PRT
<213> ORGANISM: Homo sapiens

<400> SEQUENCE: 26

Met Ala Leu Pro Val Thr Ala Leu Leu Leu Pro Leu Ala Leu Leu Leu
1               5                   10                  15

His Ala Ala Arg Pro Pro Gly Trp Phe Leu Asp Ser Pro Asp Arg Pro
            20                  25                  30

Trp Asn Pro Pro Thr Phe Ser Pro Ala Leu Leu Val Val Thr Glu Gly
        35                  40                  45

Asp Asn Ala Thr Phe Thr Cys Ser Phe Ser Asn Thr Ser Glu Ser Phe
    50                  55                  60

Val Leu Asn Trp Tyr Arg Met Ser Pro Ser Asn Gln Thr Asp Lys Leu
65                  70                  75                  80

Ala Ala Phe Pro Glu Asp Arg Ser Gln Pro Gly Gln Asp Cys Arg Phe
                85                  90                  95

Arg Val Thr Gln Leu Pro Asn Gly Arg Asp Phe His Met Ser Val Val
            100                 105                 110

Arg Ala Arg Arg Asn Asp Ser Gly Thr Tyr Leu Cys Gly Ala Ile Ser
        115                 120                 125

Leu Ala Pro Lys Ala Gln Ile Lys Glu Ser Leu Arg Ala Glu Leu Arg
    130                 135                 140

Val Thr Glu Arg Arg Ala Glu Val Pro Thr Ala His Pro Ser Pro Ser
145                 150                 155                 160

Pro Arg Pro Ala Gly Gln Phe Gln Thr Leu Val Thr Thr Thr Pro Ala
                165                 170                 175

Pro Arg Pro Pro Thr Pro Ala Pro Thr Ile Ala Ser Gln Pro Leu Ser
            180                 185                 190

Leu Arg Pro Glu Ala Cys Arg Pro Ala Ala Gly Gly Ala Val His Thr
        195                 200                 205

Arg Gly Leu Asp Phe Ala Cys Asp Ile Tyr Ile Trp Ala Pro Leu Ala
    210                 215                 220

Gly Thr Cys Gly Val Leu Leu Leu Ser Leu Val Ile Thr Leu Tyr Cys
225                 230                 235                 240

Lys Arg Gly Arg Lys Lys Leu Leu Tyr Ile Phe Lys Gln Pro Phe Met
                245                 250                 255

Arg Pro Val Gln Thr Thr Gln Glu Glu Asp Gly Cys Ser Cys Arg Phe
            260                 265                 270

Pro Glu Glu Glu Glu Gly Gly Cys Glu Leu Arg Val Lys Phe Ser Arg
        275                 280                 285

Ser Ala Asp Ala Pro Ala Tyr Lys Gln Gly Gln Asn Gln Leu Tyr Asn
    290                 295                 300

Glu Leu Asn Leu Gly Arg Arg Glu Glu Tyr Asp Val Leu Asp Lys Arg
305                 310                 315                 320

Arg Gly Arg Asp Pro Glu Met Gly Gly Lys Pro Arg Arg Lys Asn Pro
                325                 330                 335

Gln Glu Gly Leu Tyr Asn Glu Leu Gln Lys Asp Lys Met Ala Glu Ala
            340                 345                 350

Tyr Ser Glu Ile Gly Met Lys Gly Glu Arg Arg Arg Gly Lys Gly His
        355                 360                 365

Asp Gly Leu Tyr Gln Gly Leu Ser Thr Ala Thr Lys Asp Thr Tyr Asp
    370                 375                 380
```

Ala Leu His Met Gln Ala Leu Pro Pro Arg
385             390

<210> SEQ ID NO 27
<211> LENGTH: 1182
<212> TYPE: DNA
<213> ORGANISM: Homo sapiens

<400> SEQUENCE: 27

| | | | | |
|---|---|---|---|---|
| atggccctcc | ctgtcactgc | cctgcttctc | cccctcgcac | tcctgctcca cgccgctaga | 60 |
| ccacccggat | ggtttctgga | ctctccggat | cgcccgtgga | atcccccaac cttctcaccg | 120 |
| gcactcttgg | ttgtgactga | gggcgataat | gcgaccttca | cgtgctcgtt ctccaacacc | 180 |
| tccgaatcat | tcgtgctgaa | ctggtaccgc | atgagcccgt | caaaccagac cgacaagctc | 240 |
| gccgcgtttc | cggaagatcg | gtcgcaaccg | gacaggatt | gtcggttccg cgtgactcaa | 300 |
| ctgccgaatg | cagagactt | ccacatgagc | gtggtccgcg | ctaggcgaaa cgactccggg | 360 |
| acctacctgt | gcggagccat | ctcgctggcg | cctaaggccc | aaatcaaaga gagcttgagg | 420 |
| gccgaactga | gagtgaccga | gcgcagagct | gaggtgccaa | ctgcacatcc atccccatcg | 480 |
| cctcggcctg | cggggcagtt | tcagaccctg | gtcacgacca | ctccggcgcc cgcccaccg | 540 |
| actccggccc | caactatcgc | gagccagccc | ctgtcgctga | ggccggaagc atgccgccct | 600 |
| gccgccggag | gtgctgtgca | tacccgggga | ttggacttcg | catgcgacat ctacatttgg | 660 |
| gctcctctcg | ccggaacttg | tggcgtgctc | cttctgtccc | tggtcatcac cctgtactgc | 720 |
| aagcggggtc | ggaaaaagct | tctgtacatt | ttcaagcagc | ccttcatgag gcccgtgcaa | 780 |
| accacccagg | aggaggacgg | ttgctcctgc | cggttccccg | aagaggaaga aggaggttgc | 840 |
| gagctgcgcg | tgaagttctc | ccggagcgcc | gacgccccg | cctataagca gggccagaac | 900 |
| cagctgtaca | acgaactgaa | cctgggacgg | cgggaagagt | acgatgtgct ggacaagcgg | 960 |
| cgcggccggg | accccgaaat | gggcgggaag | cctagaagaa | agaaccctca ggaaggcctg | 1020 |
| tataacgagc | tgcagaagga | caagatggcc | gaggcctact | ccgaaattgg gatgaaggga | 1080 |
| gagcggcgga | ggggaaaggg | gcacgacggc | ctgtaccaag | gactgtccac cgccaccaag | 1140 |
| gacacatacg | atgccctgca | catgcaggcc | cttcccccte | gc | 1182 |

<210> SEQ ID NO 28
<211> LENGTH: 40
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (5)..(7)
<223> OTHER INFORMATION: Gly or absent
<220> FEATURE:
<221> NAME/KEY: MISC_FEATURE
<222> LOCATION: (8)..(8)
<223> OTHER INFORMATION: Ser or absent
<220> FEATURE:
<221> NAME/KEY: MISC_FEATURE
<222> LOCATION: (9)..(11)
<223> OTHER INFORMATION: Gly or absent
<220> FEATURE:
<221> NAME/KEY: MISC_FEATURE
<222> LOCATION: (12)..(12)
<223> OTHER INFORMATION: Ser or absent
<220> FEATURE:
<221> NAME/KEY: MISC_FEATURE
<222> LOCATION: (13)..(15)
<223> OTHER INFORMATION: Gly or absent
<220> FEATURE:

```
<221> NAME/KEY: MISC_FEATURE
<222> LOCATION: (16)..(16)
<223> OTHER INFORMATION: Ser or absent
<220> FEATURE:
<221> NAME/KEY: MISC_FEATURE
<222> LOCATION: (17)..(19)
<223> OTHER INFORMATION: Gly or absent
<220> FEATURE:
<221> NAME/KEY: MISC_FEATURE
<222> LOCATION: (20)..(20)
<223> OTHER INFORMATION: Ser or absent
<220> FEATURE:
<221> NAME/KEY: MISC_FEATURE
<222> LOCATION: (21)..(23)
<223> OTHER INFORMATION: Gly or absent
<220> FEATURE:
<221> NAME/KEY: MISC_FEATURE
<222> LOCATION: (24)..(24)
<223> OTHER INFORMATION: Ser or absent
<220> FEATURE:
<221> NAME/KEY: MISC_FEATURE
<222> LOCATION: (25)..(27)
<223> OTHER INFORMATION: Gly or absent
<220> FEATURE:
<221> NAME/KEY: MISC_FEATURE
<222> LOCATION: (28)..(28)
<223> OTHER INFORMATION: Ser or absent
<220> FEATURE:
<221> NAME/KEY: MISC_FEATURE
<222> LOCATION: (29)..(31)
<223> OTHER INFORMATION: Gly or absent
<220> FEATURE:
<221> NAME/KEY: MISC_FEATURE
<222> LOCATION: (32)..(32)
<223> OTHER INFORMATION: Ser or absent
<220> FEATURE:
<221> NAME/KEY: MISC_FEATURE
<222> LOCATION: (33)..(35)
<223> OTHER INFORMATION: Gly or absent
<220> FEATURE:
<221> NAME/KEY: MISC_FEATURE
<222> LOCATION: (36)..(36)
<223> OTHER INFORMATION: Ser or absent
<220> FEATURE:
<221> NAME/KEY: MISC_FEATURE
<222> LOCATION: (37)..(39)
<223> OTHER INFORMATION: Gly or absent
<220> FEATURE:
<221> NAME/KEY: MISC_FEATURE
<222> LOCATION: (40)..(40)
<223> OTHER INFORMATION: Ser or absent

<400> SEQUENCE: 28

Gly Gly Gly Ser Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa
        35                  40

<210> SEQ ID NO 29
<211> LENGTH: 20
<212> TYPE: PRT
<213> ORGANISM: Artificial Sequence
<220> FEATURE:
<223> OTHER INFORMATION: synthetic construct

<400> SEQUENCE: 29

Gly Gly Gly Gly Ser Gly Gly Gly Ser Gly Gly Gly Gly Ser Gly
1               5                   10                  15

Gly Gly Gly Ser
            20
```

-continued

<210> SEQ ID NO 30
<211> LENGTH: 15
<212> TYPE: PRT
<213> ORGANISM: Artificial Sequence
<220> FEATURE:
<223> OTHER INFORMATION: synthetic construct

<400> SEQUENCE: 30

Gly Gly Gly Gly Ser Gly Gly Gly Ser Gly Gly Gly Gly Ser
1               5                   10                  15

<210> SEQ ID NO 31
<211> LENGTH: 4
<212> TYPE: PRT
<213> ORGANISM: Artificial Sequence
<220> FEATURE:
<223> OTHER INFORMATION: synthetic construct

<400> SEQUENCE: 31

Gly Gly Gly Ser
1

<210> SEQ ID NO 32
<211> LENGTH: 373
<212> TYPE: PRT
<213> ORGANISM: Homo sapiens

<400> SEQUENCE: 32

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Ser Phe Val Leu Asn Trp Tyr
            35                  40                  45

Arg Met Ser Pro Ser Asn Gln Thr Asp Lys Leu Ala Ala Phe Pro Glu
        50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
            130                 135                 140

Gln Phe Gln Thr Leu Val Thr Thr Thr Pro Ala Pro Arg Pro Pro Thr
145                 150                 155                 160

Pro Ala Pro Thr Ile Ala Ser Gln Pro Leu Ser Leu Arg Pro Glu Ala
                165                 170                 175

Cys Arg Pro Ala Ala Gly Gly Ala Val His Thr Arg Gly Leu Asp Phe
            180                 185                 190

Ala Cys Asp Ile Tyr Ile Trp Ala Pro Leu Ala Gly Thr Cys Gly Val
        195                 200                 205

Leu Leu Leu Ser Leu Val Ile Thr Leu Tyr Cys Lys Arg Gly Arg Lys
    210                 215                 220

Lys Leu Leu Tyr Ile Phe Lys Gln Pro Phe Met Arg Pro Val Gln Thr
225                 230                 235                 240

```
Thr Gln Glu Glu Asp Gly Cys Ser Cys Arg Phe Pro Glu Glu Glu
                245                 250                 255

Gly Gly Cys Glu Leu Arg Val Lys Phe Ser Arg Ser Ala Asp Ala Pro
            260                 265                 270

Ala Tyr Lys Gln Gly Gln Asn Gln Leu Tyr Asn Glu Leu Asn Leu Gly
        275                 280                 285

Arg Arg Glu Glu Tyr Asp Val Leu Asp Lys Arg Arg Gly Arg Asp Pro
    290                 295                 300

Glu Met Gly Gly Lys Pro Arg Arg Lys Asn Pro Gln Glu Gly Leu Tyr
305                 310                 315                 320

Asn Glu Leu Gln Lys Asp Lys Met Ala Glu Ala Tyr Ser Glu Ile Gly
                325                 330                 335

Met Lys Gly Glu Arg Arg Arg Gly Lys Gly His Asp Gly Leu Tyr Gln
            340                 345                 350

Gly Leu Ser Thr Ala Thr Lys Asp Thr Tyr Asp Ala Leu His Met Gln
        355                 360                 365

Ala Leu Pro Pro Arg
    370

<210> SEQ ID NO 33
<211> LENGTH: 486
<212> TYPE: PRT
<213> ORGANISM: Mus musculus

<400> SEQUENCE: 33

Met Ala Leu Pro Val Thr Ala Leu Leu Leu Pro Leu Ala Leu Leu Leu
1               5                   10                  15

His Ala Ala Arg Pro Asp Ile Gln Met Thr Gln Thr Thr Ser Ser Leu
                20                  25                  30

Ser Ala Ser Leu Gly Asp Arg Val Thr Ile Ser Cys Arg Ala Ser Gln
            35                  40                  45

Asp Ile Ser Lys Tyr Leu Asn Trp Tyr Gln Gln Lys Pro Asp Gly Thr
        50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Gly Ser Gly Gly Gly Gly Ser Glu
130                 135                 140

Val Lys Leu Gln Glu Ser Gly Pro Gly Leu Val Ala Pro Ser Gln Ser
145                 150                 155                 160

Leu Ser Val Thr Cys Thr Val Ser Gly Val Ser Leu Pro Asp Tyr Gly
                165                 170                 175

Val Ser Trp Ile Arg Gln Pro Pro Arg Lys Gly Leu Glu Trp Leu Gly
            180                 185                 190

Val Ile Trp Gly Ser Glu Thr Thr Tyr Tyr Asn Ser Ala Leu Lys Ser
        195                 200                 205

Arg Leu Thr Ile Ile Lys Asp Asn Ser Lys Ser Gln Val Phe Leu Lys
    210                 215                 220

Met Asn Ser Leu Gln Thr Asp Asp Thr Ala Ile Tyr Tyr Cys Ala Lys
225                 230                 235                 240
```

```
His Tyr Tyr Tyr Gly Gly Ser Tyr Ala Met Asp Tyr Trp Gly Gln Gly
                245                 250                 255
Thr Ser Val Thr Val Ser Ser Thr Thr Pro Ala Pro Arg Pro Pro
            260                 265                 270
Thr Pro Ala Pro Thr Ile Ala Ser Gln Pro Leu Ser Leu Arg Pro Glu
            275                 280                 285
Ala Cys Arg Pro Ala Ala Gly Gly Ala Val His Thr Arg Gly Leu Asp
            290                 295                 300
Phe Ala Cys Asp Ile Tyr Ile Trp Ala Pro Leu Ala Gly Thr Cys Gly
305                 310                 315                 320
Val Leu Leu Leu Ser Leu Val Ile Thr Leu Tyr Cys Lys Arg Gly Arg
                325                 330                 335
Lys Lys Leu Leu Tyr Ile Phe Lys Gln Pro Phe Met Arg Pro Val Gln
                340                 345                 350
Thr Thr Gln Glu Glu Asp Gly Cys Ser Cys Arg Phe Pro Glu Glu Glu
                355                 360                 365
Glu Gly Gly Cys Glu Leu Arg Val Lys Phe Ser Arg Ser Ala Asp Ala
            370                 375                 380
Pro Ala Tyr Lys Gln Gly Gln Asn Gln Leu Tyr Asn Glu Leu Asn Leu
385                 390                 395                 400
Gly Arg Arg Glu Glu Tyr Asp Val Leu Asp Lys Arg Gly Arg Asp
                405                 410                 415
Pro Glu Met Gly Gly Lys Pro Arg Arg Lys Asn Pro Gln Glu Gly Leu
                420                 425                 430
Tyr Asn Glu Leu Gln Lys Asp Lys Met Ala Glu Ala Tyr Ser Glu Ile
                435                 440                 445
Gly Met Lys Gly Glu Arg Arg Arg Gly Lys Gly His Asp Gly Leu Tyr
            450                 455                 460
Gln Gly Leu Ser Thr Ala Thr Lys Asp Thr Tyr Asp Ala Leu His Met
465                 470                 475                 480
Gln Ala Leu Pro Pro Arg
                485

<210> SEQ ID NO 34
<211> LENGTH: 1459
<212> TYPE: DNA
<213> ORGANISM: Mus musculus

<400> SEQUENCE: 34
atggccttac cagtgaccgc cttgctcctg ccgctggcct tgctgctcca cgccgccagg      60
ccggacatcc agatgacaca gactacatcc tccctgtctg cctctctggg agacagagtc     120
accatcagtt gcagggcaag tcaggacatt agtaaatatt taaattggta tcagcagaaa     180
ccagatggaa ctgttaaact cctgatctac catacatcaa gattacactc aggagtccca     240
tcaaggttca gtggcagtgg gtctggaaca gattattctc tcaccattag caacctggag     300
caagaagata ttgccactta cttttgccaa cagggtaata cgcttccgta cacgttcgga     360
gggggaccca agctggagat cacaggtggc ggtggctcgg gcggtggtgg gtcgggtggc     420
ggcggatctg aggtgaaact gcaggagtca ggacctggcc tggtggcgcc ctcacagagc     480
ctgtccgtca catgcactgt ctcaggggtc tcattacccg actatggtgt aagctggatt     540
cgccagcctc cacgaaaggg tctggagtgg ctgggagtaa tatggggtag tgaaaccaca     600
tactataatt cagctctcaa atccagactg accatcatca aggacaactc caagagccaa     660
```

```
gttttcttaa aaatgaacag tctgcaaact gatgacacag ccatttacta ctgtgccaaa    720
cattattact acggtggtag ctatgctatg gactactggg gccaaggaac ctcagtcacc    780
gtctcctcaa ccacgacgcc agcgccgcga ccaccaacac cggcgcccac catcgcgtcg    840
cagcccctgt ccctgcgccc agaggcgtgc cggccagcgg cggggggcgc agtgcacacg    900
agggggctgg acttcgcctg tgatatctac atctgggcgc ccttggccgg gacttgtggg    960
gtccttctcc tgtcactggt tatcacccTT tactgcaaac ggggcagaaa gaaactcctg   1020
```

```
gtccttctcc tgtcactggt tatcacccTT tactgcaaac ggggcagaaa gaaactcctg   1020
tatatattca acaaccatt tatgagacca gtacaaacta ctcaagagga agatggctgt    1080
agctgccgat tccagaaga agaagaagga ggatgtgaac tgagagtgaa gttcagcagg   1140
agcgcagacg cccccgcgta caagcagggc cagaaccagc tctataacga gctcaatcta   1200
ggacgaagag aggagtacga tgttttggac aagagacgtg gccggaccc tgagatgggg    1260 ggaaagccga gaaggaagaa ccctcaggaa ggcctgtaca atgaactgca gaaagataag   1320
atggcggagg cctacagtga gattgggatg aaaggcgagc gccggagggg caaggggcac   1380
gatggccttt accagggtct cagtacagcc accaaggaca cctacgacgc ccttcacatg   1440
caggccctgc cccctcgct                                                1459

<210> SEQ ID NO 35
<211> LENGTH: 486
<212> TYPE: PRT
<213> ORGANISM: Homo sapiens

<400> SEQUENCE: 35

Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
            20                  25                  30

Ser Leu Ser Pro Gly Glu Arg Ala Thr Leu Ser Cys Arg Ala Ser Gln
        35                  40                  45

Asp Ile Ser Lys Tyr Leu Asn Trp Tyr Gln Gln Lys Pro Gly Gln Ala
    50                  55                  60

Pro Arg Leu Leu Ile Tyr His Thr Ser Arg Leu His Ser Gly Ile Pro
65                  70                  75                  80

Ala Arg Phe Ser Gly Ser Gly Ser Gly Thr Asp Tyr Thr Leu Thr Ile
                85                  90                  95

Ser Ser Leu Gln Pro Glu Asp Phe Ala Val Tyr Phe Cys Gln Gln Gly
            100                 105                 110

Asn Thr Leu Pro Tyr Thr Phe Gly Gln Gly Thr Lys Leu Glu Ile Lys
        115                 120                 125

Gly Gly Gly Gly Ser Gly Gly Gly Ser Gly Gly Gly Ser Gln
    130                 135                 140

Val Gln Leu Gln Glu Ser Gly Pro Gly Leu Val Lys Pro Ser Glu Thr
145                 150                 155                 160

Leu Ser Leu Thr Cys Thr Val Ser Gly Val Ser Leu Pro Asp Tyr Gly
                165                 170                 175

Val Ser Trp Ile Arg Gln Pro Pro Gly Lys Gly Leu Glu Trp Ile Gly
            180                 185                 190

Val Ile Trp Gly Ser Glu Thr Thr Tyr Tyr Gln Ser Ser Leu Lys Ser
        195                 200                 205

Arg Val Thr Ile Ser Lys Asp Asn Ser Lys Asn Gln Val Ser Leu Lys
    210                 215                 220

Leu Ser Ser Val Thr Ala Ala Asp Thr Ala Val Tyr Tyr Cys Ala Lys
```

```
            225                 230                 235                 240
        His Tyr Tyr Tyr Gly Gly Ser Tyr Ala Met Asp Tyr Trp Gly Gln Gly
                        245                 250                 255

Thr Leu Val Thr Val Ser Ser Thr Thr Pro Ala Pro Arg Pro Pro
                        260                 265                 270

Thr Pro Ala Pro Thr Ile Ala Ser Gln Pro Leu Ser Leu Arg Pro Glu
                    275                 280                 285

Ala Cys Arg Pro Ala Ala Gly Gly Ala Val His Thr Arg Gly Leu Asp
                290                 295                 300

Phe Ala Cys Asp Ile Tyr Ile Trp Ala Pro Leu Ala Gly Thr Cys Gly
        305                 310                 315                 320

Val Leu Leu Leu Ser Leu Val Ile Thr Leu Tyr Cys Lys Arg Gly Arg
                        325                 330                 335

Lys Lys Leu Leu Tyr Ile Phe Lys Gln Pro Phe Met Arg Pro Val Gln
                        340                 345                 350

Thr Thr Gln Glu Glu Asp Gly Cys Ser Cys Arg Phe Pro Glu Glu Glu
                    355                 360                 365

Glu Gly Gly Cys Glu Leu Arg Val Lys Phe Ser Arg Ser Ala Asp Ala
                370                 375                 380

Pro Ala Tyr Lys Gln Gly Gln Asn Gln Leu Tyr Asn Glu Leu Asn Leu
        385                 390                 395                 400

Gly Arg Arg Glu Glu Tyr Asp Val Leu Asp Lys Arg Arg Gly Arg Asp
                        405                 410                 415

Pro Glu Met Gly Gly Lys Pro Arg Arg Lys Asn Pro Gln Glu Gly Leu
                        420                 425                 430

Tyr Asn Glu Leu Gln Lys Asp Lys Met Ala Glu Ala Tyr Ser Glu Ile
                    435                 440                 445

Gly Met Lys Gly Glu Arg Arg Arg Gly Lys Gly His Asp Gly Leu Tyr
                450                 455                 460

Gln Gly Leu Ser Thr Ala Thr Lys Asp Thr Tyr Asp Ala Leu His Met
        465                 470                 475                 480

Gln Ala Leu Pro Pro Arg
                    485

<210> SEQ ID NO 36
<211> LENGTH: 1458
<212> TYPE: DNA
<213> ORGANISM: Homo sapiens

<400> SEQUENCE: 36
atggccctcc ctgtcaccgc cctgctgctt ccgctggctc ttctgctcca cgccgctcgg      60
cccgaaattg tgatgaccca gtcacccgcc actcttagcc tttcaccgg tgagcgcgca     120 accctgtctt gcagagcctc ccaagacatc tcaaaatacc ttaattggta tcaacagaag     180
cccggacagg ctcctcgcct tctgatctac acaccagcc ggctccattc tggaatccct     240
gccaggttca gcggtagcgg atctgggacc gactacaccc tcactatcag ctcactgcag     300
ccagaggact cgctgtctat tttctgtcag caagggaaca ccctgcccta cacctttgga     360
cagggcacca agctcgagat taaaggtgga ggtggcagcg gaggaggtgg gtccggcggt     420
ggaggaagcc aggtccaact ccaagaaagc ggaccgggtc ttgtgaagcc atcagaaact     480
ctttcactga cttgtactgt gagcggagtg tctctccccg attacggggt gtcttggatc     540
agacagccac cggggaaggg tctggaatgg attggagtga tttggggctc tgagactact     600
tactaccaat catccctcaa gtcacgcgtc accatctcaa aggacaactc taagaatcag     660
```

-continued

```
gtgtcactga aactgtcatc tgtgaccgca gccgacaccg ccgtgtacta ttgcgctaag    720
cattactatt atggcgggag ctacgcaatg gattactggg acagggtac tctggtcacc    780 gtgtccagca ccactacccc agcaccgagg ccacccaccc cggctcctac catcgcctcc    840
cagcctctgt ccctgcgtcc ggaggcatgt agacccgcag ctggtggggc cgtgcatacc    900
cggggtcttg acttcgcctg cgatatctac atttgggccc ctctggctgg tacttgcggg    960
gtcctgctgc tttcactcgt gatcactctt tactgtaagc gcggtcggaa gaagctgctg   1020
tacatcttta agcaacccct catgaggcct gtgcagacta ctcaagagga ggacggctgt   1080
tcatgccggt tcccagagga ggaggaaggc ggctgcgaac tgcgcgtgaa attcagccgc   1140
agcgcagatg ctccagccta caagcagggg cagaaccagc tctacaacga actcaatctt   1200
ggtcggagag aggagtacga cgtgctggac aagcggagag acgggaccc agaaatgggc   1260 gggaagccgc gcagaaagaa tccccaagag ggcctgtaca cgagctcca aaaggataag   1320 atggcagaag cctatagcga gattggtatg aaaggggaac gcagaagagg caaaggccac   1380
gacggactgt accagggact cagcaccgcc accaaggaca cctatgacgc tcttcacatg   1440
caggccctgc cgcctcgg                                                  1458
```

<210> SEQ ID NO 37
<211> LENGTH: 242
<212> TYPE: PRT
<213> ORGANISM: Homo sapiens

<400> SEQUENCE: 37

```
Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Lys Tyr
            20                  25                  30

Leu Asn Trp Tyr Gln Gln Lys Pro Gly Gln Ala Pro Arg Leu Leu Ile
        35                  40                  45

Tyr His Thr Ser Arg Leu His Ser Gly Ile Pro Ala Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln Gly Asn Thr Leu Pro Tyr
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Ser Gln Val Gln Leu Gln Glu
        115                 120                 125

Ser Gly Pro Gly Leu Val Lys Pro Ser Glu Thr Leu Ser Leu Thr Cys
    130                 135                 140

Thr Val Ser Gly Val Ser Leu Pro Asp Tyr Gly Val Ser Trp Ile Arg
145                 150                 155                 160

Gln Pro Pro Gly Lys Gly Leu Glu Trp Ile Gly Val Ile Trp Gly Ser
                165                 170                 175

Glu Thr Thr Tyr Tyr Ser Ser Ser Leu Lys Ser Arg Val Thr Ile Ser
            180                 185                 190

Lys Asp Asn Ser Lys Asn Gln Val Ser Leu Lys Leu Ser Ser Val Thr
        195                 200                 205

Ala Ala Asp Thr Ala Val Tyr Tyr Cys Ala Lys His Tyr Tyr Tyr Gly
    210                 215                 220
```

```
Gly Ser Tyr Ala Met Asp Tyr Trp Gly Gln Gly Thr Leu Val Thr Val
225                 230                 235                 240

Ser Ser

<210> SEQ ID NO 38
<211> LENGTH: 242
<212> TYPE: PRT
<213> ORGANISM: Homo sapiens

<400> SEQUENCE: 38

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Lys Tyr
            20                  25                  30

Leu Asn Trp Tyr Gln Gln Lys Pro Gly Gln Ala Pro Arg Leu Leu Ile
        35                  40                  45

Tyr His Thr Ser Arg Leu His Ser Gly Ile Pro Ala Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln Gly Asn Thr Leu Pro Tyr
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Ser Gln Val Gln Leu Gln Glu
        115                 120                 125

Ser Gly Pro Gly Leu Val Lys Pro Ser Glu Thr Leu Ser Leu Thr Cys
130                 135                 140

Thr Val Ser Gly Val Ser Leu Pro Asp Tyr Gly Val Ser Trp Ile Arg
145                 150                 155                 160

Gln Pro Pro Gly Lys Gly Leu Glu Trp Ile Gly Val Ile Trp Gly Ser
            165                 170                 175

Glu Thr Thr Tyr Tyr Gln Ser Ser Leu Lys Ser Arg Val Thr Ile Ser
        180                 185                 190

Lys Asp Asn Ser Lys Asn Gln Val Ser Leu Lys Leu Ser Ser Val Thr
    195                 200                 205

Ala Ala Asp Thr Ala Val Tyr Tyr Cys Ala Lys His Tyr Tyr Tyr Gly
210                 215                 220

Gly Ser Tyr Ala Met Asp Tyr Trp Gly Gln Gly Thr Leu Val Thr Val
225                 230                 235                 240

Ser Ser

<210> SEQ ID NO 39
<211> LENGTH: 242
<212> TYPE: PRT
<213> ORGANISM: Homo sapiens

<400> SEQUENCE: 39

Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Ile
        35                  40                  45

Gly Val Ile Trp Gly Ser Glu Thr Thr Tyr Tyr Ser Ser Ser Leu Lys
    50                  55                  60
```

```
Ser Arg Val Thr Ile Ser Lys Asp Asn Ser Lys Asn Gln Val Ser Leu
 65                  70                  75                  80

Lys Leu Ser Ser Val Thr Ala Ala Asp Thr Ala Val Tyr Tyr Cys Ala
                 85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser Gly Gly Gly Gly Ser Gly Gly Gly
            115                 120                 125

Gly Ser Gly Gly Gly Gly Ser Glu Ile Val Met Thr Gln Ser Pro Ala
130                 135                 140

Thr Leu Ser Leu Ser Pro Gly Glu Arg Ala Thr Leu Ser Cys Arg Ala
145                 150                 155                 160

Ser Gln Asp Ile Ser Lys Tyr Leu Asn Trp Tyr Gln Gln Lys Pro Gly
            165                 170                 175

Gln Ala Pro Arg Leu Leu Ile Tyr His Thr Ser Arg Leu His Ser Gly
            180                 185                 190

Ile Pro Ala Arg Phe Ser Gly Ser Gly Ser Gly Thr Asp Tyr Thr Leu
            195                 200                 205

Thr Ile Ser Ser Leu Gln Pro Glu Asp Phe Ala Val Tyr Phe Cys Gln
210                 215                 220

Gln Gly Asn Thr Leu Pro Tyr Thr Phe Gly Gln Gly Thr Lys Leu Glu
225                 230                 235                 240

Ile Lys

<210> SEQ ID NO 40
<211> LENGTH: 242
<212> TYPE: PRT
<213> ORGANISM: Homo sapiens

<400> SEQUENCE: 40

Gln Val Gln Leu Gln Glu Ser Gly Pro Gly Leu Val Lys Pro Ser Glu
 1               5                  10                  15

Thr Leu Ser Leu Thr Cys Thr Val Ser Gly Val Ser Leu Pro Asp Tyr
                 20                  25                  30

Gly Val Ser Trp Ile Arg Gln Pro Pro Gly Lys Gly Leu Glu Trp Ile
             35                  40                  45

Gly Val Ile Trp Gly Ser Glu Thr Thr Tyr Tyr Gln Ser Ser Leu Lys
 50                  55                  60

Ser Arg Val Thr Ile Ser Lys Asp Asn Ser Lys Asn Gln Val Ser Leu
 65                  70                  75                  80

Lys Leu Ser Ser Val Thr Ala Ala Asp Thr Ala Val Tyr Tyr Cys Ala
                 85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser Gly Gly Gly Gly Ser Gly Gly Gly
            115                 120                 125

Gly Ser Gly Gly Gly Gly Ser Glu Ile Val Met Thr Gln Ser Pro Ala
130                 135                 140

Thr Leu Ser Leu Ser Pro Gly Glu Arg Ala Thr Leu Ser Cys Arg Ala
145                 150                 155                 160

Ser Gln Asp Ile Ser Lys Tyr Leu Asn Trp Tyr Gln Gln Lys Pro Gly
            165                 170                 175

Gln Ala Pro Arg Leu Leu Ile Tyr His Thr Ser Arg Leu His Ser Gly
            180                 185                 190
```

```
Ile Pro Ala Arg Phe Ser Gly Ser Gly Ser Gly Thr Asp Tyr Thr Leu
            195                 200                 205

Thr Ile Ser Ser Leu Gln Pro Glu Asp Phe Ala Val Tyr Phe Cys Gln
    210                 215                 220

Gln Gly Asn Thr Leu Pro Tyr Thr Phe Gly Gln Gly Thr Lys Leu Glu
225                 230                 235                 240

Ile Lys

<210> SEQ ID NO 41
<211> LENGTH: 247
<212> TYPE: PRT
<213> ORGANISM: Homo sapiens

<400> SEQUENCE: 41

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Lys Tyr
            20                  25                  30

Leu Asn Trp Tyr Gln Gln Lys Pro Gly Gln Ala Pro Arg Leu Leu Ile
        35                  40                  45

Tyr His Thr Ser Arg Leu His Ser Gly Ile Pro Ala Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln Gly Asn Thr Leu Pro Tyr
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Gly Ser Gly Gly Gly Gly Ser Gln
        115                 120                 125

Val Gln Leu Gln Glu Ser Gly Pro Gly Leu Val Lys Pro Ser Glu Thr
    130                 135                 140

Leu Ser Leu Thr Cys Thr Val Ser Gly Val Ser Leu Pro Asp Tyr Gly
145                 150                 155                 160

Val Ser Trp Ile Arg Gln Pro Pro Gly Lys Gly Leu Glu Trp Ile Gly
                165                 170                 175

Val Ile Trp Gly Ser Glu Thr Thr Tyr Tyr Ser Ser Ser Leu Lys Ser
            180                 185                 190

Arg Val Thr Ile Ser Lys Asp Asn Ser Lys Asn Gln Val Ser Leu Lys
        195                 200                 205

Leu Ser Ser Val Thr Ala Ala Asp Thr Ala Val Tyr Tyr Cys Ala Lys
    210                 215                 220

His Tyr Tyr Tyr Gly Gly Ser Tyr Ala Met Asp Tyr Trp Gly Gln Gly
225                 230                 235                 240

Thr Leu Val Thr Val Ser Ser
                245

<210> SEQ ID NO 42
<211> LENGTH: 247
<212> TYPE: PRT
<213> ORGANISM: Homo sapiens

<400> SEQUENCE: 42

Glu Ile Val Met Thr Gln Ser Pro Ala Thr Leu Ser Leu Ser Pro Gly
1               5                   10                  15
```

Glu Arg Ala Thr Leu Ser Cys Arg Ala Ser Gln Asp Ile Ser Lys Tyr
                20                  25                  30

Leu Asn Trp Tyr Gln Gln Lys Pro Gly Gln Ala Pro Arg Leu Leu Ile
            35                  40                  45

Tyr His Thr Ser Arg Leu His Ser Gly Ile Pro Ala Arg Phe Ser Gly
        50                  55                  60

Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln Gly Asn Thr Leu Pro Tyr
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Ser Gly Gly Gly Gly Ser Gln
        115                 120                 125

Val Gln Leu Gln Glu Ser Gly Pro Gly Leu Val Lys Pro Ser Glu Thr
    130                 135                 140

Leu Ser Leu Thr Cys Thr Val Ser Gly Val Ser Leu Pro Asp Tyr Gly
145                 150                 155                 160

Val Ser Trp Ile Arg Gln Pro Pro Gly Lys Gly Leu Glu Trp Ile Gly
                165                 170                 175

Val Ile Trp Gly Ser Glu Thr Thr Tyr Tyr Gln Ser Ser Leu Lys Ser
            180                 185                 190

Arg Val Thr Ile Ser Lys Asp Asn Ser Lys Asn Gln Val Ser Leu Lys
        195                 200                 205

Leu Ser Ser Val Thr Ala Ala Asp Thr Ala Val Tyr Tyr Cys Ala Lys
210                 215                 220

His Tyr Tyr Tyr Gly Gly Ser Tyr Ala Met Asp Tyr Trp Gly Gln Gly
                225                 230                 235                 240

Thr Leu Val Thr Val Ser Ser
            245

<210> SEQ ID NO 43
<211> LENGTH: 247
<212> TYPE: PRT
<213> ORGANISM: Homo sapiens

<400> SEQUENCE: 43

Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
                20                  25                  30

Gly Val Ser Trp Ile Arg Gln Pro Pro Gly Lys Gly Leu Glu Trp Ile
            35                  40                  45

Gly Val Ile Trp Gly Ser Glu Thr Thr Tyr Tyr Ser Ser Leu Lys
        50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Glu Ile Val Met
    130                 135                 140

```
Thr Gln Ser Pro Ala Thr Leu Ser Leu Ser Pro Gly Glu Arg Ala Thr
145                 150                 155                 160

Leu Ser Cys Arg Ala Ser Gln Asp Ile Ser Lys Tyr Leu Asn Trp Tyr
                165                 170                 175

Gln Gln Lys Pro Gly Gln Ala Pro Arg Leu Leu Ile Tyr His Thr Ser
            180                 185                 190

Arg Leu His Ser Gly Ile Pro Ala Arg Phe Ser Gly Ser Gly Ser Gly
        195                 200                 205

Thr Asp Tyr Thr Leu Thr Ile Ser Ser Leu Gln Pro Glu Asp Phe Ala
    210                 215                 220

Val Tyr Phe Cys Gln Gln Gly Asn Thr Leu Pro Tyr Thr Phe Gly Gln
225                 230                 235                 240

Gly Thr Lys Leu Glu Ile Lys
                245

<210> SEQ ID NO 44
<211> LENGTH: 247
<212> TYPE: PRT
<213> ORGANISM: Homo sapiens

<400> SEQUENCE: 44

Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Ile
        35                  40                  45

Gly Val Ile Trp Gly Ser Glu Thr Thr Tyr Tyr Gln Ser Ser Leu Lys
    50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Glu Ile Val Met
    130                 135                 140

Thr Gln Ser Pro Ala Thr Leu Ser Leu Ser Pro Gly Glu Arg Ala Thr
145                 150                 155                 160

Leu Ser Cys Arg Ala Ser Gln Asp Ile Ser Lys Tyr Leu Asn Trp Tyr
                165                 170                 175

Gln Gln Lys Pro Gly Gln Ala Pro Arg Leu Leu Ile Tyr His Thr Ser
            180                 185                 190

Arg Leu His Ser Gly Ile Pro Ala Arg Phe Ser Gly Ser Gly Ser Gly
        195                 200                 205

Thr Asp Tyr Thr Leu Thr Ile Ser Ser Leu Gln Pro Glu Asp Phe Ala
    210                 215                 220

Val Tyr Phe Cys Gln Gln Gly Asn Thr Leu Pro Tyr Thr Phe Gly Gln
225                 230                 235                 240

Gly Thr Lys Leu Glu Ile Lys
                245
```

```
<210> SEQ ID NO 45
<211> LENGTH: 247
<212> TYPE: PRT
<213> ORGANISM: Homo sapiens

<400> SEQUENCE: 45

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Lys Tyr
            20                  25                  30

Leu Asn Trp Tyr Gln Gln Lys Pro Gly Gln Ala Pro Arg Leu Leu Ile
        35                  40                  45

Tyr His Thr Ser Arg Leu His Ser Gly Ile Pro Ala Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln Gly Asn Thr Leu Pro Tyr
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Ser Gly Gly Gly Gly Ser Gln
            115                 120                 125

Val Gln Leu Gln Glu Ser Gly Pro Gly Leu Val Lys Pro Ser Glu Thr
130                 135                 140

Leu Ser Leu Thr Cys Thr Val Ser Gly Val Ser Leu Pro Asp Tyr Gly
145                 150                 155                 160

Val Ser Trp Ile Arg Gln Pro Pro Gly Lys Gly Leu Glu Trp Ile Gly
                165                 170                 175

Val Ile Trp Gly Ser Glu Thr Thr Tyr Tyr Asn Ser Ser Leu Lys Ser
            180                 185                 190

Arg Val Thr Ile Ser Lys Asp Asn Ser Lys Asn Gln Val Ser Leu Lys
        195                 200                 205

Leu Ser Ser Val Thr Ala Ala Asp Thr Ala Val Tyr Tyr Cys Ala Lys
    210                 215                 220

His Tyr Tyr Tyr Gly Gly Ser Tyr Ala Met Asp Tyr Trp Gly Gln Gly
225                 230                 235                 240

Thr Leu Val Thr Val Ser Ser
            245

<210> SEQ ID NO 46
<211> LENGTH: 247
<212> TYPE: PRT
<213> ORGANISM: Homo sapiens

<400> SEQUENCE: 46

Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Ile
        35                  40                  45

Gly Val Ile Trp Gly Ser Glu Thr Thr Tyr Tyr Asn Ser Ser Leu Lys
    50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
```

```
                        85                  90                  95
Lys His Tyr Tyr Tyr Gly Gly Ser Tyr Ala Met Asp Tyr Trp Gly Gln
                100                 105                 110

Gly Thr Leu Val Thr Val Ser Ser Gly Gly Gly Gly Ser Gly Gly Gly
            115                 120                 125

Gly Ser Gly Gly Gly Gly Ser Gly Gly Gly Gly Ser Glu Ile Val Met
130                 135                 140

Thr Gln Ser Pro Ala Thr Leu Ser Leu Ser Pro Gly Glu Arg Ala Thr
145                 150                 155                 160

Leu Ser Cys Arg Ala Ser Gln Asp Ile Ser Lys Tyr Leu Asn Trp Tyr
                165                 170                 175

Gln Gln Lys Pro Gly Gln Ala Pro Arg Leu Leu Ile Tyr His Thr Ser
                180                 185                 190

Arg Leu His Ser Gly Ile Pro Ala Arg Phe Ser Gly Ser Gly Ser Gly
            195                 200                 205

Thr Asp Tyr Thr Leu Thr Ile Ser Ser Leu Gln Pro Glu Asp Phe Ala
            210                 215                 220

Val Tyr Phe Cys Gln Gln Gly Asn Thr Leu Pro Tyr Thr Phe Gly Gln
225                 230                 235                 240

Gly Thr Lys Leu Glu Ile Lys
                245

<210> SEQ ID NO 47
<211> LENGTH: 242
<212> TYPE: PRT
<213> ORGANISM: Homo sapiens

<400> SEQUENCE: 47

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Lys Tyr
                20                  25                  30

Leu Asn Trp Tyr Gln Gln Lys Pro Gly Gln Ala Pro Arg Leu Leu Ile
            35                  40                  45

Tyr His Thr Ser Arg Leu His Ser Gly Ile Pro Ala Arg Phe Ser Gly
        50                  55                  60

Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln Gly Asn Thr Leu Pro Tyr
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Ser Gln Val Gln Leu Gln Glu
        115                 120                 125

Ser Gly Pro Gly Leu Val Lys Pro Ser Glu Thr Leu Ser Leu Thr Cys
130                 135                 140

Thr Val Ser Gly Val Ser Leu Pro Asp Tyr Gly Val Ser Trp Ile Arg
145                 150                 155                 160

Gln Pro Pro Gly Lys Gly Leu Glu Trp Ile Gly Val Ile Trp Gly Ser
                165                 170                 175

Glu Thr Thr Tyr Tyr Asn Ser Ser Leu Lys Ser Arg Val Thr Ile Ser
            180                 185                 190

Lys Asp Asn Ser Lys Asn Gln Val Ser Leu Lys Leu Ser Ser Val Thr
        195                 200                 205
```

```
Ala Ala Asp Thr Ala Val Tyr Tyr Cys Ala Lys His Tyr Tyr Gly
    210                 215                 220
Gly Ser Tyr Ala Met Asp Tyr Trp Gly Gln Gly Thr Leu Val Thr Val
225                 230                 235                 240
Ser Ser
```

<210> SEQ ID NO 48
<211> LENGTH: 242
<212> TYPE: PRT
<213> ORGANISM: Homo sapiens

<400> SEQUENCE: 48

```
Gln Val Gln Leu Gln Glu Ser Gly Pro Gly Leu Val Lys Pro Ser Glu
1               5                   10                  15
Thr Leu Ser Leu Thr Cys Thr Val Ser Gly Val Ser Leu Pro Asp Tyr
            20                  25                  30
Gly Val Ser Trp Ile Arg Gln Pro Pro Gly Lys Gly Leu Glu Trp Ile
        35                  40                  45
Gly Val Ile Trp Gly Ser Glu Thr Thr Tyr Tyr Asn Ser Ser Leu Lys
    50                  55                  60
Ser Arg Val Thr Ile Ser Lys Asp Asn Ser Lys Asn Gln Val Ser Leu
65                  70                  75                  80
Lys Leu Ser Ser Val Thr Ala Ala Asp Thr Ala Val Tyr Tyr Cys Ala
                85                  90                  95
Lys His Tyr Tyr Gly Gly Ser Tyr Ala Met Asp Tyr Trp Gly Gln
            100                 105                 110
Gly Thr Leu Val Thr Val Ser Ser Gly Gly Gly Ser Gly Gly Gly
        115                 120                 125
Gly Ser Gly Gly Gly Ser Glu Ile Val Met Thr Gln Ser Pro Ala
    130                 135                 140
Thr Leu Ser Leu Ser Pro Gly Glu Arg Ala Thr Leu Ser Cys Arg Ala
145                 150                 155                 160
Ser Gln Asp Ile Ser Lys Tyr Leu Asn Trp Tyr Gln Gln Lys Pro Gly
                165                 170                 175
Gln Ala Pro Arg Leu Leu Ile Tyr His Thr Ser Arg Leu His Ser Gly
            180                 185                 190
Ile Pro Ala Arg Phe Ser Gly Ser Gly Ser Gly Thr Asp Tyr Thr Leu
        195                 200                 205
Thr Ile Ser Ser Leu Gln Pro Glu Asp Phe Ala Val Tyr Phe Cys Gln
    210                 215                 220
Gln Gly Asn Thr Leu Pro Tyr Thr Phe Gly Gln Gly Thr Lys Leu Glu
225                 230                 235                 240
Ile Lys
```

<210> SEQ ID NO 49
<211> LENGTH: 242
<212> TYPE: PRT
<213> ORGANISM: Homo sapiens

<400> SEQUENCE: 49

```
Asp Ile Gln Met Thr Gln Thr Thr Ser Ser Leu Ser Ala Ser Leu Gly
1               5                   10                  15
Asp Arg Val Thr Ile Ser Cys Arg Ala Ser Gln Asp Ile Ser Lys Tyr
            20                  25                  30
Leu Asn Trp Tyr Gln Gln Lys Pro Asp Gly Thr Val Lys Leu Leu Ile
        35                  40                  45
```

-continued

Tyr His Thr Ser Arg Leu His Ser Gly Val Pro Ser Arg Phe Ser Gly
 50                  55                  60

Ser Gly Ser Gly Thr Asp Tyr Ser Leu Thr Ile Ser Asn Leu Glu Gln
 65                  70                  75                  80

Glu Asp Ile Ala Thr Tyr Phe Cys Gln Gln Gly Asn Thr Leu Pro Tyr
                 85                  90                  95

Thr Phe Gly Gly Gly Thr Lys Leu Glu Ile Thr Gly Gly Gly Gly Ser
            100                 105                 110

Gly Gly Gly Gly Ser Gly Gly Gly Ser Glu Val Lys Leu Gln Glu
            115                 120                 125

Ser Gly Pro Gly Leu Val Ala Pro Ser Gln Ser Leu Ser Val Thr Cys
130                 135                 140

Thr Val Ser Gly Val Ser Leu Pro Asp Tyr Gly Val Ser Trp Ile Arg
145                 150                 155                 160

Gln Pro Pro Arg Lys Gly Leu Glu Trp Leu Gly Val Ile Trp Gly Ser
                165                 170                 175

Glu Thr Thr Tyr Tyr Asn Ser Ala Leu Lys Ser Arg Leu Thr Ile Ile
            180                 185                 190

Lys Asp Asn Ser Lys Ser Gln Val Phe Leu Lys Met Asn Ser Leu Gln
            195                 200                 205

Thr Asp Asp Thr Ala Ile Tyr Tyr Cys Ala Lys His Tyr Tyr Gly
210                 215                 220

Gly Ser Tyr Ala Met Asp Tyr Trp Gly Gln Gly Thr Ser Val Thr Val
225                 230                 235                 240

Ser Ser

<210> SEQ ID NO 50
<211> LENGTH: 7750
<212> TYPE: DNA
<213> ORGANISM: Artificial Sequence
<220> FEATURE:
<223> OTHER INFORMATION: synthetic construct

<400> SEQUENCE: 50

```
gcagactagt aagcttagta atcaattacg gggtcattag ttcatagccc atatatggag    60
ttccgcgtta cataacttac ggtaaatggc ccgcctggct gaccgcccaa cgacccccgc   120
ccattgacgt caataatgac gtatgttccc atagtaacgc caatagggac tttccattga   180
cgtcaatggg tggagtattt acggtaaact gcccacttgg cagtacatca agtgtatcat   240
atgccaagta cgcccctat tgacgtcaat gacggtaaat ggcccgcctg gcattatgcc   300
cagtacatga ccttatggga ctttcctact ggcagtaca tctacgtatt agtcatcgct   360
attaccatgc tgatgcggtt ttggcagtac atcaatgggc gtggatagcg gtttgactca   420
cggggatttc caagtctcca ccccattgac gtcaatggga gtttgttttg gcaccaaaat   480
caacgggact ttccaaaatg tcgtaacaac tccgccccat tgacgcaaat gggcggtagg   540
cgtgtacggt gggaggtcta tataagcaga gctggtttag tgaaccgggg tctctctggt   600
tagaccagat ctgagcctgg gagctctctg gctaactagg gaacccactg cttaagcctc   660
aataaagctt gccttgagtg cttcaagtag tgtgtgcccg tctgttgtgt gactctggta   720
actagagatc cctcagaccc ttttagtcag tgtggaaaat ctctagcagt ggcgcccgaa   780
cagggacttg aaagcgaaag taagccaga ggagatctct cgacgcagga ctcggcttgc   840
tgaagcgcgc acggcaagag gcgaggggcg gcgactggtg agtacgccaa aaatttgac   900
```

```
tagcggaggc tagaaggaga gagatgggtg cgagagcgtc ggtattaagc gggggagaat    960
tagataaatg ggaaaaaatt cggtaataag gccaggggga aagaagaagt acaagctaaa   1020
gcacatcgta tgggcaagca gggagctaga acgattcgca gttaatcctg gccttttaga   1080
gacatcagaa ggcggccgct gatcttcaga cctggaggag gcgatatgag ggacaattgg   1140
agaagtgaat tatataaata taaagtagta aaaattgaac cattaggagt agcacccacc   1200
aaggcaaaga gaagagtggt gcagagagaa aaagagcag tgggaattta aataggagct    1260
ttgttccttg ggttcttggg agcagcagga agcactatgg gcgcagcgtc aatgacgctg   1320
acggtacagg ccagacaatt attgtctgat atagtgcagc agcagaacaa tttgctgagg   1380
gctattgagg cgcaacagca tctgttgcaa ctcacagtct ggggcatcaa acagctccag   1440
gcaagaatcc tggctgtgga aagataccta aaggatcaac agctcctcct gcaggggatt   1500
tggggttgct ctggaaaact catttgcacc actgctgtgc cttggaatgc tagttggagt   1560
aataaatctc tggaacagat ttggaataac atgacctgga tggagtggga cagagaaatt   1620
aacaattaca caagcttaat acactcctta attgaagaat cgcaaaacca gcaagaaaag   1680
aatgaacaag aattattgga attagataaa tgggcaagtt tgtggaattg gtttaacata   1740
acaaattggc tgtggtatat aaaattattc ataatgatag taggaggctt ggtaggttta   1800
agaatagttt ttgctgtact ttctatagtg aatagagtta ggcagggata ttcaccatta   1860
tcgtttcaga cccacctccc aatcccgagg ggacccgaca ggcccgaagg aatagaagaa   1920
gaaggtggag agagagacag agacagatcc attcgattag tgaacggatc tcgacggtat   1980
cgattagact gtagcccagg aatatggcag ctagattgta cacatttaga aggaaaagtt   2040
atcttggtag cagttcatgt agccagtgga tatatagaag cagaagtaat tccagcagag   2100
acagggcaag aaacagcata cttcctctta aaattagcag gaagatggcc agtaaaaaca   2160
gtacatacag acaatggcag caatttcacc agtactacag ttaaggccgc ctgttggtgg   2220
gcggggatca gcaggaatt tggcattccc tacaatcccc aaagtcaagg agtaatagaa   2280
tctatgaata aagaattaaa gaaaattata ggacaggtaa gagatcaggc tgaacatctt   2340
aagacagcag tacaaatggc agtattcatc cacaatttta aaagaaaagg ggggattggg   2400
gggtacagtg caggggaaag aatagtagac ataatagcaa cagacataca aactaaagaa   2460
ttacaaaaac aaattacaaa aattcaaaat tttcgggttt attacaggga cagcagagat   2520
ccagtttggc tgcattgatc acgtgaggct ccggtgcccg tcagtgggca gagcgcacat   2580
cgcccacagt ccccgagaag ttggggggag ggtcggcaa ttgaaccggt gcctagagaa    2640
ggtggcgcgg ggtaaactgg gaaagtgatg tcgtgtactg gctccgcctt tttcccgagg   2700
gtgggggaga accgtatata agtgcagtag tcgccgtgaa cgttcttttt cgcaacgggt   2760
ttgccgccag aacacaggta agtgccgtgt gtggttcccg cgggcctggc ctctttacgg   2820
gttatgcccc ttgcgtgcct tgaattactt ccacctggct gcagtacgtg attcttgatc   2880
ccgagcttcg ggttggaagt gggtgggaga gttcgaggcc ttgcgcttaa ggagcccctt   2940
cgcctcgtgc ttgagttgag gcctggcctg ggcgctgggg ccgccgcgtg cgaatctggt   3000
ggcaccttcg cgcctgtctc gctgctttcg ataagtctct agccatttaa aattttttgat  3060
gacctgctgc gacgcttttt ttctggcaag atagtcttgt aaatgcgggc caagatctgc   3120
acactggtat ttcggttttt ggggccgcgg gcggcgacgg ggcccgtgcg tcccagcgca   3180
catgttcggc gaggcgggc ctgcgagcgc ggccaccgag aatcggacgg gggtagtctc    3240
aagctggccg gcctgctctg gtgcctggcc tcgcgccgcc gtgtatcgcc ccgccctggg   3300
```

```
cggcaaggct ggcccggtcg gcaccagttg cgtgagcgga aagatggccg cttcccggcc   3360
ctgctgcagg gagctcaaaa tggaggacgc ggcgctcggg agagcgggcg ggtgagtcac   3420
ccacacaaag gaaaagggcc tttccgtcct cagccgtcgc ttcatgtgac tccactgagt   3480
accgggcgcc gtccaggcac ctcgattagt tctcgagctt ttggagtacg tcgtctttag   3540
gttgggggga ggggtttat gcgatggagt ttccccacac tgagtgggtg gagactgaag    3600
ttaggccagc ttggcacttg atgtaattct ccttggaatt tgccctttttt gagtttggat  3660 cttggttcat tctcaagcct cagacagtgg ttcaaagttt ttttcttcca tttcaggtgt   3720
cgtgatctag aggatccgcc accatggtga gcaagggcga ggagctgttc accggggtgg   3780
tgcccatcct ggtcgagctg gacggcgacg taaacggcca caagttcagc gtgtccggcg   3840
agggcgaggg cgatgccacc tacggcaagc tgaccctgaa gttcatctgc accaccggca   3900
agctgcccgt gccctggccc accctcgtga ccaccctgac ctacggcgtg cagtgcttca   3960
gccgctaccc cgaccacatg aagcagcacg acttcttcaa gtccgccatg cccgaaggct   4020
acgtccagga gcgcaccatc ttcttcaagg acgacggcaa ctacaagacc cgcgccgagg   4080
tgaagttcga gggcgacacc ctggtgaacc gcatcgagct gaagggcatc gacttcaagg   4140
aggacggcaa catcctgggg cacaagctgg agtacaacta caacagccac aacgtctata   4200
tcatggccga caagcagaag aacggcatca aggtgaactt caagatccgc cacaacatcg   4260
aggacggcag cgtgcagctc gccgaccact accagcagaa cacccccatc ggcgacggcc   4320
ccgtgctgct gcccgacaac cactacctga gcacccagtc cgccctgagc aaagacccca   4380
acgagaagcg cgatcacatg gtcctgctgg agttcgtgac cgccgccggg atcactctcg   4440
gcatggacga gctgtacaag taagtcgaca atcaacctct ggattacaaa atttgtgaaa   4500
gattgactgg tattcttaac tatgttgctc cttttacgct atgtggatac gctgctttaa   4560
tgcctttgta tcatgctatt gcttcccgta tggctttcat tttctcctcc ttgtataaat   4620
cctggttgct gtctctttat gaggagttgt ggcccgttgt caggcaacgt ggcgtggtgt   4680
gcactgtgtt tgctgacgca accccactg gttggggcat tgccaccacc tgtcagctcc    4740
tttccgggac tttcgctttc ccctcccta ttgccacggc ggaactcatc gccgcctgcc    4800
ttgcccgctg ctggacaggg gctcggctgt tgggcactga caattccgtg gtgttgtcgg   4860
ggaagctgac gtccttttcca tggctgctcg cctgtgttgc cacctggatt ctgcgcggga   4920
cgtccttctg ctacgtccct tcggccctca atccagcgga ccttccttcc gcggcctgc    4980 tgccggctct gcggcctctt ccgcgtcttc gccttcgccc tcagacgagt cggatctccc   5040
tttgggccgc ctccccgcct ggaattcgag ctcggtacct ttaagaccaa tgacttacaa   5100
ggcagctgta gatcttagcc actttttaaa agaaaagggg ggactggaag gctaattca    5160 ctcccaacga agacaagatc tgcttttttgc ttgtactggg tctctctggt tagaccagat   5220
ctgagcctgg gagctctctg gctaactagg gaacccactg cttaagcctc aataaagctt   5280
gccttgagtg cttcaagtag tgtgtgcccg tctgttgtgt gactctggta actagagatc   5340
cctcagaccc ttttagtcag tgtggaaaat ctctagcagt agtagttcat gtcatcttat   5400
tattcagtat ttataacttg caaagaaatg aatatcagag agtgagagga acttgtttat   5460
tgcagcttat aatggttaca ataaagcaa tagcatcaca aatttcacaa ataaagcatt    5520 ttttcactg cattctagtt gtggtttgtc caaactcatc aatgtatctt atcatgtctg    5580
gctctagcta tcccgcccct aggcaccggg gaaatgtgcg cggaacccct atttgtttat   5640
```

| | |
|---|---|
| ttttctaaat acattcaaat atgtatccgc tcatgagaca ataaccctga taaatgcttc | 5700 |
| aataatattg aaaaaggaag agtatgagcc atattcaacg ggaaacgtcg aggccgcgat | 5760 |
| taaattccaa catggatgct gatttatatg ggtataaatg ggctcgcgat aatgtcgggc | 5820 |
| aatcaggtgc gacaatctat cgcttgtatg ggaagcccga tgcgccagag ttgtttctga | 5880 |
| aacatggcaa aggtagcgtt gccaatgatg ttacagatga gatggtcaga ctaaactggc | 5940 |
| tgacggaatt tatgccactt ccgaccatca agcattttat ccgtactcct gatgatgcat | 6000 |
| ggttactcac cactgcgatc cccggaaaaa cagcgttcca ggtattagaa gaatatcctg | 6060 |
| attcaggtga aaatattgtt gatgcgctgg cagtgttcct gcgccggttg cactcgattc | 6120 |
| ctgtttgtaa ttgtcctttt aacagcgatc gcgtatttcg cctcgctcag gcgcaatcac | 6180 |
| gaatgaataa cggtttggtt gatgcgagtg attttgatga cgagcgtaat ggctggcctg | 6240 |
| ttgaacaagt ctggaaagaa atgcataaac ttttgccatt ctcaccggat tcagtcgtca | 6300 |
| ctcatggtga tttctcactt gataacctta ttttgacga ggggaaatta ataggttgta | 6360 |
| ttgatgttgg acgagtcgga atcgcagacc gataccagga tcttgccatc ctatggaact | 6420 |
| gcctcggtga gttttctcct tcattacaga acggcttttt tcaaaaatat ggtattgata | 6480 |
| atcctgatat gaataaattg cagtttcatt tgatgctcga tgagttttttc taactgtcag | 6540 |
| accaagttta ctcatatata ctttagattg atttaaaact tcattttaa tttaaaagga | 6600 |
| tctaggtgaa gatccttttt gataatctca tgaccaaaat cccttaacgt gagttttcgt | 6660 |
| tccactgagc gtcagacccc gtagaaaaga tcaaaggatc ttcttgagat ccttttttc | 6720 |
| tgcgcgtaat ctgctgcttg caaacaaaaa aaccaccgct accagcggtg gtttgtttgc | 6780 |
| cggatcaaga gctaccaact ctttttccga aggtaactgg cttcagcaga gcgcagatac | 6840 |
| caaatactgt tcttctagtg tagccgtagt taggccacca cttcaagaac tctgtagcac | 6900 |
| cgcctacata cctcgctctg ctaatcctgt taccagtggc tgctgccagt ggcgataagt | 6960 |
| cgtgtcttac cgggttggac tcaagacgat agttaccgga taaggcgcag cggtcgggct | 7020 |
| gaacgggggg ttcgtgcaca gcccagct tggagcgaac gacctacacc gaactgagat | 7080 |
| acctacagcg tgagctatga gaaagcgcca cgcttcccga aggagaaag gcggacaggt | 7140 |
| atccggtaag cggcagggtc ggaacaggag agcgcacgag ggagcttcca ggggggaaacg | 7200 |
| cctggtatct ttatagtcct gtcgggtttc gccacctctg acttgagcgt cgatttttgt | 7260 |
| gatgctcgtc aggggggcgg agcctatgga aaaacgccag caacgcggcc ttttttacggt | 7320 |
| tcctggcctt ttgctggcct tttgctcaca tgttctttcc tgcgttatcc cctgattctg | 7380 |
| tggataaccg tattaccgcc tttgagtgag ctgataccgc tcgccgcagc cgaacgaccg | 7440 |
| agcgcagcga gtcagtgagc gaggaagcgg aagagcgccc aatacgcaaa ccgcctctcc | 7500 |
| ccgcgcgttg gccgattcat taatgcagct ggcacgacag gtttcccgac tggaaagcgg | 7560 |
| gcagtgagcg caacgcaatt aatgtgagtt agctcactca ttaggcaccc caggctttac | 7620 |
| actttatgct tccggctcgt atgttgtgtg gaattgtgag cggataacaa tttcacacag | 7680 |
| gaaacagcta tgaccatgat tacgccaagc gcgcaattaa ccctcactaa agggaacaaa | 7740 |
| agctggagct | 7750 |

<210> SEQ ID NO 51
<211> LENGTH: 7884
<212> TYPE: DNA
<213> ORGANISM: Artificial Sequence
<220> FEATURE:
<223> OTHER INFORMATION: synthetic construct

<400> SEQUENCE: 51

```
gcagactagt aagcttagta atcaattacg gggtcattag ttcatagccc atatatggag      60
ttccgcgtta cataacttac ggtaaatggc ccgcctggct gaccgcccaa cgaccccgc      120
ccattgacgt caataatgac gtatgttccc atagtaacgc caatagggac tttccattga     180
cgtcaatggg tggagtattt acggtaaact gcccacttgg cagtacatca agtgtatcat     240
atgccaagta cgccccctat tgacgtcaat gacggtaaat ggcccgcctg gcattatgcc     300
cagtacatga ccttatggga ctttcctact tggcagtaca tctacgtatt agtcatcgct     360
attaccatgc tgatgcggtt ttggcagtac atcaatgggc gtggatagcg gtttgactca     420
cggggatttc caagtctcca ccccattgac gtcaatggga gtttgttttg gcaccaaaat     480
caacgggact ttccaaaatg tcgtaacaac tccgccccat tgacgcaaat gggcggtagg     540
cgtgtacggt gggaggtcta taagcaga gctggtttag tgaaccgggg tctctctggt      600
tagaccagat ctgagcctgg gagctctctg gctaactagg gaacccactg cttaagcctc     660
aataaagctt gccttgagtg cttcaagtag tgtgtgcccg tctgttgtgt gactctggta     720
actagagatc cctcagaccc ttttagtcag tgtggaaaat ctctagcagt ggcgcccgaa     780
cagggacttg aaagcgaaag taaagccaga ggagatctct cgacgcagga ctcggcttgc     840
tgaagcgcgc acggcaagag gcgaggggcg gcgactggtg agtacgccaa aaattttgac     900
tagcggaggc tagaaggaga gagatgggtg cgagagcgtc ggtattaagc gggggagaat     960
tagataaatg ggaaaaaatt cggtaataag gccaggggga aagaagaagt acaagctaaa    1020
gcacatcgta tgggcaagca gggagctaga acgattcgca gttaatcctg gccttttaga    1080
gacatcagaa ggcggccgct gatcttcaga cctggaggag gcgatatgag ggacaattgg    1140
agaagtgaat tatataaata taaagtagta aaaattgaac cattaggagt agcacccacc    1200
aaggcaaaga gaagagtggt gcagagaaa aaaagagcag tgggaattta ataggagct     1260
ttgttccttg ggttcttggg agcagcagga agcactatgg gcgcagcgtc aatgacgctg    1320
acggtacagg ccagacaatt attgtctgat atagtgcagc agcagaacaa tttgctgagg    1380
gctattgagg cgcaacagca tctgttgcaa ctcacagtct ggggcatcaa acagctccag    1440
gcaagaatcc tggctgtgga agatacctaa aggatcaac agctcctcct gcagggatt     1500
tggggttgct ctggaaaact catttgcacc actgctgtgc cttggaatgc tagttggagt    1560
aataaatctc tggaacagat ttggaataac atgacctgga tggagtggga cagagaaatt    1620
aacaattaca caagcttaat acactcctta attgaagaat cgcaaaacca gcaagaaaag    1680
aatgaacaag aattattgga attagataaa tgggcaagtt tgtggaattg gtttaacata    1740
acaaattggc tgtggtatat aaaattattc ataatgatag taggaggctt ggtaggttta    1800
agaatagttt ttgctgtact ttctatagtg aatagagtta ggcagggata ttcaccatta    1860
tcgtttcaga cccacctccc aatcccgagg ggacccgaca ggcccgaagg aatagaagaa    1920
gaaggtggag agagagacag agacagatcc attcgattag tgaacggatc tcgacggtat    1980
cgattagact gtagcccagg aatatggcag ctagattgta cacatttaga aggaaaagtt    2040
atcttggtag cagttcatgt agccagtgga tatatagaag cagaagtaat tccagcagag    2100
acagggcaag aaacagcata cttcctctta aaattagcag gaagatggcc agtaaaaaca    2160
gtacatacag acaatggcag caatttcacc agtactacag ttaaggccgc ctgttggtgg    2220
gcggggatca agcaggaatt tggcattccc tacaatcccc aaagtcaagg agtaatagaa    2280
```

```
tctatgaata aagaattaaa gaaaattata ggacaggtaa gagatcaggc tgaacatctt    2340
aagacagcag tacaaatggc agtattcatc cacaatttta aaagaaaagg ggggattggg    2400
gggtacagtg caggggaaag aatagtagac ataatagcaa cagacataca aactaaagaa    2460
ttacaaaaac aaaattacaaa aattcaaaat tttcgggttt attacaggga cagcagagat    2520
ccagtttggc tgcattgatc acgtgaggct ccggtgcccg tcagtgggca gagcgcacat    2580
cgcccacagt ccccgagaag ttgggggggag ggtcggcaa ttgaaccggt gcctagagaa    2640
ggtggcgcgg ggtaaactgg gaaagtgatg tcgtgtactg gctccgcctt tttcccgagg    2700
gtgggggaga accgtatata agtgcagtag tcgccgtgaa cgttcttttt cgcaacgggt    2760
ttgccgccag aacacaggta agtgccgtgt gtggttcccg cgggcctggc ctctttacgg    2820
gttatggccc ttgcgtgcct tgaattactt ccacctggct gcagtacgtg attcttgatc    2880
ccgagcttcg ggttggaagt gggtgggaga gttcgaggcc ttgcgcttaa ggagcccctt    2940
cgcctcgtgc ttgagttgag gcctggcctg ggcgctgggg ccgccgcgtg cgaatctggt    3000
ggcaccttcg cgcctgtctc gctgctttcg ataagtctct agccatttaa aatttttgat    3060
gacctgctgc gacgctttt ttctggcaag atagtcttgt aaatgcgggc caagatctgc    3120
acactggtat ttcggttttt ggggccgcgg gcggcgacgg ggcccgtgcg tcccagcgca    3180
catgttcggc gaggcgggc ctgcgagcgc ggccaccgag aatcggacgg gggtagtctc    3240
aagctggccg gcctgctctg gtgcctggcc tcgcgccgcc gtgtatcgcc ccgccctggg    3300
cggcaaggct ggcccggtcg gcaccagttg cgtgagcgga aagatggccg cttcccggcc    3360
ctgctgcagg gagctcaaaa tggaggacgc ggcgctcggg agagcgggcg ggtgagtcac    3420
ccacacaaag gaaaagggcc tttccgtcct cagccgtcgc ttcatgtgac tccactgagt    3480
accgggcgcc gtccaggcac ctcgattagt tctcgagctt ttggagtacg tcgtctttag    3540
gttgggggga ggggttttat gcgatggagt ttccccacac tgagtgggtg gagactgaag    3600
ttaggccagc ttggcacttg atgtaattct ccttggaatt tgccctttt gagtttggat    3660 cttggttcat tctcaagcct cagacagtgg ttcaaagttt ttttcttcca tttcaggtgt    3720
cgtgatctag aggatccgcc accatggtga gcaagggcga ggagctgttc accggggtgg    3780
tgcccatcct ggtcgagctg gacggcgacg taaacggcca caagttcagc gtgtccggcg    3840
agggcgaggg cgatgccacc tacggcaagc tgaccctgaa gttcatctgc accaccggca    3900
agctgcccgt gccctggccc accctcgtga ccaccctgac ctacggcgtg cagtgcttca    3960
gccgctaccc cgaccacatg aagcagcacg acttcttcaa gtccgccatg cccgaaggct    4020
acgtccagga gcgcaccatc ttcttcaagg acgacggcaa ctacaagacc cgcgccgagg    4080
tgaagttcga gggcgacacc ctggtgaacc gcatcgagct gaagggcatc gacttcaagg    4140
aggacggcaa catcctgggg cacaagctgg agtacaacta caacagccac aacgtctata    4200
tcatggccga caagcagaag aacggcatca aggtgaactt caagatccgc cacaacatcg    4260
aggacggcag cgtgcagctc gccgaccact accagcagaa cacccccatc ggcgacggcc    4320
ccgtgctgct gcccgacaac cactacctga gcacccagtc cgccctgagc aaagaccca    4380 acgagaagcg cgatcacatg gtcctgctgg agttcgtgac cgccgccggg atcactctcg    4440
gcatggacga gctgtacaag taagtcgact aaacaggcct attgattgga aagtatgtca    4500
acgaattgtg gtctttttgg ggtttgctgc ccctttacg caatgtggat atcctgcttt    4560
aatgccttta tatgcatgta tacaagcaaa acaggctttt actttctcgc caacttacaa    4620
ggcctttcta agtaaacagt atctgaccct ttaccccgtt gctcggcaac ggcctggtct    4680
```

-continued

```
gtgccaagtg tttgctgacg caacccccac tggttggggc ttggccatag gccatcagcg      4740
catgcgtgga acctttgtgt ctcctctgcc gatccatact gcggaactcc tagccgcttg      4800
ttttgctcgc agcaggtctg gagcgaaact catcgggact gacaattctg tcgtgctctc      4860
ccgcaagtat acatcgtttc cagggctgct aggctgtgct gccaactgga tcctgcgcgg      4920
gacgtccttt gtttacgtcc cgtcggcgct gaatcccgcg gacgacccct ccggggccg       4980
cttgggctc  taccgcccgc ttctccgtct gccgtaccga ccaccacgg  ggcgcacctc      5040
tctttacgcg gactccccgt ctgtgccttc tcatctgccg gaccgtgtgc acttcgcttc      5100
acctctgcac gtcgcatgga gaccaccgtg aacgcccacc ggaacctgcc caaggtcttg      5160
cataagagga ctcttggact ttcagcaatg tcaacgaatt cgagctcggt acctttaaga      5220
ccaatgactt acaaggcagc tgtagatctt agccactttt taaaagaaaa gggggggactg     5280
gaagggctaa ttcactccca acgaagacaa gatctgcttt ttgcttgtac tgggtctctc     5340
tggttagacc agatctgagc ctgggagctc tctggctaac tagggaaccc actgcttaag     5400
cctcaataaa gcttgccttg agtgcttcaa gtagtgtgtg cccgtctgtt gtgtgactct     5460
ggtaactaga gatccctcag acccttttag tcagtgtgga aaatctctag cagtagtagt     5520
tcatgtcatc ttattattca gtatttataa cttgcaaaga aatgaatatc agagagtgag     5580
aggaacttgt ttattgcagc ttataatggt tacaaataaa gcaatagcat cacaaatttc     5640
acaaataaag catttttttc actgcattct agttgtggtt tgtccaaact catcaatgta     5700
tcttatcatg tctggctcta gctatcccgc ccctaggcac cggggaaatg tgcgcggaac     5760
ccctatttgt ttatttttct aaatacattc aaatatgtat ccgctcatga dacaataacc     5820
ctgataaatg cttcaataat attgaaaaag gaagagtatg agccatattc aacgggaaac     5880
gtcgaggccg cgattaaatt ccaacatgga tgctgattta tatgggtata aatgggctcg     5940
cgataatgtc gggcaatcag gtgcgacaat ctatcgcttg tatgggaagc ccgatgcgcc     6000
agagttgttt ctgaaacatg gcaaaggtag cgttgccaat gatgttacag atgagatggt     6060
cagactaaac tggctgacgg aatttatgcc acttccgacc atcaagcatt ttatccgtac     6120
tcctgatgat gcatggttac tcaccactgc gatccccgga aaaacagcgt tccaggtatt     6180
agaagaatat cctgattcag gtgaaaatat tgttgatgcg ctggcagtgt tcctgcgccg     6240
gttgcactcg attcctgttt gtaattgtcc ttttaacagc gatcgcgtat ttcgcctcgc     6300
tcaggcgcaa tcacgaatga ataacggttt ggttgatgcg agtgattttg atgacgagcg     6360
taatggctgg cctgttgaac aagtctggaa agaaatgcat aaacttttgc cattctcacc     6420
ggattcagtc gtcactcatg gtgatttctc acttgataac cttatttttg acgaggggaa     6480
attaataggt tgtattgatg ttggacgagt cggaatcgca gaccgatacc aggatcttgc     6540
catcctatgg aactgcctcg gtgagttttc tccttcatta cagaaacggc tttttcaaaa     6600
atatggtatt gataatcctg atatgaataa attgcagttt catttgatgc tcgatgagtt     6660
tttctaactg tcagaccaag tttactcata tatactttag attgatttaa aacttcattt     6720
ttaatttaaa aggatctagg tgaagatcct ttttgataat ctcatgacca aaatccctta     6780
acgtgagttt cgttccact  gagcgtcaga ccccgtagaa aagatcaaag gatcttcttg     6840
agatcctttt tttctgcgcg taatctgctg cttgcaaaca aaaaaaccac cgctaccagc     6900
ggtggtttgt ttgccggatc aagagctacc aactcttttt ccgaaggtaa ctggcttcag     6960
cagagcgcag ataccaaata ctgttcttct agtgtagccg tagttaggcc accacttcaa     7020
```

-continued

```
gaactctgta gcaccgccta catacctcgc tctgctaatc ctgttaccag tggctgctgc    7080
cagtggcgat aagtcgtgtc ttaccgggtt ggactcaaga cgatagttac cggataaggc    7140
gcagcggtcg ggctgaacgg ggggttcgtg cacacagccc agcttggagc gaacgaccta    7200
caccgaactg agatacctac agcgtgagct atgagaaagc gccacgcttc ccgaagggag    7260
aaaggcggac aggtatccgg taagcggcag ggtcggaaca ggagagcgca cgagggagct    7320
tccaggggga aacgcctggt atctttatag tcctgtcggg tttcgccacc tctgacttga    7380
gcgtcgattt ttgtgatgct cgtcaggggg cggagccta tggaaaaacg ccagcaacgc     7440 ggcctttta cggttcctgg ccttttgctg gcctttgct cacatgttct ttcctgcgtt      7500 atccctgat tctgtggata accgtattac cgcctttgag tgagctgata ccgctcgccg    7560
cagccgaacg accgagcgca gcgagtcagt gagcgaggaa gcggaagagc gcccaatacg    7620
caaaccgcct ctccccgcgc gttggccgat tcattaatgc agctggcacg acaggtttcc    7680
cgactggaaa gcgggcagtg agcgcaacgc aattaatgtg agttagctca ctcattaggc    7740
accccaggct ttacacttta tgcttccggc tcgtatgttg tgtggaattg tgagcggata    7800
acaatttcac acaggaaaca gctatgacca tgattacgcc aagcgcgcaa ttaaccctca    7860
ctaaagggaa caaaagctgg agct                                           7884
```

<210> SEQ ID NO 52
<211> LENGTH: 570
<212> TYPE: DNA
<213> ORGANISM: Artificial Sequence
<220> FEATURE:
<223> OTHER INFORMATION: synthetic construct

<400> SEQUENCE: 52

```
gtaatcaatt acgggtcat tagttcatag cccatatatg gagttccgcg ttacataact      60
tacggtaaat ggcccgcctg gctgaccgcc caacgacccc cgcccattga cgtcaataat    120
gacgtatgtt cccatagtaa cgccaatagg gactttccat tgacgtcaat gggtggagta    180
tttacggtaa actgcccact tggcagtaca tcaagtgtat catatgccaa gtacgccccc    240
tattgacgtc aatgacggta aatggcccgc ctggcattat gcccagtaca tgaccttatg    300
ggactttcct acttggcagt acatctacgt attagtcatc gctattacca tgctgatgcg    360
gttttggcag tacatcaatg ggcgtggata gcggtttgac tcacggggat ttccaagtct    420 ccacccatt gacgtcaatg ggagtttgtt ttggcaccaa aatcaacggg actttccaaa     480
atgtcgtaac aactccgccc cattgacgca aatgggcggt aggcgtgtac ggtgggaggt    540
ctatataagc agagctggtt tagtgaaccg                                     570
```

<210> SEQ ID NO 53
<211> LENGTH: 97
<212> TYPE: DNA
<213> ORGANISM: Human immunodeficiency virus type 1

<400> SEQUENCE: 53

```
gggtctctct ggttagacca gatctgagcc tgggagctct ctggctaact agggaaccca     60
ctgcttaagc ctcaataaag cttgccttga gtgcttc                              97
```

<210> SEQ ID NO 54
<211> LENGTH: 85
<212> TYPE: DNA
<213> ORGANISM: Human immunodeficiency virus type 1

<400> SEQUENCE: 54

```
aagtagtgtg tgcccgtctg ttgtgtgact ctggtaacta gagatccctc agacccttt      60 agtcagtgtg gaaaatctct agcag                                           85
```

<210> SEQ ID NO 55
<211> LENGTH: 18
<212> TYPE: DNA
<213> ORGANISM: Human immunodeficiency virus type 1

<400> SEQUENCE: 55

```
tggcgcccga acagggac                                                   18
```

<210> SEQ ID NO 56
<211> LENGTH: 160
<212> TYPE: DNA
<213> ORGANISM: Human immunodeficiency virus type 1

<400> SEQUENCE: 56

```
ttgaaagcga aagtaaagcc agaggagatc tctcgacgca ggactcggct tgctgaagcg      60
cgcacggcaa gaggcgaggg gcggcgactg gtgagtacgc caaaaatttt gactagcgga    120
ggctagaagg agagagatgg gtgcgagagc gtcggtatta                          160
```

<210> SEQ ID NO 57
<211> LENGTH: 10
<212> TYPE: DNA
<213> ORGANISM: Human immunodeficiency virus type 1

<400> SEQUENCE: 57

```
actggtgagt                                                            10
```

<210> SEQ ID NO 58
<211> LENGTH: 168
<212> TYPE: DNA
<213> ORGANISM: Human immunodeficiency virus type 1

<400> SEQUENCE: 58

```
atgggtgcga gagcgtcggt attaagcggg ggagaattag ataaatggga aaaaattcgg      60
taataaggcc aggggggaaag aagaagtaca agctaaagca catcgtatgg gcaagcaggg   120
agctagaacg attcgcagtt aatcctggcc ttttagagac atcagaag                 168
```

<210> SEQ ID NO 59
<211> LENGTH: 10
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (9)..(10)
<223> OTHER INFORMATION: n is absent

<400> SEQUENCE: 59

```
gcggccgcnn                                                            10
```

<210> SEQ ID NO 60
<211> LENGTH: 146
<212> TYPE: DNA
<213> ORGANISM: Human immunodeficiency virus type 1

<400> SEQUENCE: 60

```
tgatcttcag acctggagga ggcgatatga gggacaattg gagaagtgaa ttatataaat      60
```

```
ataaagtagt aaaaattgaa ccattaggag tagcacccac caaggcaaag agaagagtgg    120
tgcagagaga aaaaagagca gtggga                                         146
```

<210> SEQ ID NO 61
<211> LENGTH: 10
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (9)..(10)
<223> OTHER INFORMATION: n is absent

<400> SEQUENCE: 61

```
atttaaatnn                                                            10
```

<210> SEQ ID NO 62
<211> LENGTH: 234
<212> TYPE: DNA
<213> ORGANISM: Human immunodeficiency virus type 1

<400> SEQUENCE: 62

```
aggagctttg ttccttgggt tcttgggagc agcaggaagc actatgggcg cagcgtcaat    60
gacgctgacg gtacaggcca gacaattatt gtctgatata gtgcagcagc agaacaattt    120
gctgagggct attgaggcgc aacagcatct gttgcaactc acagtctggg gcatcaaaca    180
gctccaggca agaatcctgg ctgtggaaag atacctaaag gatcaacagc tcct          234
```

<210> SEQ ID NO 63
<211> LENGTH: 10
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (9)..(10)
<223> OTHER INFORMATION: n is absent

<400> SEQUENCE: 63

```
cctgcaggnn                                                            10
```

<210> SEQ ID NO 64
<211> LENGTH: 483
<212> TYPE: DNA
<213> ORGANISM: Human immunodeficiency virus type 1

<400> SEQUENCE: 64

```
ggatttgggg ttgctctgga aaactcattt gcaccactgc tgtgccttgg aatgctagtt    60
ggagtaataa atctctggaa cagatttgga ataacatgac ctggatggag tgggacagag    120
aaattaacaa ttcacaagc ttaatacact ccttaattga agaatcgcaa aaccagcaag    180
aaaagaatga acaagaatta ttggaattag ataaatgggc aagtttgtgg aattggttta    240
acataacaaa ttggctgtgg tatataaaat tattcataat gatagtagga ggcttggtag    300
gtttaagaat agttttttgct gtactttcta tagtgaatag agttaggcag ggatattcac    360
cattatcgtt tcagacccac ctcccaatcc cgaggggacc cgacaggccc gaaggaatag    420
aagaagaagg tggagagaga gacagagaca gatccattcg attagtgaac ggatctcgac    480
ggt                                                                  483
```

<210> SEQ ID NO 65
<211> LENGTH: 36
<212> TYPE: DNA
<213> ORGANISM: Human immunodeficiency virus type 1

<400> SEQUENCE: 65
agttaggcag ggatattcac cattatcgtt tcagac                                    36

<210> SEQ ID NO 66
<211> LENGTH: 10
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (7)..(10)
<223> OTHER INFORMATION: n is absent

<400> SEQUENCE: 66 atcgatnnnn                                                                 10

<210> SEQ ID NO 67
<211> LENGTH: 547
<212> TYPE: DNA
<213> ORGANISM: Human immunodeficiency virus type 1

<400> SEQUENCE: 67
tagactgtag cccaggaata tggcagctag attgtacaca tttagaagga aaagttatct          60
tggtagcagt tcatgtagcc agtggatata tagaagcaga agtaattcca gcagagacag         120
ggcaagaaac agcatacttc ctcttaaaat tagcaggaag atggccagta aaaacagtac         180
atacagacaa tggcagcaat ttcaccagta ctacagttaa ggccgcctgt tggtgggcgg         240
ggatcaagca ggaatttggc attccctaca atccccaaag tcaaggagta atagaatcta         300
tgaataaaga attaaagaaa attataggac aggtaagaga tcaggctgaa catcttaaga         360
cagcagtaca aatggcagta ttcatccaca atttttaaaag aaaagggggg attggggggt         420
acagtgcagg ggaaagaata gtagacataa tagcaacaga catacaaact aaagaattac         480
aaaaacaaat tacaaaaatt caaaatttttc gggtttatta cagggacagc agagatccag         540
tttggct                                                                  547

<210> SEQ ID NO 68
<211> LENGTH: 33
<212> TYPE: DNA
<213> ORGANISM: Human immunodeficiency virus type 1

<400> SEQUENCE: 68
gtttattaca gggacagcag agatccagtt tgg                                       33

<210> SEQ ID NO 69
<211> LENGTH: 10
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (7)..(10)
<223> OTHER INFORMATION: n is absent

<400> SEQUENCE: 69 ctgcatnnnn                                                                 10

<210> SEQ ID NO 70
<211> LENGTH: 10
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (7)..(10)
<223> OTHER INFORMATION: n is absent

<400> SEQUENCE: 70 tgatcannnn                                                          10

<210> SEQ ID NO 71
<211> LENGTH: 1184
<212> TYPE: DNA
<213> ORGANISM: Homo sapiens

<400> SEQUENCE: 71
cgtgaggctc cggtgcccgt cagtgggcag agcgcacatc gcccacagtc cccgagaagt    60 tgggggagg ggtcggcaat tgaaccggtg cctagagaag gtggcgcggg gtaaactggg   120
aaagtgatgt cgtgtactgg ctccgccttt ttcccgaggg tgggggagaa ccgtatataa   180
gtgcagtagt cgccgtgaac gttcttttc gcaacgggtt tgccgccaga acacaggtaa    240
gtgccgtgtg tggttcccgc gggcctggcc tctttacggg ttatgccct tgcgtgcctt    300 gaattacttc cacctggctg cagtacgtga ttcttgatcc cgagcttcgg gttggaagtg   360
ggtgggagag ttcgaggcct tgcgcttaag gagccccttc gcctcgtgct tgagttgagg   420
cctggcctgg gcgctggggc cgccgcgtgc gaatctggtg gcaccttcgc gcctgtctcg   480
ctgctttcga taagtctcta gccatttaaa attttgatg acctgctgcg acgctttttt    540
tctggcaaga tagtcttgta aatgcgggcc aagatctgca cactggtatt tcggtttttg   600
gggccgcggg cggcgacggg gcccgtgcgt cccagcgcac atgttcggcg aggcggggcc   660
tgcgagcgcg gccaccgaga atcggacggg ggtagtctca agctggccgg cctgctctgg   720
tgcctggcct cgcgccgccg tgtatcgccc cgccctgggc ggcaaggctg gcccggtcgg   780
caccagttgc gtgagcggaa agatggccgc ttccggcc tgctgcaggg agctcaaaat    840
ggaggacgcg gcgctcggga gagcgggcgg gtgagtcacc cacacaaagg aaaagggcct   900
ttccgtcctc agccgtcgct tcatgtgact ccactgagta ccgggcgccg tccaggcacc   960
tcgattagtt ctcgagcttt tggagtacgt cgtctttagg ttgggggag gggttttatg   1020 cgatggagtt tccccacact gagtgggtgg agactgaagt taggccagct tggcacttga   1080
tgtaattctc cttggaattt gccctttttg agtttggatc ttggttcatt ctcaagcctc   1140
agacagtggt tcaaagtttt tttcttccat ttcaggtgtc gtga                   1184

<210> SEQ ID NO 72
<211> LENGTH: 20
<212> TYPE: DNA
<213> ORGANISM: Homo sapiens

<400> SEQUENCE: 72
cagaacacag gtaagtgccg                                              20

<210> SEQ ID NO 73
<211> LENGTH: 19
<212> TYPE: DNA
<213> ORGANISM: Homo sapiens

```
<400> SEQUENCE: 73
tccatttcag gtgtcgtga                                                    19

<210> SEQ ID NO 74
<211> LENGTH: 10
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (7)..(10)
<223> OTHER INFORMATION: n is absent

<400> SEQUENCE: 74 tctagannnn                                                              10

<210> SEQ ID NO 75
<211> LENGTH: 10
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (7)..(10)
<223> OTHER INFORMATION: n is absent

<400> SEQUENCE: 75 ggatccnnnn                                                              10

<210> SEQ ID NO 76
<211> LENGTH: 720
<212> TYPE: DNA
<213> ORGANISM: Artificial Sequence
<220> FEATURE:
<223> OTHER INFORMATION: synthetic construct

<400> SEQUENCE: 76
atggtgagca agggcgagga gctgttcacc ggggtggtgc ccatcctggt cgagctggac        60
ggcgacgtaa acggccacaa gttcagcgtg tccggcgagg gcgagggcga tgccacctac       120
ggcaagctga ccctgaagtt catctgcacc accggcaagc tgcccgtgcc ctggcccacc       180
ctcgtgacca ccctgaccta cggcgtgcag tgcttcagcc gctaccccga ccacatgaag       240
cagcacgact tcttcaagtc cgccatgccc gaaggctacg tccaggagcg caccatcttc       300
ttcaaggacg acggcaacta caagacccgc gccgaggtga agttcgaggg cgacaccctg       360
gtgaaccgca tcgagctgaa gggcatcgac ttcaaggagg acggcaacat cctggggcac       420
aagctggagt acaactacaa cagccacaac gtctatatca tggccgacaa gcagaagaac       480
ggcatcaagg tgaacttcaa gatccgccac aacatcgagg acggcagcgt gcagctcgcc       540
gaccactacc agcagaacac ccccatcggc gacggccccg tgctgctgcc cgacaaccac       600
tacctgagca cccagtccgc cctgagcaaa gaccccaacg agaagcgcga tcacatggtc       660
ctgctggagt tcgtgaccgc cgccgggatc actctcggca tggacgagct gtacaagtaa       720

<210> SEQ ID NO 77
<211> LENGTH: 10
<212> TYPE: DNA
<213> ORGANISM: Artificial Sequence
<220> FEATURE:
<223> OTHER INFORMATION: synthetic construct
<220> FEATURE:
```

<221> NAME/KEY: misc_feature
<222> LOCATION: (7)..(10)
<223> OTHER INFORMATION: n is absent

<400> SEQUENCE: 77 gtcgacnnnn    10

<210> SEQ ID NO 78
<211> LENGTH: 591
<212> TYPE: DNA
<213> ORGANISM: Artificial Sequence
<220> FEATURE:
<223> OTHER INFORMATION: synthetic construct

<400> SEQUENCE: 78
atcaacctct ggattacaaa atttgtgaaa gattgactgg tattcttaac tatgttgctc    60
cttttacgct atgtggatac gctgctttaa tgcctttgta tcatgctatt gcttcccgta   120
tggctttcat tttctcctcc ttgtataaat cctggttgct gtctctttat gaggagttgt   180
ggcccgttgt caggcaacgt ggcgtggtgt gcactgtgtt tgctgacgca accccactg    240
gttgggcat tgccaccacc tgtcagctcc tttccgggac tttcgctttc cccctcccta   300
ttgccacggc ggaactcatc gccgcctgcc ttgcccgctg ctggacaggg gctcggctgt   360
tgggcactga caattccgtg gtgttgtcgg ggaagctgac gtcctttcca tggctgctcg   420
cctgtgttgc cacctggatt ctgcgcggga cgtccttctg ctacgtccct tcggccctca   480
atccagcgga ccttccttcc cgcggcctgc tgccggctct gcggcctctt ccgcgtcttc   540
gccttcgccc tcagacgagt cggatctccc tttgggccgc ctccccgcct g            591

<210> SEQ ID NO 79
<211> LENGTH: 726
<212> TYPE: DNA
<213> ORGANISM: Artificial Sequence
<220> FEATURE:
<223> OTHER INFORMATION: synthetic construct

<400> SEQUENCE: 79
taaacaggcc tattgattgg aaagtatgtc aacgaattgt gggtcttttg gggtttgctg    60
ccccttttac gcaatgtgga tatcctgctt taatgccttt atatgcatgt atacaagcaa   120
aacaggcttt tactttctcg ccaacttaca aggcctttct aagtaaacag tatctgaccc   180
tttaccccgt tgctcggcaa cggcctggtc tgtgccaagt gtttgctgac gcaaccccca   240
ctggttgggg cttggccata ggccatcagc gcatgcgtgg aacctttgtg tctcctctgc   300
cgatccatac tgcggaactc ctagccgctt gttttgctcg cagcaggtct ggagcgaaac   360
tcatcgggac tgacaattct gtcgtgctct cccgcaagta tacatcgttt ccagggctgc   420
taggctgtgc tgccaactgg atcctgcgcg gacgtccttt tgtttacgtc ccgtcggcgc   480
tgaatcccgc ggacgacccc tcccggggcc gcttggggct ctaccgcccg cttctccgtc   540
tgccgtaccg accgaccacg gggcgcacct ctctttacgc ggactcccg tctgtgcctt   600
ctcatctgcc ggaccgtgtg cacttcgctt cacctctgca cgtcgcatgg agaccaccgt   660
gaacgcccac cggaacctgc ccaaggtctt gcataagagg actcttggac tttcagcaat   720
gtcaac                                                              726

<210> SEQ ID NO 80
<211> LENGTH: 10
<212> TYPE: DNA
<213> ORGANISM: Artificial Sequence

```
<220> FEATURE:
<223> OTHER INFORMATION: synthetic construct
<220> FEATURE:
<221> NAME/KEY: misc_feature
<222> LOCATION: (7)..(10)
<223> OTHER INFORMATION: n is absent

<400> SEQUENCE: 80 gaattcnnnn                                                          10

<210> SEQ ID NO 81
<211> LENGTH: 10
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (7)..(10)
<223> OTHER INFORMATION: n is absent

<400> SEQUENCE: 81 gagctcnnnn                                                          10

<210> SEQ ID NO 82
<211> LENGTH: 10
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (7)..(10)
<223> OTHER INFORMATION: n is absent

<400> SEQUENCE: 82 ggtaccnnnn                                                          10

<210> SEQ ID NO 83
<211> LENGTH: 64
<212> TYPE: DNA
<213> ORGANISM: Human immunodeficiency virus type 1

<400> SEQUENCE: 83
ctttaagacc aatgacttac aaggcagctg tagatcttag ccactttta aaagaaaagg    60 gggg                                                                64

<210> SEQ ID NO 84
<211> LENGTH: 55
<212> TYPE: DNA
<213> ORGANISM: Human immunodeficiency virus type 1

<400> SEQUENCE: 84
actggaaggg ctaattcact cccaacgaag acaagatctg cttttttgctt gtact       55

<210> SEQ ID NO 85
<211> LENGTH: 97
<212> TYPE: DNA
<213> ORGANISM: Human immunodeficiency virus type 1

<400> SEQUENCE: 85
gggtctctct ggttagacca gatctgagcc tgggagctct ctggctaact agggaaccca   60
ctgcttaagc ctcaataaag cttgccttga gtgcttc                            97

<210> SEQ ID NO 86
```

```
<211> LENGTH: 85
<212> TYPE: DNA
<213> ORGANISM: Human immunodeficiency virus type 1

<400> SEQUENCE: 86
aagtagtgtg tgcccgtctg ttgtgtgact ctggtaacta gagatccctc agaccctttt    60
agtcagtgtg gaaaatctct agcag                                          85

<210> SEQ ID NO 87
<211> LENGTH: 129
<212> TYPE: DNA
<213> ORGANISM: Artificial Sequence
<220> FEATURE:
<223> OTHER INFORMATION: synthetic construct

<400> SEQUENCE: 87
aacttgttta ttgcagctta taatggttac aaataaagca atagcatcac aaatttcaca    60
aataaagcat tttttcact gcattctagt tgtggtttgt ccaaactcat caatgtatct    120
tatcatgtc                                                           129

<210> SEQ ID NO 88
<211> LENGTH: 810
<212> TYPE: DNA
<213> ORGANISM: Artificial Sequence
<220> FEATURE:
<223> OTHER INFORMATION: synthetic construct

<400> SEQUENCE: 88
atgagccata ttcaacggga aacgtcgagg ccgcgattaa attccaacat ggatgctgat    60
ttatatgggt ataaatgggc tcgcgataat gtcgggcaat caggtgcgac aatctatcgc   120
ttgtatggga agcccgatgc gccagagttg tttctgaaac atggcaaagg tagcgttgcc   180
aatgatgtta cagatgagat ggtcagacta aactggctga cggaatttat gccacttccg   240
accatcaagc attttatccg tactcctgat gatgcatggt tactcaccac tgcgatcccc   300
ggaaaaacag cgttccaggt attagaagaa tatcctgatt caggtgaaaa tattgttgat   360
gcgctggcag tgttcctgcg ccggttgcac tcgattcctg tttgtaattg tccttttaac   420
agcgatcgcg tatttcgcct cgctcaggcg caatcacgaa tgaataacgg tttggttgat   480
gcgagtgatt ttgatgacga gcgtaatggc tggcctgttg aacaagtctg gaaagaaatg   540
cataaacttt tgccattctc accggattca gtcgtcactc atggtgattt ctcacttgat   600
aaccttattt ttgacgaggg gaaattaata ggttgtattg atgttggacg agtcggaatc   660
gcagaccgat accaggatct tgccatccta tggaactgcc tcggtgagtt ttctccttca   720
ttacagaaac ggcttttca aaaatatggt attgataatc ctgatatgaa taaattgcag   780
tttcatttga tgctcgatga gttttctaa                                    810

<210> SEQ ID NO 89
<211> LENGTH: 620
<212> TYPE: DNA
<213> ORGANISM: Artificial Sequence
<220> FEATURE:
<223> OTHER INFORMATION: synthetic construct

<400> SEQUENCE: 89
agatcaaagg atcttcttga gatccttttt ttctgcgcgt aatctgctgc ttgcaaacaa    60
aaaaaccacc gctaccagcg gtggtttgtt tgccggatca gagctaccaa actcttttc   120 cgaaggtaac tggcttcagc agagcgcaga taccaaatac tgttcttcta gtgtagccgt   180
```

| | |
|---|---|
| agttaggcca ccacttcaag aactctgtag caccgcctac ataccgct ctgctaatcc | 240 |
| tgttaccagt ggctgctgcc agtggcgata agtcgtgtct taccgggttg gactcaagac | 300 |
| gatagttacc ggataaggcg cagcggtcgg gctgaacggg gggttcgtgc acacagccca | 360 |
| gcttggagcg aacgacctac accgaactga gatacctaca gcgtgagcta tgagaaagcg | 420 |
| ccacgcttcc cgaagggaga aaggcggaca ggtatccggt aagcggcagg gtcggaacag | 480 |
| gagagcgcac gagggagctt ccaggggaa acgcctggta tctttatagt cctgtcgggt | 540 |
| ttcgccacct ctgacttgag cgtcgatttt tgtgatgctc gtcaggggg cggagcctat | 600 |
| ggaaaaacgc cagcaacgcg | 620 |

<210> SEQ ID NO 90
<211> LENGTH: 7523
<212> TYPE: DNA
<213> ORGANISM: Artificial Sequence
<220> FEATURE:
<223> OTHER INFORMATION: synthetic construct

<400> SEQUENCE: 90

| | |
|---|---|
| gtaatcaatt acggggtcat tagttcatag cccatatatg gagttccgcg ttacataact | 60 |
| tacggtaaat ggcccgcctg gctgaccgcc caacgacccc cgcccattga cgtcaataat | 120 |
| gacgtatgtt cccatagtaa cgccaatagg gactttccat tgacgtcaat gggtggagta | 180 |
| tttacggtaa actgcccact tggcagtaca tcaagtgtat catatgccaa gtacgccccc | 240 |
| tattgacgtc aatgacggta aatggcccgc ctggcattat gcccagtaca tgaccttatg | 300 |
| ggactttcct acttggcagt acatctacgt attagtcatc gctattacca tgctgatgcg | 360 |
| gttttggcag tacatcaatg ggcgtggata gcggtttgac tcacggggat ttccaagtct | 420 |
| ccaccccatt gacgtcaatg ggagtttgtt ttggcaccaa aatcaacggg actttccaaa | 480 |
| atgtcgtaac aactccgccc cattgacgca aatgggcggt aggcgtgtac ggtgggaggt | 540 |
| ctatataagc agagctggtt tagtgaaccg ggtctctct ggttagacca gatctgagcc | 600 |
| tgggagctct ctggctaact agggaaccca ctgcttaagc ctcaataaag cttgccttga | 660 |
| gtgcttcaag tagtgtgtgc ccgtctgttg tgtgactctg gtaactagag atccctcaga | 720 |
| cccttttagt cagtgtggaa aatctctagc agtggcgccc gaacagggac ttgaaagcga | 780 |
| aagtaaagcc agaggagatc tctcgacgca ggactcggct tgctgaagcg cgcacggcaa | 840 |
| gaggcgaggg gcggcgactg gtgagtacgc caaaatttt gactagcgga ggctagaagg | 900 |
| agagagatgg gtgcgagagc gtcggtatta agcggggag aattagataa atgggaaaaa | 960 |
| attcggtaat aaggccaggg ggaaagaaga agtacaagct aaagcacatc gtatgggcaa | 1020 |
| gcagggagct agaacgattc gcagttaatc ctggcctttt agagacatca gaaggcggcc | 1080 |
| gctgatcttc agacctggag gaggcgatat gagggacaat tggagaagtg aattatataa | 1140 |
| atataaagta gtaaaattg aaccattagg agtagcaccc accaaggcaa agagaagagt | 1200 |
| ggtgcagaga gaaaaagag cagtgggaat ttaaatagga gctttgttcc ttgggttctt | 1260 |
| gggagcagca ggaagcacta tgggcgcagc gtcaatgacg ctgacggtac aggccagaca | 1320 |
| attattgtct gatatagtgc agcagcagaa caatttgctg agggctattg aggcgcaaca | 1380 |
| gcatctgttg caactcacag tctggggcat caaacagctc caggcaagaa tcctggctgt | 1440 |
| ggaaagatac ctaaaggatc aacagctcct cctgcagggg atttgggtt gctctggaaa | 1500 |
| actcatttgc accactgctg tgccttggaa tgctagttgg agtaataaat ctctggaaca | 1560 |

```
gatttggaat aacatgacct ggatggagtg ggacagagaa attaacaatt acacaagctt    1620
aatacactcc ttaattgaag aatcgcaaaa ccagcaagaa aagaatgaac aagaattatt    1680
ggaattagat aaatgggcaa gtttgtggaa ttggtttaac ataacaaatt ggctgtggta    1740
tataaaatta ttcataatga tagtaggagg cttggtaggt ttaagaatag ttttgctgt     1800 actttctata gtgaatagag ttaggcaggg atattcacca ttatcgtttc agacccacct    1860
cccaatcccg aggggacccg acaggcccga aggaatagaa gaagaaggtg gagagagaga    1920
cagagacaga tccattcgat tagtgaacgg atctcgacgg tatcgatact agtacaaatg    1980
gcagtattca tccacaattt taaaagaaaa ggggggattg gggggtacag tgcaggggaa    2040
agaatagtag acataatagc aacagacata caaactaaag aattacaaaa acaaattaca    2100
aaaattcaaa attttcgggt ttattacagg gacagcagag atccactttg gctgcattga    2160
tcacgtgagg ctccggtgcc cgtcagtggg cagagcgcac atcgcccaca gtccccgaga    2220
agttgggggg aggggtcggc aattgaaccg gtgcctagag aaggtggcgc ggggtaaact    2280
gggaaagtga tgtcgtgtac tggctccgcc ttttcccga gggtggggga gaaccgtata     2340
taagtgcagt agtcgccgtg aacgttcttt ttcgcaacgg gtttgccgcc agaacacagg    2400
taagtgccgt gtgtggttcc cgcgggcctg gcctctttac gggttatggc ccttgcgtgc    2460
cttgaattac ttccacctgg ctgcagtacg tgattcttga tcccgagctt cgggttggaa    2520
gtgggtggga gagttcgagg ccttgcgctt aaggagcccc ttcgcctcgt gcttgagttg    2580
aggcctggcc tgggcgctgg ggccgccgcg tgcgaatctg gtggcacctt cgcgcctgtc    2640
tcgctgcttt cgataagtct ctagccattt aaaattttg atgacctgct gcgacgcttt     2700
ttttctggca agatagtctt gtaaatgcgg gccaagatct gcacactggt atttcggttt    2760
ttggggccgc gggcggcgac ggggcccgtg cgtcccagcg cacatgttcg gcgaggcggg    2820
gcctgcgagc gcggccaccg agaatcggac gggggtagtc tcaagctggc cggcctgctc    2880
tggtgcctgg cctcgcgccg ccgtgtatcg ccccgcccctg gcggcaagg ctggcccggt     2940 cggcaccagt tgcgtgagcg gaaagatggc cgcttcccgg ccctgctgca gggagctcaa    3000
aatggaggac gcgcgctcg ggagagcggg cgggtgagtc acccacacaa aggaaaaggg     3060
cctttccgtc ctcagccgtc gcttcatgtg actccacgga gtaccgggcg ccgtccaggc    3120
acctcgatta gttctcgagc ttttggagta cgtcgtcttt aggttggggg gaggggtttt    3180
atgcgatgga gtttccccac actgagtggg tggagactga agttaggcca gcttggcact    3240
tgatgtaatt ctccttggaa tttgcccttt ttgagtttgg atcttggttc attctcaagc    3300
ctcagacagt ggttcaaagt ttttttcttc catttcaggt gtcgtgatct agaggatccg    3360
ccaccatggt gagcaaggc gaggagctgt tcaccgggt ggtgcccatc ctggtcgagc       3420
tggacggcga cgtaaacggc cacaagttca gcgtgtccgg cgagggcgag ggcgatgcca    3480
cctacggcaa gctgaccctg aagttcatct gcaccaccgg caagctgccc gtgccctggc    3540
ccaccctcgt gaccaccctg acctacggcg tgcagtgctt cagccgctac cccgaccaca    3600
tgaagcagca cgacttcttc aagtccgcca tgcccgaagg ctacgtccag gagcgcacca    3660
tcttcttcaa ggacgacggc aactacaaga cccgcgccga ggtgaagttc gagggcgaca    3720
ccctggtgaa ccgcatcgag ctgaagggca tcgacttcaa ggaggacggc aacatcctgg    3780
ggcacaagct ggagtacaac tacaacagcc acaacgtcta tatcatggcc gacaagcaga    3840
agaacggcat caaggtgaac ttcaagatcc gccacaacat cgaggacggc agcgtgcagc    3900
tcgccgacca ctaccagcag aacaccccca tcggcgacgg ccccgtgctg ctgcccgaca    3960
```

```
accactacct gagcacccag tccgccctga gcaaagaccc caacgagaag cgcgatcaca    4020
tggtcctgct ggagttcgtg accgccgccg ggatcactct cggcatggac gagctgtaca    4080
agtaagtcga ctaaacaggc ctattgattg gaaagtatgt caacgaattg tgggtctttt    4140
ggggtttgct gccccttta cgcaatgtgg atatcctgct ttaatgcctt tatatgcatg     4200
tatacaagca aaacaggctt ttactttctc gccaacttac aaggcctttc taagtaaaca    4260
gtatctgacc ctttacccg ttgctcggca acggctggt ctgtgccaag tgtttgctga     4320
cgcaaccccc actggttggg cttggccat aggccatcag cgcatgcgtg aacctttgt     4380
gtctcctctg ccgatccata ctgcggaact cctagccgct tgttttgctc gcagcaggtc    4440
tggagcgaaa ctcatcggga ctgacaattc tgtcgtgctc tcccgcaagt atacatcgtt    4500
tccagggctg ctaggctgtg ctgccaactg gatcctgcgc gggacgtcct ttgtttacgt    4560
cccgtcggcg ctgaatcccg cggacgaccc ctcccggggc cgcttggggc tctaccgccc    4620
gcttctccgt ctgccgtacc gaccgaccac ggggcgcacc tctctttacg cggactcccc    4680
gtctgtgcct tctcatctgc cggaccgtgt gcacttcgct tcacctctgc acgtcgcatg    4740
gagaccaccg tgaacgccca ccggaacctg cccaaggtct tgcataagag gactcttgga    4800
cttttcagcaa tgtcaacgaa ttcgagctcg gtacctttaa gaccaatgac ttacaaggca    4860
gctgtagatc ttagccactt tttaaaagaa aaggggggac tggaagggct aattcactcc    4920
caacgaagac aagatctgct ttttgcttgt actgggtctc tctggttaga ccagatctga    4980
gcctgggagc tctctggcta actagggaac ccactgctta agcctcaata aagcttgcct    5040
tgagtgcttc aagtagtgtg tgcccgtctg ttgtgtgact ctggtaacta gagatccctc    5100
agacccttt agtcagtgtg aaaatctct agcagtagta gttcatgtca tcttattatt    5160
cagtatttat aacttgcaaa gaaatgaata tcagagagtg agaggaactt gtttattgca    5220
gcttataatg gttacaaata aagcaatagc atcacaaatt tcacaaataa agcattttt    5280
tcactgcatt ctagttgtgg tttgtccaaa ctcatcaatg tatcttatca tgtctggctc    5340
tagctatccc gccccctaggc accggggaaa tgtgcgcgga acccctattt gtttatttt    5400
ctaaatacat tcaaatatgt atccgctcat gagacaataa ccctgataaa tgcttcaata    5460
atattgaaaa aggaagagta tgagccatat tcaacgggaa acgtcgaggc cgcgattaaa    5520
ttccaacatg gatgctgatt tatatgggta taaatgggct cgcgataatg tcgggcaatc    5580
aggtgcgaca atctatcgct tgtatgggaa gcccgatgcg ccagagttgt ttctgaaaca    5640
tggcaaaggt agcgttgcca atgatgttac agatgagatg gtcagactaa actggctgac    5700
ggaatttatg ccacttccga ccatcaagca ttttatccgt actcctgatg atgcatggtt    5760
actcaccact gcgatcccg gaaaaacagc gttccaggta ttagaagaat atcctgattc    5820
aggtgaaaat attgttgatg cgctggcagt gttcctgcgc cggttgcact cgattcctgt    5880
ttgtaattgt cctttaaca gcgatcgcgt atttcgcctc gctcaggcgc aatcacgaat    5940
gaataacggt ttggttgatg cgagtgattt tgatgacgag cgtaatggct ggcctgttga    6000
acaagtctgg aaagaaatgc ataaactttt gccattctca ccggattcag tcgtcactca    6060
tggtgatttc tcacttgata accttatttt tgacgagggg aaattaatag gttgtattga    6120
tgttggacga gtcggaatcg cagaccgata ccaggatctt gccatcctat ggaactgcct    6180
cggtgagttt tctccttcat tacagaaacg gctttttcaa aaatatggta ttgataatcc    6240
tgatatgaat aaattgcagt ttcatttgat gctcgatgag ttttttctaac tgtcagacca    6300
```

```
agtttactca tatatacttt agattgattt aaaacttcat ttttaattta aaaggatcta    6360
ggtgaagatc cttttttgata atctcatgac caaaatccct taacgtgagt tttcgttcca   6420
ctgagcgtca gacccccgtag aaaagatcaa aggatcttct tgagatcctt tttttctgcg   6480
cgtaatctgc tgcttgcaaa caaaaaaacc accgctacca gcggtggttt gtttgccgga   6540
tcaagagcta ccaactcttt ttccgaaggt aactggcttc agcagagcgc agataccaaa   6600
tactgttctt ctagtgtagc cgtagttagg ccaccacttc aagaactctg tagcaccgcc   6660
tacataccct gctctgctaa tcctgttacc agtggctgct gccagtggcg ataagtcgtg   6720
tcttaccggg ttggactcaa gacgatagtt accggataag gcgcagcggt cgggctgaac   6780
ggggggttcg tgcacacagc ccagcttgga gcgaacgacc tacaccgaac tgagatacct   6840
acagcgtgag ctatgagaaa gcgccacgct tcccgaaggg agaaaggcgg acaggtatcc   6900
ggtaagcggc agggtcggaa caggagagcg cacgagggag cttccagggg gaaacgcctg   6960
gtatctttat agtcctgtcg ggtttcgcca cctctgactt gagcgtcgat ttttgtgatg   7020
ctcgtcaggg gggcggagcc tatggaaaaa cgccagcaac gcggcctttt tacgttcct    7080 ggccttttgc tggccttttg ctcacatgtt ctttcctgcg ttatcccctg attctgtgga   7140
taaccgtatt accgcctttg agtgagctga taccgctcgc cgcagccgaa cgaccgagcg   7200
cagcgagtca gtgagcgagg aagcggaaga gcgcccaata cgcaaaccgc ctctccccgc   7260
gcgttggccg attcattaat gcagctggca cgacaggttt cccgactgga aagcgggcag   7320
tgagcgcaac gcaattaatg tgagttagct cactcattag gcaccccagg ctttacactt   7380
tatgcttccg gctcgtatgt tgtgtggaat tgtgagcgga taacaatttc acacaggaaa   7440
cagctatgac catgattacg ccaagcgcgc aattaaccct cactaaaggg aacaaaagct   7500
ggagctgcag actagtaagc tta                                           7523
```

<210> SEQ ID NO 91
<211> LENGTH: 10
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (7)..(10)
<223> OTHER INFORMATION: n is absent

<400> SEQUENCE: 91

```
actagtnnnn                                                            10
```

<210> SEQ ID NO 92
<211> LENGTH: 181
<212> TYPE: DNA
<213> ORGANISM: Human immunodeficiency virus type 1

<400> SEQUENCE: 92

```
agtacaaatg gcagtattca tccacaattt taaaagaaaa ggggggattg ggggtacag     60 tgcagggaa agaatagtag acataatagc aacagacata caaactaaag aattacaaaa    120
acaaattaca aaaattcaaa attttcgggt ttattacagg gacagcagag atccactttg    180
g                                                                    181
```

<210> SEQ ID NO 93
<211> LENGTH: 178
<212> TYPE: DNA
<213> ORGANISM: Human immunodeficiency virus type 1

<400> SEQUENCE: 93

| acaaatggca gtattcatcc acaattttaa aagaaaaggg gggattgggg ggtacagtgc | 60 |
| --- | --- |
| aggggaaaga atagtagaca taatagcaac agacatacaa actaaagaat tacaaaaaca | 120 |
| aattacaaaa attcaaaatt ttcgggttta ttacagggac agcagagatc cactttgg | 178 |

<210> SEQ ID NO 94
<211> LENGTH: 33
<212> TYPE: DNA
<213> ORGANISM: Human immunodeficiency virus type 1

<400> SEQUENCE: 94

| gtttattaca gggacagcag agatccactt tgg | 33 |
| --- | --- |

<210> SEQ ID NO 95
<211> LENGTH: 1184
<212> TYPE: DNA
<213> ORGANISM: Homo sapiens

<400> SEQUENCE: 95

| cgtgaggctc cggtgcccgt cagtgggcag agcgcacatc gcccacagtc cccgagaagt | 60 |
| --- | --- |
| tggggggagg ggtcggcaat tgaaccggtg cctagagaag gtggcgcggg gtaaactggg | 120 |
| aaagtgatgt cgtgtactgg ctccgccttt tccccgaggg tggggagaa ccgtatataa | 180 |
| gtgcagtagt cgccgtgaac gttctttttc gcaacgggtt tgccgccaga acacaggtaa | 240 |
| gtgccgtgtg tggttcccgc gggcctggcc tctttacggg ttatggccct tgcgtgcctt | 300 |
| gaattacttc cacctggctg cagtacgtga ttcttgatcc cgagcttcgg gttggaagtg | 360 |
| ggtgggagag ttcgaggcct tgcgcttaag gagccccttc gcctcgtgct tgagttgagg | 420 |
| cctggcctgg gcgctgggc cgccgcgtgc gaatctggtg gcaccttcgc gcctgtctcg | 480 |
| ctgctttcga taagtctcta gccatttaaa attttttgatg acctgctgcg acgcttttt | 540 |
| tctggcaaga tagtcttgta aatgcgggcc aagatctgca cactggtatt tcggtttttg | 600 |
| gggccgcggg cggcgacggg gcccgtgcgt cccagcgcac atgttcggcg aggcggggcc | 660 |
| tgcgagcgcg gccaccgaga atcggacggg ggtagtctca agctggccgg cctgctctgg | 720 |
| tgcctggcct cgcgccgccg tgtatcgccc cgccctgggc ggcaaggctg gcccggtcgg | 780 |
| caccagttgc gtgagcggaa agatggccgc ttccgggccc tgctgcaggg agctcaaaat | 840 |
| ggaggacgcg gcgctcggga gagcgggcgg gtgagtcacc cacacaaagg aaaagggcct | 900 |
| ttccgtcctc agccgtcgct tcatgtgact ccacggagta ccgggcgccg tccaggcacc | 960 |
| tcgattagtt ctcgagcttt tggagtacgt cgtctttagg ttgggggag gggttttatg | 1020 |
| cgatggagtt tccccacact gagtgggtgg agactgaagt taggccagct tggcacttga | 1080 |
| tgtaattctc cttggaattt gccctttttg agtttggatc ttggttcatt ctcaagcctc | 1140 |
| agacagtggt tcaaagtttt tttcttccat ttcaggtgtc gtga | 1184 |

<210> SEQ ID NO 96
<211> LENGTH: 10
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (7)..(10)
<223> OTHER INFORMATION: n is absent

```
<400> SEQUENCE: 96 gccaccnnnn                                                            10

<210> SEQ ID NO 97
<211> LENGTH: 218
<212> TYPE: DNA
<213> ORGANISM: Artificial Sequence
<220> FEATURE:
<223> OTHER INFORMATION: synthetic construct

<400> SEQUENCE: 97
tagtagttca tgtcatctta ttattcagta tttataactt gcaaagaaat gaatatcaga      60
gagtgagagg aacttgttta ttgcagctta taatggttac aaataaagca atagcatcac    120
aaatttcaca aataaagcat tttttcact gcattctagt tgtggtttgt ccaaactcat     180
caatgtatct tatcatgtct ggctctagct atcccgcc                            218
```